US012161890B2

(12) United States Patent
Zanini et al.

(10) Patent No.: US 12,161,890 B2
(45) Date of Patent: Dec. 10, 2024

(54) ANTIBODIES AGAINST DENGUE VIRUS AND RELATED METHODS

(71) Applicants: CZ Biohub SF, LLC, San Francisco, CA (US); The Board of Trustees of the Leland Stanford Junior University, Stanford, CA (US)

(72) Inventors: Fabio Zanini, Stanford, CA (US); Derek Croote, Stanford, CA (US); Makeda L. Robinson, Stanford, CA (US); Leslie Goo, San Francisco, CA (US); Stephen R. Quake, San Francisco, CA (US); Shirit Einav, Stanford, CA (US); Krista McCutcheon, San Francisco, CA (US); Eric Waltari, San Francisco, CA (US)

(73) Assignees: CZ Biohub SF, LLC, San Francisco, CA (US); The Board of Trustees of the Leland Stanford Junior University, Stanford, CA (US)

( * ) Notice: Subject to any disclaimer, the term of this patent is extended or adjusted under 35 U.S.C. 154(b) by 827 days.

(21) Appl. No.: 17/265,704

(22) PCT Filed: Aug. 7, 2019

(86) PCT No.: PCT/US2019/045427
§ 371 (c)(1),
(2) Date: Feb. 3, 2021

(87) PCT Pub. No.: WO2020/033491
PCT Pub. Date: Feb. 13, 2020

(65) Prior Publication Data
US 2021/0188948 A1 Jun. 24, 2021

Related U.S. Application Data

(60) Provisional application No. 62/715,628, filed on Aug. 7, 2018.

(51) Int. Cl.
*A61P 31/14* (2006.01)
*G01N 33/563* (2006.01)
(Continued)

(52) U.S. Cl.
CPC ............ *G01N 33/563* (2013.01); *A61P 31/14* (2018.01); *G01N 33/56983* (2013.01);
(Continued)

(58) Field of Classification Search
CPC .............. C07K 16/10; C07K 2317/565; C07K 2317/76; C07K 16/1081; G01N 33/563;
(Continued)

(56) References Cited

U.S. PATENT DOCUMENTS 7,622,113 B2   11/2009  Lai et al.
9,334,331 B2 *  5/2016  Igawa ................... C07K 16/36
(Continued)

FOREIGN PATENT DOCUMENTS

WO        2004067567        8/2004

OTHER PUBLICATIONS

Janeway CA Jr, Travers P, Walport M, et al. Immunobiology: The Immune System in Health and Disease. 5th edition. New York: Garland Science; 2001. The interaction of the antibody molecule with specific antigen. (Year: 2001).*

(Continued)

*Primary Examiner* — Joanne Hama
*Assistant Examiner* — Pratik Thapa
(74) *Attorney, Agent, or Firm* — Kilpatrick Townsend & Stockton LLP

(57) ABSTRACT

Provided are antibodies or antigen binding portions thereof that specifically bind Dengue virus, various compositions of such antibodies or antigen binding portions thereof, and methods of their use. Provided are such antibodies, fragments of such antibodies retaining Dengue virus-binding (Continued)

ability, pharmaceutical compositions including such antibodies or antigen binding fragments thereof, and diagnostic compositions including such antibodies or antigen binding fragments thereof. Also provided are isolated nucleic acids encoding such antibodies, amino acid sequences of such antibodies, and host cells transformed therewith. Additionally, provided are prophylactic, therapeutic, and diagnostic methods employing the antibodies and nucleic acids of the disclosure.

11 Claims, 24 Drawing Sheets

Specification includes a Sequence Listing.

(51) Int. Cl.
  *G01N 33/569* (2006.01)
  *A61K 39/00* (2006.01)
(52) U.S. Cl.
  CPC .. *A61K 2039/505* (2013.01); *C07K 2317/565* (2013.01); *G01N 2333/185* (2013.01)
(58) Field of Classification Search
  CPC ....... G01N 33/56983; G01N 2333/185; A61K 2039/505; A61P 31/14
  See application file for complete search history.

(56) References Cited

U.S. PATENT DOCUMENTS

| | | | | |
|---|---|---|---|---|
| 10,421,807 | B2* | 9/2019 | Gonzales | ............. A61P 17/08 |
| 2017/0029489 | A1 | 2/2017 | Macary et al. | |

OTHER PUBLICATIONS

Clark LA, Demarest SJ, Eldredge J, Jarpe MB, Li Y, Simon K, van Vlijmen HW. Influence of canonical structure determining residues on antibody affinity and stability. J Struct Biol. Feb. 2014; 185(2):223-7. doi: 10.1016/j.jsb.2013.08.009. Epub Aug. 29, 2013. PMID: 23994046. (Year: 2013).*

Chiu ML, Goulet DR, Teplyakov A, Gilliland GL. Antibody Structure and Function: The Basis for Engineering Therapeutics. Antibodies (Basel). Dec. 3, 2019;8(4):55. doi: 10.3390/antib8040055. PMID: 31816964; PMCID: PMC6963682. (Year: 2019).*

Hummer AM, Abanades B, Deane CM. Advances in computational structure-based antibody design. Curr Opin Struct Biol. Jun. 2022;74:102379. doi: 10.1016/j.sbi.2022. 102379. Epub Apr. 28, 2022. PMID: 35490649. (Year: 2022).*

De Genst E, Saerens D, Muyldermans S, Conrath K. Antibody repertoire development in camelids. Dev Comp Immunol. 2006;30(1-2):187-98. doi: 10.1016/j.dci.2005.06.010. PMID: 16051357. (Year: 2006).*

Malia TJ, Teplyakov A, Ernst R, Wu SJ, Lacy ER, Liu X, Vandermeeren M, Mercken M, Luo J, Sweet RW, Gilliland GL. Epitope mapping and structural basis for the recognition of phosphorylated tau by the anti-tau antibody AT8. Proteins. Apr. 2016;84(4):427-34. doi: 10.1002/prot.24988. (Year: 2016).*

Multiplexed Sequencing with the Illumina Genome Analyzer System, Illumina® Sequencing, Available online at https://www.illumina.com/documents/products/datasheets/datasheet_sequencing_multiplex.pdf, Dec. 2, 2008, 4 pages.

Zanini et al., Figures and Figure Supplements—Single-cell Transcriptional Dynamics of Flavivirus Infection, Microbiology and Infectious Disease, eLife, vol. 7, 2018, pp. 1-21.

Zanini et al., Single-Cell Transcriptional Dynamics of Flavivirus Infection, Microbiology and Infectious Disease, eLife, vol. 7, Feb. 16, 2018, pp. 1-21.

Zanini et al., Virus-Inclusive Single-cell RNA Sequencing Reveals the Molecular Signature of Progression to Severe Dengue, Proceedings of the National Academy of Sciences of the United States of America, vol. 115, No. 52, Dec. 26, 2018, pp. E12363-E12369.

Zanini et al., Virus-Inclusive Single-cell RNA Sequencing Reveals the Molecular Signature of Progression to Severe Dengue: Supplementary Information, Proceedings of the National Academy of Sciences of the United States of America, vol. 115, No. 52, Dec. 7, 2018, 30 pages.

Budigi et al., "Neutralization of Antibody-Enhanced Dengue Infection by VIS513, A Pan Serotype Reactive Monoclonal Antibody Targeting Domain III of The Dengue E Protein", PLOS Neglected Tropical Diseases, vol. 12, No. 2, Feb. 9, 2018, 20 pages.

Lu et al., "Potent Neutralization Ability of a Human Monoclonal Antibody Against Serotype 1 Dengue Virus", Frontiers in Microbiolog, vol. 9, No. 1214, Jun. 6, 2018, 10 pages.

PCT/US2019/045427 , "International Search Report and Written Opinion", Jan. 6, 2020, 13 pages.

PCT/US2019/045427 , "Invitation to Pay Additional Fees and, Where Applicable, Protest Fee", Nov. 4, 2019, 3 pages.

* cited by examiner

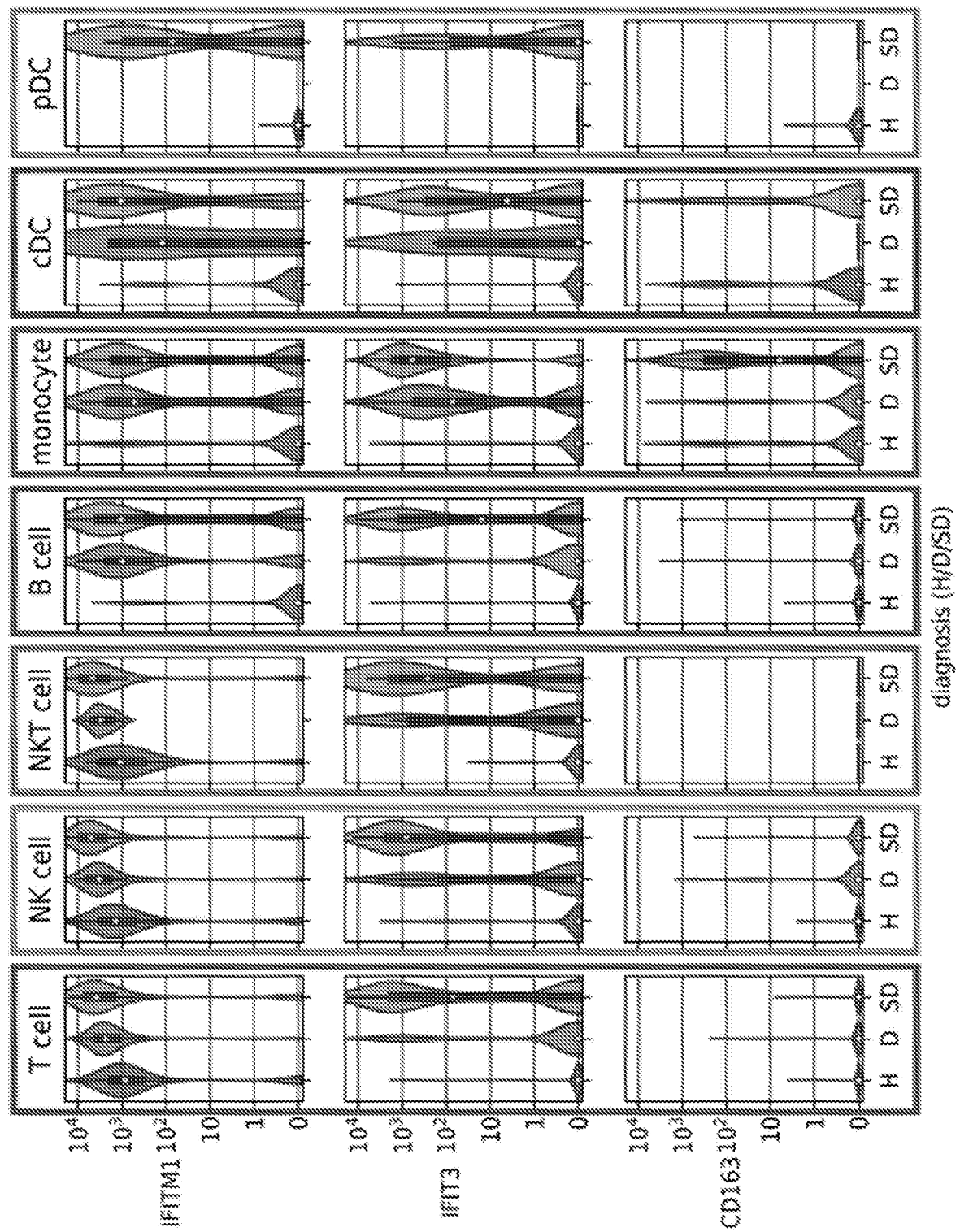

FIG. 12B — Sequence alignment of Founder VDJ, J9 mAb v1, and J8 mAb (Kabat/Chothia numbering; CDR H1, CDR H2, and CDR H3 boxed).

Positions 1–36 (CDR H1 boxed: 26–35A)

| Position | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 35A | 36 |
|---|---|---|---|---|---|---|---|---|---|---|---|---|---|---|---|---|---|---|---|---|---|---|---|---|---|---|---|---|---|---|---|---|---|---|---|---|---|
| FOUNDER VDJ | Q | V | Q | L | V | Q | S | G | A | E | V | K | K | P | G | S | S | V | K | V | S | C | K | A | S | G | G | T | F | S | S | Y | A | I | S |   | W |
| J9 mAb v1 |   |   |   |   |   |   |   |   | A | E | V | R | K | P | G | S | S | V | K | V | S | C | K | T | S | G | G | S | L | N | S | Y | G | I | S |   | W |
| J8 mAb |   |   |   |   |   |   |   |   | A | E | V | K | K | P | G | S | S | V | K | V | S | C | K | A | S | G | G | T | F | S | S | N | S | V | T |   | W |

Positions 37–67 (CDR H2 boxed: 50–65)

| Position | 37 | 38 | 39 | 40 | 41 | 42 | 43 | 44 | 45 | 46 | 47 | 48 | 49 | 50 | 51 | 52 | 52A | 53 | 54 | 55 | 56 | 57 | 58 | 59 | 60 | 61 | 62 | 63 | 64 | 65 | 66 | 67 |
|---|---|---|---|---|---|---|---|---|---|---|---|---|---|---|---|---|---|---|---|---|---|---|---|---|---|---|---|---|---|---|---|---|
| FOUNDER VDJ | V | R | Q | A | P | G | Q | G | L | E | W | M | G | G | I | I |   | P | I | F | G | T | A | N | Y | A | Q | K | F | Q | G | R | V |
| J9 mAb v1 | V | R | Q | A | P | G | Q | G | L | E | W | M | G | G | I | I |   | P | F | F | G | T | V | I | Y | S | D | N | Y | Q | G | R | A |
| J8 mAb | V | R | Q | A | P | G | H | G | L | E | W | M | G | T | I | I |   | P | F | F | G | T | R | H | Y | A | D | N | F | Q | G | R | V |

Positions 68–92

| Position | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 |
|---|---|---|---|---|---|---|---|---|---|---|---|---|---|---|---|---|---|---|---|---|---|---|---|---|---|---|---|---|
| FOUNDER VDJ | T | I | T | T | D | E | S | T | S | T | A | Y | M | E | L | S | S | L | R | S | E | D | T | A | V | Y | Y | C |
| J9 mAb v1 | S | F | S | S | D | E | S | T | T | T | A | Y | M | E | L | R | S | L | R | S | E | D | T | A | V | Y | Y | C |
| J8 mAb | T | V | T | T | D | E | S | T | T | T | V | Y | M | E | L | S | S | L | R | S | D | D | T | A | V | Y | Y | C |

Positions 93–113 (CDR H3 boxed: 95–102)

| Position | 93 | 94 | 95 | 96 | 97 | 98 | 99 | 100 | 100A | 100B | 100C | 100D | 100E | 100F | 101 | 102 | 103 | 104 | 105 | 106 | 107 | 108 | 109 | 110 | 111 | 112 | 113 |
|---|---|---|---|---|---|---|---|---|---|---|---|---|---|---|---|---|---|---|---|---|---|---|---|---|---|---|---|
| FOUNDER VDJ | A | R | Y | C | S | S | T | S | C | Y | D | N | W | F | D | P | W | G | Q | G | T | L | V | T | V | S | S |
| J9 mAb v1 | A | R | Y | C | Y | S | A | S | C | Y | H | N | W | F | D | P | W | G | Q | G | T | L | V | T | V | S | T |
| J8 mAb | A | R | S | C | E | S | P | S | C | Y | H | N | W | F | D | P | W | G | Q | G | T | L | V | T | V | T | S |

FIG. 12B

ANTIBODIES AGAINST DENGUE VIRUS AND RELATED METHODS

CROSS-REFERENCE TO RELATED APPLICATIONS

This application is a 371 application and claims the benefit of PCT Application No. PCT/US2019/045427, filed Aug. 7, 2019, which claims the benefit of priority of U.S. Provisional Application No. 62/715,628, filed Aug. 7, 2018, each of which are incorporated herein by reference in their entireties.

STATEMENT AS TO RIGHTS TO INVENTIONS MADE UNDER FEDERALLY SPONSORED RESEARCH AND DEVELOPMENT

This invention was made with Government support under Contract No. AI057229, awarded by the National Institutes of Health. The Government has certain rights in the invention.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named 103182-1142280-001310WO-_SL.txt, created on Aug. 6, 2019, and having a size of 245,798 bytes and is filed concurrently with the specification. The sequence listing contained in this ASCII formatted document is part of the specification and is herein incorporated by reference in its entirety.

BACKGROUND

Dengue virus (DEW) is a major threat to global health, estimated to infect 400 million people annually in over 100 countries. The four serotypes of DENV (1-4) are transmitted by a mosquito vector. There are currently no approved antivirals available for dengue treatment. The majority of symptomatic patients present with dengue fever; a flu like illness. Five to twenty percent of these patients progress to severe dengue (SD), manifested by bleeding, plasma leakage, shock, organ failure, and sometimes death. Early administration of supportive care reduces mortality in patients with SD, however, there are no accurate means to predict which patients will progress to SD. The currently utilized warning signs to identify dengue patients at risk of progressing to severe disease are based on clinical parameters that appear late in the disease course and are neither sensitive nor specific. This promotes ineffective patient triage and resource allocation and continued morbidity and mortality. There are currently no biomarkers to effectively predict disease progression.

BRIEF SUMMARY

The disclosure provides antibodies or antigen binding portions thereof that specifically bind to Dengue virus antigens.

In some embodiments, the antibody or antigen binding fragment thereof has a heavy chain variable region that includes (i) a CDRH1 comprising SEQ ID NOs: 153 or 154; (ii) a CDRH2 comprising SEQ ID NOs: 189 or 190; and (iii) a CDRH3 comprising SEQ NO:222, and a light chain variable region that includes (i) a CDRL1 comprising SEQ ID NO:257; (ii) a CDRL2 comprising SEQ ID NOs: 285 or 286; and (iii) a CDRL3 comprising SEQ ID NOs: 298 or 299.

In some embodiments, the antibody or antigen binding fragment thereof has a heavy chain variable region that includes (i) a CDRH1 comprising SEQ NO:155; (ii) a CDRH2 comprising SEQ ID NO:191; and (iii) a CDRH3 comprising SEQ ID NO:223; and a light chain variable region that includes (i) a CDRL1 comprising SEQ ID NO:258; (ii) a CDRL2 comprising SEQ ID NO:287; and (iii) a CDRL3 comprising SEQ NO: 300.

In some embodiments, the antibody or antigen binding fragment thereof has a heavy chain variable region that includes (i) a CDRH1 comprising SEQ ID NOs: 156, 157, or 158; (ii) a CDRH2 comprising SEQ ID NOs: 192, 193, or 194; and (iii) a CDRH3 comprising SEQ ID NOs: 224, 225, or 226; and a light chain variable region that includes (i) a CDRL1 comprising SEQ ID NOs: 259, 260, or 261; (ii) a CDRL2 comprising SEQ ID NO:288; and (iii) a CDRL3 comprising SEQ ID NOs: 301 or 302.

In some embodiments, the antibody or antigen binding fragment thereof has a heavy chain variable region that includes (i) a CDRH1 comprising SEQ ID NOs: 159 or 160; (ii) a. CDRH2 comprising SEQ ID NO:19;5; and (iii) a CDRH3 comprising SEQ ID NOs: 227 or 228; and a light chain variable region that includes (i) a CDRL1 comprising SEQ ID NO:262; (ii) a CDRL2 comprising SEQ ID NO:289; and (iii) a CDRL3 comprising SEQ ID NOs: 303 or 304.

In some embodiments, the antibody or antigen binding fragment thereof has a heavy chain variable region that includes (i) a CDRH1 comprising SEQ ID NOs: 161 or 162; (ii) a CDRH2 comprising SEQ ID NOs: 196 or 197; and (iii) a CDRH3 comprising SEQ ID NOs: 229 or 230; and a light chain variable region that includes (i) a CDRL1 comprising SEQ ID NOs: 263 or 264; (ii) a CDRL2 comprising SEQ NOs: 288 or 290; and (iii) a CDRL3 comprising SEQ NOs: 305 or 306.

In some embodiments, the antibody or antigen binding fragment thereof has a heavy chain variable region that includes (i) a CDRH1 comprising SEQ NOs: 163 or 164; (ii) a CDRH2 comprising SEQ ID NOs: 198 or 199; and (iii) a CDRH3 comprising SEQ NOs: 231 or 232; and a light chain variable region that includes (i) a CDRL1 comprising SEQ NOs: 265 or 266; (ii) a CDRL2 comprising SEQ ID NOs: 291; and (iii) a CDRL3 comprising SEQ ID NOs: 307 or 308.

In some embodiments, the antibody or antigen binding fragment thereof has a heavy chain variable region comprising (i) a CDRH1 comprising SEQ ID NOs: 163, 164, or 443; (ii) a CDRH2 comprising SEQ ID NOs: 198, 199, or 444; and (iii) a CDRH3 comprising SEQ ID NOs: 231, 232, or 445.

In some embodiments, the antibody or antigen binding fragment thereof has a heavy chain variable region that includes (i) a CDRH1 comprising SEQ NO:165; (ii) a CDRH2 comprising SEQ ID NO:200; and (iii) a CDRH3 comprising SEQ ID NO:233; and a light chain variable region that includes (i) a CDRL1 comprising SEQ ID NO:267; (ii) a CDRL2 comprising SEQ ID NO:285; and (iii) a CDRL3 comprising SEQ ID NO:309.

In some embodiments, the antibody or antigen binding fragment thereof has a heavy chain variable region that includes (i) a CDRH1 comprising SEQ ID NO:166; (ii) a CDRH2 comprising SEQ ID NO:201; and (iii) a CDRH3 comprising SEQ ID NO:234; and a light chain variable region that includes (i) a CDRL1 comprising SEQ ID NO:257; (ii) a CDRL2 comprising SEQ ID NO:285; and (iii) a CDRL3 comprising SEQ ID NO:310.

In some embodiments, the antibody or antigen binding fragment thereof has a heavy chain variable region that includes (i) a CDRH1 comprising SEQ ID NOs: 167, 168, 169, or 170; (ii) a CDRH2 comprising SEQ ID NOs: 202, 203, or 204; and (iii) a CDRH3 comprising SEQ ID NOs: 235, 236, 237, or 238; and a light chain variable region that includes (i) a CDRL1 comprising SEQ ID NOs:268, 269, 270, or 271; (ii) a CDRL2 comprising SEQ ID NOs: 292 or 293; and (iii) a CDRL3 comprising SEQ ID NOs: 311, 312, 313, or 314.

In some embodiments, the antibody or antigen binding fragment thereof has a heavy chain variable region that includes (i) a CDRH1 comprising SEQ ID NOs: 171, 172, 173, 174, 175, or 176; (ii) a CDRH2 comprising SEQ ID NOs: 205, 206, 207, 208, or 209; and (iii) a CDRH3 comprising SEQ ID NOs: 239, 240, 241, 242, 243, or 244; and a light chain variable region that includes (i) a CDRL1 comprising SEQ ID NOs: 272, 273, 274, or 446; (ii) a CDRL2 comprising SEQ ID NOs: 292 or 294; and (iii) a CDRL3 comprising SEQ ID NOs: 315 or 316.

In some embodiments, the antibody or antigen binding fragment thereof has a heavy chain variable region that includes (i) a CDRH1 comprising SEQ ID NOs: 177 or 178; (ii) a CDRH2 comprising SEQ ID NOs: 210 or 211; and (iii) a CDRH3 comprising SEQ ID NOs: 245 or 246; and a light chain variable region that includes (i) a CDRL1 comprising SEQ ID NOs: 275 or 276; (ii) a CDRL2 comprising SEQ ID NO:295; and (iii) a CDRL3 comprising SEQ ID NO:317.

In some embodiments, the antibody or antigen binding fragment thereof has a heavy chain variable region that includes (i) a CDRH1 comprising SEQ ID NOs: 179 or 180; (ii) a CDRH2 comprising SEQ ID NO:212; and (iii) a CDRH3 comprising SEQ ID NOs: 247 or 248; and a light chain variable region that includes (i) a CDRL1 comprising SEQ ID NOs: 277 or 278; (ii) a CDRL2 comprising SEQ ID NO:296; and (in) a CDRL3 comprising SEQ ID NO:318.

In some embodiments, the antibody or antigen binding fragment thereof has a heavy chain variable region that includes (i) a CDRH1 comprising SEQ ID NOs: 181 or 182; (ii) a CDRH2 comprising SEQ ID NOs: 213 or 214; and (iii) a CDRH3 comprising SEQ ID NOs: 249 or 250; and a light chain variable region that includes (i) a CDRL1 comprising SEQ ID NO:279; (ii) a CDRL2 comprising SEQ ID NOs: 285 or 297; and (iii) a CDRL3 comprising SEQ ID NOs: 319 or 320.

In some embodiments, the antibody or antigen binding fragment thereof has a heavy chain variable region that includes (i) a CDRH1 comprising SEQ ID NO:183; (ii) a CDRH2 comprising SEQ TD NOs: 215 or 216; and (iii) a CDRH3 comprising SEQ ID NOs: 251 or 252; and a light chain variable region that includes (i) a CDRL1 comprising SEQ ID NOs: 280 or 281; (ii) a CDRL2 comprising SEQ ID NO:288; and (iii) a CDRL3 comprising SEQ ID NO:321.

In some embodiments, the antibody or antigen binding fragment thereof has a heavy chain variable region that includes (i) a CDRH1 comprising SEQ ID NOs: 184, 185, or 186; (ii) a CDRH2 comprising SEQ ID NOs: 217, 218, or 219; and (iii) a CDRH3 comprising SEQ ID NOs: 253 or 254; and a light chain variable region that includes (i) a CDRL1 comprising SEQ ID NO:282; (ii) a CDRL2 comprising SEQ ID NOs: 291 or 294; and (iii) a CDRL3 comprising SEQ ID NOs: 322, 323, or 324.

In some embodiments, the antibody or antigen binding fragment thereof has a heavy chain variable region that includes (i) a CDRH1 comprising SEQ NOs: 187 or 188; (ii) a CDRH2 comprising SEQ ID NOs: 220 or 221; and (iii) a CDRH3 comprising SEQ NOs: 255 or 256; and a light chain variable region that includes (i) a CDRL1 comprising SEQ NOs: 283 or 284; (ii) a CDRL2 comprising SEQ ID NO:294; and (iii) a CDRL3 comprising SEQ ID NOs: 325 or 326.

In some embodiments, the antibody or antigen binding fragment thereof has a heavy chain variable region that includes an amino acid sequence that is at least 90% identical to SEQ ID NOs: 1 or 2; and a light chain variable region that includes an amino acid sequence that is at least 90% identical to SEQ ID NOs: 77 or 78.

In some embodiments, the antibody or antigen binding fragment thereof has a heavy chain variable region that includes an amino acid sequence that is at least 90% identical to SEQ ID NO:3; and a light chain variable region that includes an amino acid sequence that is at least 90% identical to SEQ ID NO:79.

In some embodiments, the antibody or antigen binding fragment thereof has a heavy chain variable region that includes an amino acid sequence that is at least 90% identical to SEQ II) NOs: 4, 5, or 6; and a light chain variable region that includes an amino acid sequence that is at least 90% identical to SEQ ID NOs:80, 81, or 82.

In some embodiments, the antibody or antigen binding fragment thereof has a heavy chain variable region that includes an amino acid sequence that is at least 90% identical to SEQ ID NOs: 7 or 8; and a light chain variable region that includes an amino acid sequence that is at least 90% identical to SEQ ID NOs: 83 or 84.

In some embodiments, the antibody or antigen binding fragment thereof has a heavy chain variable region that includes an amino acid sequence that is at least 90% identical to SEQ ID NOs: 9 or 10; and a light chain variable region that includes an amino acid sequence that is at least 90% identical to SEQ ID NOs: 85 or 86.

In some embodiments, the antibody or antigen binding fragment thereof has a heavy chain variable region that includes an amino acid sequence that is at least 90% identical to SEQ ID NOs: 11 or 12; and (b) a light chain variable region that includes an amino acid sequence that is at least 90% identical to SEQ ID NOs: 87 or 88.

In some embodiments, the antibody or antigen binding fragment thereof has a heavy chain variable region comprising an amino acid sequence that is at least 90% identical to SEQ ID NOs: 11, 12, 440, 441, or 442 and comprising G26 and G27 in CDRH1, W47, M48, G49, P52a, F54, G55, and T56 in CDRH2, and S100, C100a, Y100b, H100, W100e, F100f, D101, and P102 in CDRH3.

In some embodiments, the antibody or antigen binding fragment thereof has a heavy chain variable region comprising an amino acid sequence that is at least 90% identical to SEQ ID NO:439 and comprising G26 and G27 in CDRH1, W47, M48, G49, P52a, F'54, G55, and T56 in CDRH2, and S100, C100a, Y100b, D100 or H100, W100e, F100f, D101, and P102 in CDRH3.

In some embodiments, the antibody or antigen binding fragment thereof has a heavy chain variable region that includes an amino acid sequence that is at least 90% identical to SEQ ID NOs: 13 or 14; and a light chain variable region that includes an amino acid sequence that is at least 90% identical to SEQ ID NOs: 89 or 90.

In some embodiments, the antibody or antigen binding fragment thereof has a heavy chain variable region that includes an amino acid sequence that is at least 90% identical to SEQ ID NOs: 15, 16, 17, 18, or 19; and a light chain variable region that includes an amino acid sequence that is at least 90% identical to SEQ ID NOs: 91, 92, 9:3, 94, or 95.

In some embodiments, the antibody or antigen binding fragment thereof has a heavy chain variable region that includes an amino acid sequence that is at least 90% identical to SEQ ID NOs: 20, 21, 22, 23, 24, or 25; and a light chain variable region that includes an amino acid sequence that is at least 90% identical to SEQ ID NOs: 96, 97, 98, 99, 100, or 101.

In some embodiments, the antibody or antigen binding fragment thereof has a heavy chain variable region that includes an amino acid sequence that is at least 90% identical to SEQ ID NOs: 26 or 27; and a light chain variable region that includes an amino acid sequence that is at least 90% identical to SEQ ID NOs: 102 or 103.

In some embodiments, the antibody or antigen binding fragment thereof has a heavy chain variable region that includes an amino acid sequence that is at least 90% identical to SEQ ID NOs: 28 or 29; and a light chain variable region that includes an amino acid sequence that is at least 90% identical to SEQ ID NOs: 104 or 105.

In some embodiments, the antibody or antigen binding fragment thereof has a heavy chain variable region that includes an amino acid sequence that is at least 90% identical to SEQ ID NOs: 30 or 31; and a light chain variable region that includes an amino acid sequence that is at least 90% identical to SEQ ID NOs: 106 or 107.

In some embodiments, the antibody or antigen binding fragment thereof has a heavy chain variable region that includes an amino acid sequence that is at least 90% identical to SEQ ID NOs: 32 or 33; and a light chain variable region that includes an amino acid sequence that is at least 90% identical to SEQ ID NOs: 108 or 109.

In some embodiments, the antibody or antigen binding fragment thereof has a heavy chain variable region that includes an amino acid sequence that is at least 90% identical to SEQ ID NOs: 34, 35, or 36; and a light chain variable region that includes an amino acid sequence that is at least 90% identical to SEQ NOs: 110, 111, or 112.

In some embodiments, the antibody or antigen binding fragment thereof has a heavy chain variable region that includes an amino acid sequence that is at least 90% identical to SEQ II) NOs: 37 or 38; and a light chain variable region that includes an amino acid sequence that is at least 90% identical to SEQ ID NOs: 113 or 114.

Also provided is a pharmaceutical preparation that includes a pharmaceutically acceptable carrier; and an isolated antibody or antigen binding portion thereof as described herein.

Also provided is a diagnostic preparation that includes a pharmaceutically acceptable carrier; and an isolated antibody or antigen binding portion thereof as described herein.

In addition, provided is a method for the treatment of dengue virus disease that includes the step of administering to a subject a therapeutically effective amount of a pharmaceutical preparation that includes a pharmaceutically acceptable carrier and an isolated antibody or antigen binding portion thereof as described herein.

Also provided is a method for prophylactically treating dengue virus disease that includes the step of administering to a subject a prophylactically effective amount of a pharmaceutical preparation that includes a pharmaceutically acceptable carrier and an isolated antibody or antigen binding portion thereof as described herein.

Also provided is a method for the diagnosis of dengue virus disease that includes the steps of (a) administering to a subject an effective amount of a diagnostic preparation that includes a pharmaceutically acceptable carrier and an isolated antibody or antigen binding portion thereof as described herein, and (b) detecting binding of the isolated antibody or antigen binding portion thereof as a determination of the presence of dengue virus disease.

Lastly, also provided is a method of detecting the presence of dengue virus in a biological sample that includes the steps of (a) contacting said sample with a diagnostic preparation that includes a pharmaceutically acceptable carrier and an isolated antibody or antigen binding portion thereof as described herein, and (b) detecting an amount of binding of the isolated antibody or antigen binding portion thereof as a determination of the presence of said dengue virus.

BRIEF DESCRIPTION OF THE DRAWINGS

The present application includes the following figures. The figures are intended to illustrate certain embodiments and/or features of the compositions and methods, and to supplement any description(s) of the compositions and methods. The figures do not limit the scope of the compositions and methods, unless the written description expressly indicates that such is the case.

FIG. 1A shows a two-dimensional representation of the cells color coded by the expression level of cell type specific marker genes or the abundance of virus reads within the cell (>30 virus reads per million reads in samples from two severe dengue patients, p1-026-1 and p1-036-1). FIG. 1B shows the number of cells analyzed for each cell type from each subject. FIG. 1C show t-Distributed Stochastic Neighbor Embedding (tSNE) visualizations within T, NK, B cells, and monocytes, highlighting broad cell subtypes.

FIG. 2A-2E show differential expression across disease severity and cell types shows hallmarks predictive of severe dengue according to certain aspects of this disclosure. FIG. 2A shows genes that are overexpressed in subjects prior to progressing to severe dengue across cell types and subtypes. Density (light to dark) indicates the average logfold change; size of the dot indicates lower P-value in a distribution statistical comparison (2 sample Kolmogorov-Smirnov). FIG. 2B shows many inflammatory genes such as IFITM1 are expressed ubiquitously during both mild and severe dengue infection (Y axis=counts per million). FIG. 2C shows that other genes such as IFIT3 are specifically expressed prior to the development of severe dengue in various types of lymphocytes (Y axis=counts per million). FIG. 2D shows that a number of genes show double specificity for both severe dengue and a single cell type, for instance CD163 in monocytes (Y axis=counts per million). FIG. 2E shows averaging across cells within specific cell types and subtypes indicates promising candidate predictors of severe dengue as assessed by ROC curves at increasing discriminatory thresholds for gene expression versus disease severity. The numbers after the gene name indicate log 2 fold changes of average expression in patients progressing to severe dengue versus other dengue patients, indicating an overexpression of these genes by a hundred fold or more in our cohort. H: healthy subject, D: dengue, SD: severe dengue. Each data line is marked with a number corresponding to a gene on each graph as noted in the legend.

FIG. 3A shows the fraction of DENV-associated cells across cell types from the two subjects and relative amount of virus RNA from each cell. FIG. 3B shows a tSNE visualization of the B cells from the two subjects. The expression level of DENV RNA and MS4A1 (CD20), JCHAIN, IGHM, TCL1A, and TYROBP are highlighted. FIG. 3C shows differential expression of genes in B cells. FIG. 3D show the fractional identity of heavy chain V loci to their germline counterparts in virus-associated IgM, bystander IgM, and IgG B cells from the subjects 1-026-1 and 1-036-1. Top line, IgM virus; middle line, IgM no virus; bottom line, IgM. FIG. 3E shows coverage (upper line across graph) and minor allele frequency (MAF, lower vertical lines) along the DENV genome in the viral reads from all cells from patient sample 1-026-1 show the genetic diversity of the virus population. FIG. 3F shows site specific Shannon entropy of a cross-sectional DENV serotype 3 alignment does not correlate with entropy from the viral reads of patient sample 1-026-1. Only sites with a coverage of 500 or more reads are considered (dashed green line in panel E). FIG. 3G shows that B cells that are not associated with DENV (bystanders) but derived from subjects with virus-associated cells (B, right plot for each gene) show a clear interferon response compared with B cells derived from healthy controls (H, left plot for each gene). FIG. 3H shows a graph of heavy chain CDR3 antibody clonality illustrating the clonal expansion of IgG1 plasmablasts in patients 1-013-1 and 1-020-1. Each dot is a unique antibody sequence, larger size corresponds to more somatic hypermutation. IgM and IgA1 clones are circled and labeled.

FIG. 12B shows an amino acid alignment of the founder heavy chain VDJ with the J8 and J9 mAb sequences (SEC) ID NOs: 439, 440, and 441, respectively) according to certain aspects of this disclosure. The VDJ recombination of the founder clone for the J8/J9 lineage is shown on the top row. Residues in bold are mutations conserved in clones throughout the entire lineage.

DETAILED DESCRIPTION

Figure 1A:
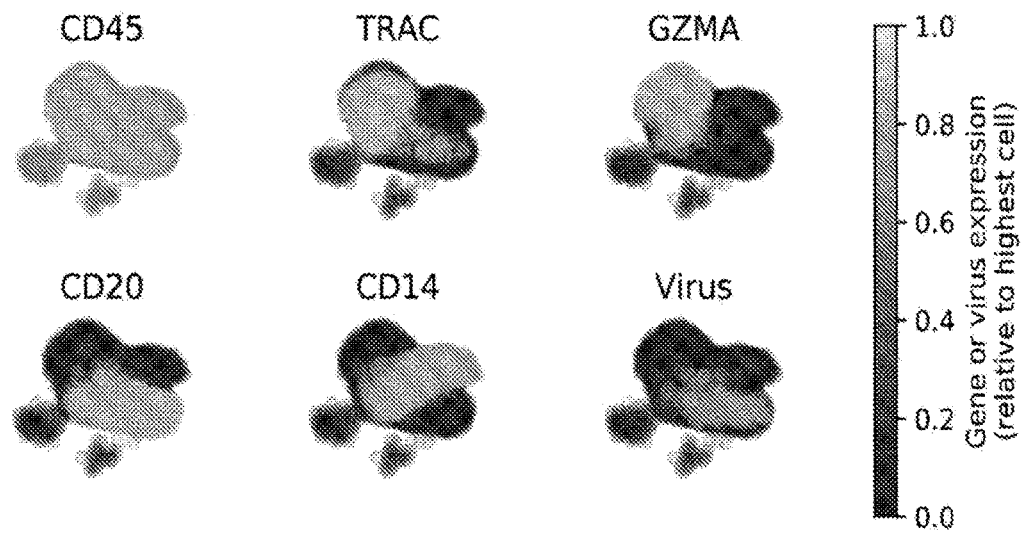
FIG. 1A-1C show an overview of the types of peripheral mononuclear blood cells (PBMCs) surveyed according to certain aspects of this disclosure.

As used in the disclosure and the appended claims, the singular forms "a," "an," and "the" are intended to include the plural forms as well, unless the context clearly indicates otherwise. Also as used herein, "and/or" refers to and encompasses any and all possible combinations of one or more of the associated listed items, as well as the lack of combinations when interpreted in the alternative ("or").

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, compositions, formulations and methodologies which are described in the publication and which might be used in connection with the presently described invention.

Provided in this disclosure are antibodies or antigen binding portions thereof that specifically bind Dengue virus (one or more of type 1, 2, 3, or 4), various compositions of such antibodies or antigen binding portions thereof, and methods of their use. The disclosure provides such antibodies, fragments of such antibodies retaining Dengue virus-binding ability, pharmaceutical compositions including such antibodies or antigen binding fragments thereof, and diagnostic compositions including such antibodies or antigen binding fragments thereof. This disclosure further provides for isolated nucleic acids encoding such antibodies, amino acid sequences of such antibodies, and host cells transformed therewith. Additionally, this disclosure provides for prophylactic, therapeutic, and diagnostic methods employing the antibodies and nucleic acids of the disclosure. While the disclosure is not bound by any particular theory or mechanism of action, the antibodies or antigen binding portions thereof described herein, when bound to a Dengue virus antigen in a subject infected with Dengue virus, may target an immune response in the subject against cells infected with the virus. Thus, such antibodies or antigen binding portions thereof may be used as therapeutic agents to treat subjects infected with Dengue virus. Such antibodies or antigen binding portions thereof may also be used diagnostically to identify subjects that are infected with Dengue virus.

A. Dengue Virus

Dengue (DENV) viruses belong to the flavivirus genus of the family Flaviviridae and are of four serotypes, DENV 1-4. Dengue viruses are positive strand RNA viruses which code for ten genes. The genes are translated as a polyprotein which is cleaved b host and viral proteinases. The DENV envelope glycoprotein (E) is the major surface-exposed DEW antigen and is a principal target against which neutralizing antibodies are directed. The three-dimensional structure of the E glycoprotein has been determined at 2 Å resolution for tick-borne encephalitis virus and recently for dengue type 2 virus (Rey, P. A. et al. (1995) *Nature* 375: 291-298, Modis, Y. et al. (2003) *Proc. Natl. Acad. USA* 100:6986-6994 These studies showed that the monomeric E polypeptide is folded into three distinct domains and that the E glycoprotein consists of a flat, elongated dimer structure, with an interdomain ligand-binding pocket. The membrane protein also appears on the virion surface and is required for the proper processing of E. Dengue virus prM and E structural proteins and nonstructural NS1 protein are glycosylated. The prM glycoprotein is further cleaved by the cellular enzyme furin following viral assembly, generating M, which is present in the mature virus (Stadler, K. et al. (1997) *J. Virol.* 71:8475-8481). Flavivirus prM and E form heterodimers, which are assembled into viral particles during infection (Wengler, G. and Wengler, G. (1989) *J. Virol.* 63:2521-2526). In this manner, the prM serves to protect the functional integrity of E from acid-induced conformational change (Heinz, F. X. et al. 1994 *Virology* 198:109-117; Holzmann, H. et al. 1995 *Arch. Virol.* 140:21.3-221). The E glycoprotein is responsible for cell attachment, possibly mediated by a receptor, and for fusion with the cell membranes following viral entry.

Dengue infection produces fever, rash, and joint pain in humans. A more severe and life-threatening form of dengue is characterized by hemorrhagic fever and hemorrhagic shock (severe dengue (SD)). Passive immunization with clinically acceptable dengue virus neutralizing antibodies is an option for prevention and treatment of Dengue virus infection. In particular, highly efficient neutralizing antibodies may be useful for consideration as a possible therapy for severe dengue virus infection. Neutralizing antibodies specific for the E glycoprotein have been shown to be capable of protecting against dengue virus infection. Some such neutralizing antibodies specifically bind to F dimer or trimer epitopes that bridge two or three envelope protein subunits that make up the 90 repeating dimers on the mature virion. Monoclonal antibodies reactive to flavivirus envelope proteins have been shown to mediate protection against homologous virus challenge in animal models (Mathews, J. H. and Roehrig, J. T. 11984) *J. Immunol.* 132:1533-1537; Brandriss, M. W. et al. (1986) *J. Gen. Virol.* 67:229-234, Gould, E. A. et. al. (1986) *J. Gen. Virol.* 67:591-595; Kaufman, B. M. et al. (1987) *Am. Trop. Med. Hyg.* 36:427-434; Kimura-Kuroda, S., and Yasui, K. (1988) *J. Virol.* 141:3606-3510). In most cases, protection by passive immunization has been correlated with the ability of these antibodies to neutralize the virus in vitro. Protection against dengue virus challenge was also demonstrated in mice following passive immunization with monoclonal or polyclonal antibodies specific to prM (Bray, M., and C. J. Lai. 1991 *Virology* 185:505-508; Kaufman, B M et al. 1987 *Am. J. Trop. Med. Hyg.* 36:427-434) or NS1 (Falgout, B. et al. 1990. *J. Virol.* 64:4356-4363 Henchal, E. A. et al. 1988 *J. Gen. Virol.* 69:2101-2107).

Biomarkers for early detection of SD based on molecular features of the patients blood have been proposed. These efforts have focused on two experimental techniques: (i) flow cytometry of fixed blood cell populations (Durbin A. P., et al, (2008) *Virology* 376:429-435), and (ii) gene expression in bulk RNA extracted from blood or peripheral mononuclear blood cells (PBMCs) (Ubol S, et al. (2008) *J Infect Dis.* 197:1459-11167; Fink J, et al. (2007) *PLoS Negl Trop Dis.* 1:e86; Sessions O. M., et al. (2013) *PLoS Negl Trop Dis.* 7:e2107; Nikolayeva T, et al. (2018) *J Infect Dis.* 217:1690-1698). Although useful, these studies suffer from several limitations. The majority of these studies identified genes whose altered expression is associated with but does not precede the onset of SD and therefore cannot be used as prognostic biomarkers. From a technical standpoint, flow cytometry has a high throughput but is constrained to a few protein markers that are selected a priori, making it excellent for separating known, discrete cell populations but less appropriate for screening the complex, dynamic landscape of cell types, subtypes, and states characteristic of immune responses. Transcriptomics performed on bulk cell populations can screen thousands of genes but its resolution is limited, because it cannot capture tissue heterogeneity. Averaging the signal over various cell populations is confounded by changes both in abundances of cell types and activation states. Coupling fluorescence activated cell sorting (FACS) with single cell transcriptomics can potentially combine the advantages of both approaches (Darmanis S, et al. (2017) *Cell Reports* 21: 1399-1410). It has also been challenging to identify DENV-associated and DENV-infected immune cells in humans.

B. Antibodies

The present disclosure provides compositions and methods for treating and diagnosing a Dengue virus infection (Dengue fever). Antibodies or antigen binding portions thereof that specifically or selectively bind Dengue virus antigens are provided. As used herein, the terms specifically binds to, specific for, selectively binds and selective for a Dengue virus antigen or an epitope on a Dengue virus protein mean binding that is measurably different from a non-specific or non-selective interaction. Specific binding can be measured, for example, by determining binding of a molecule compared to binding of a control molecule. Specific binding can also be determined by competition with a control molecule that is similar to the target, such as an excess of non-labeled target. In that case, specific binding is indicated if the binding of the labeled target to a probe is competitively inhibited by the excess non-labeled target.

An antibody, as used herein, can refer to an intact antibody (e.g., an intact immunoglobulin) and antibody fragment, for example, an antigen binding fragment. Antigen binding fragments comprise at least one antigen binding domain. One example of an antigen binding domain is an antigen binding domain formed by a $V_H$-$V_L$ dimer. Antibodies and antigen binding fragments can be described by the antigen to which they specifically bind.

The $V_H$ and $V_L$ regions can be further subdivided into regions of hypervariability (hypervariable regions (HVRs), also called complementarity determining regions (CDRs)) interspersed with regions that are more conserved. The more conserved regions are called framework regions (FRs). Each $V_H$ and $V_L$ generally comprises three CDRs and four FRs, arranged in the following order (from N-terminus to C-terminus): FR1-CDR1-FR2-CDR2-FR3-CDR3-FR4. The CDRs are involved in antigen binding, and confer antigen specificity, and binding affinity to the antibody. (See Kabat et al, (1991) *Sequences of Proteins of Immunological Interest* 5th ed., Public Health Service, National Institutes of Health, Bethesda, MD) CDR sequences on the heavy chain ($V_H$) may be designated as CDRH1, 2, 3, while CDR sequences on the light chain ($V_v$) may be designated as CDRL1, 2, 3.

Provided herein are antibodies or antigen binding portions thereof that specifically bind to Dengue virus antigens. Dengue virus antigen-specific antibodies were identified from two subjects diagnosed with Dengue fever as described in Example 1. Heavy chain CDR sequences encompassed by this disclosure are set forth in Table 3. Light chain CDR sequences are set forth in Table 4.

In some embodiments, the antibody or antigen binding fragment thereof comprises a heavy chain variable region comprising (i) a CDRH1 comprising SEQ ID NOs: 153 or 154; (ii) a CDRH2 comprising SEQ ID NOs: 189 or 190; and (iii) a CDRH3 comprising SEQ ID NO:222; and a light chain variable region comprising (i) a CDRL1 comprising SEQ ID NO:257; (ii) a CDRL2 comprising SEQ NOs: 285 or 286; and (iii) a CDRL3 comprising SEQ ID NOs: 298 or 299.

In some embodiments, the antibody or antigen binding fragment thereof comprises a heavy chain variable region comprising (i) a CDRH1 comprising SEQ ID NO:155; (ii) a CDRH2 comprising SEQ ID NO: 191; and (iii) a CDRH3 comprising SEQ ID NO:223; and a light chain variable region comprising (i) a CDRL1 comprising SEQ ID NO:258; (ii) a CDRL2 comprising SEQ ID NO:287; and (iii) a CDRL3 comprising SEQ ID NO: 300.

In some embodiments, the antibody or antigen binding fragment thereof comprises a heavy chain variable region comprising (i) a CDRH1 comprising SEQ ID NOs: 156, 157, or 158; (ii) a CDRH2 comprising SEQ ID NOs: 192, 193, or 194; and (iii) a CDRH3 comprising SEQ ID NOs: 224, 225, or 226; and a light chain variable region comprising (i) a CDRL1 comprising SEQ ID NOs: 259, 260, or 261; (ii) a CDRL2 comprising SEQ ID NO:288; and (iii) a CDRL3 comprising SEQ ID NOs: 301 or 302.

In some embodiments, the antibody or antigen binding fragment thereof comprises a heavy chain variable region comprising (i) a CDRH1 comprising SEQ NOs: 159 or 160; (ii) a CDRH2 comprising SEQ ID NO:195; and (iii) a CDRH3 comprising SEQ TD NOs: 227 or 228; and a light chain variable region comprising (i) a CDRL1 comprising SEQ TD NO:262; (ii) a CDRL2 comprising SEQ ID NO:289; and (iii) a CDRL3 comprising SEQ ID NOs: 303 or 304.

In some embodiments, the antibody or antigen binding fragment thereof comprises a heavy chain variable region comprising (i) a CDRH1 comprising SEQ ID NOs: 161 or 162; (ii) a. CDRH2 comprising SEQ ID NOs: 196 or 197; and (iii) a CDRH3 comprising SEQ ID NOs: 229 or 230; and a light chain variable region comprising (i) a CDRL1 comprising SEQ ID NOs: 263 or 264; (ii) a CDRL2 comprising SEQ ID NOs: 288 or 290; and (iii) a CDRL3 comprising SEQ ID NOs: 305 or 306.

In some embodiments, the antibody or antigen binding fragment thereof comprises a heavy chain variable region comprising (i) a CDRH1 comprising SEQ ID NOs: 163 or 164; (ii) a CDRH2 comprising SEQ ID NOs: 198 or 199; and (iii) a CDRH3 comprising SEQ ID NOs: 231 or 232; and a light chain variable region comprising (i) a CDRL1 comprising SEQ ID NOs: 265 or 266; (ii) a CDRL2 comprising SEQ ID NOs: 291; and (iii) a CDRL3 comprising SEQ ID NOs: 307 or 308.

In some embodiments, the antibody or antigen binding fragment thereof comprises a heavy chain variable region comprising (i) a CDRH1 comprising SEQ ID NOs: 163, 164, or 443; (ii) a CDRH2 comprising SEQ NOs: 198, 199, or 444; and (iii) a CDRH3 comprising SEQ ID NOs: 231, 232, or 445.

In some embodiments, the antibody or antigen binding fragment thereof comprises a heavy chain variable region comprising (i) a CDRH1 comprising SEQ ID NO:165; (ii) a CDRH2 comprising SEQ ID NO:200; and (iii) a CDRH3 comprising SEQ ID NO:233; and a light chain variable region comprising (i) a CDRL1 comprising SEQ ID NO:267; (ii) a CDRL2 comprising SEQ ID NO:285; and (iii) a CDRL3 comprising SEQ NO: 309.

In some embodiments, the antibody or antigen binding fragment thereof has a heavy chain variable region that includes (i) a CDRH1 comprising SEQ ID NO:166; (ii) a CDRH2 comprising SEQ ID NO:201; and (iii) a CDRH3 comprising SEQ ID NO:234; and a light chain variable region that includes (i) a CDRL1 comprising SEQ ID NO:257; (ii) a CDRL2 comprising SEQ ID NO:285; and (iii) a CDRL3 comprising SEQ ID NO:310.

In some embodiments, the antibody or antigen binding fragment thereof comprises a heavy chain variable region comprising (i) a CDRH1 comprising SEQ ID NOs: 167, 168, 169, or 170; (ii) a CDRH2 comprising SEQ ID NOs: 202, 203, or 204; and (iii) a CDRH3 comprising SEQ ID NOs:235, 236, 237, or 238; and a light chain variable region comprising (i) a CDRL1 comprising SEQ ID NOs:268, 269, 270, or 271; (ii) a CDRL2 comprising SEQ ID NOs: 292 or 293; and (iii) a CDRL3 comprising SEQ ID NOs: 311, 312, 313, or 314.

In some embodiments, the antibody or antigen binding fragment thereof comprises a heavy chain variable region comprising (i) a CDRH1 comprising SEQ ID NOs: 171, 172, 173, 174, 175, or 176; (ii) a CDRH2 comprising SEQ ID NOs: 205, 206, 207, 208, or 209; and (iii) a CDRH3 comprising SEQ ID NOs: 239, 240, 241, 242, 243, or 244; and a light chain variable region comprising (i) a CDRL1 comprising SEQ ID NOs: 272, 273, 274, or 446; (ii) a CDRL2 comprising SEQ ID NOs: 292 or 294; and (iii) a CDRL3 comprising SEQ ID NOs: 315 or 316.

In some embodiments, the antibody or antigen binding fragment thereof comprises a heavy chain variable region comprising (i) a CDRH1 comprising SEQ ID NOs: 177 or 178; (ii) a CDRH2 comprising SEQ ID NOs: 210 or 211; and (iii) a CDRH3 comprising SEQ NOs: 245 or 246; and a light chain variable region comprising (i) a CDRL1 comprising SEQ ID NOs: 275 or 276; (ii) a CDRL2 comprising SEQ ID NO:295; and (iii) a CDRL3 comprising SEQ ID NO:317.

In some embodiments, the antibody or antigen binding fragment thereof comprises a heavy chain variable region comprising (i) a CDRH1 comprising SEQ TD NOs: 179 or 180; (ii) a CDRH2 comprising SEQ ID NO:212; and (iii) a CDRH3 comprising SEQ ID NOs: 247 or 248; and a light chain variable region comprising (i) a CDRL1 comprising SEQ ID NOs: 277 or 278; (ii) a CDRL2 comprising SEQ TD NO:296; and (iii) a CDRL3 comprising SEQ ID NO:318.

In some embodiments, the antibody or antigen binding fragment thereof comprises a heavy chain variable region comprising (i) a CDRH1 comprising SEQ ID NOs: 181 or 182; (ii) a CDRH2 comprising SEQ ID NOs: 213 or 214; and (iii) a CDRH3 comprising SEQ ID NOs: 249 or 250; and a light chain variable region comprising (i) a CDRL1 comprising SEQ ID NO:279; (ii) a CDRL2 comprising SEQ ID NOs: 285 or 297; and (iii) a CDRL3 comprising SEQ TD NOs: 319 or 320.

In some embodiments, the antibody or antigen binding fragment thereof comprises a heavy chain variable region comprising (i) a CDRH1 comprising SEQ ID NO:183; (ii) a CDRH2 comprising SEQ ID NOs:215 or 216; and (iii) a CDRH3 comprising SEQ ID NOs: 251 or 252; and a light chain variable region comprising (i) a CDRL1 comprising SEQ TD NOs: 280 or 281; (ii) a CDRL2 comprising SEQ ID NO:288; and (in) a CDRL3 comprising SEQ TD NO:321.

In some embodiments, the antibody or antigen binding fragment thereof comprises a heavy chain variable region comprising (i) a CDRH1 comprising SEQ ID NOs: 184, 185, or 186; (ii) a CDRH2 comprising SEQ ID NOs:217, 218, or 219; and (iii) a CDRH3 comprising SEQ ID NOs: 253 or 254; and a light chain variable region comprising (i) a CDRL1 comprising SEQ ID NO:282; (ii) a CDRL2 comprising SEQ II) NOs: 291 or 294; and (iii) a CDRL3 comprising SEQ II) NOs: 322, 323, or 324.

In some embodiments, the antibody or antigen binding fragment thereof comprises a heavy chain variable region comprising (i) a CDRH1 comprising SEQ ID NOs: 187 or 188; (ii) a CDRH2 comprising SEQ ID NOs: 220 or 221; and (iii) a CDRH3 comprising SEQ II) NOs: 255 or 256; and a light chain variable region comprising (i) a CDRL1 comprising SEQ ID NOs: 283 or 284; (ii) a CDRL2 comprising SEQ NO:294; and (iii) a CDRL3 comprising SEQ ID NOs: 325 or 326.

In some embodiments, the antibody or antigen binding fragment thereof comprises a heavy chain variable region comprising an amino acid sequence that is at least 90% identical to SEQ ID NOs: 1 or 2; and a light chain variable region comprising an amino acid sequence that is at least 90% identical to SEQ ID NOs: 77 or 78.

In some embodiments, the antibody or antigen binding fragment thereof comprises a heavy chain variable region comprising an amino acid sequence that is at least 90% identical to SEQ II) NO:3; and a light chain variable region comprising an amino acid sequence that is at least 90% identical to SEQ ID NO:79.

In some embodiments, the antibody or antigen binding fragment thereof comprises a heavy chain variable region comprising an amino acid sequence that is at least 90% identical to SEQ II) NOs: 4, 5, or 6; and a light chain variable region comprising an amino acid sequence that is at least 90% identical to SEQ ID NOs: 80, 81, or 82.

In some embodiments, the antibody or antigen binding fragment thereof comprises a heavy chain variable region comprising an amino acid sequence that is at least 90% identical to SEQ ID NOs: 7 or 8; and a light chain variable region comprising an amino acid sequence that is at least 90% identical to SEQ ID NOs: 83 or 84.

In some embodiments, the antibody or antigen binding fragment thereof comprises a heavy chain variable region comprising an amino acid sequence that is at least 90% identical to SEQ ID NOs: 9 or 10; and a light chain variable region comprising an amino acid sequence that is at least 90% identical to SEQ ID NOs: 85 or 86.

In some embodiments, the antibody or antigen binding fragment thereof comprises a heavy chain variable region comprising an amino acid sequence that is at least 90% identical to SEQ ID NOs: 11 or 12; and (b) a light chain variable region comprising an amino acid sequence that is at least 90% identical to SEQ NOs: 87 or 88.

In some embodiments, the antibody or antigen binding fragment thereof comprises a heavy chain variable region comprising an amino acid sequence that is at least 90% identical to SEQ ID NOs: 11, 12, 440, 441, or 442 and comprising G26 and G27 in CDRH1, W47, M48, G49, P52a, F54, G55, and T56 in CDRH2, and S100, C100a, Y100b, H100, W100e, F100f, D101, and P102 in CDRH3.

In some embodiments, the antibody or antigen binding fragment thereof comprises a heavy chain variable region comprising an amino acid sequence that is at least 90% identical to SEQ NO:439 and comprising G26 and G27 in CDRH1, W47, M48, G49, P52a, F54, G55, and T56 in CDRH2, and S100, C100a, Y100b, D100 or H100, W100e, F100f, D101, and P102 in CDRH3.

In some embodiments, the antibody or antigen binding fragment thereof comprises a heavy chain variable region comprising an amino acid sequence that is at least 90% identical to SEQ ID NOs: 13 or 14; and a light chain variable region comprising an amino acid sequence that is at least 90% identical to SEQ ID NOs: 89 or 90.

In some embodiments, the antibody or antigen binding fragment thereof comprises a heavy chain variable region comprising an amino acid sequence that is at least 90% identical to SEQ ID NOs: 1:5, 16, 17, 18, or 19; and a light chain variable region comprising an amino acid sequence that is at least 90% identical to SEQ ID NOs: 91, 92, 93, 94, or 95.

In some embodiments, the antibody or antigen binding fragment thereof comprises a heavy chain variable region comprising an amino acid sequence that is at least 90% identical to SEQ ID NOs: 20, 21, 22, 23, 24, or 25; and a light chain variable region comprising an amino acid sequence that is at least 90% identical to SEQ ID NOs: 96, 97, 98, 99, 100, or 101.

In some embodiments, the antibody or antigen binding fragment thereof comprises a heavy chain variable region comprising an amino acid sequence that is at least 90% identical to SEQ ID NOs: 26 or 27; and a light chain variable region comprising an amino acid sequence that is at least 90% identical to SEQ ID NOs: 102 or 103.

In some embodiments, the antibody or antigen binding fragment thereof comprises a heavy chain variable region comprising an amino acid sequence that is at least 90% identical to SEQ ID NOs: 28 or 29; and a light chain variable region comprising an amino acid sequence that is at least 90% identical to SEQ ID NOs: 104 or 105.

In some embodiments, the antibody or antigen binding fragment thereof comprises a heavy chain variable region comprising an amino acid sequence that is at least 90% identical to SEQ ID NOs: 30 or 31; and a light chain variable region comprising an amino acid sequence that is at least 90% identical to SEQ ID NOs: 106 or 107.

In some embodiments, the antibody or antigen binding fragment thereof comprises a heavy chain variable region comprising an amino acid sequence that is at least 90% identical to SEQ ID NOs: 32 or 33; and a light chain variable region comprising an amino acid sequence that is at least 90% identical to SEQ ID NOs: 108 or 109.

In some embodiments, the antibody or antigen binding fragment thereof comprises a heavy chain variable region comprising an amino acid sequence that is at least 90% identical to SEQ ID NOs: 34, 35, or 36; and a light chain variable region comprising an amino acid sequence that is at least 90% identical to SEQ ID NOs: 110, 111, or 112.

In some embodiments, the antibody or antigen binding fragment thereof comprises a heavy chain variable region comprising an amino acid sequence that is at least 90% identical to SEQ ID NOs: 37 or 38; and a light chain variable region comprising an amino acid sequence that is at least 90% identical to SEQ ID NOs: 113 or 114.

In each case, where a specific amino acid sequence is recited, embodiments comprising a sequence having at least 90% (e.g. 90%, 91%, 92%, 93%, 94%, 95%, 96%, 97%, 98%, or 99%) identity to the recited sequence (e.g., SEQ ID NOs: 153-326 and 443-445) are also provided.

The disclosure also provides an antibody or antigen binding portion thereof that specifically binds to a Dengue virus antigen, wherein the antibody or antigen binding portion thereof comprises a heavy chain variable region comprising an amino acid sequence that is at least 90% identical (for example, at least 90%, 91%, 92%, 93%, 94%, 95%, 96%, 97%, 98% or 99% identical) to any of SEQ ID NOs: 1-38 and 440-442 and a light chain variable region comprising an amino acid sequence that is at least 90% identical (for example, at least 90%, 91%, 92%, 93%, 94%, 95%, 96%, 97%, 98% or 99% identical) to any of SEQ ID NOs: 77-114. Table 1 provides the sequences for SEQ ID Nos: 1-38. Table 2 provides the sequences for SEQ ID Nos: 77-114.

In some embodiments, the antibody or antigen binding portion thereof comprises the heavy chain variable region comprises an amino acid sequence that is at least 90% identical (for example, at least 90%, 91%, 92%, 93%, 94%, 95%, 96%, 97%, 98% or 99% identical) to any of SEQ ID NOs: 1-38 and 440-442.

Variants of the specific antibody sequences described herein are contemplated. For example, variants of the J8/J9 and associated founder heavy chain sequence are contemplated that have at leas 90% identity thereto. In some embodiments, such variants retain G26 and G27 in CDRH1, W47, M48, G49, P52a, F54, G55, and T56 in CDRH2, and S100, C100a, Y100b, H100 or D100, W100e, F100f, D101, and P102 in CDRH3

In some embodiments, provided are nucleic acid sequences encoding antibodies or antigen binding fragments thereof that specifically bind to Dengue virus antigens. Exemplary heavy chain nucleic acid sequences are set forth in SEQ ID NOs: 39-76. Exemplary light chain nucleic acid sequences are set forth in SEQ ID NOs: 115-152. In some embodiments, provided are nucleic acid sequences comprising a sequence having at least 80% (e.g. 80%, 81%, 82%, 83%, 84%, 85%, 86%, 87%, 88%, 89%, 90%, 91%, 92%, 93%, 94%, 95%, 96%, 97%, 98%, or 99%) identity to the recited sequence (e.g., SEQ ID NO: 39-76 or 115-152) are also provided.

TABLE 1

Heavy chains full Amino Acid and DNA sequences

| antibody id | VDJ amino acid | VDJ nucleotides |
|---|---|---|
| 1001701405_P4 | SEQ ID NO: 1<br>QVQLVQSGAEVKKPGASVKVSCR<br>ASGNSFSGYGISWVRQAPGQGLEW<br>MGWLTPYTDNRKYAEDLQGRVTM<br>TIDTSTRTAYMELRSLRSDDTAFYY<br>CATGGPNFWSGHNWLDPWGQGTL<br>VTVSS | SEQ ID NO: 39<br>CAGGTTCAGCTGGTGCAGTCTGGTGCTGAGGTGAAGAAGCCTGGGGCCTCAGTGAAGGTC<br>TCCTGCAGGGCTTCTGGTAACAGCTTTTCCGGCTATGGTATCAGCTGGGTGCGACAGGCCC<br>CTGGACAAGGGCTTGAGTGGATGGGGTGGCTCACCCCTTACACTGATAACAGAAAGTATG<br>CAGAGGACCTCCAGGGCAGAGTCACCATGACCATAGACACATCCACGAGGACGGCCTACA<br>TGGAGCTGAGGAGCCTGAGATCTGACGACACGGCCTTTTATTACTGTGCGACGGGGGGAC<br>CAAATTTTTGGAGTGGCCACAACTGGCTCGACCCCTGGGGCCAGGGAACCCTGGTCACCGT<br>CTCCTCAG |
| 1001701403_J13 | SEQ ID NO: 2<br>QVQLVQSGAEVKKPGASVKVSCM<br>ASGHTFSGYGISWVRQAPGQGLEW<br>MGWSTPYTGKIEYAEKFQGRVTMT<br>IDTSTGTAYMELRSLRSDDTAFYYC<br>ATGGPNFWSGHNWLDPWGQGTLV<br>TVSS | SEQ ID NO: 40<br>CAGGTTCAGCTGGTGCAGTCTGGAGCTGAGGTGAAGAAGCCTGGGGCCTCAGTGAAGGTC<br>TCCTGCATGGCTTCTGGTCACACCTTTAGCGGCTATGGTATCAGCTGGGTGCGACAGGCCC<br>CTGGACAAGGGCTTGAGTGGATGGGATGGAGCACCCCTTACACTGGAAAGATAGAGTATG<br>CAGAGAAATTCCAGGGCAGAGTCACCATGACCATAGACACATCCACGGGGACGGCCTACA<br>TGGAGCTGAGGAGCCTGAGATCTGACGACACGGCCTTTTATTACTGTGCGACGGGGGGAC<br>CAAATTTTTGGAGTGGCCACAATTGGCTCGACCCCTGGGGCCAGGGAACCCTGGTCACCGT<br>CTCCTCAG |

TABLE 1-continued

Heavy chains full Amino Acid and DNA sequences

| antibody id | VDJ amino acid | VDJ nucleotides |
|---|---|---|
| 1001701503_I7 | SEQ ID NO: 3<br>QVQLVQSGAEVKKPGATVKVSCK<br>ASGYTFTSFAVNWVRQAPGQSFEW<br>MGWINIGSGNTKYSQKFQGRVTIT<br>GDTSASTAYMELSSLRSEDTAVYY<br>CARALFGLVAVASPFDNWGQGTL<br>VTVSS | SEQ ID NO: 41<br>CAGGTCCAGCTTGTGCAGTCTGGGGCTGAGGTGAAGAAGCCTGGGGCCACAGTGAAGGTT<br>TCCTGCAAGGCTTCTGGATACACCTTCACGAGTTTTGCTGTGAACTGGGTGCGCCAGGCCC<br>CCGGACAAAGTTTTGAGTGGATGGGATGGATCAACATTGGCAGTGGTAACACAAAATATT<br>CACAGAAGTTCCAGGGCAGAGTCACCATTACCGGGGACACATCCGCGAGCACAGCGTACA<br>TGGAACTGAGCAGCCTGAGATCTGAAGACACGGCTGTATATTACTGTGCGAGAGCACTGT<br>TTGGGTTGGTGGCAGTTGCTTCACCTTTTGACAACTGGGGCCAGGGAACCCTGGTCACCGT<br>CTCCTCAG |
| 1001701403_C4 | SEQ ID NO: 4<br>QAQLVQSGAEVKKPGSSVKLSCKA<br>SGGTFTSYAINWVRQAPGQGLEW<br>MGEINVIFGSTKYAQKFHGRVTIAT<br>DESTGTVYMELRTLRLDDTGVYYC<br>ARADEMATAQGFYAFDIWGQGTM<br>VTVSS | SEQ ID NO: 42<br>CAGGCCCAGCTGGTGCAGTCTGGGGCTGAGGTGAAGAAGCCTGGGTCTTCAGTGAAGCTT<br>TCCTGCAAGGCTTCTGGAGGCACCTTCACCAGCTATGCTATCAACTGGGTGCGACAGGCCC<br>CTGGACAAGGGCTTGAGTGGATGGGAGAGATCAACGTAATTTTTGGTTCAACAAAATACG<br>CACAGAAGTTCCACGGCAGAGTCACTATTGCCACGGACGAATCCACGGGCACAGTCTACA<br>TGGAACTGAGAACTCTAAGACTTGACGACACGGGCGTGTATTACTGTGCGAGAGCGGACG<br>AGATGGCCACAGCTCAAGGATTCTATGCTTTTGATATCTGGGGCCAAGGGACAATGGTCAC<br>CGTCTCTTCAG |
| 1001701403_J2 | SEQ ID NO: 5<br>QAQLVQSGAEVKKPGSSVKVSCKA<br>SGGTTSYGVDWVRQAPGQGLEW<br>MGGINVVFGSVKYAQKFQGRVTIT<br>KDDSRTTVYMEVRSLRSEDTAMY<br>YCARADEMATIEGFYAFDIWGQGT<br>MITVSS | SEQ ID NO: 43<br>CAGGCCCAGCTGGTGCAGTCTGGGGCTGAGGTGAAGAAGCCTGGGTCCTCAGTGAAGTC<br>TCCTGCAAGGCTTCTGGAGGCAGCTTCACCAGTTATGGTGTCGACTGGGTGCGACAGGCCC<br>CTGGACAAGGGCTTGAGTGGATGGGTGGGATAAATGTTGTCTTTGGCTCAGTAAAATACG<br>CACAGAAGTTCCAGGGCAGAGTCACGATCACCAAGGACGATTCCAGGACTACAGTCTACA<br>TGGAGGTGAGGAGCCTGAGATCTGAGGACACGGCCATGTATTACTGTGCGAGAGCGGACG<br>AGATGGCTACAATTGAAGGGTTCTATGCATTTGATATCTGGGGCCAAGGGACAATGATCA<br>CCGTCTCCTCAG |
| 1001701405_N2 | SEQ ID NO: 6<br>QAQLVVQSGAEVKKPGSSVKVSCKA<br>SGGTFTSYGIDWVRQAPGQGLEWV<br>GGINPIFGSTKYPQKFQGRVTCSTD<br>ESTSTAYMELRSERSEDTAMYYCA<br>RADEMATTGGFYAFDIWGQGTMV<br>TVSS | SEQ ID NO: 44<br>CAGGCCCAGTTGGTGCAGTCTGGGGCTGAGGTGAAGAAGCCTGGGTCCTCAGTGAAGGTC<br>TCCTGCAAGGCTTCTGGAGGCACGTTCACCAGCTATGGGATCGACTGGGTGCGACAGGCC<br>CCTGGACAGGGGCTTGAGTGGGTGGGGGGATCAACCCCATCTTTGGTTCGACAAATTAC<br>CCACAGAAGTTTCAAGGCAGAGTCACGGTTAGCACGGACGAATCCACGAGCACAGCCTAC<br>ATGGAGTTGAGAAGCCTGAGATCTGAGGACACGGCCATGTATTACTGTGCGAGAGCGGAC<br>GAGATGGCTACAACTGGAGGCTTCTATGCTTTTGATATCTGGGGCCAGGGGACAATGGTCA<br>CCGTCTCCTCAG |
| 1001701503_L8 | SEQ ID NO: 7<br>QVHLVQSGAEVKKPGSSVKVSCKT<br>SGGTFTNYPITWVRQAPGQGLEWM<br>GGILPILDTANYAQEFQGRVTIADE<br>STSTAYMELSNLRSEDTAVYYCA<br>RVYFDSGGYFDSWGQGTLVTVSS | SEQ ID NO: 45<br>CAGGTGCACCTGGTGGAGTCTGGGGCTGAGGTGAAGAAGCCTGGGTCCTCGGTGAAGGTC<br>TCCTGCAAGACTTCTGGAGGCACCTTCACCAACTATCCTATCACCTGGGTGCGACAGGCCC<br>CTGGACAAGGGCTTGAGTGGATGGGAGGGATCCTCCCTATCCTTGATACAGCTAACTACGC<br>ACAGGAGTTCCAGGGCAGAGTCACGATTACCGCGGACGAATCCACGAGCACAGCCTACAT<br>GGAGCTGAGCAACCTGAGATCTGAGGACACGGCCGTGTATTACTGTGCGAGAGTTTACTTT<br>GATAGTGGTGGTTATTTTGACTCCTGGGGCCAGGGAACCCTGGTCACCGTCTCCTCAG |
| 1001701503_H1 | SEQ ID NO: 8<br>QVHLVQSGAECKKPGSSVKVSCKT<br>SGGTFTKYPITWVRQAPGQGLEWM<br>GGILPILDTANYAQEFQGRVTITAD<br>ESTSTAYMELSNERSEDTAVYYCA<br>RVYYDSGGYFDSWGQGTLVTVSS | SEQ ID NO: 46<br>CAGGTGCACCTGGTGCAGTCTGGGGCTGAGGTGAAGAAGCCTGGGTCCTCGGTGAAGGTC<br>TCCTGCAAGACTTCTGGAGGCACCTTCACCAAGTATCCTATCACCTGGGTGCGACAGGCCC<br>CTGGACAAGGGCTTGAGTGGATGGGAGGGATCCTCCCTATCCTTGATACAGCTAACTACGC<br>ACAGGAGTTCCAGGGCAGAGTCACGATTACCGCGGACGAATCCACGAGCACAGCCTACAT<br>GGAGCTGAGCAACCTGAGATCTGAGGACACGGCCGTGTATTACTGTGCGAGAGTTTACTA<br>TGATAGTGGTGGTTATTTTGACTCCTGGGGCCAGGGAACCCTGGTCACCGTCTCCTCAG |
| 1001701405_M6 | SEQ ID NO: 9<br>QVQLVQSGAEVKKPGSSVKVSCKA<br>SGGTFSNYAFSWVRQAPGQGLEW<br>MGRIIPIFGTPKYAQKFQGRVTITRD<br>ESTSTAYMELSSLRSEDTAVYYCA<br>RSPWHSSGWFPSDYWGQGTLVTVS<br>S | SEQ ID NO: 47<br>CAGGTCCAGCTGGTGCAGTCTGGGGCTGAGGTGAAGAAGCCTGGGTCCTCGGTGAAGGTC<br>TCCTGCAAGGCTTCTGGAGGCACCTTCAGCAACTATGCTTTCAGCTGGGTGCGACAGGCCC<br>CTGGACAAGGGCTTGAGTGGATGGGAAGGATCATCCCTATCTTTGGTACACCAAAGTACG<br>CCCAGAAGTTCCAGGGCAGAGTCACGATTACCAGGGACGAATCCACGAGCACAGCCTACA<br>TGGAGCTGAGCAGCCTGAGATCGGAGGACACGGCCGTGTATTACTGTGCGAGAAGCCCCT<br>GGCACAGCAGTGGCTGGTTCCCTTCTGACTACTGGGGCCAGGGAACCCTGGTCACCGTCTC<br>CTCAG |
| 1001701403_H3 | SEQ ID NO: 10<br>QVQLVQSGAELKKPGSSVKVSCKS<br>SGGTFRNYSFSWVRQAPGQGLEW<br>MGRSIPIFGTAKYAQKFQGRVTITT<br>DESTSTAYMDLSSLRSEDTAVYYC<br>ARSPWHNSGWFPLDSWGQGTLVT<br>VSS | SEQ ID NO: 48<br>CAGGTCCAGCTGGTGCAGTCTGGGGCTGAGTTGAAGAAGCCTGGGTCCTCGGTGAAGGTC<br>TCCTGCAAGTCTTCTGGAGGCACCTTCAGGAACTACAGTTTCAGCTGGGTGCGACAGGCCC<br>CTGGACAAGGGCTTGAGTGGATGGGAAGGAGTATCCCTATCTTTGGTACAGCAAAATACG<br>CACAGAAGTTCCAGGGCAGAGTCACGATTACAACGGACGAATCCACGAGCACAGCCTACA<br>TGGACTTGAGCAGCCTAAGATCTGAGGACACGGCCGTGTATTACTGTGCGAGAAGCCCCT<br>GGCATAACAGTGGCTGGTTCCCTCTTGACTCCTGGGGCCAGGGAACCCTGGTCACCGTCTC<br>CTCAG |
| 1001701405_J8 | SEQ ID NO: 11<br>QVQLVQSGAEVKKPGSSVKVSCKA<br>SGGTFSSNSVTWVRQAPGHGLEW<br>MGTIIPFFGTRHYADNFQGRVTVTT<br>DESTTTVYMELSSLRSDDTAVYYC | SEQ ID NO: 49<br>CAGGTCCAACTGGTGCAATCTGGGGCTGAGGTGAAGAAGCCTGGGTCCTCAGTGAAGGTC<br>TCCTGCAAGGCTTCTGGAGGCACCTTCAGCAGCAATTCTGTCACCTGGGTGCGGCAGGCCC<br>CTGGACACGGGCTTGAGTGGATGGGAACAATCATCCCTTTCTTTGGTACAAGACACTACGC<br>AGACAACTTTCAGGGCAGAGTCACAGTCACCACGGACGAATCCACGACCACGGTGTACAT |

TABLE 1-continued

Heavy chains full Amino Acid and DNA sequences

| antibody id | VDJ amino acid | VDJ nucleotides |
|---|---|---|
| | ARSCESPSCYHNWFDPWGQGTLVT VTS | GGAGCTGAGCAGCCTGAGATCTGACGACACGGCCGTGTATTACTGTGCGCGATCTTGTGA GAGTCCCAGTTGTTACCACAACTGGTTCGACCCCTGGGGCCAGGGAACCCTGGTCACCGTC ACCTCAG |
| 1001701405_ J9 | SEQ ID NO: 12<br>QVQLVQSGAEVRKPGSSVKVSCKT SGGGSLNSYGISWVRQAPGGQGLEW MGGIIPFFGTVIYSDNYQGRASFSSD ESTTTAYMELRSLRSEDTAVYYCA RYCYSASCYHNWFDPWGQGTLVT VST | SEQ ID NO: 50<br>CAGGTCCAGCTGGTGGAGTCTGGGGCTGAGGTGAGGAAGCCTGGGTCCTCAGTGAAGGTC TCCTGCAAGACTTCTGGAGGCTCCCTCAACAGTTATGGCATCAGTTGGGTGCGACAGGCCC CTGGTGGACAAGGGCTTGAGTGGATGGGAGGGATCATCCCTTTCTTTGGTACAGTTATCTA TTCAGACAATTACCAGGGCAGAGCCTCGTTTTCCTCGGACGAATCTACGACCACAGCCTAC ATGGAGCTGAGAAGCCTAAGATCTGAGGACACGGCCGTGTATTACTGTGCGAGATATTGT TATAGTGCCAGTTGTTATCACAACTGGTTCGACCCCTGGGGCCAGGGAACCCTGGTCACCG TCTCCACAG |
| 1001701403_ J3 | SEQ ID NO: 13<br>QVQLVQSGAEVKKPGSSVKVSCEA SGVSLSSYGISWVRQAPGRGLEWM GGIIPFFGTRNYAHDFEGRLTITTDE STRTVYMELSSLRSEDTAVYYCAR RNAKGGYSGGNWFDPWGQGTPVT VSS | SEQ ID NO: 51<br>CAGGTCCAGCTGGTGGAGTCTGGGGCTGAGGTGAAGAAGCCTGGGTCCTCAGTGAAGGTC TCCTGCAGGGCCTCTGGAGTCAGCCTCAGCAGCTATGGTATCAGCTGGGTGCGACAGGCCC CTGGACGGGGCCTTGAGTGGATGGGAGGGATCATCCCTTTCTTTGGAACAAGAAACTACG CACATGACTTCGAGGGCCGACTCACGATTACCACGGACGAATCTACGCACAGTATATA TGGAGCTGAGTAGCCTGAGATCTGAGGACACGGCCGTGTATTATTGTGCGAGGAGAAACG CGAAGGGGGGTTATTCCGGAGGGAACTGGTTCGACCCCTGGGGCCAGGGAACCCCGGTCA CCGTCTCCTCAG |
| 1001701403_ P4 | SEQ ID NO: 14<br>QVQLVQSGAEVKKPGSSVRVSCTA SGGTFSSLAISWVRQAPGQGLEWM GGLIPVFGIPNYAEDFQGRVTITAD ESTRTAYMDLSSLSADDTAVYYCA RRSGKGGYSGGNWPDPWGQGTLV TVSS | SEQ ID NO: 52<br>CAGGTCCAGCTGGTGCAGTCTGGGGCTGAGGTGAAGAAGCCTGGGTCCTCAGTGAGGGTC TCCTGCACGGCTTCTGGAGGCACCTTCAGTAGTCTTGCCATCAGCTGGGTGCGGCAGGCCC CTGGACAAGGCCTTGAGTGGATGGGAGGGCTCATCCCTGTCTTTGGTATACCAAACTACGC AGAGGACTTCCAGGGCAGAGTCACGATTACCGCGGACGAATCCACGAGGACGGCCTACAT GGACCTGAGCAGCCTGAGCGCTGACGACACGGCCGTGTATTACTGTGCGAGGAGAAGTGG GAAGGGGGGTTATTCCGGAGGGAACTGGTTCGACCCCTGGGGCCAGGGAACCCTGGTCAC CGTCTCCTCAG |
| 1001701403_ M11 | SEQ ID NO: 15<br>QVQLVQSGSEVKKPGSSVRVSCRA SGGTFNSLPISWLRQAPGQGPEWM GRIIPFTATPTYAEKFQGRVTITADE STATAYMELSNLRSDDTAVYYCAR DLNFYDSSGYHFARWFDPWGQGT LVTVSS | SEQ ID NO: 53<br>CAGGTCCAGCTGGTCCAGTCTGGGTCTGAGGTGAAGAAGCCTGGGTCCTCGGTGAGGGTC TCCTGCAGGGCTTCTGGAGGCACCTTCAACAGTTTGCCTATCAGCTGGCTGCGACAGGCCC CTGGACAAGGGCCTGAGTGGATGGGAAGGATCATCCCTTTCTTTGCGACACCAACGTACG CAGAGAAGTTCCAGGGCAGAGTCACCATTACCGCGGACGAATCCACGGCCACAGCCTACA TGGAGCTGAGCAACCTGAGATCCGACGACACGGCCGTATATTACTGTGCGAGAGATCTAA ATTTTTATGATAGTAGTGGTTATCACTTCGCGCGGTGGTTCGACCCCTGGGGCCAGGGAAC CTGGTCACCGTCTCCTCAG |
| 1001701403_ M4 | SEQ ID NO: 16<br>QVQLVQSGAEVKKPGSSVKVSCTT SGGTLSSYPISWVRQAPGQGLEWM GRITPFFGTTNYAEQFQGRITITTDE STSTAYMELSSLRSEDTAVYYCAR DVHYSSSGYTHFGRWFDPWGQGT LVTVSS | SEQ ID NO: 54<br>CAGGTCCAGTTGGTGCAGTCTGGGGCTGAGGTGAAGAAGCCTGGGTCCTCGGTGAAGGTC TCCTGCACGACTTCCGGAGGCACCCTCAGCAGTTATCCTATCAGCTGGGTGCGACAGGCCC CTGGACAAGGGCTTGAGTGGATGGGAAGGATCACTCCTTTCTTTGGTACAACAAACTACG AGAGCAGTTCCAGGGCAGAATCACGATCACCACGGACGAATCCACGAGCACGGCATATAT GGAGCTGAGCAGCCTGAGATCTGAGGACACGGCCGTCTATTACTGTGCGAGAGATGTCCA CTACTCAGATAGTAGTGGTTATCACTTCGGGCGGTGGTTCGACCCCTGGGGCCAGGGAACT CTGGTCACCGTCTCCTCAG |
| 1001701405_ L3 | SEQ ID NO: 17<br>QVQLVQSGSEVKKPGSSVRVSCRA SGGTFSSLAISWVRQAPGQGPEWM GRIIPFFATPSYAENFQGRVTITADE STSTAYMELSNLRSDDTAVYYCAR DLNFYDSSGYHFARWFDPWGQGT LVTVSS | SEQ ID NO: 55<br>CAGGTCCAGCTGGTCCAGTCTGGGTCTGAGGTGAAGAAGCCTGGGTCCTCGGTGAGGGTC TCCTGCAGGGCTTCTGGAGGCACCTTCAGCAGCTTGGCTATCAGCTGGGTGCGACAGGCCC CTGGACAAGGGCCTGAGTGGATGGGAAGGATCATCCCTTTCTTTGCTACACCAAGCTACG AGAGAACTTCCAGGGCAGAGTCACGATTACCGCGGACGAATCCACGAGCACAGCCTACAT GGAGCTGAGCAACCTGAGATCTGACGACACGGCCGTGTATTACTGTGCGAGAGATCTAAA TTTCTATGATAGTAGTGGTTATCACTTCGCGCGGTGGTTCGACCCCTGGGGCCAGGGAACC CTGGTCACCGTCTCCTCAG |
| 1001701405_ K11 | SEQ ID NO: 18<br>QVQLVQSGAEVKKPGSSVKVSCKV SGGTFSSSPISWVRQAPGQGPEWM GRIIPFFGSPSYAEQFQDRVTITTDE STTTAYMELRSLRSEDTAVYYCAR DVNYYDSSGYHFGRWFDPWGQGT LVTVSS | SEQ ID NO: 56<br>CAGGTCCAGCTAGTGCAGTCTGGGGCTGAGGTGAAGAAGCCTGGGTCCTCGGTGAAGGTC TCCTGCAAGGTTTCTGGAGGCACCTTCAGCAGCTCTCCTATCAGCTGGGTTCGACAGGCCC CTGGACAAGGGTTTGAGTGGATGGGAAGGATCATCCCTTTCTTTGGTTCACCAAGCTACGC AGAGCAGTTCCAGGGCAGAGTCACAATTACCACGGACGAATCCACGACTACAGCCTACAT GGAGCTGCGCAGCCTGAGATCTGAGGACACGGCCGTGTATTACTGTGCGAGAGATGTTAA TTATTACGATAGTAGTGGTTATCACTTCGGGCGGTGGTTCGACCCCTGGGGCCAGGGAACC CTGGTCACCGTCTCCTCAG |
| 1001701403_ O4 | SEQ ID NO: 19<br>QVQLVQSGAEVKKPGSSVKVSCKV SGGTFSSSPISWVRQAPGQGPEWM GRIIPFFGSPTYAEQFQGRVTITTDE STSTAYMELSSLRSADTAVYYCAR DVNYYDSSGYHFGRWFDPWGQGT LVTVSS | SEQ ID NO: 57<br>CAGGTCCAGCTAGTGCAGTCTGGGGCTGAGGTGAAGAAGCCTGGGTCGTCGGTAAAGGTC TCCTGCAAGGTTTCTGGAGGCACCTTCAGCAGCTCTCCTATCAGCTGGGTTCGACAGGCCC CTGGACAAGGGTTTGAGTGGATGGGAAGGATCATCCCTTTTTTGGTTCACCAACCTACG AGAGCAGTTCCAGGGCAGAGTCACAATCACCACGGACGAATCTACGAGTACAGCCTACAT GGAGCTGAGCAGCCTGAGATCTGCGGACACGGCCGTCTATTACTGTGCGAGAGATGTTAA TTATTACGATAGTAGTGGTTATCACTTCGGGCGGTGGTTCGACCCCTGGGGCCAGGGAACC CTGGTCACCGTCTCCTCAG |

TABLE 1-continued

Heavy chains full Amino Acid and DNA sequences

| antibody id | VDJ amino acid | VDJ nucleotides |
|---|---|---|
| 1001701405_<br>I11 | SEQ ID NO: 20<br>QVQLVESGGGVVQPGRSLRLSCAA<br>SGFPFSGYAMHWVRQAPGKGLEW<br>VAFISYDGSDKYYADSVKGRFTISR<br>DNSENTLHLQMNSLRAEDTAVYYC<br>AKNYGSGSLNWFDAWGQGTLVTV<br>SS | SEQ ID NO: 58<br>CAGGTGCAGCTGGTGGAGTCTGGGGGAGGCGTGGTCCAGCCTGGGAGGTCCCTGAGACTC<br>TCCTGTGCAGCCTCTGGATTCCCCTTCAGTGGCTATGCTATGCACTGGGTCCGCCAGGCTCC<br>AGGCAAGGGGCTGGAGTGGGTGGCTTTTATATCATATGATGGAAGCGATAAATACTACGC<br>AGACTCCGTGAAGGGCCGATTCACCATCTCCAGAGACAATTCCGAAAACACGTTGCATCT<br>GCAAATGAACAGCCTGAGAGCTGAGGACACGGCTGTGTATTACTGTGCGAAGAACTATGG<br>TTCGGGGAGTTTGAACTGGTTCGACGCCTGGGGCCAGGGAACCCTGGTCACCGTCTCCTCA<br>G |
| 1001701405_<br>C1 | SEQ ID NO: 21<br>QVQLVESGGGVVQPGGSLRLSCAA<br>SGFPFRSYAMHWVRQAPGKGLEW<br>VAFISYDGTNTYYADSVKGPPTISR<br>DNSKNTLYLQMNSLRAEDTAVYY<br>CAKNYGSGSQNWFDSWGQGTLVT<br>VSS | SEQ ID NO: 59<br>CAGGTGCAGCTGGTGGAGTCTGGGGGAGGCGTGGTCCAGCCTGGGGGGTCCCTGAGACTC<br>TCCTGTGCAGCCTCTGGATTCCCCTTCAGGAGCTATGCTATGCACTGGGTCCGCCAGGCTC<br>CAGGCAAGGGCTGGAGTGGGTGGCTTTCATATCATATGATGGAACAATACATACTACG<br>CAGACTCCGTGAAGGGCCCATTCACCATCTCCAGAGACAATTCCAAGAACACGTGTACCT<br>GCAAATGAACAGCCTCAGAGCTGAGGACACGGCTGTTTATTACTGTGCGAAGAATTATGG<br>TTCGGGGAGCCAGAACTGGTTCGATTCCTGGGGCCAGGGAACCCTGGTCACCGTCTCCTCA<br>G |
| 1001701405_<br>G5 | SEQ ID NO: 22<br>QVRLVESGGGVVQPGRSLRLSCAG<br>SGFSFSTYAMHWVRQAPGKGLEW<br>VALIYYDGSNKYYADSVKGRFTISR<br>DNSKNTVYLQMNSLRPEDTAVYFC<br>AKNYGSGSLNWYDAWGQGTLVIV<br>SS | SEQ ID NO: 60<br>CAGGTGCGGCTGGTGGAGTCTGGGGGAGGCGTGGTCCAGCCTGGGAGGTCCCTGAGACTC<br>TCCTGTGCAGGCTCTGGATTCTCCTTCAGTACCTATGCTATGCACTGGGTCCGCCAGGCTCC<br>AGGCAAGGGGCTGGAGTGGGTGGCACTTATATACTATGATGGAAGCAATAAATACTACGC<br>GGACTCTGTGAAGGGCCGATTCACCATCTCCAGAGACAATTCCAAGAATACGGTGTATTTG<br>CAAATGAACAGCCTGAGACCTGAGGACACGGCTGTGTATTTCTGTGCGAAGAACTATGGT<br>TCGGGGAGTTTGAACTGGTACGACGCCTGGGGCCAGGGAACCCTGGTCATCGTTTCCTCAG |
| 1001701403_<br>P2 | SEQ ID NO: 23<br>QVQLVESGGGVVQPGRSLRLSCAA<br>SGFTFSNYALHWVRQAPGKGLEW<br>VALIYDGSRKYYADSVKGRFTISR<br>DNSKNTLHLQMNSVREDTAVYY<br>CAKNYGSGTLNWFDAWGQGTLVT<br>VSS | SEQ ID NO: 61<br>CAGGTGCAACTGGTGGAGTCTGGGGGAGGCGTGGTCCAGCCTGGGAGGTCCCTGAGACTC<br>TCCTGTGCAGCCTCTGGATTCACCTTCAGTAACTATGCTCTGCACTGGGTCCGCCAGGCTCC<br>AGGCAAGGGGCTCGAGTGGGTGGCACTTATATACTATGATGGAAGCAGAAATACTATGC<br>AGACTCCGTGAAGGGCCGATTCACCATCTCCAGAGACAATTCCAAGAACACGCTCCATCT<br>GCAAATGAACAGCGTGAGAGTTGAGGACACGGCTGTCTATTACTGTGCGAAGAACTATGG<br>TTCGGGGACCTTGAACTGGTTCGACGCCTGGGGCCAGGGAACCCTGGTCACCGTCTCCTCA<br>G |
| 1001701403_<br>A7 | SEQ ID NO: 24<br>QVQLVESGGGVVQPGRSLRLSCVG<br>SEFPPKAYAMHWVRQAPGKGLEW<br>VAFISYDGSNTYYADSVKGRFSLSR<br>DNSKNTLYLDMNPLRPEDTAVYYC<br>AKNYGSGSLNWFDSWGQGTLLTV<br>SA | SEQ ID NO: 62<br>CAGGTGCAACTTGTGGAGTCTGAATTCCCCTTCAAGGCCTATGCTATGCACTGGGTCCGCCAGGCTC<br>TCCTGTGTAGGCTCTGAATTCCCCTTCAAGGCCTATGCTATGCACTGGGTCCGCCAGGCTC<br>CAGGCAAGGGCCTGGAGTGGGTGGCATTTATATCATATGATGGATCCAATACATATTATGC<br>AGACTCCGTGAAGGGCCGATTCAGCCTCTCCAGGGACAATTCGAAGAACACCCTGTATCT<br>AGACATGAACCCCCTGAGACCTGAAGACACGGCTGTGTATTATTGTGCGAAGAATTACGG<br>TTCGGGGAGTTTGAATTGGTTCGACTCTTGGGGCCAGGGGACCCTGCTCACCGTCTCCGCA<br>G |
| 1001701405_<br>L9 | SEQ ID NO: 25<br>QVQLVESGGGVVRPGRSLRVSCAA<br>SGFTFSNFAMHWVRQAPGKGLEW<br>VALIYYDGSNKYYADSVRGRFTISR<br>DNSKNTLYLQMNSLRPDDTAVYY<br>CAKNYGSGTLNWFDSWGQGTLVT<br>VSS | SEQ ID NO: 63<br>CAGGTGCAACTGGTGGAGTCTGGGGGAGGCGTGGTCCGGCCTGGGAGGTCCCTGCGAGTC<br>TCCTGTGCAGCCTCTGGATTCACCTTCAGTAATTTTGCAATGCACTGGGTCCGCCAGGCTCC<br>AGGCAAGGGGCTGGAGTGGGTGGCACTTATATATTATGATGGAAGCAATAAATATTACGC<br>AGACTCCGTGAGGGGCCGATTCACCATCTCCAGAGACAATTCCAAGAACACACTGTATCT<br>GCAAATGAACAGCCTGAGACCTGACGACACGGCTGTGTATTACTGTGCGAAAAACTACGG<br>TTCGGGGACTTTGAATTGGTTCGACTCCTGGGGCCAGGGAACCCTGGTCACCGTCTCCTCA<br>G |
| 1001701405_<br>E9 | SEQ ID NO: 26<br>QVQLVESGGGVVQPGRSLTLSCAD<br>SGFTFTTDAMHWVRQAPGKGLEW<br>VAVISYDGTEKYYGDSVEGRFTISR<br>DNSKNTLFLQMSDLRPRDSAVYFC<br>AREGTYSGIVTGQSQSPSSYMDVW<br>GKGTTVIVSS | SEQ ID NO: 64<br>CAGGTGCAGCTGGTGGAGTCTGGGGGAGGCGTGGTCCAGCCTGGGAGGTCCCTGACACTC<br>TCCTGTGCAGACTCTGGATTCACCTTCACAACCGATGCTATGCACTGGGTCCGTCAGGCTC<br>CAGGCAAGGGGCTGGAGTGGGTGGCCGTCATATCATATGATGGAACCGAGAAATACTATG<br>GAGACTCCGTGGAGGGCCGATTCACCATCTCCAGAGACAATTCCAAGAACACGCTGTTTCT<br>GCAAATGAGCGACCTAAGGCCTCGGCTGTGTATTTCTGTGCGAGAGAGGGAAC<br>CTACAGTGGAATTGTGACTGGCCAATCCCCTCTTCATACATGGACGTCTGGGGC<br>AAAGGGACTACGGTCATCGTCTCCTCAG |
| 1001701403_<br>I8 | SEQ ID NO: 27<br>QVQLVESGGGVVQPGRSLRLSCAD<br>SGFTFRTDAMHWVRQAPGKGLEW<br>VAVISYDGSEKYYGDSVEGRFTISR<br>DNSKNTLFLQMNALRPGDTAVYFC<br>AREGTYSGIVTGQSQSPSSYMAVW<br>GKGTTVIVSS | SEQ ID NO: 65<br>CAGGTGCAGTTGGTGGAGTCTGGGGGAGGCGTGGTCCAGCCTGGGAGGTCCCTGAGACTC<br>TCCTGTGCAGATTCTGGATTCACCTTCAGAACCGACGCTATGCACTGGGTCCGTCAGGCCC<br>CAGGCAAGGGGCTGGAGTGGGTGGCCGTCATATCATATGATGGATCCGAGAAATATTATG<br>GAGACTCCGTGGAGGGCCGATTCACCATCTCCAGAGACAATTCCAAGAACACGCTGTTTCT<br>GCAAATGAACGCCCTGAGACCTGGGGACACGGCTGTATATTCTGTGCGAGAGAGGGAAC<br>CTACAGTGGAATTGTGACTGGCCAATCCCAATCGCCCTCCTTCATACATGGCCGTCTGGGGC<br>AAAGGGACTACGGTCATCGTCTCCTCAG |
| 1001701503_<br>E1 | SEQ ID NO: 28<br>EVQLVESGGGLVPPGGSLRLSCAAS<br>GFTFDSYWMSWVRQAPGKGLEWV<br>ANIKLIDGSEKCYDSVKGRFTISRD<br>NAKNSLFLQMNSLRAEDTAVYYC | SEQ ID NO: 66<br>GAGGTGCAGCTGGTGGAGTCTGGGGGAGGCTTGGTCCCGCCTGGGGGGTCCCTGAGACTC<br>TCCTGTGCAGCCTCTGGATTCACCTTTGATAGTTATTGGATGAGCTGGGTCCGCCAGGCTC<br>CAGGGAAGGGGCTGGAGTGGGTGGCCAACATAAAGCTAGATGGAAGTGAGAAATGCTAT<br>GTGGACTCTGTGAAGGGCCGATTCACCATCTCCAGAGACAACGCCAAGAACTCACTGTTTC |

TABLE 1-continued

Heavy chains full Amino Acid and DNA sequences

| antibody id | VDJ amino acid | VDJ nucleotides |
|---|---|---|
| | ARVASHPSLFSPYYFDYWGQGTLV TVSS | TGCAAATGAACAGCCTGAGAGCCGAGGACACGGCTGTCTATTACTGTGCGAGAGTCGCTA GTCACCCAAGCTTGTTTTCACCCTACTACTTTGACTACTGGGGCCAGGGAACCCTGGTCAC CGTCTCCTCAG |
| 1001701503_ F10 | SEQ ID NO: 29 EVQLVESGGGLVPPGGSLKVSCAA SGFTFDNYWMSWVRQAPGKGLEW VANIKLDGSEKCYVDSVKGRFTISR DNARNSLFLQMNSLRAEDTAVYYC ARVASHPTLFSPYYFDYWGQGTLV TVSS | SEQ ID NO: 67 GAGGTGCAGCTGGTGGAGTCTGGGGGAGGCTTGGTCCCGCCTGGGGGGTCCCTAAAAGTC TCCTGTGCAGCCTCTGGATTCACCTTTGACAACTATTGGATGAGCTGGGTCCGCCAGGCTC CAGGGAAGGGGCTGGAGTGGGTGGCCAACATAAAGCTAGATGGAAGTGAGAAATGCTAT GTGGACTCTGTGAAGGGCCGATTCACCATCTCCAGAGACAACAGCCAGGAACTCACTGTTTC TGCAAATGAACAGCCTGAGAGCCGAGGACACGGCTGTCTATTACTGTGCGAGAGTCGCTA GTCACCCAACTTTGTTTTCACCCTACTACTTTGACTACTGGGGCCAGGGAACCCTGGTCACT GTCTCCTCAG |
| 1001701405_ N8 | SEQ ID NO: 30 QVQLQQWGAGLLKPSETLSLTCGV SDGPLIGYYWAWIRQTPGKGLEWI GEITHSGNTNYNPSLESRVTISVDTS KNQFSLKVNSVTAADTAVYYCAR GPGGTSTSCYRCWFDPWGQGTLVT VSS | SEQ ID NO: 68 CAGGTGCAGCTGCAACAGTGGGGCGCAGGACTGTTGAAGCTTCGGAGACCTTGTCCCTC ACCTGCGGTGTCTCTGATGGGCCCCTCATTGGTTACTACTGGGCCTGGATCCGCCAGACCC CAGGGAAGGGGCTGGAGTGGATTGGGGAGATCACTCATAGTGGAAACACCAACTACAACC CGTCCCTCGAGAGTCGAGTCACCATTTCCGTTGACACGTCCAAGAACCAGTTCTCCCTGAA GGTGAACTCTGTTACCGCCGCGGACACGGCTGTCTATTATTGTGCGAGAGGCCCCGGGGG GACTAGCACCAGTTGTTATAGGTGTTGGTTCGACCCCTGGGGCCAGGGAACCCTGGTCACC GTCTCCTCAG |
| 1001701403_ F4 | SEQ ID NO: 31 QVQLQQWGAGLLKPSETLSLTCAV HGGPLIGYYWSWIRQTPEKGLEWI GEITHSGSTNYNPSLKSRVTISVDTS KNHFSLKLTSVTAADTAVYYCARG PGGTSTSCYQCWFDPWGQGTLVTV SS | SEQ ID NO: 69 CAGGTGCAGCTACAGCAATGGGGCGCAGGACTGTTGAAGCTTCGGAGACCCTGTCCCTC ACCTGCGCTGTCCATGGTGGGCCCTTGATTGGTTACTACTGGAGCTGGATCCGCCAGACCC CAGAGAAGGGGCTGGAGTGGATTGGGGAAATCACTCATAGTGGAAGCACCAACTACAACC CGTCCCTCAAGAGTCGAGTCACCATATCAGTAGACACGTCCAAGAACCACTTCTCCCTCAA GCTGACGTCTGTGACCGCCGCGGACACGGCTGTGTATTACTGTGCGAGGGGCCCCGGGGG CACAAGTACCAGCTGCTATCAATGTTGGTTCGACCCCTGGGGCCAGGGAACCCTGGTCACC GTCTCCTCAG |
| 1001701503_ K2 | SEQ ID NO: 32 QVQLQESGPGLVKPSETLSLTCTVS GGSISSSSYYWGWIRQPPGKGLEWI GSLYYSGSTYYNPSLKSRVTISVDT SKNQFSLKLYSVTAADTAVYYCAG QDYSGTYYDYFDYWGQGALVTVS S | SEQ ID NO: 70 CAGGTGCAGCTGCAGGAGTCGGGCCCAGGACTGGTGAAGCCTTCGGAGACCCTGTCACTC ACCTGCACTGTCTCTGGTGGCTCCATCAGCAGTAGTAGTTATTACTGGGGCTGGATCCGCC AGCCCCCAGGGAAGGGGCTGGAGTGGATTGGGAGTCTCTATTATAGTGGGAGCACCTACT ACAACCCGTCCCTCAAGAGTCGAGTCACCATATCCGTAGACACGTCCAAGAACCAGTTCTC CCTGAAGCTGTACTCTGTGACCGCCGCAGACACGGCTGTGTATTACTGTGCGGGACAGGAC TATAGTGGGACTTACTATGACTACTTTGACTACTGGGGCCAGGGAGCCCTGGTCACCGTCT CCTCAG |
| 1001701503_ A5 | SEQ ID NO: 33 QVQLQESGPGLVKPSETLSLTCTVS GGSISSSSYYWGWIRQPPGKGLEWI GSMYYSGSTYYNPSLKSRVTISVDT SKNQFSLKLSSVTAADTAVYYCAG QDYSGTYYDYFNWGQGTLVTVS S | SEQ ID NO: 71 CAGGTGCAGCTGCAGGAGTCGGGCCCAGGACTGGTGAAGCCTTCGGAGACCCTGTCACTC ACCTGCACTGTCTCTGGTGGCTCCATCAGCAGTAGTAGTTATTACTGGGGCTGGATCCGCC AGCCCCCAGGGAAGGGGCTGGAGTGGATTGGGAGTATGTATTATAGTGGGAGCACCTACT ACAACCCGTCCCTCAAGAGTCGAGTCACCATATCCGTAGACACGTCCAAGAACCAGTTCTC CCTGAAGCTGAGCTCTGTGACCGCCGCAGACACGGCTGTGTATTACTGTGCGGGACAGGA CTATAGTGGGACTTACTATGACTACTTTAACTACTGGGGCCAGGGAACCCTGGTCACCGTC TCCTCAG |
| 1001701503_ B10 | SEQ ID NO: 34 QLQLQESGPGLVKPSETLSLTCTVS GGSINTRSYYWGWIRQPPGKGLEW IGSIFYTGSTYYNPSLKSRVTISVDT SNNQFSLRLSSVTAADTAVYYCAR QDRNWFDSWGQGTLVTVSS | SEQ ID NO: 72 CAGCTGCAGCTGCAGGAGTCGGGCCCAGGACTGGTGAAGCCTTCGGAGACCCTGTCCCTC ACCTGCACTGTCTCTGGTGGCTCCATCAACACTAGGAGTTACTACTGGGGCTGGATCCGCC AGCCTCCAGGGAAGGGGCTGGAGTGGATTGGGAGTATCTTTTATACTGGGAGCACCTACT ACAACCCGTCCCTCAACTAGTCGAGTCACCATATCCGTAGACACGTCCAACAACCAGTTCTC CCTGAGGCTGAGCTCTGTGACCGCCGCAGACACGGCTGTGTATTACTGTGCGAGACAGGA CAGAAACTGGTTCGACTCCTGGGGCCAGGGAACCCTGGTCACCGTCTCCTCAG |
| 1001701403_ M1 | SEQ ID NO: 35 QLQLQESGPGLVKPSATLSLTCTVS RGSISTNDHSWGWIRQPPGKGLEW VGSLHHSGNTYYNPSLKSRLTISLD TSETQFSLNLSSVTAADTAVYYCV RQNRNWFDSWGQGTLVSVSS | SEQ ID NO: 73 CAACTGCAGCTGCAGGAGTCGGGCCCAGGACTAGTGAAGCCTTCGGCGACCCTGTCCCTC ACCTGCACTGTCTCTCGTGGCTCCATCAGCACTAATGATCATTCTTGGGGCTGGATCCGCC AGCCCCCAGGGAAGGGACTGGAGTGGGTTGGCAGTCTTCATCATTCTGGGAACACCTACT ACAACCCGTCCCTCAAGAGTCGGCTCACCATATCACTGACACGTCCGAGACCCAGTTCTC CCTGAACCTGAGCTCTGTGACCGCCGCGGACACGGCCGTCTATTATTGTGTGAGACAGAAT CGGAACTGGTTCGACTCCTGGGGCCAGGGAACCCTGGTCAGCGTCTCGTCAG |
| 1001701503_ D8 | SEQ ID NO: 36 QLQLQESGPGLVKPSETLSLTCTVS GGSISRSSTYFWGWIRQPPGKGLE WIGSVSYSGSTYYNPSLKSRVSVSV DTSRKQFSLKLTSVTAADTAVYYC ARQDRNWFDSWGQGTLVTVSS | SEQ ID NO: 74 CAGCTGCAGCTGCAGGAGTCGGGCCCAGGACTGGTGAAGCCTTCGGAGACCCTGTCCCTC ACCTGCACTGTCTCTGGTGGCTCCATCAGTAGGAGTAGTACTTACTTCTGGGGCTGGATCC GCCAGCCCCCAGGGAAGGGGCTGGAGTGGATTGGGAGTGTCTCTTATAGTGGGAGCCCTT ACTACAACCCGTCCCTCAAGAGTCGAGTCAGCGTATCCGTAGACACGTCCAGGAAGCAGT TCTCCCTGAAGCTGACGTCTGTGACCGCCGCGGACACGGCTGTGTATTACTGTGCGAGACA GGACAGAAACTGGTTCGACTCCTGGGGCCAGGGAACCCTGGTCACCGTCTCCTCAG |
| 1001701403_ P10 | SEQ ID NO: 37 QVQLQESGPGLVKPSETLSLTCTVS GDSITSYYWSWIRQPPGQGLEWIG | SEQ ID NO: 75 CAGGTGCAGCTGCAGGAGTCGGGCCCAGGACTGGTGAAGCCTTCGGAGACCCTGTCCCTC ACCTGCACTGTCTCTGGTGACTCCATCACTAGTTACTACTGGAGTTGGATCAGGCAGCCCC |

TABLE 1-continued

Heavy chains full Amino Acid and DNA sequences

| antibody id | VDJ amino acid | VDJ nucleotides |
|---|---|---|
| | YIYYSGGTNYNPSLKSRVVMSLDT SRNQFSLKLNSLTAADTAVYYCAS ALNYFDSSGPGGVAMGGGFDSWG QGALVTVSS | CAGGGCAGGGACTGGAGTGGATTGGCTATATCTATTACAGTGGGGGCACCAACTACAACC CCTCCCTCAAGAGTCGAGTCGTCATGTCACTGGACACGTCGAGGAATCAGTTCTCCCTGAA GCTGAACTCTCTGACCGCTGCGGACACGGCCGTGTATTATTGTGCGAGCGCCTTGAATTAT TTTGATAGTAGTGGCCCCGGTGGCGTCGCGATGGGGGGGGGATTTGACTCCTGGGGCCAG GGAGCCCTGGTCACCGTCTCCTCAG |
| 1001701403_L2 | SEQ ID NO: 38<br>QVQHQESGPGLVKPSETLSLTCTVS GDSISSYYWNWIRQAPGKGLEWLG YINYSGNTDYNTSLKSRATISLDTS KNQFSLKLSSVTTADTAVYYCAGA LYYFDSRGPGGVAMGGGFDSWGQ GTLVTVSS | SEQ ID NO: 76<br>CAGGTGCAGCATCAGGAGTCGGGCCCAGGCCTGGTGAAGCCTTCGGAGACCCTGTCCCTC ACCTGCACTGTCTCTGGTGACTCCATCAGTAGTTACTACTGGAACTGGATCCGGCAGGCCC CAGGGAAGGGACTGGAGTGGCTTGGGTATATAAATTACAGTGGGAACACCGACTACAACA CCTCCCTCAAGAGTCGACTATATCACTAGACACGTCGAAGAACCAGTTCTCCCTGAA ACTGAGCTCCGTGACCACTGCGGATACGGCCGTCTATTACTGTGCGGGCGCCTTGTATTAC TTTGATAGTCGTGGCCCCGGTGGCGTCGCGATGGGGGGGGGTTTGACTCCTGGGGCCAG GGAACCCTGGTCACCGTCTCCTCAG |

TABLE 2

Light chains full Amino Acid and DNA sequences

| antibody id | VJ amino acid | VJ nucleotides |
|---|---|---|
| 1001701405_P4 | SEQ ID NO: 77<br>QSALTQPASVSGSPGQSITISCTGTS SDVGGYNYVSWYQQHPGKVPKLM IYDVSNRPSGVSNRFSGSKSGNTAS LTISGLQAEDEADYYCSSYTRSSTL LFGGGTKLTVL | SEQ ID NO: 115<br>CAGTCTGCCCTGACTCAGCCTGCCTCCGTGTCTGGGTCTCCTGGACAGTCGATCACCATCTC CTGCACTGGAACCAGCAGTGACGTTGGTGGTTATAACTATGTCTCCTGGTACCAACAACAC CCAGGCAAAGTCCCCAAACTCATGATTTATGATGTCAGTAATCGGCCCTCAGGGGTTCTA ATCGCTTCTCTGGCTCCAAGTCTGGCAACACGGCCTCCCTGACCATCTCTGGGCTCCAGGC TGAGGACGAGGCTGATTATTACTGCAGCTCATATACAAGGAGCAGCACCCTCCTATTCGGC GGAGGGACCAAGCTGACCGTCCTAG |
| 1001701403_I13 | SEQ ID NO: 78<br>QSALTQPASVSGSPGQSITISCTGTS SDVGGYNYVSWYQQHPGKAPKLM IFDVNNRPSGVSTRFSGSKSGNTAS LTISGLQAEDEADYYCTSFTKSTTL LFGGGTKLTVL | SEQ ID NO: 116<br>CAGTCTGCCCTGACTCAGCCTGCCTCCGTGTCTGGGTCTCCTGGACAGTCGATCACCATCTC CTGCACTGGAACCAGCAGTGACGTTGGTGGTTATAACTATGTCTCCTGGTACCAACAACAC CCAGGCAAAGCCCCCAAACTCATGATTTTTGATGTCAATAATCGGCCCTCAGGGGTTCTA CTCGCTTCTCTGGCTCCAAGTCTGGCAACACGGCCTCCCTGACCATCTCTGGGCTCCAGGC TGAGGACGAGGCTGATTATTACTGCACCTCATTTACAAAGAGCACCACTCTCCTATTTGGC GGAGGGACCAAGCTGACCGTCCTAG |
| 1001701503_I7 | SEQ ID NO: 79<br>DIQMTQSPSSLSASVGDRVTITCRA SQSIAGYLNWYQQKPGKAPELLIYS ASTLQSGFPSRFNGHGSGTDFTLTIT SLQPEDFATYYCQQSFRTPTTFGGG TRVEIK | SEQ ID NO: 117<br>GACATCCAGATGACCCAGTCTCCATCCTCCCTGTCTGCATCTGTAGGAGACAGAGTCACCA TCACTTGCCGGGCCAGCCAGAGCATTGCCGGCTATTTAAATTGGTATCAGCAGAAACCAG GAAAAGCCCCTGAGCTCCTGATCTACTCTGCATCCACTTTGCAAAGTGGATTCCCTTCAAG GTTCAATGGCCATGGATCTGGGACAGATTTCACTCTCACCATCACCAGTCTGCAACCTGAG GATTTTGCAACTTACTACTGTCAACAGAGTTTCAGAACCCCCACCACTTTTCGGCGGAGGGA CCAGGGTGGAGATCAAAC |
| 1001701403_C4 | SEQ ID NO: 80<br>DIQMTQSPSTLSASVGDRVTITCRA SQSIGTWLAWYQQKPGKAPKLLIY KASSLERGVPSRFSGSGSETEFTLTI SSLQPDDFATYYCQQYNSYWTFGQ GTKVEIK | SEQ ID NO: 118<br>GACATCCAGATGACCCAGTCTCCTTCCACCCTGTCTGCATCTGTAGGAGACAGAGTCACCA TCACTTGCCGGGCCAGTCAGAGTATTGGTACCTGGTTGGCCTGGTATCAGCAGAAACCAGG GAAAGCCCCTAAACTCCTGATCTATAAGGCGTCCAGTTTAGAAAGGGGGGTCCCATCAAG GTTCAGCGGCAGTGGATCTGAGACAGAATTCACTCTCACCATCAGCAGCCTGCAGCCTGAT GATTTTGCAACTTATTACTGCCAACAGTATAATAGTTATTGGACGTTCGGCCAGGGGACCA AGGTGGAAATCAAAC |
| 1001701403_J2 | SEQ ID NO: 81<br>DIQMTQSPSTLSASVGDSVITIVRA SQSISSWLAWYQQKPGKAPKLLIY KASSLERGVPSRFSGSGSGTEFTLTI DSLQPDDFATYYCQQYNTYWTFG QGTKVEIK | SEQ ID NO: 119<br>GACATCCAGATGACCCAGTCTCCTTCCACCCTGTCTGCATCTGTAGGAGACAGCGTCACCA TCACTTGCCGGGCCAGTCAGAGTATTAGTAGTTGGTTGGCCTGGTATCAGCAGAAACCAGG GAAAGCCCCTAAGCTCCTGATCTATAAGGCGTCTAGTTTAGAAAGAGGGGTCCCATCAAG GTTCAGCGGCAGTGGATCTGGGACAGAATTCACTCTCACCATCGACAGCCTGCAGCCTGAT GATTTTGCAACTTATTACTGCCAACAATATAATACTTATTGGACGTTCGGCCAAGGGACCA AGGTGGAAATCAAAC |
| 1001701405_N2 | SEQ ID NO: 82<br>DIQMTQSPSTLSASVGDRVTITCRA SQSVSSWLAWYQQKPGKAPKLLIY KASRLESGVPSRFSGSGSETEFTLTI SSLQPDDFATYYCQQYNSYWTFGQ GTKVEIK | SEQ ID NO: 120<br>GACATCCAGATGACCCAGTCTCCTTCCACCCTGTCTGCATCTGTAGGAGACAGAGTCACCA TCACTTGCCGGGCCAGTCAGAGTGTTAGTTCCTGGTTGGCCTGGTATCAGCAGAAACCAGG GAAAGCCCCTAAACTCCTGATCTATAAGGCGTCGTTAGAAAGTGGGGTCCCATCAAGG TTCAGCGGCAGTGGATCTGAGACAGAATTCACTCTCACCATCAGCAGCCTGCAGCCTGATG ATTTTGCAACTTATTACTGCCAACAGTATAATAGTTATTGGACGTTCGGCCAGGGGACCAA GGTGGAAATCAAAC |
| 1001701503_L8 | SEQ ID NO: 83<br>QSVLTQPPSVSGAPGQRVTISCTGS SSNIGAGYDVHWYQQLPGTAPKLL IYGYSNRPSGVPDRFSGSKSGTSAS | SEQ ID NO: 121<br>CAGTCTGTGCTGACGCAGCCGCCCTCAGTGTCTGGGGCCCAGGGCAGAGGGTCACCATCT CCTGCACTGGGAGCAGCTCCAACATCGGGGCAGGTTATGATGTACACTGGTACCAGCAAC TTCCAGGAACAGCCCCCAAACTCCTCATCTATGGTTACAGCAATCGGCCCTCAGGGGTCCC |

TABLE 2-continued

Light chains full Amino Acid and DNA sequences

| antibody id | VJ amino acid | VJ nucleotides |
|---|---|---|
| | LAITGLQAEDEADYYCQSYDSSLSG HVVFGGGTKLTVL | TGACCGATTCTCTGGCTCCAAGTCTGGCACCTCAGCCTCCCTGGCCATCACTGGGCTCCAG GCTGAGGATGAGGCTGATTATTACTGCCAGTCCTATGACAGCAGCCTGAGTGGTCATGTGG TATTCGGCGGAGGGACCAAGCTGACCGTCCTAG |
| 1001701503_ H1 | SEQ ID NO: 84<br>QSVLTQPPSVSGAPGQRVTISCTGS SSNIGAGYDVHWYQQLPGTAPKLL IYGYSNRPSGVPDRFSGSKSGTSAS LAITGLQAEDEADYYCQSYDSSLSG HVIFGGGTKVTVL | SEQ ID NO: 122<br>CAGTCTGTGCTGACGCAGCCGCCCTCAGTGTCTGGGGCCCCAGGGCAGAGGGTCACCATCT CCTGCACTGGGAGCAGCTCCAACATCGGGGCAGGTTATGATGTACACTGGTACCAGCAAC TTCCAGGAACAGCCCCCAAACTCCTCATCTATGGTTACAGCAATCGGCCCTCAGGGGTCCC TGACCGATTCTCTGGCTCCAAGTCTGGCACCTCAGCCTCCCTGGCCATCACTGGGCTCCAG GCTGAGGATGAGGCTGATTATTACTGCCAGTCCTATGACAGCAGCCTGAGTGGTCATGTGA TATTCGGCGGAGGGACCAAGGTGACCGTCCTAG |
| 1001701405_ M6 | SEQ ID NO: 85<br>QSVLTQPPSVSGAPGQRVTISCTGG SSNIGAGYDVHWYQKLPGTAPKLL IFGKNNRPSGVPDRFSGSKSGTSAS LAITGLRAEDEAEYYCQSFDSLSGY AVFGGGTQLTVL | SEQ ID NO: 123<br>CAGTCTGTGCTGACGCAGCCGCCCTCAGTGTCTGGGGCCCCAGGGCAGAGGGTCACCATCT CCTGCACTGGGGGCAGCTCCAACATCGGGGCGGGTTATGATGTACACTGGTACCAGAAGC TTCCAGGAACAGCCCCCAAACTCCTCATCTTTGGTAAGAACAATCGACCCTCAGGGGTCCC TGACCGATTCTCTGGCTCCGAAGTCTGGCACCTCAGCCTCCCTGGCCATCACTGGGCTCCGG GCTGAGGATGAGGCTGAGTATTACTGCCAGTCCTTTGACAGCCTGAGTGGCTATGCTGTGT TCGGAGGAGGCACCCAACTGACCGTCCTCG |
| 1001701403_ H3 | SEQ ID NO: 86<br>DIQMTQSPSTLPASVGDRVTITCRA SQSIDSWLAWFQQKPGKAPKLLISK ASTLENGVPSRFSGSGSGTEFTLTIS SLQPDDEATYYCQQYSSYSPWTFG QGTKVEIK | SEQ ID NO: 124<br>GACATCCAGATGACCCAGTCTCCTTCCACCCTGCCTGCATCTGTAGGAGACAGAGTCACCA TCACTTGCCGGGCCAGTCAGAGTATTGATAGCTGGTTGGCCTGGTTTCAGCAGAAACCAGG GAAAGCCCCTAAGCTTCTGATCTCTAAGGCGTCTACCTTAGAAAATGGGGTCCCATCAAGG TTCAGCGGCAGTGGATCTGGGACAGAATTCACTCTCACCATCAGCAGCCTGCAGCCTGATG ATTTTGCAACTTATTACTGCCAACAGTATAGTAGTTATTCTCCGTGGACGTTCGGCCAAGG GACCAAGGTGGAAATCAAAC |
| 1001701405_ J8 | SEQ ID NO: 87<br>DIVLTQSPATLSLSPGERATLSCRAS QSVSSYLAWYQQKPGQAPRLLIYD ASNRASGIPARFSGSGSGTDFTLTIS SLEPEDEAVYYCQHRSNWPPRVYT FGQGTKLEIK | SEQ ID NO: 125<br>GATATTGTGTTGACACAGTCTCCAGCCACCCTGTCTTTGTCTCCAGGGGAAAGAGCCACCC TCTCCTGCAGGGCCAGTCAGAGTGTTAGCAGCTACTTAGCCTGGTACCAACAGAAACCTGG CCAGGCTCCCAGGCTCCTCATCTATGATGCATCCAACAGGGCCTCTGGCATCCCAGCCAGA TTCAGTGGCAGTGGGTCTGGGACAGACTTCACTCTCACCATCAGCAGCCTAGAGCCTGAAG ATTTTGCAGTTTATTACTGTCAGCACCGTAGCAACTGGCCTCCCCGGGTGTACACTTTTGGC CAGGGGACCAAGCTGGAGATCAAAC |
| 1001701405_ J9 | SEQ ID NO: 88<br>DIVLTQSPATLSLSPGERATLSCRAS QSVGSSLAWYQQKPGQAPRLLIYD ASKRASGFPARFSGSGSGTDFTLTIS SLEPGDFAVYYCQQRSSWPPYMYT FGQGTKLEIK | SEQ ID NO: 126<br>GACATTGTGTTGACACAGTCTCCAGCCACCCTGTCTTTGTCTCCAGGGGAAAGAGCCACCC TCTCCTGCAGGGCCAGTCAGAGTGTTGGCAGTTCCTTGGCCTGGTACCAACAGAAACCTGG CCAGGCTCCCAGACTCCTCATCTATGATGCATCCAAGAGGGCCTCTGGCTTCCCAGCCAGG TTCAGTGGCAGTGGGTCTGGGACAGACTTCACTCTCACCATCAGCAGCCTAGAGCCTGGAG ATTTTGCAGTTTATTATGTCAGCAGCGTAGCAGCTGGCCTCCATACATGTACACTTTTGGC CAGGGGACCAAGCTGGAGATCAAAC |
| 1001701403_ J3 | SEQ ID NO: 89<br>QSALTQPASVSGSPGQSITIACTGTS SDVGGYNFVSWYQQHPGEAPRLLI FDVSNRPSGVSNRFSGSKSGNTASL TISGLQAEDEADYFCSSYTSRSSRT YVFGTGTRVTVL | SEQ ID NO: 127<br>CAGTCTGTGCTGACTCAGCCTGCCTCCGTGTCTGGGTCTCCTGGACAGTCGATCACCATCG CCTGCACTGGAACCAGCAGTGACGTCGGTGGTTATAACTTTGTCTCCTGGTATCAACAACA CCCAGGCGAAGCCCCCAGACTTCTCATTTTTGATGTCAGTAATCGGCCCTCAGGGGTCTCT AATCGCTTCTCTGGCTCCAAGTCTGGCAACACGGCCTCCCTGACCATCTCCGGACTTCAGG CTGAGGACGAGGCTGATTATTTTTGCAGCTCATACACAAGTCGCAGCTCCCGGACTTACGT CTTCGGAACTGGGACCAGGGTCACCGTCCTAG |
| 1001701403_ P4 | SEQ ID NO: 90<br>QSALTQPASVSGSPGQSITISCTGSS SDVGGYNYVSWYQQHPGKAPKLLI FDVSNRPSGVSNRFSGSKSSNTASL TISGLQAEDEADYYCSSYTARTSRT YVFGSGTKVTVL | SEQ ID NO: 128<br>CAGTCTGCCCTGACTCAGCCTGCCTCCGTGTCTGGGTCGCCTGGACAGTCGATCACCATCT CCTGCACTGGAAGCAGCAGTGACGTTGGTGGTTATAACTATGTCTCCTGGTACCAGCAACA CCCAGGCAAAGCCCCCAAACTCCTGATTTTTGATGTCAGTAATCGGCCCTCAGGGGTTTCT AATCGCTTCTCTGGCTCCAAGTCTAGCAACACGGCCTCCCTGACCATCTCTGGGCTCCAGG CTGAGGACGAGGCTGATTATTACTGCAGCTCATATACAGCCAGGACCTCCCGGACTTATGT CTTCGGAAGTGGGACCAAGGTCACCGTCCTAG |
| 1001701403_ M11 | SEQ ID NO: 91<br>EKVMTQSPASLSVSPGERATFSCRA SQSVNNNLAWYQQKPGQAPRLLIY GASSRVTGIPARFSGSGSGTEFTLTI SSLQSEDFAVYYCQQYNNWPPTFG QGTKLDIK | SEQ ID NO: 129<br>GAAAAAGTGATGACGCAGTCTCCAGCCTCCCTGTCTGTGTCTCCAGGGGAAAGAGCCACC TTCTCCTGCAGGGCCAGTCAGAGTGTTAACAACAACTTAGCCTGGTACCAGCAGAAAACCT GGCCAGGCTCCCAGGCTCCTCATCTATGGTGCATCCTCCAGGGTCACTGGTATCCCAGCCA GGTTCAGTGGCAGTGGGTCTGGGACAGAGTTCACTCTCACCATCAGCAGCCTGCAGTCTGA AGATTTTGCAGTTTATTACTGTCAGCAGTATAATAACTGGCCTCCGACTTTTGGCCAGGGG ACCAAGCTGGATATCAAAC |
| 1001701403_ M4 | SEQ ID NO: 92<br>EIVMTQSPATLSVSPGERATLSCRA SQSVGNNLAWYQQKPGQAPRLLIY GASTRTTGIPARFSGSGSGTFFTLTI SSLQSEDFAVYYCQQCNNWPPTFG QGTNLEIK | SEQ ID NO: 130<br>GAAATAGTGATGACGCAGTCTCCAGCCACCCTGTCTGTGTCTCCAGGGGAAAGAGCCACC CTCTCCTGCAGGGCCAGTCAGAGTGTTGGCAACAATTTAGCCTGGTACCAGCAGAAACCTG GCCAGGCTCCCAGGCTCCTCATCTATGGTGCATCCACCAGGACCACTGGTATCCCAGCCAG GTTCAGTGGCAGTGGGTCTGGGACAGAGTTCACTCTCACCATCAGCAGCCTGCAGTCTGAA GATTTTGCAGTTTATTACTGTCAGCAGTGTTATAACTGGCCTCCGACTTTTGGCCAGGGGA CCAACCTGGAGATCAAAC |

TABLE 2-continued

Light chains full Amino Acid and DNA sequences

| antibody id | VJ amino acid | VJ nucleotides |
|---|---|---|
| 1001701405_L3 | SEQ ID NO: 93<br>EKVMTQSPATLSVSPGERATFSCRA<br>SQSVSSNLAWYQQKPGQAPRLLIY<br>GASNRVTGIPARFSGSGSGTEFTLTI<br>SSLQSEDFAVVYCQQYDNWPPTFG<br>QGTKLDIK | SEQ ID NO: 131<br>GAAAAAGTGATGACGCAGTCTCCAGCCACCCTGTCTGTGTCTCCAGGGGAAAGAGCCACC<br>TTCTCCTGCAGGGCCAGTCAGAGTGTCAGCAGCAACTTAGCCTGGTACCAGCAGAAGCCT<br>GGCCAGGCTCCCAGGCTCCTCATCTATGGTGCATCCAACAGGGTCACTGGTATCCCAGCCA<br>GGTTCAGTGGCAGTGGGTCTGGGACAGAGTTCACTCTCACCATCAGCAGCCTGCAGTCTGA<br>AGATTTTGCAGTTTATTACTGTCAGCAGTATGATAACTGGCCTCCGACTTTTGGCCAGGGG<br>ACCAAGCTGGATATCAAAC |
| 1001701405_K11 | SEQ ID NO: 94<br>EIVMTQSPATLSVSPGERATLSCRA<br>SQSISSNLVWYQQKPGQAPRLLIYR<br>ASTRVTGIPARFSGSGSGTEFTLTIS<br>SLLSEDFAIYYCQQFYNWPPTFGQG<br>TKLEIK | SEQ ID NO: 132<br>GAAATAGTGATGACGCAGTCTCCAGCCACCCTGTCTGTGTCTCCAGGGGAAAGAGCCACC<br>CTCTCCTGCAGGGCCAGTCAGAGTATTAGCAGCAACTTAGTCTGGTACCAGCAGAAACCTG<br>GCCAGGCTCCCAGGCTCCTCATCTATCGTGCATCCACCAGGGTCACTGGTATCCCAGCCAG<br>GTTCAGTGGCAGTGGGTCTGGGACAGAGTTCACTCTCACCATCAGCAGCCTGCTGTCTGAA<br>GATTTTGCAATTTATTACTGTCAGCAGTTTTATAACTGGCCTCCGACTTTTGGCCAGGGGAC<br>CAAGCTGGAAATCAAAC |
| 1001701403_O4 | SEQ ID NO: 95<br>EIVMTQSPATLSVSPGERATLSCRA<br>SQSISSNLVWYQQKPGQAPRLLIYR<br>ASTRVTGIPARFSGSGSGTEFTLTIS<br>SLLSEDFAVYYCQQFYNWPPTFGQ<br>GTKLEIK | SEQ ID NO: 133<br>GAAATAGTGATGACGCAGTCTCCAGCCACCCTGTCTGTGTCTCCAGGGGAAAGAGCCACC<br>CTCTCCTGCAGGGCCAGTCAGAGTATTAGCAGCAACTTAGTCTGGTACCAGCAGAAACCTG<br>GCCAGGCTCCCAGGCTCCTCATCTATCGTGCATCCACCAGGGTCACTGGTATCCCAGCCAG<br>GTTCAGTGGCAGTGGGTCTGGGACAGAGTTCACTCTCACCATCAGCAGCCTGCTGTCTGAA<br>GATTTTGCAGTTTATTACTGTCAGCAGTTTTATAACTGGCCTCCGACTTTTGGCCAGGGGAC<br>CAAGCTGGAAATCAAAC |
| 1001701405_J11 | SEQ ID NO: 96<br>EIVMTQSPATLSVSPGERATLSCRA<br>SQSVGSNLAWYQQKPGQTPRLLIY<br>GASTRATGIPARFSGSGSGTDFTLTI<br>SSLQSEDFAVYYCQQYNNWWTFG<br>LGTKVEIK | SEQ ID NO: 134<br>GAAATAGTGATGACGCAGTCTCCAGCCACCCTGTCTGTGTCTCCAGGGGAAAGAGCCACC<br>CTCTCCTGCAGGGCCAGTCAGAGTGTTGGCAGCAACTTAGCCTGGTACCAGCAGAAACCT<br>GGCCAGACTCCCAGGCTCCTCATCTATGGTGCCTCCACCAGGGCCACTGGTATCCCAGCCA<br>GGTTCAGTGGCAGTGGGTCTGGGACAGACTTCACTCTCACCATCAGCAGCCTGCAGTCTGA<br>GGATTTTGCAGTTTATTACTGTCAGCAGTATAATAACTGGTGGACGTTCGGCCTAGGGACC<br>AAGGTGGAAATCAAAC |
| 1001701405_C1 | SEQ ID NO: 97<br>EIVVTQSPATLSVSLGERATLSCRA<br>SQNIGSNLAWYQQKPGQAPRLLIY<br>GASTRATGTPARFSGSGSETEFTLTI<br>SSLQSEDFAVYYCQQYNNWWTFG<br>QGTKVEIK | SEQ ID NO: 135<br>GAAATAGTGGTGACGCAGTCTCCAGCCACCCTGTCTGTGTCTCTGGGGGAAAGAGCCACC<br>CTCTCCTGCAGGGCCAGTCAGAACATTGGCAGCAACTTAGCCTGGTACCAGCAGAAACCT<br>GGCCAGGCTCCCAGGCTCCTCATCTACGGTGCATCCACCAGGGCCACTGGTACCCCAGCCA<br>GGTTCAGTGGCAGTGGGTCTGAGACAGAGTTCACTCTCACCATCAGCAGCCTGCAGTCTGA<br>GGATTTTGCAGTTTATTACTGTCAGCAGTATAATAACTGGTGGACGTTCGGCCAAGGGACC<br>AAGGTGGAAATCAAAC |
| 1001701405_G5 | SEQ ID NO: 98<br>EVVVTQSPATLSVSPGERATLSCRA<br>SQSVGSNLAWYQQKPGQAPRLLLY<br>GASTRATGIPARFSGSGSGTEFTLTI<br>SSLQSEDFAVYYCQQYNNLWTFGQ<br>GTKVEIK | SEQ ID NO: 136<br>GAAGTAGTGGTGACGCAGTCTCCAGCCACCCTGTCTGTGTCTCCAGGGGAAAGAGCCACC<br>CTCTCCTGCAGGGCCAGTCAGAGTGTTGGCAGCAACTTAGCCTGGTACCAGCAGAAACCT<br>GGCCAGGCTCCCAGGCTCCTCCTCTATGGTGCATCCACCAGGGCCACTGGTATCCCAGCCA<br>GGTTCAGTGGCAGTGGGTCTGGGACAGAGTTCACTCTCACCATCAGCAGCCTGCAGTCTGA<br>AGATTTTGCAGTTTATTACTGTCAGCAGTATAATAACTTGTGGACGTTCGGCCAAGGGACC<br>AAGGTGGAAATCAAAC |
| 1001701403_P2 | SEQ ID NO: 99<br>EIVMTQSPATLSVSPGERATLSCRA<br>SQSIGSNLAWYQQKPGQAPTLLIYA<br>ASTRATGIPARFSGSGSWTEFNLTIN<br>SLQSEDFAVYYCQQYNNWWTFGQ<br>GTKVEIK | SEQ ID NO: 137<br>GAAATAGTGATGACGCAGTCTCCAGCCACCCTGTCTGTGTCTCCAGGGGAAAGAGCCACC<br>CTCTCCTGCAGGGCCAGTCAGAGTATTGGCAGCAACTTAGCCTGGTACCAACAGAAACCT<br>GGCCAGGCTCCCACGCTCCTCATCTATGCTGCGTCCACCAGGGCCACTGGTATCCCGGCCA<br>GGTTCAGTGGCAGTGGGTCTTGGACAGAGTTCAATCTCACCATCAACAGCCTGCAGTCTGA<br>AGATTTTGCAGTTTATTACTGTCAGCAATATAATAACTGGTGGACGTTCGGCCAAGGGACC<br>AAGGTGGAAATCAAAC |
| 1001701403_A7 | SEQ ID NO: 100<br>EIVMTQSPVTVSVSPGERATLSCRV<br>SQSVGSNLAWYQQKPGQAPRLLIY<br>AASTRATGVPARFSGSKSGTEFTLT<br>ISSLQPEDLAVYYCQQYNNWWTFG<br>QGTKVEIK | SEQ ID NO: 138<br>GAAATAGTGATGACGCAGTCTCCAGTCACCGTGTCTGTGTCTCCAGGGGAAAGAGCCACC<br>CTCTCGTGCAGGGTCAGTCAGAGTGTTGGCAGCAACTTAGCCTGGTACCAGGAGAAACCT<br>GGCCAGGCTCCCAGGCTTCTCATCTATGCTGCATCCACCAGGGCCACTGGTGTCCCAGCCA<br>GGTTCAGTGGCAGTAAGTCTGGGACAGAGTTCACTCTCACCATCAGCAGCCTGCAGCCTGA<br>AGATTTAGCAGTTTATTACTGTCAGCAGTATAATAACTGGTGGACGTTCGGCCAAGGGACC<br>AAGGTGGAAATCAAAC |
| 1001701405_L9 | SEQ ID NO: 101<br>EIVMTQSPATLSVSPGERPTLSCRAS<br>QNIGRNLAWYQQKPGQAPRLLIYG<br>ASTRATGVPARFSGSGSETEFNLTI<br>NSLQSEDLAVYYCQQYNNWWTFG<br>QGTKVEIK | SEQ ID NO: 139<br>GAGATAGTGATGACGCAGTCTCCAGCCACCCTGTCTGTGTCTCCAGGGGAAAGACCCACC<br>CTCTCCTGCAGGGCCAGTCAGAATATTGGCAGGAATTTAGCCTGGTACCAGCAGAAACCT<br>GGCCAGGCTCCCAGGCTCCTCATCTATGGTGCATCCACCAGGGCCACTGGTGTCCCAGCCA<br>GGTTCAGTGGCAGTGGGTCTGAGACAGAGTTCAATCTCACAATCAACAGCCTGCAGTCTG<br>AAGATCTTGCAGTTTATTACTGTCAGCAGTATAATAACTGGTGGACGTTCGGCCAAGGGAC<br>CAAGGTGGAAATCAAAC |
| 1001701405_E9 | SEQ ID NO: 102<br>QSVLTQPPSVSGAPGQRVTISCTGT<br>SSNIGAGYDVHWYQQFPGKAPKLL<br>IFGNNNRPSGVPDRFSGSKSGTSAS | SEQ ID NO: 140<br>CAGTCTGTGCTGACGCAGCCGCCCTCAGTGTCTGGGGCCCCAGGGCAGAGGGTCACCATCT<br>CCTGCACTGGGACCAGCTCCAACATCGGGGCAGGTTATGATGTTCACTGGTACCAGCAGTT<br>TCCAGGAAAAGCCCCCAAACTCCTCATCTTTGGGAACAACAACCGGCCCTCAGGGGTCCCT |

TABLE 2-continued

Light chains full Amino Acid and DNA sequences

| antibody id | VJ amino acid | VJ nucleotides |
|---|---|---|
| | LAITGLQAEDDADYYCQSYDNSLK AVFGGGTRLTVL | GACCGATTCTCTGGCTCCAAGTCTGGCACCTCAGCCTCCCTGGCCATCACTGGGCTCCAGG CTGAGGATGACGCTGATTATTACTGCCAGTCCTATGACAACAGCCTGAAGGCGGTATTCGG CGGAGGGACCAGGCTGACCGTCCTAG |
| 1001701403_ I8 | SEQ ID NO: 103 QSVLTQPPSVSGAPGQRITISCTGTS SNLGAGFDVHWYQQLPGKAPELLI FGNNNRPSGVPDRFSGSKSGTSASL AITGLQAEDEADYYCQSYDNSLKA VFGGGTRLTVL | SEQ ID NO: 141 CAGTCTGTGCTGACGCAGCCGCCCTCAGTGTCTGGGGCCCGAGGGCAGAGGATCACCATCT CCTGCACTGGGACCAGCTCCAACCTCGGGGCAGGTTTTGATGTTCACTGGTATCAGCAGCT TCCAGGAAAAGCCCCCGAACTCCTCATCTTTGGGAACAACAACCGGCCCTCAGGGGTCCCT GACCGATTCTCTGGCTCCAAGTCTGGCACCTCAGCCTCCCTGGCCATCACTGGGCTCCAGG CTGAGGATGAGGCTGATTATTACTGCCAGTCCTATGACAACAGCCTGAAGGCGGTATTCGG CGGAGGGACCAGGCTGACCGTCCTAG |
| 1001701503_ 31 | SEQ ID NO: 104 QTVVTQEPSFSVSPGGTVTLTCGLS SGSVSTTHYPSWYQRTPGQAPRTLI YTTNTRSSGVPDRFSGSILGNKAAL TITGAQADDESDYYCVLYMGRGIS VTGGGTKLTVL | SEQ ID NO: 142 CAGACTGTGGTGACCCAGGAGCCATCGTTCTCAGTGTCCCCTGGAGGGAGAGTCACACTCA CTTGTGGCTTGAGCTCTGGCTCAGTCTCTACTACTCACTACCCCAGCTGGTACCAGCGGAC CCCAGGCCAGGCTCCACGCACGCTCATCTACACCACAAACACTCGCTCTTCTGGGGTCCCT GATCGCTTCTCTGGCTCCATCCTAGGGAACAAAGCTGCCCTCACCATCACGGGGGCCCAGG CAGATGATGAATCTGATTATTACTGTGTGCTGTATATGGGTCGTGGCATTTCGGTGTTCGG CGGAGGGACCAAGCTGACCGTCCTAG |
| 1001701503_ F10 | SEQ ID NO: 105 QTVVTQEPSFSVSPGGTVTLTCGLS SGSVSITHYPSWYRQTPGQAPRTLI YTTNTRSSGVPDRFSGSILGNKAAL TITGAQADDESDYYCVLYMGRGIS VFGGGTKLTVL | SEQ ID NO: 143 CAGACTGTGGTGACCCAGGAGCCATCGTTCTCAGTGTCCCCTGGAGGGACAGTCACACTCA CTTGTGGCTTGAGCTGGCTCAGTCTCTATTACTCACTACCCCAGCTGGTATCGGCAGACC CCAGGCCAGGCTCCACGCACGCTCATCTACACCACAAACACTCGCTCTTCTGGGGTCCCTG ATCGCTTCTCTGGCTCCATCCTAGGGAACAAAGCTGCCCTCACCATCACGGGGGCCCAGGC AGATGATGAATCTGATTATTACTGTGTGCTGTATATGGGTCGTGGCATTTCGGTGTTTGGC GGAGGGACCAAGCTGACCGTCCTAG |
| 1001701405_ N8 | SEQ ID NO: 106 QSALTQPASVSGSPGQSITISCTGTS SDVGGYNFVSWYQHHPGNAPKLLI YGVTDRPSGVSKRFSGSRSGNTASL TISGLQSEDEADYYCSSYTTFITRG WIFGGGTRLTVL | SEQ ID NO: 144 CAGTCTGCCCTGACTCAGCCTGCCTCCGTGTCTGGGTCTCCTGGACAGTCGATCACCATCTC CTGCACTGGAACCAGCAGTGACGTTGGTGGTTATAACTTTGTCTCCTGGTACCAACACCAC CCAGGCAACGCCCCCAAACTCCTGATTTATGGTGTCACTGATCGGCCCTCAGGGGTCTCTA AACGATTCTCAGGTTCCAGGTCTGGCAACACGGCCTCCCTGACCATCTCTGGGCTCCAGTC TGAGGACGAGGCTGATTATTACTGCAGCTCATATACAACCTTCATCACCCGCGGTTGGATT TTCGGCGGAGGGACCAGACTGACCGTCCTAG |
| 1001701403_ F4 | SEQ ID NO: 107 QSALTQPASVSGSPGQSITISCTGTS SDVGGYNFVSWYQQPGKAPKLII YDVSNRPSGVSDRFSGSKSGNTASL TISGLQAEDEADYYCSSYTASSTRN FVFGTGTQVTVL | SEQ ID NO: 145 CAGTCTGCCCTGACTCAGCCTGCCTCCGTGTCTGGGTCTCCTGGACAGTCGATCACGATCT CCTGCACTGGAACCAGCAGTGACGTTGGTGGTTATAACTTTGTCTCCTGGTACCAACAACA GCCAGGCAAAGCCCCCAAACTCATCATTTATGATGTCAGTAATCGGCCCTCAGGGGTTTCT GATCGCTTCTCTGGCTCCAAGTCTGGCAACACGGCCTCCCTGACCATCTCTGGGCTCCAGG CTGAGGACGAGGCTGATTATTACTGCAGCTCATATACAGCCAGCAGCACTCGAAATTTTGT CTTCGGAACTGGGACCCAGGTCACCGTCCTAG |
| 1001701503_ K2 | SEQ ID NO: 108 DIQMTQSPSTLSASVGDRVTITCRA SQSFSTWLAWYQQKPGKAPKLLIY KASSLESGVPSRFSGSGSGTEFTLTI SSLQPDDFATYYCQQYDTYSTFGQ GTKVEVK | SEQ ID NO: 146 GACATCCAGATGACCCAGTCTCCTTCCACCCTGTCTGCATCTGTAGGAGACAGAGTCACCA TCACTTGCCGGGCCAGTCAGAGTTTTAGTACTTGGTTGGCCTGGTATCAGCAGAAACCAGG GAAAGCCCCTAAGCTCCTGATCTATAAGGCGTCTAGTTTAGAAAGTGGGGTCCCATCAAG GTTCAGCGGCAGTGGATCTGGGACAGAATTCACTCTCACCATCAGCAGCCTGCAGCCTGAT GATTTTGCAACTTATTACTGCCAACAGTATGATACTTATTCGACGTTCGGCCAAGGGACCA AGGTGGAAGTCAAAC |
| 1001701503_ 15 | SEQ ID NO: 109 DIQMTQSPSTLSASVGDRVTITCRA SQSFSSWLAWYQQKPGKAPKLLIY KASSLESGVPSRFSGSGSGTEFTLTI SSLQPDDFATYYCQQYDTYSTFGQ GTKVEVK | SEQ ID NO: 147 GACATCCAGATGACCCAGTCTCCTTCCACCCTGTCTGCATCTGTAGGAGACAGAGTCACCA TCACTTGCCGGGCCAGTCAGAGTTTTAGTAGTTGGTTGGCCTGGTATCAGCAGAAACCAGG GAAAGCCCCTAAGCTCCTGATCTATAAGGCGTCTAGTTTAGAAAGTGGGGTCCCATCAAG GTTCAGCGGCAGTGGATCTGGGACAGAATTCACTCTCACCATCAGCAGCCTGCAGCCTGAT GATTTTGCAACTTATTACTGCCAACAGTATGATACTTATTCGACGTTCGGCCAAGGGACCA AGGTGGAAGTCAAAC |
| 1001701503_ B10 | SEQ ID NO: 110 DIQLTQSPSFLSASVRDRVTITCRAS QGISTYLAWYQQKPGKAPKLLIYA ASTLQSGVPSRFSGSGSGTDFTLTIS SLQPEDFATYYCQHLSNYLFTFGPG TKVDIK | SEQ ID NO: 148 GACATCCAGTTGACCCAGTCTCCATCCTTCCTGTCTGCATCTGTAGGAGACAGAGTCACCA TCACTTGCCGGGCCAGTCAGGGCATTAGCACTTATTTAGCCTGGTATCAGCAAAAACCAGG GAAAGCCCCTAAGCTCCTGATCTATGCTGCATCCACTTTGCAAAGTGGGGTCCCATCAAGG TTCAGCGGCAGTGGATCTGGGACAGACTTCACTCTCACAATCAGCAGCCTGCAGCCTGAA GATTTTGCAACTTATTACTGTCAACACCTTAGTAATTACCTGTTCACTTTCGGCCCTGGGAC CAAAGTGGATATCAAAC |
| 1001701403_ M1 | SEQ ID NO: 111 DIQLTQSPSFLSASVGDRVTITCRAS QGISTYLAWYQQKPGKAPKLLIYD ASTLQSGVPSRFSGSGSGTEFTLTIS SLQPEDFATYYCQQLNNYVFTFGP GTKVDIK | SEQ ID NO: 149 GACATCCAGTTGACCCAGTCTCCATCCTTCCTGTCTGCATCTGTAGGAGACAGAGTCACCA TCACTTGCCGGGCCAGTCAGGGCATTAGCACTTATTTAGCCTGGTATCAGCAAAAACCAGG GAAAGCCCCTAAGCTCCTGATCTATGATGCATCCACTTTGCAAAGTGGGGTCCCATCAAGG TTCAGCGGCAGTGGATCTGGGACAGAATTCACTCTCACAATCAGCAGCCTGCAGCCTGAA GATTTTGCAACTTATTACTGTCAACAGCTTAATAATTACGTTTTCACTTTCGGCCCTGGGAC CAAAGTGGATATCAAAC |

TABLE 2-continued

Light chains full Amino Acid and DNA sequences

| antibody id | VJ amino acid | VJ nucleotides |
|---|---|---|
| 1001701503_P8 | SEQ ID NO: 112<br>DVQLTQSPSFLSASVGHRVTITCRA<br>SQGISTYLAWYQQKPGKAPKLLIY<br>DASTLQSGVPSRFSGSGSGTEFTLTI<br>SSLQPEDFATYYCQQLSSYVFTFGP<br>GTKVDIK | SEQ ID NO: 150<br>GACGTCCAGTTGACCCAGTCTCCATCCTTCCTGTCTGCATCTGTAGGACACAGAGTCACCA<br>TCACTTGCCGGGCCAGTCAGGGCATTAGCACTTATTTAGCCTGGTATCAGCAAAAGCCAGG<br>GAAAGCCCCTAAGCTCCTGATCTATGATGCATCCACTTTGCAAAGTGGGGTCCCATCAAGG<br>TTCAGCGGCAGTGGATCTGGGACAGAATTCACTCTCACAATCAGCAGCCTGCAGCCTGAA<br>GATTTTGCAACTTATTACTGTCAACAGCTTAGTAGTTACGTATTCACTTTCGGCCCTGGGAC<br>CAAAGTGGATATCAAAC |
| 1001701403_P10 | SEQ ID NO: 113<br>DMQMTQSPSSLSASVGDRVTITCR<br>ASQSISTYLNWYQQKAGKAPKLLI<br>YAASSLQSGVPSRFSGSGSGTDFTL<br>TISSLQPEDFATYYCQQSYSTPLFG<br>QGTKVEIK | SEQ ID NO: 151<br>GACATGCAGATGACCCAGTCTCCATCCTCCCTGTCTGCATCTGTAGGAGACAGAGTCACCA<br>TCACTTGCCGGGCAAGTCAGAGCATTAGCACCTTATTTAAATTGGTATCAGCAGAAAGCAG<br>GGAAAGCCCCTAAACTCCTGATCTATGCTGCATCAAGTTTGCAAAGTGGGGTCCCATCACG<br>GTTCAGTGGCAGTGGATCTGGGACAGATTTCACTCTCACCATCAGCAGTCTGCAACCTGAA<br>GATTTTGCAACTTACTACTGTCAACAGAGTTACAGTACCCCCCTGTTCGGCCAAGGGACCA<br>AGGTGGAAATCAAAC |
| 1001701403_L2 | SEQ ID NO: 114<br>DIQMTQSPSSLSASVGDRVTITCRA<br>SQNINNYLNWYQQRPGKPPNLLIY<br>AASTLQAGVPSRFSGRGSGTDFTLT<br>ISSLQPEDFATYYCQQSYGSPLFGQ<br>GTKVEIK | SEQ ID NO: 152<br>GACATTCCAGATGACCCAGTCTCCATCCTCCCTGTCTGCATCTGTAGGAGACAGGGTCACCA<br>TCACTTGCCGGGCAAGCCAGAACATTAACAACTATTTAAATTGGTATCAACAGAGACCAG<br>GGAAACCCCCTAACCTCCTGATCTATGCTGCATCTACTTTGCAAGCTGGGGTCCCATCAAG<br>GTTCAGTGGCCGTGGATCTGGGACAGATTTCACTCTCACCATCAGCAGTCTGCAACCTGAA<br>GATTTTGCTACTTACTACTGTCAGCAAAGTTACGGTAGTCCCCTGTTCGGCCAAGGGACCA<br>AGGTGGAAATCAAAC |

TABLE 3

Heavy chains CDR amino acid sequences and antibody lineages

| antibody id | lineage | isotype | V | J | CDR1 | CDR2 |
|---|---|---|---|---|---|---|
| 1001701405_P4 | 32 | IGHG1 | IGHV1-18*01 | IGHJ5*02 | GNSFSGYG (SEQ ID NO: 153) | LTPYTDNR (SEQ ID NO: 189) |
| 1001701403_I13 | 32 | IGHG1 | IGHV1-18*01 | IGHJ-5*02 | GHTFSGYG (SEQ ID NO: 154) | STPYTGKI (SEQ ID NO: 190) |
| 1001701503_I7 | 127 | IGHG1 | IGHV1-3*01 | IGHJ4*02 | GYTFTSFA (SEQ ID NO: 155) | INIGSGNT (SEQ ID NO: 191) |
| 1001701403_C4 | 186 | IGHG1 | IGHV1-69*13 | IGHJ3*02 | GGTFTSYA (SEQ ID NO: 156) | INVIFGST (SEQ ID NO: 192) |
| 1001701403_J2 | 186 | IGHG1 | IGHV1-69*13 | IGHJ-3*02 | GGSFTSYG (SEQ ID NO: 157) | INVVFGSV (SEQ ID NO: 193) |
| 1001701405_N2 | 186 | IGHG1 | IGHV1-69*13 | IGHJ-3*02 | GGTFTSYG (SEQ ID NO: 158) | INPIFGST (SEQ ID NO: 194) |
| 1001701503_L8 | 201 | IGHG1 | IGHV1-69*01 | IGHJ4*02 | GGTFTNYP (SEQ ID NO: 159) | ILPILDTA (SEQ ID NO: 195) |
| 1001701503_H1 | 201 | IGHG1 | IGHV1-69*01 | IGHJ4*02 | GGTFTKYP (SEQ ID NO: 160) | ILPILDTA (SEQ ID NO: 195) |
| 1001701405_M6 | 215 | IGHG1 | IGHV1-69*05 | IGHJ4*02 | GGTFSNYA (SEQ ID NO: 161) | IIPIFGTP (SEQ ID NO: 196) |
| 1001701403_H3 | 215 | IGHG1 | IGHV1-69*05 | IGHJ4*02 | GGTFRNYS (SEQ ID NO: 162) | SIPIFGTA (SEQ ID NO: 197) |
| 1001701405_J8 | 243 | IGHG1 | IGHV1-69*05 | IGHJ5*02 | GGTFSSNS (SEQ ID NO: 163) | IIPFFGTR (SEQ ID NO: 198) |
| 1001701405_J9 | 243 | IGHG1 | IGHV1-69*13 | IGHJ5*02 | GGSLNSYG (SEQ ID NO: 164) | IIPFFGTV (SEQ ID NO: 199) |
| 100170403_J3 | 248 | IGHG1 | IGHV1-69*05 | IGHJ5*02 | GVSLSSYG (SEQ ID NO: 165) | IIPFFGTR (SEQ ID NO: 200) |
| 1001701403_P4 | 248 | IGHG1 | IGHV1-69*13 | IGHJ5*02 | GGTFSSLA (SEQ ID NO: 166) | LIPVFGIP (SEQ ID NO: 201) |
| 1001701403_M11 | 254 | IGHG1 | IGHV1-69*15 | IGHJ5*02 | GGTFNSLP (SEQ ID NO: 167) | IIPFFATP (SEQ ID NO: 202) |
| 1001701403_M4 | 254 | IGHG1 | IGHV1-69*15 | IGHJ5*02 | GGTLSSYP (SEQ ID NO: 168) | ITPFFGTT (SEQ ID NO: 203) |
| 1001701405_L3 | 254 | IGHG1 | IGHV-69*15 | IGHJ5*02 | GGTFSSLA (SEQ ID NO: 169) | IIPFFATP (SEQ ID NO: 202) |
| 1001701405_K11 | 254 | IGHG1 | IGHV1-6995 | IGHJ5*02 | GGTFSSSP (SEQ ID NO: 170) | IIPFFGSP (SEQ ID NO: 204) |

TABLE 3-continued

Heavy chains CDR amino acid sequences and antibody lineages

| | | | | | | |
|---|---|---|---|---|---|---|
| 1001701403_O4 | 254 | IGHG1 | IGHV1-69*15 | IGHJ5*02 | GGTFSSSP (SEQ ID NO: 170) | IIPFFGSP (SEQ ID NO: 204) |
| 1001701405_I11 | 746 | IGHG1 | IGHV3-30-3*01 | IGHJ5*02 | GFPFSGYA (SEQ ID NO: 171) | ISYDGSDK (SEQ ID NO: 205) |
| 1001701405_C1 | 746 | IGHG1 | IGHV3-30-3*01 | IGHJ5*01 | GFPFRSYA (SEQ ID NO: 172) | ISYDGTNT (SEQ ID NO: 206) |
| 1001701405_G5 | 746 | IGHG1 | IGHV3-30-3*01 | IGHJ5*02 | GFSFSTYA (SEQ ID NO: 173) | IYYDGSNK (SEQ ID NO: 207) |
| 1001701403_P2 | 746 | IGHG1 | IGHV3-30-3*01 | IGHJ5*02 | GFTFSNYA (SEQ ID NO: 174) | IYYDGSRK (SEQ ID NO: 208) |
| 1001701403_A7 | 746 | IGHG1 | IGHV3-30-3*01 | IGHJ5*01 | EFPFKAYA (SEQ ID NO: 175) | ISYDGSNT (SEQ ID NO: 209) |
| 1001701405_L9 | 746 | IGHG1 | IGHV3-30-3*02 | IGHJ5*01 | GFTFSNFA (SEQ ID NO: 176) | IYYDGSNK (SEQ ID NO: 207) |
| 1001701405_E9 | 755 | IGHG1 | IGHV3-30-3*01 | IGHJ6*03 | GFTFTTDA (SEQ ID NO: 177) | ISYDGTEK (SEQ ID NO: 210) |
| 1001701403_I8 | 755 | IGHG1 | IGHV3-30-3*01 | IGHJ6*03 | GFTFRTDA (SEQ ID NO: 178) | ISYDGSEK (SEQ ID NO: 211) |
| 1001701503_E1 | 962 | IGHG1 | IGHV3-7*01 | IGHJ4*02 | GTFDSYW SEQ ID NO: 179) | IKLDGSEK (SEQ ID NO: 212) |
| 1001701503_F10 | 962 | IGHG1 | IGHV3-7*01 | IGHJ4*02 | GFTFDNYW (SEQ ID NO: 180) | IKLDGSEK (SEQ ID NO: 212) |
| 1001701405_N8 | 1152 | IGHG1 | IGHV4-34*02 | IGHJ5*02 | DGPLIGYY (SEQ ID NO: 181) | ITHSGNT (SEQ ID NO: 213) |
| 1001701403_F4 | 1152 | IGHG1 | IGHV4-34*01 | IGHJ5*02 | GGPLIGWY (SEQ ID NO: 182) | ITHSGST (SEQ ID NO: 214) |
| 1001701503_K2 | 1227 | IGHA1 | IGHV4-39*01 | IGHJ4*02 | GGSISSSSYY (SEQ ID NO: 183) | LYYSGST (SEQ ID NO: 215) |
| 1001701503_A5 | 1227 | IGHA1 | IGHV4-39*01 | IGHJ4*02 | GGSISSSSYY (SEQ ID NO: 183) | MYYSGST (SEQ ID NO: 216) |
| 1001701503_B10 | 1255 | IGHG1 | IGHV4-39*01 | IGHJ5*01 | GGSINTRSYY- (SEQ ID NO: 184) | IFYTGST (SEQ ID NO: 217) |
| 1001701403_M1 | 1255 | IGHG1 | IGHV4-39*07 | IGHJ5*01 | RGSISTNDHS- (SEQ ID NO: 185) | LHHSGNT (SEQ ID NO: 218) |
| 1001701503_D8 | 1255 | IGHG1 | IGHV4-39*01 | IGHJ5*01 | GGSISRSSTYF (SEQ ID NO: 186) | VSYSGST (SEQ ID NO: 219) |
| 1001701403_P10 | 1353 | IGHG1 | IGHV4-59*01 | IGHJ4*02 | GDSITSYY (SEQ ID NO: 187) | IYYSGGT (SEQ ID NO: 220) |
| 1001701403_L2 | 1353 | IGHG1 | IGHV4-59*01 | IGHJ4*02 | GDSISSYY (SEQ ID NO: 188) | INYSGNT (SEQ ID NO: 221) |

| antibody id | CDR3 | Median percent amino acid identity for CDR3 seqs |
|---|---|---|
| 1001701405_P4 | ATGGPNFWSGHNWLDP (SEQ ID NO: 222) | 100% |
| 1001701403_I13 | ATGGPNFWSGHNWDP (SEQ ID NO: 222) | |
| 1001701503_I7 | ARALFGLVAVASPFDN (SEQ ID NO: 223) | 100% |
| 1001701403_C4 | ARADEMATAQGFYAFDI (SEQ ID NO: 224) | 88% |
| 1001701403_J2 | ARADEMATIEGFYAFDI (SEQ ID NO: 225) | |
| 1001701405_N2 | ARADEMATTGGFYAFDI (SEQ ID NO: 226) | |
| 1001701503_L8 | ARVYFDSGGYFDS (SEQ ID NO: 227) | 92% |
| 1001701503_H1 | ARVYYDSGGYFDS (SEQ ID NO: 228) | |
| 1001701405_M6 | ARSPWHSSGWFPSDY (SEQ ID NO: 229) | 80% |
| 1001701403_H3 | ARSPWHNSGWFPLDS (SEQ ID NO: 230) | |

TABLE 3-continued

Heavy chains CDR amino acid sequences and antibody lineages

| | | |
|---|---|---|
| 1001701405_J8 | ARSCESPSCYHNWFDP (SEQ ID NO: 231) | 81% |
| 1001701405_J9 | ARYCYSASCYHNWFDP (SEQ ID NO: 232) | |
| 1001701403_J3 | ARRNAKGGYSGGNWFDP (SEQ ID NO: 233) | 88% |
| 1001701403_P4 | ARRSGKGGYSGGNWFDP (SEQ ID NO: 234) | |
| 1001701403_M11 | ARDLNFYDSSGYHFARWFDP (SEQ ID NO: 235) | 85% |
| 1001701403_M4 | ARDVHYSDSSGYHFGRWFDP (SEQ ID NO: 236) | |
| 1001701405_L3 | ARDLNFYDSSGYHFARWFDP (SEQ ID NO: 237) | |
| 1001701405_K11 | ARDVNYYDSSGYHFGRWFDP (SEQ ID NO: 238) | |
| 1001701403_O4 | ARDVNYYDSSGYHFGRWFDP (SEQ ID NO: 238) | 86% |
| 1001701405_I11 | AKNYGSGSLNWFDA (SEQ ID NO: 239) | |
| 1001701405_C1 | AKNYGSGSQNWFDS (SEQ ID NO: 240) | |
| 1001701405_G5 | AKNYGSGSLNWYDA (SEQ ID NO: 241) | |
| 1001701403_P2 | AKNYGSGTLNWFDA (SEQ ID NO: 242) | |
| 1001701403_A7 | AKNYGSGSLNWFDS (SEQ ID NO: 243) | |
| 1001701405_L9 | AKNYGSGTLNWFDS (SEQ ID NO: 244) | |
| 1001701405_E9 | AREGTYSGIVTGQSQSPSSYMDV (SEQ ID NO: 245) | 96% |
| 1001701403_I8 | AREGTYSGIVTGQSQSPSSYMAV (SEQ ID NO: 246) | |
| 1001701503_E1 | ARVASHPSLFSPYYFDY (SEQ ID NO: 247) | 94% |
| 1001701503_F10 | ARVASHPTLFSPYYFDY (SEQ ID NO: 248) | |
| 1001701405_N8 | ARGPGGTSTSCYRCWFDP (SEQ ID NO: 249) | 94% |
| 1001701403_F4 | ARGPGGTSTSCYQCWFDP (SEQ ID NO: 250) | |
| 1001701503_K2 | AGQDYSGTYYDYFDY (SEQ ID NO: 251) | 93% |
| 1001701503_A5 | AGQDYSGTYYDYFNY (SEQ ID NO: 252) | |
| 1001701503_B10 | ARQDRNWFDS (SEQ ID NO: 253) | 80% |
| 1001701403_M1 | VRQNRNWFDS (SEQ ID NO: 254) | |
| 1001701503_D8 | ARQDRNWFDS (SEQ ID NO: 253) | |
| 1001701403_P10 | ASALNYFDSSGPGGVAMGGGFDS (SEQ ID NO: 255) | 87% |
| 1001701403_L2 | AGALYYFDSRGPGGVAMGGGFDS (SEQ ID NO: 256) | |

TABLE 4

Light chains CDR amino acid sequences and antibody lineages

| antibody id | lineage | V | J | isotype | CDR1 | CDR2 |
|---|---|---|---|---|---|---|
| 1001701405_P4 | 32 | IGLV2-14*01 | IGLJ2*01 | IGLC | SSDVGGYNY (SEQ ID NO: 257) | DVS (SEQ ID NO: 285) |
| 1001701403_I13 | 32 | IGLV2-14*01 | IGLJ2*01 | IGLC | SSDVGGYNY (SEQ ID NO: 257) | DVN (SEQ ID NO: 286) |

TABLE 4-continued

Light chains CDR amino acid sequences and antibody lineages

| | | | | | | |
|---|---|---|---|---|---|---|
| 1001701503_I7 | 127 | IGKC | IGKV1-39*01 | IGKL4*01 | QSIAGY (SEQ ID NO: 258) | SAS (SEQ ID NO: 287) |
| 1001701403_C4 | 186 | IGKC | IGKV1-5*03 | IGKJ1*01 | QSIGTW (SEQ ID NO: 259) | KAS (SEQ ID NO: 288) |
| 1001701403_J2 | 186 | IGKC | IGKV1-5*03 | IGKJ1*01 | QSISSW (SEQ ID NO: 260) | KAS (SEQ ID NO: 288) |
| 1001701405_N2 | 186 | IGKC | IGKV1-5*03 | IGKJ1*01 | QSVSSW (SEQ ID NO: 261) | KAS (SEQ ID NO: 288) |
| 1001701503_L8 | 201 | IGLC | IGLV1-40*01 | IGLJ2*01 | SSNIGAGYD (SEQ ID NO: 262) | GYS (SEQ ID NO: 289) |
| 1001701503_H1 | 201 | IGLC | IGLV1-40*01 | IGLJ2*01 | SSNIGAGYD (SEQ ID NO: 262) | GYS (SEQ ID NO: 289) |
| 1001701405_M6 | 215 | IGLC | IGLV1-40*01 | IGLJ7*01 | SSNIGAGYD (SEQ ID NO: 263) | GKN (SEQ ID NO: 290) |
| 1001701403_H3 | 215 | IGKC | IGKV1-5*03 | IGKJI*01 | QSIDSW--- (SEQ ID NO: 264) | KAS (SEQ ID NO: 288) |
| 1001701405_J8 | 243 | IGKC | IGKV3-11*01 | IGKJ2*01 | QSVSSY (SEQ ID NO: 265) | DAS (SEQ ID NO: 291) |
| 1001701405_J9 | 243 | IGKC | IGKV3-11*01 | IGKJ2*01 | QSVGSS (SEQ ID NO: 266) | DAS (SEQ ID NO: 291) |
| 1001701403_J3 | 248 | IGLC | IGLV2-14*01 | IGLJ1*01 | SSDVGGYNF (SEQ ID NO: 267) | DVS (SEQ ID NO: 285) |
| 1001701403_P4 | 248 | IGLC | IGLV2-14*01 | IGLJ1*01 | SSDVGGYNY (SEQ ID NO: 257) | DVS (SEQ ID NO: 285) |
| 1001701403_M11 | 254 | IGKC | IGKV3-15*01 | IGKJ2*01 | QSVNNN (SEQ ID NO: 268) | GAS (SEQ ID NO: 292) |
| 1001701403_M4 | 254 | IGKC | IGKV3-15*01 | IGKJ2*01 | QSVGNN (SEQ ID NO: 269) | GAS (SEQ ID NO: 292) |
| 1001701405_L3 | 254 | IGKC | IGKV3-15*01 | IGKJ2*01 | QSVSSN (SEQ ID NO: 270) | GAS (SEQ ID NO: 292) |
| 1001701405_K11 | 254 | IGKC | IGKV3-15*01 | IGKJ2*01 | QSISSN (SEQ ID NO: 271) | RAS (SEQ ID NO: 293) |
| 1001701403_O4 | 254 | IGKC | IGKV3-15*01 | IGKJ2*01 | QSISSN (SEQ ID NO: 271) | RAS (SEQ ID NO: 293) |
| 1001701405_I11 | 746 | IGKC | IGKV3-15*01 | IGKJ1*01 | QSVGSN (SEQ ID NO: 272) | GAS (SEQ ID NO: 292) |
| 1001701405_C1 | 746 | IGKC | IGKV3-15*01 | IGKJI*01 | QNIGSN (SEQ ID NO: 273) | GAS (SEQ ID NO: 292) |
| 1001701405_G5 | 746 | IGKC | IGKV3-15*01 | IGKJ1*01 | QSVGSN (SEQ ID NO: 272) | GAS (SEQ ID NO: 292) |
| 1001701403_P2 | 746 | IGKC | IGKV3-15*01 | IGKJ1*01 | QSIGSN (SEQ ID NO: 446) | AAS (SEQ ID NO: 294) |
| 1001701403_A7 | 746 | IGKC | IGKV3-15*01 | IGKJ1*01 | QSVGSN (SEQ ID NO: 272) | AAS (SEQ ID NO: 294) |
| 1001701405_L9 | 746 | IGKC | IGKV3-15*01 | IGKJ1*01 | QNIGRN (SEQ ID NO: 274) | GAS (SEQ ID NO: 292) |
| 1001701405_E9 | 755 | IGLC | IGLV1-40*01 | IGLJ2*01 | SSNIGAGYD (SEQ ID NO: 275) | GNN (SEQ ID NO: 295) |
| 1001701403_I8 | 755 | IGLC | IGLV1-40*01 | IGLJ2*01 | SSNLGAGFD (SEQ ID NO: 276) | GNN (SEQ ID NO: 295) |
| 1001701503_E1 | 962 | IGLC | IGLV8-61*01 | IGLJ3*02 | SGSVSTTHY (SEQ ID NO: 277) | TTN (SEQ ID NO: 296) |

TABLE 4-continued

Light chains CDR amino acid sequences and antibody lineages

| | | | | | | |
|---|---|---|---|---|---|---|
| 1001701503_F10 | 962 | IGLC | IGLV8-61*01 | IGLJ3*02 | SGSVSITHY (SEQ ID NO: 278) | TTN (SEQ ID NO: 296) |
| 1001701405_N8 | 1152 | IGLC | IGLV2-14*01 | IGLJ3*02 | SSDVGGYNF (SEQ ID NO: 279) | GVT (SEQ ID NO: 297) |
| 1001701403_F4 | 1152 | IGLC | IGLV2-14*01 | IGLJ1*01 | SSDVGGYNF (SEQ ID NO: 279) | DVS (SEQ ID NO: 285) |
| 1001701503_K2 | 1227 | IGKC | IGKV1-5*03 | IGKJ1*01 | QSFSTW (SEQ ID NO: 280) | KAS (SEQ ID NO: 288) |
| 1001701503_A5 | 1227 | IGKC | IGKV1-5*03 | IGKJ1*01 | QSFSSW (SEQ ID NO: 281) | KAS (SEQ ID NO: 288) |
| 1001701503_B10 | 1255 | IGKC | IGKV1-9*01 | IGKJ3*01 | QGISTY (SEQ ID NO: 282) | AAS (SEQ ID NO: 294) |
| 1001701403_M1 | 1255 | IGKC | IGKV1-9*01 | IGKJ3*01 | QGISTY (SEQ ID NO: 282) | DAS (SEQ ID NO: 291) |
| 1001701503_D8 | 1255 | IGKC | IGKV1-9*01 | IGKJ3*01 | QGISTY (SEQ ID NO: 282) | DAS (SEQ ID NO: 291) |
| 1001701403_P10 | 1353 | IGKC | IGKV1-39*01 | IGKJ1*01 | QSISTY (SEQ ID NO: 283) | AAS (SEQ ID NO: 294) |
| 1001701403_L2 | 1353 | IGKC | IGKV1-39*01 | IGKJ1*01 | QNINNY (SEQ ID NO: 284) | AAS (SEQ ID NO: 294) |

| antibody id | CDR3 |
|---|---|
| 1001701405_P4 | SSYTRSSTLL (SEQ ID NO: 298) |
| 1001701403_I13 | TSFTKSTTLL (SEQ ID NO: 299) |
| 1001701503_I7 | QQSFRTPTT (SEQ ID NO: 300) |
| 1001701403_C4 | QQYNSYWT (SEQ ID NO: 301) |
| 1001701403_J2 | QQYNTYWT (SEQ ID NO: 302) |
| 1001701405_N2 | QQYNSYWT (SEQ ID NO: 301) |
| 1001701503_L8 | QSYDSSLSGHVV (SEQ ID NO: 303) |
| 1001701503_H1 | QSYDSSLSGHVI (SEQ ID NO: 304) |
| 1001701405_M6 | QSFDSLSGYAV (SEQ ID NO: 305) |
| 1001701403_H3 | QQYSYSPWT- (SEQ ID NO: 306) |
| 1001701405_J8 | QHRSNWPPRVYT (SEQ ID NO: 307) |
| 1001701405_J9 | QQRSSWPPYMYT (SEQ ID NO: 308) |
| 1001701403_J3 | SSYTSRSSRTYV (SEQ ID NO: 309) |
| 1001701403_P4 | SSYTARTSRTYV (SEQ ID NO: 310) |
| 1001701403_M11 | QQYNNWPPT (SEQ ID NO: 311) |
| 1001701403_M4 | QQCYNWPPT (SEQ ID NO: 312) |
| 1001701405_L3 | QQYDNWPPT (SEQ ID NO: 313) |
| 1001701405_K11 | QQFYNWPPT (SEQ ID NO:314) |
| 1001701403_O4 | QQFYNWPPT (SEQ ID NO: 314) |
| 1001701405_I11 | QQYNNWWT (SEQ ID NO: 315) |
| 1001701405_C1 | QQYNNWWT (SEQ ID NO: 315) |
| 1001701405_G5 | QQYNNLWT (SEQ ID NO: 316) |

TABLE 4-continued

Light chains CDR amino acid sequences and antibody lineages

| | | |
|---|---|---|
| | 1001701403_P2 | QQYNNWWT (SEQ ID NO: 315) |
| | 1001701403_A7 | QQYNNWWT (SEQ ID NO: 315) |
| | 1001701405_L9 | QQYNNWWT (SEQ ID NO: 315) |
| | 1001701405_E9 | QSYDNSLKAV (SEQ ID NO: 317) |
| | 1001701403_I8 | QSYDNSLKAV (SEQ ID NO: 317) |
| | 1001701503_E1 | VLYMGRGISV (SEQ ID NO: 318) |
| | 1001701503_F10 | VLYMGRGISV (SEQ ID NO: 318) |
| | 1001701405_N8 | SSYTTFITRGWI (SEQ ID NO: 319) |
| | 1001701403_F4 | SSYTASSTRNFV (SEQ ID NO: 320) |
| | 1001701503_K2 | QQYDTYST (SEQ ID NO: 321) |
| | 1001701503_A5 | QQYDTYST (SEQ ID NO: 321) |
| | 1001701503_B10 | QHLSNYLFT (SEQ ID NO: 322) |
| | 1001701403_M1 | QQLNNYVFT (SEQ ID NO: 323) |
| | 1001701503_D8 | QQLSSYVFT (SEQ ID NO: 324) |
| | 1001701403_P10 | QQSYSTPL (SEQ ID NO: 325) |
| | 1001701403_L2 | QQSYGSPL (SEQ ID NO: 326) |

The amino acid residue sequences provided herein are set forth in single-letter amino acid code which can be used interchangeably with three-letter amino acid code. An amino acid refers to any monomer unit that can be incorporated into a peptide, polypeptide, or protein. The twenty natural or genetically encoded alpha-amino acids are as follows: alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V). The structures of these twenty natural amino acids are shown in, e.g., Stryer et al., Biochemistry, 5$^{th}$ ed., Freeman and Company (2002). The term amino acid also includes unnatural amino acids, modified amino acids (e.g., having modified side chains and/or backbones), and amino acid analogs.

The terms identical or percent identity, in the context of two or more nucleic acids or polypeptide sequences, refer to two or more sequences or subsequences that are the same or have a specified percentage of nucleotides or amino acid residues that are the same (e.g., 90%, or 95?/or greater identity over a specified region), when compared and aligned for maximum correspondence over a comparison window, or designated region as measured using one of the following sequence comparison algorithms or by manual alignment and visual inspection.

Identity or similarity with respect to a sequence is defined as the percentage of amino acid residues in the candidate sequence that are identical (i.e., same residue) with the starting amino acid residues, after aligning the sequences and introducing gaps, if necessary, to achieve the maximum percent sequence identity. Methods of alignment of sequences for comparison are well known in the art. Optimal alignment of sequences for comparison can be conducted, for example, by the local homology algorithm of Smith and Waterman (*Adv. Appl. Math.* 2:482, 1970), by the homology alignment algorithm of Needleman and Wunsch (*J. Mol. Biol.* 48:443, 1970), by the search for similarity method of Pearson and Lipman (*Proc. Natl. Acad. Sci. USA* 85:2444, 1988), by computerized implementations of these algorithms (e.g., GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

As with all peptides, polypeptides, and proteins, including fragments thereof, it is understood that additional modifications in the amino acid sequence of the Dengue virus antigen-specific antibodies or antigen binding fragments thereof described herein, for example, in the heavy chain variable region and/or light chain variable region, can occur that do not alter the nature or function of the antibodies or antigen binding fragments thereof. Such modifications include conservative amino acids substitutions, such that each recited sequence optionally contains one or more conservative amino acid substitutions. The list provided below identifies groups that contain amino acids that are conservative substitutions for one another; these groups are exemplary as other conservative substitutions are known to those of skill in the art.

| | |
|---|---|
| 1) | Alanine (A), Glycine (G); |
| 2) | Aspartic acid (D), Glutamic acid (E); |
| 3) | Asparagine (N), Glutamine (Q); |
| 4) | Arginine (R), Lysine (K); |
| 5) | Isoleucine (I), Leucine (L), Methionine (M), Valine (V); |
| 6) | Phenylalanine (F), Tyrosine (Y), Tryptophan (W); |

| | |
|---|---|
| 7) | Serine (S), Threonine (T); and |
| 8) | Cysteine (C), Methionine (M) |

By way of example, when an aspartic acid at a specific residue is mentioned, also contemplated is a conservative substitution at the residue, for example, glutamic acid, Non-conservative substitutions, for example, substituting a proline with glycine, are also contemplated.

In some instances, the affinity of Dengue virus antigen-specific antibodies or antigen binding fragments thereof may be optimized through mutations to increase or decrease affinity as desired based on one or more of the known characteristics of the binding interaction with the cognant Dengue virus antigen, the structure of either or both of the antibodies or fragments thereof, or the Dengue virus antigen. In some instances, the mutations permits facile elution of purified antibodies or fragments thereof under desirable elution conditions during isolation and purification.

Methods of generating and screening for antibodies and antigen binding fragments thereof as provided in this disclosure are described in the Examples and are well-known in the art. Methods of further modifying antibodies for enhanced properties (e.g., enhanced affinity, chimerization, humanization) as well as generating antigen binding fragments, as described herein, are also well-known in the art.

The present disclosure also encompasses antibodies or fragments thereof that bind to the same epitope of Dengue virus antigens as the antibodies disclosed herein. Such antibodies can be identified using routine techniques known in the art, including, for example, competitive binding assays.

The term epitope, as used herein, means a component of an antigen capable of specific binding to an antibody or antigen binding fragment thereof. Such components optionally comprise one or more contiguous amino acid residues and/or one or more non-contiguous amino acid residues. Epitopes frequently consist of surface-accessible amino acid residues and/or sugar side chains and can have specific three-dimensional structural characteristics, as well as specific charge characteristics. Conformational and non-conformational epitopes are distinguished in that the binding to the former but not the latter is lost in the presence of denaturing solvents. An epitope can comprise amino acid residues that are directly involved in the binding, and other amino acid residues, which are not directly involved in the binding. The epitope to which an antigen binding protein binds can be determined using known techniques for epitope determination such as, for example, testing for antigen binding protein binding to antigen variants with different point mutations.

The present disclosure also provides chimeric antibodies. The term chimeric antibody refers to an antibody in which a component of the heavy and/or light chain is derived from a particular source or species, while the remainder of the heavy and/or light chain is derived from a different source or species.

A human antibody is one that possesses an amino acid sequence corresponding to that of an antibody produced by a human or a human cell, or derived from a non-human source that utilizes a human antibody repertoire or human antibody-encoding sequences (e.g., obtained from human sources, genetically modified non-human sources or designed de novo), Human antibodies specifically exclude humanized antibodies.

Humanized forms of non-human antibodies are chimeric antibodies that contain minimal sequence derived from the non-human antibody. A humanized antibody is generally a human immunoglobulin (recipient antibody) in which residues from one or more CDRs are replaced by residues from one or more CDRs of a non-human antibody (donor antibody). The donor antibody can be any suitable non-human antibody, such as a mouse, rat, rabbit, chicken, or non-human primate antibody having a desired specificity, affinity, or biological effect. In some instances, selected framework region residues of the recipient antibody are replaced by the corresponding framework region residues from the donor antibody. Humanized antibodies can also comprise residues that are not found in either the recipient antibody or the donor antibody. Such modifications can be made to further refine antibody function. (See Jones et al. (1986) *Nature,* 321:522-525; Riechmann et al. (1988) *Nature,* 332: 323-329; and Presta, (1992) *Curr Op Struct Biol.,* 2:593-596).

In some embodiments, the antibody or antigen binding fragment thereof provided herein can include a heavy (H) chain variable domain sequence (abbreviated herein as VH), and a light (L) chain variable domain sequence (abbreviated herein as VL). In some embodiments, an antibody molecule comprises or consists of a heavy chain and a light chain (referred to as a half antibody). In another example, an antibody molecule includes two heavy (H) chain variable domain sequences and two light (L) chain variable domain sequence, thereby forming two antigen binding sites, such as Fab, Fab', $F(ab)_2$, Fc, Fd, Fd', Fv, single chain antibodies (scFv, for example), single variable domain antibodies, diabodies (Dab) (bivalent and bispecific), and chimeric (e.g., humanized) antibodies, which may be produced by the modification of whole antibodies or synthesized de novo using recombinant DNA technologies. These functional antibody fragments retain the ability to selectively bind with their respective antigen. Antibodies and antibody fragments can be from any class of antibodies including, but not limited to, IgG, IgA IgM, IgD, and IgE, and from any subclass (e.g., IgG1, IgG2, IgG3, and IgG4) of antibodies. The preparation of antibody molecules can be monoclonal or polyclonal. An antibody molecule can also be a human, humanized, CDR-grafted, or an in vitro generated antibody. The antibody can have a heavy chain constant region chosen from, e.g., IgG1, IgG2, IgG3, or IgG4. The antibody can also have a light chain chosen from either kappa or lambda light chains.

As used herein, the term monoclonal antibody refers to an antibody from a population of substantially homogeneous antibodies. A population of substantially homogeneous antibodies comprises antibodies that are the same or substantially similar and that bind the same epitope(s), except for variants that can normally arise during production of the monoclonal antibody. Such variants are generally present in only minor amounts. A monoclonal antibody is typically obtained by a process that includes the selection of a single antibody from a plurality of antibodies. For example, the selection process can be the selection of a unique clone from a plurality of clones, such as a pool of yeast clones, phage clones, bacterial clones, mammalian cell clones, hybridoma clones, or other recombinant DNA clones. The selected antibody can be further altered, for example, to improve affinity for the target, for example, by affinity maturation, to humanize the antibody, to improve its production in cell culture, and/or to reduce its immunogenicity in a subject.

Antigen binding fragments of an antibody molecule are well known in the art, and include, for example, (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a diabody (dAb) fragment, which consists of a VH domain; (vi) a camelid or camelized variable domain; (vii) a single chain Fv (scFv) (see e.g., Bird et al. (1988) *Science* 242:423-426; Huston et al. (1988) *Proc. Natl. Acad. Sci. USA* 85:5879-5883); (viii) a single domain antibody. These antibody fragments are obtained using conventional techniques known to those skilled in the art, and the fragments are screened for utility in the same manner as are intact antibodies.

In certain embodiments, antibodies and antibody compositions as provided herein are distinguishable from naturally occurring antibodies and compositions in one or more respects. Such distinguishable antibodies and compositions may be referred to as "synthetic," or may be identified by the proviso that the antibody or composition "is not naturally occurring" or affirmatively as "non-naturally occurring," As used herein the terms "corresponding antibody," and "corresponding to" describes the relationship between (1) an antibody characterized by six specific CDR sequences and produced by immune cells of a study subject described in the Examples below and (2) a synthetic antibody comprising the same six CDR sequences. Synthetic antibodies of this disclosure may differ in structure from naturally occurring antibodies with the same CDRs. That is, synthetic antibodies identified by specified CDRs may be structurally different from antibodies comprising the specified CDRs that are produced by cells of the study subject described in the Examples below. Possible differences for synthetic antibodies include variable region sequences that differ corresponding naturally occurring antibodies, different light chain sequences (i.e. lambda type instead of kappa type or vice versa), different isotypes, different allotypes, and different constant domain variants. These differences are discussed in more detail below.

In one approach, an antibody heavy chain comprises the CDRs of a clone described herein with the proviso that the antibody heavy chain does not comprise the heavy chain variable region sequence associated with the clone described herein. For illustration, in one embodiment an antibody that comprises the CDRs of Clone J9 does not have a heavy chain variable region that comprises SEQ ID NO:12. In another approach, an antibody light chain comprises the CDRs of a clone described herein with the proviso that the antibody light chain does not comprise the light chain variable region sequence associated with the clone described herein. For illustration, in one embodiment an antibody that comprises the CDRs of Clone J9 does not have a light chain variable region that comprises SEQ ID NO:88. In one approach both the heavy chain and the light chain variable region of an antibody of the invention have an amino acid sequence other than the sequence disclosed herein.

In some embodiments the synthetic antibody with specified CDRs is an isotype other the isotype(s) found associated with the study subject from which B cells with the specified CDRs was derived. In some embodiments the antibody disclosed herein is an isotype other than IgG1. In some embodiments the antibody disclosed herein is an isotype other than IgG2. In some embodiments the antibody disclosed herein is an isotype other than IgG3. In some embodiments the antibody disclosed herein is an isotype other than IgG4. In some embodiments the antibody disclosed herein is an isotype other than IgM. In some embodiments the antibody disclosed herein is an isotype other than IgA. In some embodiments the synthetic antibody comprises lambda type light chains. In some embodiments the synthetic antibody comprises kappa type light chains.

In some embodiments, the monoclonal antibody comprises a heavy chain variable region sequence and a light chain variable region sequence that are derived from an immunoglobulin producing human B cell, and further comprises a kappa or lambda light chain constant region. In some embodiments, the light chain constant region (kappa or lambda) is from the same type of light chain (i.e., kappa or lambda) as the light chain variable region that was derived from the immunoglobulin producing human B cell; as a non-limiting example, if an IgE-producing human B cell comprises a kappa light chain, then the monoclonal antibody that is produced can comprise the light chain variable region from the IgE-producing B cell and further comprises a kappa light chain constant region.

In some embodiments, the monoclonal antibody comprises a heavy chain variable region sequence and a light chain variable region sequence that are derived from an immunoglobulin-producing human B cell, and further comprises a heavy chain constant region having an IgG isotype IgG4), an IgA isotype (e.g., IgA1), an IgM isotype, an IgD isotype, or that is derived from an IgG, IgA, IgM, or IgD isotype (e.g., is a modified IgG4 constant region). It will be appreciated by a person of ordinary skill in the art that the different heavy chain isotypes (IgA, IgD, IgE, IgG, and IgM) have different effector functions that are mediated by the heavy chain constant region, and that for certain uses it may be desirable to have an antibody that has the effector function of a particular isotype IgG).

In some embodiments, the monoclonal antibody comprises a native (i.e., wild-type) human IgG, IgA, IgM, or IgD constant region. In some embodiments, the monoclonal antibody comprises a native human IgG1 constant region, a native human IgG2 constant region, a native human IgG3 constant region, a native human IgG4 constant region, a native human IgA1 constant region, a native human IgA2 constant region, a native human IgM constant region, or a native human IgD constant region. In some embodiments, the monoclonal antibody comprises a heavy chain constant region that comprises one or more modifications. It will be appreciated by a person of ordinary skill in the art that modifications such as amino acid substitutions can be made at one or more residues within the heavy chain constant region that modulate effector function. In some embodiments, the modification reduces effector function, e.g., results in a reduced ability to induce certain biological functions upon binding to an Fc receptor expressed on an effector cell that mediates the effector function. In some embodiments, the modification (e.g., amino acid substitution) prevents in vivo Fab arm exchange, which can introduce undesirable effects and reduce the therapeutic efficacy of the antibody. See, e.g., Silva et al., *J Biol Chem,* 2015, 280:5462-5469

In some embodiments, the monoclonal antibody comprises a native (i.e., wild-type) human IgM constant region, human IgD constant region, human IgG constant region that is derived from IgG1, IgG2, IgG3, or IgG4, or human IgA constant region that is derived from IgA1 or IgA2 and comprises one or more modifications that modulate effector function. Ini some embodiments the monoclonal antibody comprises a human IgM constant region, human IgD constant region, human IgG constant region that is derived from IgG1, IgG2, IgG3, or IgG4, or human IgA constant region that is derived from IgA1 or IgA2. In some embodiments, the monoclonal antibody comprises a native i.e., wild-type) human IgM constant region, human IgD constant region, human IgG constant region that is derived from IgG1, IgG2, IgG3, or IgG4, or human IgA constant region that is derived from IgA1 or IgA2 and comprises one, two, three, four, five, six, seven, eight, nine, ten or more modifications (e.g., amino acid substitutions). In some embodiments the constant regions includes variations (e.g., one, two, three, four, five, six, seven, eight, nine, ten or more amino acid substitutions) that reduce effector function.

In some embodiments the synthetic antibody with specified CDRs is an allotype other the allotype(s) found associated with the study subject from which B cells with the specified CDRs was derived. In some embodiments, the synthetic antibody of the invention comprises an allotype selected from those listed in Table 5, below, which is different from an allotype of antibodies from the corresponding study subject. In some embodiments the synthetic antibody of the invention comprises any individual allotype selected from those listed in Table 5, with the proviso that the allotype differs from the corresponding allotype of antibodies from a study subject.

TABLE 5

Human immunoglobulin allotypes

Isotype/type

| Heavy chains | | | | Light chains |
|---|---|---|---|---|
| IgG1 | IgG2 | IgG3 | IgA | |
| Allotypes | | | | |
| G1m | G2m | G3m | A2m | Km |
| 1 (a) | 23 (n) | 21 (g1) | 1 | 1 |
| 2 (x) |  | 28 (g5) | 2 | 2 |
|  | 3 (f) | 11 (b0) |  | 3 |
|  | 17 (z) | 5 (b1) |  |  |
|  |  | 13 (b3) |  |  |
|  |  | 14 (b4) |  |  |
|  |  | 10 (b5) |  |  |
|  |  | 15 (s) |  |  |
|  |  | 16 (t) |  |  |
|  |  | 6 (c3) |  |  |
|  |  | 24 (c5) |  |  |
|  |  | 26 (u) |  |  |
|  |  | 27 (v) |  |  |

NB: Alphabetical notation given within brackets. From: Jefferis and Marie-Paule Lefranc, 2009, "Human immunoglobulin allotypes: Possible implications for immunogenicity" mAbs 1(4): 332-338, incorporated herein by reference.

In some embodiments, a monoclonal antibody comprises CDR sequences, a heavy chain variable region, and/or a light chain variable region from an antibody from a B cell as described herein (e.g., as disclosed in Tables 1-2) and further comprises a heavy chain constant region and/or a light chain constant region that is heterologous to the antibody from the B cell from which the CDR sequences and/or variable region sequences are derived. For example, in some embodiments, the monoclonal antibody comprises the CDR sequences and/or variable region sequences of an antibody from a B cell, and further comprises a heavy chain constant region and a light chain constant region that is heterologous to the antibody from the B cell (e.g., the heavy chain constant region and/or light chain constant region is a wild-type or modified IgG1, IgG2, IgG3, or IgG4 constant region, or the heavy chain constant region and/or light chain constant region comprises one or more modifications (e.g., amino acid substitutions) relative to the native constant region of the antibody from the IgE B cell.

Synthetic antibodies of this disclosure may comprise variations in heavy chain constant regions to change the properties of the synthetic antibody relative to the corresponding naturally occurring antibody. Exemplary changes include mutations to modulate antibody effector function (e.g., complement-based effector function or FcγR-based effector function), alter half-like, modulate coengagement of antigen and FcγRs, introduce or remove glycosylation motifs (glyco-engineering). See Fonseca et al., 2018, "Boosting half-life and effector functions of therapeutic antibodies by Fc-engineering: An interaction-function review" *Int J Biol Macromol.* 19:306-311; Wang et al., 2018; "IgG Fc engineering to modulate antibody effector functions" *Protein Cell* 2018, 9(1):63-73, Schlothauer, 2016, "Novel human IgG1 and IgG4 Fc-engineered antibodies with completely abolished immune effector functions," *Protein Engineering, Design and Selection* 29(10):457-466; Tam et al., 2017, "Functional, Biophysical, and Structural Characterization of Human IgG1 and IgG4 Fc Variants with Ablated Immune Functionality" *Antibodies* 6, 12, each incorporated herein by reference for all purposes.

In some embodiments, the heavy chain variable region and/or the light chain variable region of the monoclonal antibody has an identical sequence to the heavy chain variable region and/or the light chain variable region encoded by the immunoglobulin producing single B cell from the human subject having Dengue. In some embodiments, the heavy chain variable region and/or the light chain variable region of the monoclonal antibody comprises one or more modifications, e.g., amino acid substitutions, deletions, or insertions.

The heavy chain variable region sequence and/or light chain variable region sequence of an antibody described herein can be engineered to comprise one or more variations in the heavy chain variable region sequence and/or light chain variable region sequence. In some embodiments, the engineered variation(s) improves the binding affinity of the antibody for a Dengue virus (e.g., DEN-1, DEN-2, DEN-3, DEN-4). In some embodiments, the engineered variation(s) improves the cross-reactivity of the antibody for a second Dengue virus.

In some embodiments, the engineered variation is a variation in one or more CDRs, e.g., an amino acid substitution in a heavy chain CDR and/or a light chain CDR as described herein. In some embodiments, the engineered variation is a variation in one or more framework regions, e.g., an amino acid substitution in a heavy chain framework region and/or a light chain framework region. In some embodiments, the engineered variation is a reversion of a region of the heavy chain and/or light chain sequence to the inferred naïve sequence. Methods for determining an inferred naive immunoglobulin sequence are described in the art. See, e.g., Magnani et al., *PLoS Negl Trop Dis,* 2017, 11:e0005655, doi:10.1371/journal.pntd.0005655

In some embodiments, affinity maturation is used to engineer further mutations that enhance the binding affinity of the antibody for a Dengue virus or enhance the cross-reactivity of the antibody for a second Dengue virus. Methods for performing affinity maturation are known in the art. See, e.g., Renaut et al., *Methods Mol Biol,* 2012, 907:451-461.

Antibody molecules can also be single domain antibodies. Single domain antibodies can include antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, rat, guinea, pig, human, camel, llama, fish, shark, goat, rabbit, and bovine. Single domain antibodies are described, for example, in International Application Publication No. WO 94/04678. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in Camelidae species (e.g., camel, llama, dromedary, alpaca and guanaco) or other species besides Camelidae.

In some embodiments, an antigen binding fragment can also be or can also comprise, e.g., a non-antibody, scaffold protein. These proteins are generally obtained through combinatorial chemistry-based adaptation of preexisting antigen-binding proteins. For example, the binding site of human transferrin for human transferrin receptor can be diversified using the system described herein to create a diverse library of transferrin variants, some of which have acquired affinity for different antigens. See, e.g., Ali et al. (1999) *J. Biol. Chem.* 274:24066-24073. The portion of human transferrin not involved with binding the receptor remains unchanged and serves as a scaffold, like framework regions of antibodies, to present the variant binding sites. The libraries are then screened, as an antibody library is screened, and in accordance with the methods described herein, against a target antigen of interest to identify those variants having optimal selectivity and affinity for the target antigen. See, e.g., Hey et al. (2005) *TRENDS Biotechnol* 23(10):514-522.

One of skill in the art would appreciate that the scaffold portion of the non-antibody scaffold protein can include, e.g., all or part of the Z domain of *S. aureus* protein A, human transferrin, human tenth fibronectin type 111 domain, kunitz domain of a human trypsin inhibitor, human CTLA-4, an ankyrin repeat protein, a human lipocalin (e.g., anticalins, such as those described in, e.g., International Application Publication No. WO2015/104406), human crystallin, human ubiquitin, or a trypsin inhibitor from *E. elaterium*.

Synthetic antibody compositions of this disclosure may differ from naturally occurring compositions in at least one or more of the following respects: (i) composition comprises antibodies that are purified, i.e., separated from tissue or cellular material with which they are associated in the human body, and optionally in a manufactured excipient or medium; and/or (ii) antibody compositions of the invention contain a single species of antibody (are monoclonal) such that all antibodies in the composition have the same structure and specificity.

C. Expression and Purification of Antibodies

The Dengue virus antigen-specific antibodies or antigen binding fragments thereof disclosed herein may be produced by recombinant expression in a human or non-human cell. Synthetic antibody-producing cells include non-human cells expressing heavy chains, light chains, or both heavy and light chains; human cells that are not immune cells heavy chains, light chains, or both heavy and light chains; and human B cells that produce heavy chains or light chains, but not both heavy and light chains. Synthetic antibodies of this disclosure may be are heterologously expressed, in vitro or in vivo, in cells other than human B cells, such as non-human cells and human cells other than B cells, optionally other than immune cells, and optionally in cells other than cells in a B cell lineage.

The Dengue virus antigen-specific antibodies or antigen binding fragments thereof disclosed herein can be produced using a variety of techniques known in the art of molecular biology and protein chemistry. For example, a nucleic acid encoding the antibody or antigen binding fragment thereof can be inserted into an expression vector that contains transcriptional and translational regulatory sequences, which include, e.g., promoter sequences, ribosomal binding sites, transcriptional start and stop sequences, translational start and stop sequences, transcription terminator signals, polyadenylation signals, and enhancer or activator sequences. The regulatory sequences include a promoter and transcriptional start and stop sequences. In addition, the expression vector can include more than one replication system, such that it can be maintained in two different organisms; for example, in mammalian or insect cells for expression and in a prokaryotic host for cloning and amplification.

Several possible vector systems are available for the expression of cloned heavy chain and light chain polypeptides from nucleic acids in mammalian cells. One class of vectors relies upon the integration of the desired gene sequences into the host cell genome. Cells that have stably integrated DNA can be selected by simultaneously introducing drug resistance genes such as *E. coli* gpt (Mulligan and Berg (1981) *Proc Natl Acad Sci USA* 78:2072) or Tn5 neo (Southern and Berg (1982) *Mol Appl Genet* 1:327). The selectable marker gene can be either linked to the DNA gene sequences to be expressed or introduced into the same cell by co-transfection (Wigler et al. (1979) *Cell* 16:77). A second class of vectors utilizes DNA elements that confer autonomously replicating capabilities to an extrachromosomal plasmid. These vectors can be derived from animal viruses, such as bovine papillomavirus (Sarver et al. (1982) *Proc Natl Acad Sci USA,* 79:7147), CMV, polyoma virus (Deans et al. (1984) *Proc Natl Acad Sci USA* 81:1 or SV40 virus (Lusky and Botchan (1981) *Nature* 293:79).

The expression vectors can be introduced into cells in a manner suitable for subsequent expression of the nucleic acid. The method of introduction is largely dictated by the targeted cell type, discussed below. Exemplary methods include CaPO$_4$ precipitation, liposome fusion, cationic liposomes, electroporation, nucleoporation, viral infection, dextran-mediated transfection, polybrene-mediated transfection, protoplast fusion, and direct microinjection.

Appropriate host cells for the expression of antibodies or antigen binding fragments thereof include yeast, bacteria, insect, plant, and mammalian cells. Of particular interest are bacteria such as *E. coli*, fungi such as *Saccharomyces cerevisiae* and *Pichia pastoris*, insect cells such as SF9, mammalian cell lines (e.g., human cell lines), as well as primary cell lines.

In some embodiments, an antibody or fragment thereof can be expressed in, and purified from, transgenic animals (e.g., transgenic mammals). For example, an antibody can be produced in transgenic non-human mammals (e.g., rodents) and isolated from milk as described in, e.g., Houdebine (2002) *Curr Opin Biotechnol* 13(6):625-629; van Kuik-Romeijn et al. (2000) *Transgenic Res* 9(2):155-159; and Pollock et al, (1999) *J Immunol Methods* 231(1-2):147-157.

The antibodies and fragments thereof can be produced from the cells by culturing a host cell transformed with the expression vector containing nucleic acid encoding the antibodies or fragments, under conditions, and for an amount of time, sufficient to allow expression of the proteins. Such conditions for protein expression vary with the choice of the expression vector and the host cell and are easily ascertained by one skilled in the art through routine experimentation. For example, antibodies expressed in *E. coli* can be refolded from inclusion bodies (see, e.g., Hou et al. (1998) *Cytokine* 10:319-30). Bacterial expression systems and methods for their use are known in the art (see Ausubel et al. (1988) *Current Protocols in Molecular Biology*, Wiley & Sons; and Green and Sambrook (012) *Molecular Cloning—A Laboratory Manual*, 4th Ed., Cold Spring Harbor Laboratory Press, New York (2001)). The choice of codons, suitable expression vectors and suitable host cells vary depending on a number of factors, and may be easily optimized as needed. An antibody (or fragment thereof) described herein can be expressed in mammalian cells or in other expression systems including but not limited to yeast, baculovirus, and in vitro expression systems (see, e.g., Kaszubska et al. (2000) *Protein Expression and Purification* 18:213-220).

In vitro methods are also suitable for preparing monovalent antibodies. or fragments. Digestion of antibodies to produce fragments thereof, particularly, Fab fragments, can be accomplished using routine techniques known in the art. For instance, digestion can be performed using papain. Examples of papain digestion are described in International Application Publication No. WO 94/29348, U.S. Pat. No. 4,342,566, and Harlow and Lane, Antibodies, A Laboratory Manual, Cold Spring Harbor Publications, New York, (1988). Papain digestion of antibodies typically produces two identical antigen binding fragments, called Fab fragments, each with a single antigen binding site, and a residual Fc fragment. Pepsin treatment yields a fragment, called the F(ab')2 fragment that has two antigen combining sites and is still capable of cross-linking antigen.

The Fab fragments produced in antibody digestion can also contain the constant domains of the light chain and the first constant domain of the heavy chain. Fab' fragments differ from Fab fragments by the addition of a few residues at the carboxy terminus of the heavy chain domain including one or more cysteines from the antibody hinge region. The F(ab')2 fragment is a bivalent fragment comprising two Fab' fragments linked by a disulfide bridge at the hinge region. Fab'-SH is the designation herein for Fab' in which the cysteine residue(s) of the constant domains bear a free thiol group.

One method of producing proteins comprising the provided antibodies or fragments is to link two or more peptides or polypeptides together by protein chemistry techniques. For example, peptides or polypeptides can be chemically synthesized using currently available laboratory equipment using either Fmoc (9-fluorenylmethyl-oxycarbonyl) or Boc (tert-butyloxycarbonoyl) chemistry (Applied. Biosystems, Inc.; Foster City, CA). Those of skill in the art readily appreciate that a peptide or polypeptide corresponding to the antibody provided herein, for example, can be synthesized by standard chemical reactions. For example, a peptide or polypeptide can be synthesized and not cleaved from its synthesis resin whereas the other fragment of an antibody can be synthesized and subsequently cleaved from the resin, thereby exposing a terminal group that is functionally blocked on the other fragment. By peptide condensation reactions, these two fragments can be covalently joined via a peptide bond at their carboxyl and amino termini, respectively, to form an antibody, or fragment thereof. (Grant G A (1992) Synthetic Peptides: A User Guide. W.H. Freeman and Co., N.Y. (1992); Bodansky M and Trost B., Ed. (1993) Principles of Peptide Synthesis. Springer Verlag Inc., NY). Alternatively, the peptide or polypeptide can by independently synthesized in vivo. Once isolated, these independent peptides or polypeptides may be linked to form an antibody or fragment thereof via similar peptide condensation reactions.

For example, enzymatic ligation of cloned or synthetic peptide segments can allow relatively short peptide fragments to be joined to produce larger peptide fragments, polypeptides or whole protein domains (Abrahmsen et al., *Biochemistry*, 30:4151 (1991)). Alternatively, native chemical ligation of synthetic peptides can be utilized to synthetically construct large peptides or polypeptides from shorter peptide fragments. This method consists of a two step chemical reaction (Dawson et al., *Science*, 266:776 779 (1994)). The first step is the chemoselective reaction of an unprotected synthetic peptide a thioester with another unprotected peptide segment containing an amino terminal Cys residue to give a thioester linked intermediate as the initial covalent product. Without a change in the reaction conditions, this intermediate undergoes spontaneous, rapid intramolecular reaction to form a native peptide bond at the ligation site. Application of this native chemical ligation method to the total synthesis of a protein molecule is illustrated by the preparation of human interleukin 8 (IL-8) (Baggiolini et al., *FEBS Lett.* 307:97-101 (1992); Clark et al., *J. Biol. Chem.* 269:16075 (1994); Clark et al., *Biochemistry* 30:3128 (1991); Rajarathnam et al., *Biochemistry* 33:6623-30 (1994)).

Alternatively, unprotected peptide segments can be chemically linked where the bond formed between the peptide segments as a result of the chemical ligation is an unnatural (non-peptide) bond (Schnolzer et al., *Science* 256:221 (1992)). This technique has been used to synthesize analogs of protein domains as well as large amounts of relatively pure proteins with full biological activity (deLisle et al., Techniques in Protein Chemistry IV. Academic Press, New York, pp. 257-267 (1992)).

Recombinant techniques can also be used to modify antibodies or antigen binding fragments thereof. For example, amino acids found to not contribute to either the activity or the binding specificity or affinity of the antibody can be deleted without a loss in the respective activity. Insertions, deletions, substitutions, or other selected modifications of particular regions or specific amino acids residues, provided the activity of the fragment is not significantly altered or impaired compared to the non-modified antibody, or antigen binding fragment thereof can be made. Such methods are readily apparent to a skilled practitioner in the art and can include site specific mutagenesis of the nucleic acid encoding the antibody or fragment thereof. (Zoller et al., *Nucl. Acids Res.* 10:6487-500 (1982)).

Following expression, the antibodies and fragments thereof can be isolated. An antibody or fragment thereof can be isolated or purified in a variety of ways known in the art depending on what other components are present in the sample. Standard purification methods include electrophoretic, molecular, immunological, and chromatographic techniques, including ion exchange, hydrophobic, affinity, and reverse-phase HPLC chromatography. For example, an antibody can be purified using a standard anti-antibody column (e.g., a protein-A or protein-G-column). Ultrafiltration and diafiltration techniques, in conjunction with protein concentration, are also useful. See, e.g., Scopes (1994) *Protein Purification*, $3^{rd}$ edition, Springer-Verlag, New York City, New York. The degree of purification necessary varies depending on the desired use. In some instances, no purification of the expressed antibody or fragments thereof is necessary.

Methods for determining the yield or purity of a purified antibody or fragment thereof are known in the art and include, e.g., Bradford assay, UV spectroscopy, Biuret protein assay, Lowry protein assay, amino black protein assay, high pressure liquid chromatography (HPLC), mass spectrometry (MS), and gel electrophoretic methods (e.g., using a protein stain such as Coomassie Blue or colloidal silver stain).

D. Modification of Antibodies

Any of the Dengue virus antigen-specific antibodies or antigen binding fragments thereof described herein can be modified. The modifications can be covalent or non-covalent modifications. Such modifications can be introduced into the antibodies or antigen binding fragments by, e.g., reacting targeted amino acid residues of the polypeptide with an organic derivatizing agent that is capable of reacting with selected side chains or terminal residues. Suitable sites for modification can be chosen using any of a variety of criteria including, e.g., structural analysis or amino acid sequence analysis of the antibodies or fragments. In some instances, the Dengue virus antigen-specific antibodies or antigen binding fragments may be labeled by a variety of means for use in diagnostic and/or pharmaceutical applications.

In some embodiments, the antibodies or antigen binding fragments thereof can be conjugated to a heterologous moiety. The heterologous moiety can be, e.g., a heterologous polypeptide, a therapeutic agent (e.g., a toxin or a drug), or a detectable label such as, but not limited to, a radioactive label, an enzymatic label, a fluorescent label, a heavy metal label, a luminescent label, or an affinity tag such as biotin or streptavidin. Suitable heterologous polypeptides include, e.g., an antigenic tag (e.g., FLAG (DYKDDDDK) (SEQ ID NO:339), polyhistidine (6-His; HHHHHH (SEQ ID NO:340)), hemagglutinin (HA; YPYDVPDYA (SEQ ID NO:341)), glutathione-S-transferase (GST), or maltose-binding protein (MBP)) for use in purifying the antibodies or fragments. Heterologous polypeptides also include polypeptides (e.g., enzymes) that are useful as diagnostic or detectable markers, for example, luciferase, a fluorescent protein (e.g., green fluorescent protein (GFP)), or chloramphenicol acetyl transferase (CAT). Suitable radioactive labels include, e.g., $^{32}P$, $^{33}P$, $^{14}C$, $^{125}I$, $^{131}I$, $^{35}S$, and $^{3}H$. Suitable fluorescent labels include, without limitation, fluorescein, fluorescein isothiocyanate (FITC), green fluorescent protein (GFP), DyLight™ 488, phycoerythrin (PE), propidium iodide (PI), PerCP, PE-Alexa Fluor® 700, Cy5, allophycocyanin, and Cy7. Luminescent labels include, e.g., any of a variety of luminescent lanthanide (e.g., europium or terbium) chelates. For example, suitable europium chelates include the europium chelate of diethylene triamine pentaacetic acid (DTPA) or tetraazacyclododecane-1,4,7,10-tetraacetic acid (DOTA). Enzymatic labels include, e.g., alkaline phosphatase, CAT, luciferase, and horseradish peroxidase. Another labeling technique which may result in greater sensitivity consists of coupling the antibodies to low molecular weight haptens. These haptens can then be specifically altered by means of a second reaction. For example, it is common to use haptens such as biotin, which reacts with avidin, or dinitrophenol, pyridoxal, or fluorescein, which can react with specific antihapten antibodies.

Two proteins (e.g., an antibody and a heterologous moiety) can be cross-linked using any of a number of known chemical cross linkers. Examples of such cross linkers are those that link two amino acid residues via a linkage that includes a "hindered" disulfide bond. In these linkages, a disulfide bond within the cross-linking unit is protected (by hindering groups on either side of the disulfide bond) from reduction by the action, for example, of reduced glutathione or the enzyme disulfide reductase. One suitable reagent, 4-succinimidyloxycarbonyl-α-methyl-α(2-pyridyldithio) toluene (SHPT), forms such a linkage between two proteins utilizing a terminal lysine on one of the proteins and a terminal cysteine on the other. Heterobifunctional reagents that cross-link by a different coupling moiety on each protein can also be used. Other useful cross-linkers include, without limitation, reagents which link two amino groups (e.g., N-5-azido-2-nitrobenzoyloxysuccinimide), two sulfhydryl groups (e.g., 1,4-bis-maleimidobutane), an amino group and a sulfhydryl group (e.g., m-maleimidobenzoyl-N-hydroxysuccinimide ester), an amino group and a carboxyl group (e.g., 4-[p-azidosalicylamido]butylamine), and an amino group and a guanidinium group that is present in the side chain of arginine (e.g., p-azidophenyl glyoxal monohydrate).

In some embodiments, a radioactive label can be directly conjugated to the amino acid backbone of the antibody. Alternatively, the radioactive label can be included as part of a larger molecule (e.g., $^{125}I$ in meta-[$^{125}I$]iodophenyl-N-hydroxysuccinimide ([$^{125}I$]mIPNHS), which binds to free amino groups to form meta-iodophenyl (mIP) derivatives of relevant proteins (see, e.g., Rogers et al. (1997) *J Nucl Med* 38:1221-1229) or chelate (e.g., to DOTA or DTPA), which is in turn bound to the protein backbone. Methods of conjugating the radioactive labels or larger molecules/chelates containing them to the antibodies or antigen binding fragments described herein are known in the art. Such methods involve incubating the proteins with the radioactive label under conditions (e.g., pH, salt concentration, and/or temperature) that facilitate binding of the radioactive label or chelate to the protein (see, e.g., U.S. Pat. No. 6,001,329).

Methods for conjugating a fluorescent label (sometimes referred to as a fluorophore) to a protein (e.g., an antibody) are known in the art of protein chemistry. For example, fluorophores can be conjugated to free amino groups (e.g., of lysines) or sulfhydryl groups (e.g., cysteines) of proteins using succinimidyl (NHS) ester or tetrafluorophenyl (TFP) ester moieties attached to the fluorophores. In some embodiments, the fluorophores can be conjugated to a heterobifunctional cross-linker moiety such as sulfo-SMCC. Suitable conjugation methods involve incubating an antibody protein or fragment thereof with the fluorophore under conditions that facilitate binding of the fluorophore to the protein. See, e.g., Welch and Redvanly (2003) *Handbook of Radiopharmaceuticals: Radiochemistry and Applications*, John Wiley and Sons.

In some embodiments, the antibodies or fragments can be modified, e.g., with a moiety that improves the stabilization and/or retention of the antibodies in circulation, e.g., in blood, serum, or other tissues. For example, the antibody or fragment can be PEGylated as described in, e.g., Lee et al. (1999) *Bioconjug Chem* 10(6): 973-8; Kinstler et al. (2002) *Advanced Drug Deliveries Reviews* 54:477-485; and Roberts et al, (2002) *Advanced Drug Delivery Reviews* 54:459-476, or HESylated (Fresenius Kabi, Germany) (see, e.g., Pavisić et al. (2010) *Int J Pharm* 387(1-2):110-119). The stabilization moiety can improve the stability, or retention of, the antibody (or fragment) by at least 1.5 (e.g., at least 2, 5, 10, 15, 20, 25, 30, 40, or 50 or more) fold.

In some embodiments, the antibodies or antigen-binding fragments thereof described herein can be glycosylated. In some embodiments, an antibody or antigen-binding fragment thereof described herein can be subjected to enzymatic or chemical treatment, or produced from a cell, such that the antibody or fragment has reduced or absent glycosylation. Methods for producing antibodies with reduced glycosylation are known in the art and described in, e.g., U.S. Pat. No. 6,933,368; Wright et al. (1991) *EMBO J* 10(10):2717-2723; and Co et al. (1993) *Mol Immunol* 30:1361.

The materials for use in the assay of the disclosure are ideally suited for the preparation of a kit. Such a kit may comprise a carrier means being compartmentalized to receive in close confinement one or more container means such as vials, tubes, and the like, each of the container means comprising one of the separate elements to be used in the method. For example, one of the container means may comprise a monoclonal antibody of the invention that is, or can be, detectably labeled. The kit may also have containers containing buffer(s) and/or a container comprising a reporter-means, such as a biotin-binding protein, such as avidin or streptavidin, bound to a reporter molecule, such as an enzymatic or fluorescent label.

E. Pharmaceutical Compostions and Formulations

Compositions comprising a Dengue virus antigen-specific antibody or antigen binding fragment thereof of the present disclosure and a pharmaceutically acceptable carrier are also provided. The compositions may further comprise a diluent, solubilizer, emulsifier, preservative, and/or adjuvant to be used with the methods disclosed herein. Such compositions can be used in a subject infected with a Dengue virus that would benefit from any of the Dengue virus antigen-specific antibodies or antigen binding fragments thereof described herein.

In certain embodiments, acceptable formulation materials preferably are nontoxic to recipients at the dosages and concentrations employed. In certain embodiments, the formulation material(s) are for s.c. and/or I.V. administration. In certain embodiments, the pharmaceutical composition can contain formulation materials for modifying, maintaining or preserving, for example, the pH, osmolality, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides, disaccharides, and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (Allen (2012) *Remington—The Science and Practice of Pharmacy,* 22d Edition, Lloyd V, Allen, ed., The Pharmaceutical Press). In certain embodiments, the optimal pharmaceutical composition is determined by one skilled in the art depending upon, for example, the intended route of administration, delivery format and desired dosage. See, for example, Allen (2012) *Remington—The Science and Practice of Pharmacy,* 22d Edition, Lloyd V, Allen, ed., The Pharmaceutical Press. In certain embodiments, such compositions may influence the physical state, stability, rate of in vivo release and/or rate of in vivo clearance of the Dengue virus antigen-specific antibody or antigen binding fragment thereof.

In certain embodiments, the primary vehicle or carrier in a pharmaceutical composition can be either aqueous or non-aqueous in nature. For example, in certain embodiments, a suitable vehicle or carrier can be water for injection, physiological saline solution or artificial cerebrospinal fluid, possibly supplemented with other materials common in compositions for parenteral administration. In certain embodiments, the saline comprises isotonic phosphate-buffered saline. In certain embodiments, neutral buffered saline or saline mixed with serum albumin are further exemplary vehicles. In certain embodiments, pharmaceutical compositions comprise a pH controlling buffer such phosphate-buffered saline or acetate-buffered saline. In certain embodiments, a composition comprising a Dengue virus antigen-specific antibody or antigen binding fragment thereof disclosed herein can be prepared for storage by mixing the selected composition having the desired degree of purity with optional formulation agents (see Allen (2012) *Remington—The Science and Practice of Pharmacy,* 22d Edition, Lloyd V, Allen, ed., The Pharmaceutical Press) in the form of a lyophilized cake or an aqueous solution. Further, in certain embodiments, a composition comprising a Dengue virus antigen-specific antibody or antigen binding fragment thereof disclosed herein can be formulated as a lyophilizate using appropriate excipients. In some instances, appropriate excipients may include a cryo-preservative, a bulking agent, a surfactant, or a combination of any thereof. Exemplary excipients include one or more of a polyol, a disaccharide, or a polysaccharide, such as, for example, mannitol, sorbitol, sucrose, trehalose, and dextran 40. In some instances, the cryo-preservative may be sucrose or trehalose. In some instances, the bulking agent may be glycine or mannitol. In one example, the surfactant may be a polysorbate such as, for example, polysorbate-20 or polysorbate-80.

In certain embodiments, the pharmaceutical composition can be selected for parenteral delivery. In certain embodiments, the compositions can be selected for inhalation or for delivery through the digestive tract, such as orally. The preparation of such pharmaceutically acceptable compositions is within the ability of one skilled in the art.

In certain embodiments, the formulation components are present in concentrations that are acceptable to the site of administration. In certain embodiments, buffers are used to maintain the composition at physiological pH or at a slightly lower pH, typically within a pH range of from about 5 to about 8. For example, the pH may be 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8. 6.9, 6.9, 7.0, 7.1, 7.2, 7.3, 7.4, 7.5, 7.6, 7.7, 7.8, 7.9, 8.0, 8.1, 8.2, 8.3, 8.4, or 8.5. In some instances, the pH of the pharmaceutical composition may be in the range of 6.6-8.5 such as, for example, 7.0-8.5, 6.6-7.2, 6.8-7.2, 6.8-7.4, 7.2-7.8, 7.0-7.5, 7.5-8.0, 7.2-8.2, 7.6-8.5, or 7.8-8.3. In some instances, the pH of the pharmaceutical composition may be in the range of 5.5-7.5 such as, for example, 5.5-5.8, 5.5-6.0, 5.7-6.2, 5.8-6.5, 6.0-6.5, 6.2-6.8, 6.5-7.0, 6.8-7.2, or 6.8-7.5. In some instances, the pH of the pharmaceutical composition may be in the range of 4.0-5.5 such as, for example, 4.0-4.3, 4.0-4.5, 4.2-4.8, 4.5-4.8, 4.5-5.0, 4.8-5.2, or 5.0-5.5.

In certain embodiments when parenteral administration is contemplated, a therapeutic composition can be in the form of a pyrogen-free, parenterally acceptable aqueous solution comprising a Dengue virus antigen-specific antibody or antigen binding fragment thereof in a pharmaceutically acceptable vehicle. In certain embodiments, a vehicle for parenteral injection is sterile distilled water in which a Dengue virus antigen-specific antibody or antigen binding fragment thereof is formulated as a sterile, isotonic solution and properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that can provide for the controlled or sustained release of the product which can then be delivered via a depot injection. In certain embodiments, hyaluronic acid can also be used, and can have the effect of promoting sustained duration in the circulation. In certain embodiments, implantable drug delivery devices can be used to introduce the desired molecule.

In certain embodiments, a pharmaceutical composition can be formulated for inhalation. In certain embodiments, a Dengue virus antigen-specific antibody or antigen binding fragment thereof can be formulated as a dry powder for inhalation. In certain embodiments, an inhalation solution comprising a Dengue virus antigen-specific antibody or antigen binding fragment thereof can be formulated with a propellant for aerosol delivery. In certain embodiments, solutions can be nebulized. Pulmonary administration is further described in International Application Publication No. WO/1994/020069, which describes pulmonary delivery of chemically modified proteins.

In certain embodiments, it is contemplated that formulations can be administered orally. In certain embodiments, a Dengue virus antigen-specific antibody or antigen binding fragment thereof that is administered in this fashion can be formulated with or without carriers customarily used in compounding solid dosage forms, such as tablets and capsules. In certain embodiments, a capsule can be designed to release the active portion of the formulation at the point in the gastrointestinal tract when bioavailability is maximized and pre-systemic degradation is minimized. In certain embodiments, at least one additional agent can be included to facilitate absorption of a Dengue virus antigen-specific antibody or antigen binding fragment thereof. In certain embodiments, diluents, flavorings, low melting point waxes, vegetable oils, lubricants, suspending agents, tablet disintegrating agents, and binders can also be employed.

In certain embodiments, a pharmaceutical composition can involve an effective quantity of a Dengue virus antigen-specific antibody or antigen binding fragment thereof in a mixture with non-toxic excipients suitable for the manufacture of tablets. In certain embodiments, by dissolving the tablets in sterile water or other appropriate vehicle, solutions can be prepared in unit-dose form. In certain embodiments, suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions can be selected by one skilled in the art, including formulations involving a Dengue virus antigen-specific antibody or antigen binding fragment thereof in sustained- or controlled-delivery formulations. In certain embodiments, techniques for formulating a variety of other sustained- or controlled-delivery means, such as liposome carriers, bio-erodible microparticles or porous beads and depot injections, are also known to those skilled in the art. See for example, International Application Publication No. WO/1993/015722, which describes the controlled release of porous polymeric microparticles for the delivery of pharmaceutical compositions. In certain embodiments, sustained-release preparations can include semipermeable polymer matrices in the form of shaped articles, e.g., films, or microcapsules. Sustained release matrices can include polyesters, hydrogels, polylactides (see, e.g., U.S. Pat. Nos. 3,773,919; 5,594,091; 8,383,153; 4,767,628; International Application Publication No. WO1998043615, Cabo, E. et al. (201:5) $Eur.$ $Polymer$ $J$ 65:252-267 and European Patent No. EP 058,481), including, for example, chemically synthesized polymers, starch based polymers, and polyhydmxyalkanoates (PHAs), copolymers of L-glutamic acid and gamma ethyl-L-glutamate (Sidman et al. (1993) $Biopolymers$ 22:547-556), poly (2-hydroxyethyl-methacrylate) (Langer et al. (1981) $J$ $Biomed$ $Mater$ $Res.$ 15: 167-277; and Langer (1982) $Chem$ $Tech$ 12:98-105), ethylene vinyl acetate (Hsu and Langer (1985) $J$ $Biomed$ $Materials$ $Res$ 19(4):445-460) or poly-D(−)-3-hydroxybutyric acid (European Patent No. EP0133988). In certain embodiments, sustained release compositions can also include liposomes, which can be prepared by any of several methods known in the art. (See, e.g., Eppstein et al. (1985) $Prot.$ $Natl.$ $Acad.$ $Sci.$ $USA$ 82:3688-3692; European Patent No. EP 036,676; and U.S. Pat. Nos. 4,619,794 and 4,615,885).

The pharmaceutical composition to be used for in vivo administration typically is sterile. In certain embodiments, sterilization is accomplished by filtration through sterile filtration membranes. In certain embodiments, where the composition is lyophilized, sterilization using this method can be conducted either prior to or following lyophilization and reconstitution. In certain embodiments, the composition for parenteral administration can be stored in lyophilized form or in a solution. In certain embodiments, parenteral compositions generally are placed into a container having a sterile access port, for example, an intravenous solution bag or vial having a stopper pierceable by a hypodermic injection needle.

In certain embodiments, once the pharmaceutical composition has been formulated, it can be stored in sterile vials as a solution, suspension, gel, emulsion, solid, or as a dehydrated or lyophilized powder. In certain embodiments, such formulations can be stored either in a ready-to-use form or in a form (e.g., lyophilized) that is reconstituted prior to administration.

In certain embodiments, kits are provided for producing a single-dose administration unit. In certain embodiments, the kit can contain both a first container having a dried protein and a second container having an aqueous formulation. In certain embodiments, kits containing single and multi-chambered pre-filled syringes are included.

In certain embodiments, the effective amount of a pharmaceutical composition comprising a Dengue virus antigen-specific antibody or antigen binding fragment thereof to be employed therapeutically depends, for example, upon the therapeutic context and objectives. One skilled in the art will appreciate that the appropriate dosage levels for treatment, according to certain embodiments, vary depending, in part, upon the molecule delivered, the indication for which a Dengue virus antigen-specific antibody or antigen binding fragment thereof is being used, the route of administration, and the size (body weight, body surface or organ size) and/or condition (the age and general health) of the patient. The clinician can titer the dosage and modify the route of administration to obtain the optimal therapeutic effect.

The clinician also selects the frequency of dosing, taking into account the pharmacokinetic parameters of the Dengue virus antigen-specific antibody or antigen binding fragment thereof in the formulation used. In certain embodiments, a clinician administers the composition until a dosage is reached that achieves the desired effect. In certain embodiments, the composition can therefore be administered as a single dose or as two or more doses (which may or may not contain the same amount of the desired molecule) over time, or as a continuous infusion via, for example, an implantation device or catheter. Further refinement of the appropriate dosage is routinely made by those of ordinary skill in the art and is within the ambit of tasks routinely performed by them. In certain embodiments, appropriate dosages can be ascertained through use of appropriate dose-response data.

In certain embodiments, the route of administration of the pharmaceutical composition is in accord with known methods, e.g. orally, through injection by intravenous, intraperitoneal, intracerebral (intra-parenchymal), intracerebral, intraventricular, intramuscular, subcutaneously, intra-ocular, intraarterial, intraportal, or intralesional routes; by sustained release systems or by implantation devices. In certain embodiments, the compositions can be administered by bolus injection or continuously by infusion, or by implantation device. In certain embodiments, individual elements of a combination therapy may be administered by different routes.

In certain embodiments, the composition can be administered locally, e.g., during surgery or topically. Optionally local administration is via implantation of a membrane, sponge, or another appropriate material onto which the desired molecule has been absorbed or encapsulated. In certain embodiments, where an implantation device is used, the device can be implanted into any suitable tissue or organ, and delivery of the desired molecule can be via diffusion, timed-release bolus, or continuous administration.

In certain embodiments, it can be desirable to use a pharmaceutical composition comprising a Dengue virus antigen-specific antibody or antigen binding fragment thereof in an ex vivo manner. In such instances, cells that have been removed from a subject may be exposed to a pharmaceutical composition comprising a Dengue virus antigen-specific antibody or antigen binding fragment thereof after which the cells are subsequently implanted back into the subject.

In certain embodiments, a Dengue virus antigen-specific antibody or antigen binding fragment thereof can be delivered by implanting certain cells that have been genetically engineered, using methods such as those described herein, to express and secrete the polypeptides. In certain embodiments, such cells can be animal or human cells, and can be autologous, heterologous, or xenogeneic. In certain embodiments, the cells can be immortalized. In certain embodiments, in order to decrease the chance of an immunological response, the cells can be encapsulated to avoid infiltration of surrounding tissues. In certain embodiments, the encapsulation materials are typically biocompatible, semi-permeable polymeric enclosures or membranes that allow the release of the protein product(s) but prevent the destruction of the cells by a subject's immune system or by other detrimental factors from the surrounding tissues.

F. Method of Use of Dengue Virus Antigen-Specific Antibodies

1. In Vitro Detection and Diagnostics

The Dengue virus antigen-specific antibody or antigen binding fragment thereof provided in this disclosure are suited for in vitro use, for example, in immunoassays in which they can be utilized in liquid phase or bound to a solid phase carrier. In addition, the in these immunoassays can be detectably labeled in various ways. Examples of types of immunoassays which can utilize the monoclonal antibodies of the invention are competitive and non-competitive immunoassays in either a direct or indirect format. Examples of such immunoassays are the radioimmunoassay (RIA) and the sandwich (immunometric) assay. Detection of antigens using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The monoclonal antibodies of the invention can be bound to many different carriers and used to detect the presence of dengue virus. Examples of well-known carriers include glass, polystyrene, polypropylene, polyethylene, dextran, nylon, amylase, natural and modified cellulose, polyacrylamide, agarose and magnetite. The nature of the carrier can be either soluble or insoluble for purposes of the invention. Those skilled in the art will know of other suitable carriers for binding monoclonal antibodies, or will be able to ascertain such, using routine experimentation.

For purposes of this disclosure, Dengue virus may be detected by the provided antibodies fragments thereof when the virus is present in biological fluids and tissues from a subject that may be infected with Dengue virus. Any sample containing a detectable amount of Dengue virus can be used. A sample can be a liquid such as urine, saliva, cerebrospinal fluid, blood, serum or the like; a solid or semi-solid such as tissues, feces, or the like; or, alternatively, a solid tissue such as those commonly used in histological diagnosis.

Another approach to assessing whether a subject is infected with Dengue virus is to determine if the B cell receptor (BCR) repertoire of the subject includes a coding sequence for one of the Dengue specific antibodies provided in this disclosure. An exemplary method of this type of sequence analysis is described in Example 13. RNA from whole blood or B cells (PBMCs) can be used as the template for the amplification of CDR sequences. CDRs of the heavy chain, light chain, or both may be sequenced, with analysis of either or both of lambda or kappa chain sequences. Primer pools are designed to result in wide-spread amplification of the BCR V(D)JC sequences in the sample. Reverse transcription is then performed to create cDNA sequences corresponding to the BCR coding sequences, which may be amplified for subsequent sequence analysis. Next generation sequencing of the amplified cDNA library can then be performed. Sequence analysis is used to assess the identity of the BCR V(D)JC sequences in the sample and to determine the percent identity thereof to the Dengue specific antibodies described herein. Various commercial services are also available for performing BCR repertoire analysis (e.g., Magic™ BCR Repertoire Analysis by Creative Biolabs). The presence of BCR sequences encoding the Dengue specific antibodies described in this disclosure in the subject's sample is indicative that the subject has a Dengue virus infection or has previously been exposed to Dengue virus.

2. In Vivo Detection

In using the provided antibodies and fragments thereof for the in vivo detection of Dengue virus antigens, the detectably labeled antibody or fragment thereof is given in a dose which is diagnostically effective. The term "diagnostically effective" means that the amount of detectably labeled monoclonal antibody is administered in sufficient quantity to enable detection of the site having the Dengue virus antigen for which the antibodies are specific.

The concentration of detectably labeled antibody or fragment thereof which is administered should be sufficient such that the binding to Dengue virus is detectable compared to the background. Further, it is desirable that the detectably labeled antibody or fragment thereof be rapidly cleared from the circulatory system in order to give the best target-to-background signal ratio.

As a rule, the dosage of detectably labeled antibody or fragment thereof for in vivo diagnosis will vary depending on such factors as age, sex, and extent of disease of the individual. The dosage of monoclonal antibody can vary from about 0.01 mg/kg to about 50 mg/kg, preferably 0.1 mg/kg to about 20 mg/kg, most preferably about 0.1 mg/kg to about 2 mg/kg. Such dosages may vary, for example, depending on whether multiple injections are given, on the tissue being assayed, and other factors known to those of skill in the art.

For in vivo diagnostic imaging, the type of detection instrument available is a major factor in selecting an appropriate radioisotope. The radioisotope chosen must have a type of decay which is detectable for the given type of instrument. Still another important factor in selecting a radioisotope for in vivo diagnosis is that the half-life of the radioisotope be long enough such that it is still detectable at the time of maximum uptake by the target, but short enough such that deleterious radiation with respect to the host is acceptable. Ideally, a radioisotope used for in vivo imaging will lack a particle emission but produce a large number of photons in the 140-250 keV range, which may be readily detected by conventional gamma cameras. For in vivo diagnosis, radioisotopes may be bound to immunoglobulin either directly or indirectly by using an intermediate functional group. Intermediate functional groups which often are used to bind radioisotopes which exist as metallic ions are the bifunctional chelating agents such as diethylenetriamine-pentacetic acid (DTPA) and ethylenediaminetetra-acetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr and $^{201}$Tl.

The Dengue virus antigen-specific antibodies and antigen binding fragments thereof can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr and $^{56}$Fe.

The provided antibodies and antigen binding fragments can be used in vitro and in vivo to monitor the course of Dengue virus disease therapy. Thus, for example, by measuring the increase or decrease in the number of cells infected with Dengue virus or changes in the concentration of Dengue virus present in the body or in various body fluids, it would be possible to determine whether a particular therapeutic regimen aimed at ameliorating Dengue virus disease is effective.

3. Therapeutic Methods

As described herein, the present disclosure provides a method of treating a subject infected with a Dengue virus, comprising administering to the subject a therapeutically effective amount of a Dengue virus antigen-specific antibody or antigen binding fragment thereof of the present disclosure. In some embodiments, the subject has or is determined to have a Dengue virus infection.

The Dengue virus antigen-specific antibodies and antigen binding fragments thereof can also be used as a prophylactic therapy for Dengue virus disease. The provided antibodies and fragments thereof may be used either in prophylactic and therapeutic administration as well as either by passive immunization with substantially purified polypeptide products and gene therapy by transfer of polynucleotide sequences encoding the product or part thereof. Thus, the provided antibodies and fragments thereof can be administered to high-risk subjects in order to lessen the likelihood and/or severity of Dengue virus disease or administered to subjects already evidencing active Dengue virus infection.

The compositions described herein are useful in, inter alia, methods for treating a Dengue virus infection in a subject. As used herein, the term subject means a mammalian subject. Exemplary subjects include, but are not limited to humans, monkeys, dogs, cats, mice, rats, cows, horses, camels, goats and sheep. In some embodiments, the subject is a human. In some embodiments, the subject has or is suspected to have a Dengue virus infection. In some embodiments, the subject is diagnosed with a Dengue virus infection. In some embodiments, the subject is a human that is suspected of having a Dengue virus infection.

As used herein, administer or administration refers to the act of injecting or otherwise physically delivering a substance as it exists outside the body (e.g., a Dengue virus antigen-specific antibody or antigen binding fragment provided herein or a construct encoding same) into a patient, such as by mucosal, intradermal, intravenous, intramuscular, subcutaneous delivery and/or any other method of physical delivery described herein or known in the art. When a disease, or a symptom thereof, is being treated, administration of the substance typically occurs after the onset of the disease or symptoms thereof. When a disease, or symptoms thereof, are being prevented, administration of the substance typically occurs before the onset of the disease or symptoms thereof.

The compositions can be administered to a subject, e.g., a human subject, using a variety of methods that depend, in part, on the route of administration. The route can be, e.g., intravenous injection or infusion (IV), subcutaneous injection (SC), intraperitoneal (IP) injection, intramuscular injection (IM), intradermal injection (ID), subcutaneous, transdermal, intracavity, oral, intracranial injection, or intrathecal injection (IT). The injection can be in a bolus or a continuous infusion. Techniques for preparing injectate or infusate delivery systems containing antibodies are well known to those of skill in the art. Generally, such systems should utilize components which will not significantly impair the biological properties of the antibodies, such as the paratope binding capacity (see, for example, *Remington's Pharmaceutical Sciences*, 18th edition, 1990, Mack Publishing). Those of skill in the art can readily determine the various parameters and conditions for producing antibody injectates or infusates without resort to undue experimentation.

Administration can be achieved by, e.g., topical administration, local infusion, injection, or by means of an implant. The implant can be of a porous, non-porous, or gelatinous material, including membranes, such as sialastic membranes, or fibers. The implant can be configured for sustained or periodic release of the composition to the subject. See, e.g., U.S. Patent Application Publication No. 20080241223; U.S. Pat. Nos. 5,501,856; 5,164,188; 4,863,457; and 3,710,795. The composition can be delivered to the subject by way of an implantable device based on, e.g., diffusive, erodible, or convective systems, e.g., osmotic pumps, biodegradable implants, electrodiffusion systems, electroosmosis systems, vapor pressure pumps, electrolytic pumps, effervescent pumps, piezoelectric pumps, erosion-based systems, or electromechanical systems. In some embodiments, a Dengue virus antigen-specific antibody or antigen binding fragment of the present disclosure is therapeutically delivered to a subject by way of local administration.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and the like.

Treating or treatment of any disease or disorder refers to ameliorating a disease or disorder that exists in a subject or a symptom thereof. The term ameliorating refers to any therapeutically beneficial result in the treatment of a disease state, e.g., a Dengue virus infection, lessening in the severity or progression, promoting remission or durations of remission, or curing thereof. Thus, treating or treatment includes ameliorating at least one physical parameter or symptom. Treating or treatment includes modulating the disease or disorder, either physically (e.g., stabilization of a discernible symptom) or physiologically (e.g., stabilization of a physical parameter) or both. Treating or treatment includes delaying or preventing metastasis. Thus, in the disclosed methods, treatment can refer to a 10%, 20%, 30%, 40%, 50%, 60%, 70%, 80%, 90%, or 100% reduction in the severity of an established disease or condition or symptom of the disease or condition. For example, a method for treating a Dengue virus infection in a subject by administering an antibody as described in this disclosure is considered to be a treatment if there is a 10% reduction in one or more symptoms of the cancer in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

The principal symptoms of Dengue virus infection include high fever and at least two of the following: severe headache, severe eye pain (behind the eyes), joint pain, pain in muscles or bones or both, rash, mild bleeding manifestation (e.g., nose or gum bleed, petechiae, easy bruising), or low white cell count. Severe Dengue: virus disease includes one or more of severe abdominal pain, persistent vomiting, red spots or patches on skin, bleeding from nose or gums, vomiting blood, black tarry stools, drowsiness, irritability, pale skin, cold skin, clammy skin, or difficulty breathing. Dengue hemorrhagic fever (DHF) is characterized by a fever that lasts from 2 to 7 days, with general signs and symptoms consistent with Dengue fever. When the fever declines, warning signs may develop. This marks the beginning of a 24 to 48 hour period when the smallest blood vessels (capillaries) become excessively permeable ("leaky"), allowing the fluid component to escape from the blood vessels into the peritoneum (causing ascites) and pleural cavity (leading to pleural effusions). This may lead to failure of the circulatory system and shock, and possibly death without prompt, appropriate treatment. In addition, a subject with DHF has a low platelet count and hemorrhagic manifestations, tendency to bruise easily or have other types of skin hemorrhages, bleeding nose or gums, and possibly internal bleeding.

As used herein, a "prophylactically effective amount" of a Dengue virus antigen-specific antibody or antigen binding fragment thereof is a dosage large enough to produce the desired effect in the protection of individuals against dengue virus infection for a reasonable period of time, such as one to two months or longer following administration. A prophylactically effective amount is not, however, a dosage so large as to cause adverse side effects, such as hyperviscosity syndromes, pulmonary edema, congestive heart failure, and the like. Generally, a prophylactically effective amount may vary with the subject's age, condition, and sex, as well as the extent of the disease in the subject and can be determined by one of skill in the art. Other factors can include, e.g., other medical disorders concurrently or previously affecting the subject, the general health of the subject, the genetic disposition of the subject, diet, time of administration, rate of excretion, drug combination, and any other additional therapeutics that are administered to the subject. The dosage of the prophylactically effective amount may be adjusted by the individual physician or veterinarian in the event of any complication. In some instances, a prophylactically effective amount may vary from about 0.01 mg/kg to about 50 mg/kg, preferably from about 0.1 mg/kg to about 20 mg/kg, most preferably from about 0.2 mg/kg to about 2 mg/kg, in one or more administrations (priming and boosting).

As used herein, the term "therapeutically effective amount" or effective amount refers to an amount of a Dengue virus antigen-specific antibody or antigen binding fragment thereof that, when administered to a subject, is effective to treat a disease or disorder such that the symptoms of Dengue virus disease are ameliorated or the likelihood of infection is decreased. A therapeutically effective amount is not, however, a dosage so large as to cause adverse side effects, such as hyperviscosity syndromes, pulmonary edema, congestive heart failure, and the like. A suitable dose of an antibody or fragment thereof described herein, which dose is capable of treating a Dengue virus infection in a subject, can depend on a variety of factors including the particular construct used and whether it is used concomitantly with other therapeutic agents. For example, a different dose of a whole Dengue virus antigen-specific antibody may be required to treat a subject with a Dengue virus infection as compared to the dose of a fragment of a Dengue virus antigen-specific antibody (e.g., Fab' antibody fragment) required to treat the same subject. Other factors affecting the dose administered to the subject include, e.g., the type or extent of the infection. For example, a subject that has had a previous Dengue virus infection may require administration of a different dosage of Dengue virus antigen-specific antibody or antigen binding fragment thereof than a subject who has not previously had a Dengue virus infection. Generally, a therapeutically effective amount may vary with the subject's age, condition, and sex, as well as the extent of the disease in the subject and can be determined by one of skill in the art. Other factors can include, e.g., other medical disorders concurrently or previously affecting the subject, the general health of the subject, the genetic disposition of the subject, diet, time of administration, rate of excretion, drug combination, and any other additional therapeutics that are administered to the subject. It should also be understood that a specific dosage and treatment regimen for any particular subject also depends upon the judgment of the treating medical practitioner (e.g., doctor or nurse). A therapeutically effective amount is also one in which any toxic or detrimental effects of the composition are outweighed by the therapeutically beneficial effects. The dosage of the therapeutically effective amount may be adjusted by the individual physician or veterinarian in the event of any complication. In some instances, a therapeutically effective amount may vary from about 0.01 mg/kg to about 50 mg/kg, preferably from about 0.1 mg/kg to about 20 mg/kg, most preferably from about 0.2 mg/kg to about 2 mg/kg, in one or more dose administrations daily, for one or several days. In some instances, the Dengue virus antigen-specific antibody or antigen binding fragment thereof is administered for 2 to 5 or more consecutive days in order to avoid "rebound" of virus replication from occurring.

A pharmaceutical composition can include a therapeutically effective amount or a prophylactically effective amount of a Dengue virus antigen-specific antibody or antigen binding fragment thereof described herein. Such effective amounts can be readily determined by one of ordinary skill in the art as described above. Considerations include the effect of the administered Dengue virus antigen-specific antibody or antigen binding fragment thereof, or the combinatorial effect of the Dengue virus antigen-specific antibody or antigen binding fragment thereof with one or more additional active agents, if more than one agent is used in or with the pharmaceutical composition.

Suitable human doses of any of the Dengue virus antigen-specific antibody or antigen binding fragment thereof described herein can further be evaluated in, e.g., Phase I dose escalation studies. See, e.g., van Gurp et al, (2008) *Am J Transplantation* 8(8):1711-1718; Hanouska et al. (2007) *Clin Cancer Res* 13(2, part 1):523-531; and Hetherington et al. (2006) *Antimicrobial Agents and Chemotherapy* 50(10): 3499-3500.

Toxicity and therapeutic efficacy of such Dengue virus antigen-specific antibodies or antigen binding fragments thereof can be determined by known pharmaceutical procedures in cell cultures or experimental animals (e.g., animal models of any of the cancers described herein). These procedures can be used, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. A Dengue virus antigen-specific antibody or antigen binding fragment thereof that exhibits a high therapeutic index is preferred. While constructs that exhibit toxic side effects may be used, care should be taken to design a delivery system that targets such constructs to the site of affected tissue and to minimize potential damage to normal cells and, thereby, reduce side effects.

The data obtained from the cell culture assays and animal studies can be used in formulating a range of dosage for use in humans. The dosage of a Dengue virus antigen-specific antibody or antigen binding fragment thereof lies generally within a range of circulating concentrations of the Dengue virus antigen-specific antibody or antigen binding fragment that include the $ED_{50}$ with little or no toxicity. The dosage may vary within this range depending upon the dosage form employed and the route of administration utilized. For Dengue virus antigen-specific antibodies or antigen binding fragments thereof described herein, the therapeutically effective dose can be estimated initially from cell culture assays. A dose can be formulated in animal models to achieve a circulating plasma concentration range that includes the $EC_{50}$ (i.e., the concentration of the construct—e.g., antibody—which achieves a half-maximal inhibition of symptoms) as determined in cell culture. Such information can be used to more accurately determine useful doses in humans. Levels in plasma may be measured, for example, by high performance liquid chromatography. In some embodiments, e.g., where local administration is desired, cell culture or animal models can be used to determine a dose required to achieve a therapeutically effective concentration within the local site.

In some embodiments, a Dengue virus antigen-specific antibody or antigen binding fragment thereof described herein can be administered to a subject as a monotherapy. Alternatively, the Dengue virus antigen-specific antibody or antigen binding fragment thereof can be administered in conjunction with other therapies for viral infection (combination therapy). For example, the composition can be administered to a subject at the same time, prior to, or after, a second therapy. In some embodiments, the Dengue virus antigen-specific antibody or antigen binding fragment thereof and the one or more additional active agents are administered at the same time. Optionally, the Dengue virus antigen-specific antibody or antigen binding fragment thereof is administered first in time and the one or more additional active agents are administered second in time. In some embodiments, the one or more additional active agents are administered first in time and the Dengue virus antigen-specific antibody or antigen binding fragment thereof is administered second in time. Optionally, the Dengue virus antigen-specific antibody or antigen binding fragment thereof and the one or more additional agents are administered simultaneously in the same or different routes. For example, a composition comprising the Dengue virus antigen-specific antibody or antigen binding fragment thereof optionally contains one or more additional agents.

There is currently no specific medication approved for treatment of a Dengue virus infection. Subjects that may have a Dengue virus infection are generally administered analgesics (pain relievers) with acetaminophen but generally not administered analgesics containing ibuprofen, naproxen, or aspirin or other aspirin containing drugs. There is also no specific medication for Severe Dengue (SD). If a clinical diagnosis is made early, a subject with SD may be treated using fluid replacement therapy. However, monoclonal antibody therapeutics, small molecule anti-viral drugs, peptide inhibitors, and gene therapy approaches are under development and known in the art and could be used in combination therapy with the Dengue virus antigen-specific antibodies or antigen binding fragments thereof described herein. Antiviral approaches explored thus far have targeted both structural and nonstructural proteins of Dengue virus. The search for small-molecule inhibitors that target viral entry has focused on the multifunctional enzymes NS3 and NS5 (see, e.g., Wang QY, et al. (2009) Antimicrob Agents Chemother 53:1823-1831; Luo D, et al. (2015) Antiviral Res 118:148-

158; Schmidt et al. (2012) PLOS Pathog 8: e1002627; de Wispelaere et al. (2018). Cell Chem Biol doi.org/10.1016/j.chembiol.2018.05.011, in press). In addition, the C protein and NS4B are also being explored as drug targets (see, e.g., Byrd CM, et al. (2013) Antimicrob Agents Chemother 57:15-25; Becker G L, et al. (2012) J Biol Chem 287:21992-2003; Scaturro P, et al. (2014) J Virol 88:11540-11555; van Cleef KW, et al. (2013) Antiviral Res 99:165-171). The most advanced therapeutics against virus entry are therapeutic antibodies, which are at various stages of clinical development (see, e.g., Robinson LN, et al. (2015) Cell 162:493-504; Teoh E P, et al. (2012) Sci Transl Med 4: 139ra83). Peptide inhibitors are also under development. See, e.g., Panya, A., et al. (2014) Chem Biol & Drug Design 84 (2): 148-457.

A Dengue virus antigen-specific antibody or antigen binding fragment thereof described herein can replace or augment a previously or currently administered therapy. For example, upon treating with a Dengue virus antigen-specific antibody or antigen binding fragment thereof, administration of the one or more additional active agents can cease or diminish; e.g., be administered at lower levels or dosages. In some embodiments, administration of the previous therapy can be maintained. In some embodiments, a previous therapy is maintained until the level of the Dengue virus antigen-specific antibody or antigen binding fragment thereof reaches a level sufficient to provide a therapeutic effect.

Monitoring a subject (e.g., a human patient) for an improvement of a Dengue viral infection, as defined herein, means evaluating the subject for a change in a disease parameter, e.g., a reduction in one or more symptoms of Dengue virus infection exhibited by the subject. In some embodiments, the evaluation is performed at least one (1) hour, e.g., at least 2, 4, 6, 8, 12, 24, or 48 hours, or at least 1 day, 2 days, 4 days, 10 days, 13 days, 20 days or more, or at least 1 week. 2 weeks, 4 weeks, 10 weeks, 13 weeks, 20 weeks or more, after an administration. The subject can be evaluated in one or more of the following periods: prior to beginning of treatment; during the treatment; or after one or more elements of the treatment have been administered. Evaluation can include evaluating the need for further treatment, e.g., evaluating whether a dosage, frequency of administration, or duration of treatment should be altered. It can also include evaluating the need to add or drop a selected therapeutic modality, e.g., adding or dropping any of the treatments for a viral infection described herein.

EXAMPLES

Example 1. Virus-Inclusive Single Cell RNA Sequencing

Virus-inclusive single cell RNA-seq approach (viscRNA-Seq) was used to profile transcriptomes of thousands of single PBMCs derived early in the course of disease from six dengue patients and four healthy controls, and to characterize distinct DENV-associated leukocytes. viscRNA-Seq is an approach to sequence and quantify the whole transcriptome of single cells together with the viral RNA (vRNA) from the same cell. viscRNA-Seq permits investigation of virus-host interactions in an unbiased, high-throughput manner, keeping information on cell-to-cell variability (i.e. cell state) and creating statistical power by the large number of single cell replicates while avoiding essential gene restrictions. Using this method, gene expression may be correlated with virus level in the same cell. Use of this method is described in Zanini, F. et al. (2018) eLIFE 7:e32942, which is incorporated herein in its entirety for all purposes.

In this study, FACS was coupled with viscRNA-Seq to identify virus-associated cells from human patients and studied the molecular signatures preceding the development of SD infection. The use of antibodies against surface proteins during FACS enabled enrichment for specific cell populations. Moreover, since viscRNA-Seq requires no genetic manipulation of the cells of interest, this approach enabled high-resolution screening of the whole human transcriptome for changes in gene expression at the single cell level.

A. Materials & Methods

Colombia cohort ethics statement. All work with human subjects was approved by the Stanford University Administrative Panel on Human Subjects in Medical Research (Protocol 35460) and the Fundación Valle del Lili Ethics committee in biomedical research (Cali/Colombia). All subjects, their parents or legal guardians provided written informed consent, and subjects between 6 to 17 years of age and older provided assent.

Study population and sample collection. Blood samples were collected from individuals presenting to the emergency room or clinics at the Fundación Valle del LAE in Cali (Colombia) between March 2016 and June 2017. Enrollment criteria include: i) age greater than 2 years; ii) presentation with an acute febrile illness of less than 7 day duration associated with one or more of the following signs or symptoms: headache, rash, arthralgia, myalgia, retro-orbital pain, abdominal pain, positive tourniquet test, petechiae, and bleeding; and iii) a positive dengue IgM antibody and/or NS1 antigen by the SD BIOLINE Dengue Duo combo device (Standard Diagnostic Inc., Korea) (Wang and Sekaran, 2010).

Patients were classified by infectious diseases specialists as having dengue, dengue with warning signs or severe dengue according to 2009 WHO criteria [22,43] upon both presentation and prior to their discharge. Patients presenting with severe dengue were excluded from the study. Discharge diagnoses were also blindly classified by infectious diseases specialists according to the 1997 WHO criteria into DF, DHF, and/or DSS criteria. Demographics and clinical information were collected at the time of presentation. The first day of fever (fever day 0) was defined by the patients or their relatives. Symptoms, signs, and laboratory studies (including complete blood count, chemistry, and liver function tests) were documented by healthcare professionals.

The first venous blood sample was collected upon enrollment on the first day of presentation. 10-40 ml of whole blood were collected in 1-4 tubes. Serum samples were obtained for additional assays. Samples transport, reception, and processing were strictly controlled using personal data assistants (PDAs) with barcode scanners.

PBMCs isolation. PBMCs were isolated using SepMate tubes (Stemcell Technologies) according to the manufacturer's instructions. Briefly, whole blood was diluted 1:1 with phosphate-buffered saline (PBS) and added to a SepMate tube, which contained 15 ml of Ficoll. Tubes were then centrifuged for 10 minutes at 1,200 g, after which the PBMC layer was poured off into a fresh tube and washed with PBS. Tubes were then centrifuged at 250×g for 10 minutes and resuspended in freezing media. Cryovials containing PBMCs were then placed in a CoolCell at −80 C for 24 hours prior to being transferred to liquid nitrogen for storage.

Confirmation of dengue diagnosis—qRT-PCR assays for detection of dengue and other microbial pathogens. To confirm the diagnosis of dengue and differentiate from infection with the co-circulating arboviruses, Zika virus and chikungunya virus, serum samples were screened with a qualitative, single-reaction, multiplex real-time reverse transcriptase PCR (rRT-PCR) that detects Zika, chikungunya, and dengue virus RNA (Waggoner J J, et al. (2016) *Emerg Inject Dis.* 22:1295-1297). To identify the specific DENV serotype and determine the virus load, samples positive for DENS' in the screening assay were serotyped and quantitated using a separate DEW multiplex rRT-PCR (Waggoner J J. et al. (2013) *PLoS Negl Trop Dis.* 7:e2116).

Confirmation of dengue diagnosis—Multiplexed serological assays on a plasmonic-gold platform. Multiplexed antigen microarrays including DENV-2 whole virus particles spotted in triplicate were fabricated on pGOLD slides (Nirmidas Biotech, California) and serologic testing performed, as described (Zhang B, et al. (2017) *Nat Med.* 23:548-550). Briefly, for DEW IgG and IgM testing, each well was incubated with human sera (400 times dilution) for 40 min, followed by incubation of a mixture of anti-human IgG-IRDye680 conjugate and anti-human IgM-IRDye800 conjugate for 15 min (Vector-Laboratories, Burlingame, CA). Each well was washed between incubation procedures. The biochip was then scanned with a MidaScan-IR near-infrared scanner. IRDye680 and IRDye800 fluorescence images were generated, and the median fluorescence signal for each channel on each microarray spot was quantified by MidaScan software. For each sample, each antigen and each channel, the average of the three median fluorescence signals for three spots was calculated and normalized by positive and negative reference samples through a two-point calibration. Previously defined cutoffs based on mean levels+3 S.D. were used (Zhang B, et al. (2017)). DENV IgG avidity was performed as above in duplicate wells, except that following primary incubation, one well was incubated with 10 M urea for 10 min. Then, anti-human IgG-IRDye680 conjugate was applied to each well and incubated for 15 min. DENV IgG avidity was calculated by dividing the normalized DENV IgG result of the sample tested with urea treatment by the normalized DENV IgG result of the sample without urea treatment. High avidity (>0.6) is indicative of a past infection, whereas low avidity (<0.6) is consistent with a recent infection.

Fluorescence activated cell sorting. Cells were thawed in a water bath at 37° C. in media containing 10% DMSO. 9 ml of warm media were added and cells were spun 300 g×8 mins. The supernatant was discarded and 2 ml of media were added, then cells were spun again. The supernatant was discarded and cells were resuspend in 100 µl Phosphate Buffer solution (PBS) 1% BSA (bovine serum albumin). 5 µl of Human TruStain FcX™ (Fc Receptor Blocking Solution) from Biolegend were added and cells were incubated for 15 mins at room temperature. 300 µl of PBS were added for a total volume of 405 µl. The cell suspension was split in 3 or 4 aliquots (100 µl/aliquot, see below) and the specific antibody mix (3 µl/antibody, total ~10-30 was added to each aliquot (see below). Cells were incubated for 45 mins on ice, then 1 ml PBS was added. 1 µl of SytoxBlue (ThermoFisher) was added to stain dead cells and the cells were incubated 5 mins at room temperature. Cells were filtered through a 35-40 µm filter into FACS tubes, 1 ml PBS was added (total volume ~2 ml) and cells were flown on a Sony SH800 cell sorter with a 100 µm chip. When it became available, targeted mode for the calibration of the instrument was used.

Two sets of antibody panels were developed for this study. The first group of panels (Table 6a) was used for patient samples 3-013-1, 3-027-1, 1-008-1, 1-013-1, 1-020-1, 1-026-1, and 3-018-1, the second group (Table 6b) for patient samples 3-006-1, 1-010-1, 1-036-1. Colors for both sets of panels adhere as much as possible to the following design principles and are set forth in Table 6A and Table 6B:

LINEAGED (violet/blue—noted by "1" below): Common negative selection for dead stain (sytox blue), CD235a (red blood cells), plus abundant cell types that are not in the focal aliquot. For instance, in the monocyte aliquot we want to exclude T, NK, and B cells.

ANCHOR (green—noted by "2" below): Common positive selection gate for the focal aliquot, so we can select blue− green+ and color bleeding is not such a big problem. For instance, CD2 is anchoring both T cells and NK cells.

SPECIFIC 1 (orange—noted by "3" below) and SPECIFIC 2 (infrared—noted by "4" below): Aliquot-specific antibodies that will be plotted against one another to distinguish 2 or more subpopulations.

TABLE 6A

First Set of FACS antibody panels

| Aliquot 1 (T/NK/NKT) | Aliquot 2 (B/DC) | Aliquot 3 (myeloid) |
| --- | --- | --- |
| (1) CD235a - BV421 | (1) CD235a - BV421 | (1) CD235a - BV421 |
| (1) CD19 - BV421 | (1) CD3 - BV421 | (1) CD3 - BV421 |
| (2) CD2 - FITC | (2) HLA-DR - FITC | (1) CD19 - BV421 |
| (3) CD3 - APC | (3) CD19 - APC | (2) CD14 - FITC |
| (4) CD56 - BV785 | (4) CD11c - PE/Cy7 | (3) CD11b - APC |
|  | (4) CD123 - BV785 | (4) CD66b - PE/Cy7 |
| Total: 15 µl | Total: 18 µl | Total: 18 µl |

Panels: T: T cells; NK: natural killer cells; NKT: natural killer T cells; B: B cells; DC: dendritic cells; myeloid: myeloid cells.

TABLE 6B

Second Set of FACS antibody panels

| Aliquot 1 (T/NK/NKT) | Aliquot 2 (B/cDC) | Aliquot 3 (myeloid) | Aliquot 4 (pDC) |
| --- | --- | --- | --- |
| (1) CD235a - BV421 | (1) CD235a - BV421 | (1) CD235a - BV421 | (1) CD235a - BV421 |
| (1) CD19 - BV421 | (1) CD3 - BV421 | (1) CD3 - BV421 | (1) CD3 - BV421 |
| (2) CD2 - FITC | (1) CD16 - BV421 | (1) CD19 - BV421 | (1) CD19 - BV421 |
| (3) CD3 - APC | (1) CD14 - BV421 | (1) CD56 - BV421 | (1) CD14 - BV421 |
| (4) CD56 - BV785 | (1) CD56 - BV421 | (2) CD14 - FITC | (1) CD16 - BV421 |
|  | (2) HLA-DR - FITC | (3) CD16 - APC | (1) CD56 - BV421 |
|  | (3) CD19 - APC | (4) CD66b - PE/Cy7 | (2) HLA-DR - FITC |
|  | (3) CD20 - APC |  | (3) Axl(orCD2) - APC |
|  | (4) CD11c - PE/Cy7 |  | (4) CD123 - BV785 |
| Total: 15 µl | Total: 27 µl | Total: 21 µl | Total: 27 µl |

Panels: T: T cells; NK: natural killer cells; NKT: natural killer T cells; B: B cells; cDC: classical dendritic cells; myeloid: myeloid cells; pDC: plasmacytoid dendritic cells.

The expected ratio of abundances for the various cell types was generally observed: T cells were most abundant, followed in similar proportions by B cells, monocytes, and NK cells. Dendritic cells were less abundant.

viscRNA-Seq protocol. viscRNA-Seq was performed as described in Zanini, F. et al. (2018) *eLIFE* 7:e32942. Briefly, 384-well (Biorad HSP384) lysis plates containing capture oligos for polyadenylated mRNA and a DENV-specific capture oligo were prepared beforehand and stored at −80 C and cells were sorted into them (lysis volume 0.5 μl). Reverse transcription, template switching and 23 cycles of PCR were done to generate and amplify the cDNA. On some plates, cDNA quantification was performed using the Quant-iT™ PicoGreen™ dsDNA Assay Kit (ThermoFisher) and normalization to 0.4 ng/ul was achieved using automated liquid handling robots. Sequencing libraries were prepared using the Nextera XT kit (illumina) or equivalent in-house reagents with 10-12 cycles of amplification after tagmentation. The DNA was purified using Ampure XP (Agencourt) magnetic beads at a ratio of 0.75-0.8× for two or three times in a row to ensure primer removal, and libraries were quantified on a Bioanalyzer 2100 (Agilent).

Sequencing. Libraries were sequenced on NextSeq 500 or NovaSeq machines (illumina) using 75 or 100 base paired-end reads, respectively. To avoid "index hopping" on the latter platform, 15,360 custom multiplex barcodes, developed at Chan Zuckerberg Biohub, were used to uniquely barcode both ends of the tagmented DNA, so that a double recombination event is required to generate cross contamination. See description of barcodes in Quake S R, et al. (2018) *Nature* 562:367-372. Sequencing coverage was around 500,000 to 5,000,000 read pairs per cell.

Bioinformatics data analysis. Custom Python 3.6 scripts were used for the analysis and are available at github.com/iosonofabio/Zanini_et_al_DENV_patients_2018. The following software was routinely used for this study: numpy (van der Walt 5, et al. (2011) *Computing in Science Engineering* 13: 22-30), seaborn (Waskom M, et al. seaborn: v0.5.0 (November 2014), available at doi:10.5281/zenodo.12710), and scikit-learn (Pedregosa F, et al. (2011) *J Mach Learn Res.* 12: 2825-2830), and pandas (McKinney W. (2011) pandas: a Foundational Python Library for Data Analysis and Statistics, Python for High Performance and Scientific Computing, available at www.dlr.de/sc/Portaldata/15/Resources/dokumente/pyhpc2011/submissions/pyhpc2011_submission_9.pdf), and matplotlib (Hunter J D. (2007) *Comput Sci Eng* 9:90-95).

Read mapping/assembling and gene counting. The sequencing reads were demultiplexed using bcl2fastq 2.19 (Illumina), mapped to the human genome reference GRCh38 from Ensembl augmented with ERCC spike-in controls using STAR aligner (Dobin A, et al. (2013) *Bioinformatics* 29: 15-21). Human genes were counted using htseq-count from the HTSeq library (Anders S. et al. (2015) *Bioinformatics* 31: 166-169), which is currently maintained by one of the inventors (F. Zanini). Unmapped reads were mapped to a serotype specific DENV reference using Stampy (Lunter G & Goodson M. (2011) *Genome Res.* 21:936-939) inside a singularity container (Kurtzer G M, et al. (2017) *PLoS One* 12:e0177459) and filtered to trim short CIGAR sections off the read edges using custom Python scripts (see below), Filtered viral reads were assembled using vicuna (Yang X, et al. (2012) *BMC Genomics* 13: 475) followed by a semi-automatic merge of the contigs onto the closest reference found by NCBI BLAST (i.e. a complete genome from the same serotype). Viral reads were then remapped against this hybrid reference and single nucleotide polymorphism frequencies were computed by custom scripts after trimming again short CIGAR codes off the read edges.

B and T cell receptor assembly and clonality graph construction. Sequencing reads belonging to cells within the B cluster were assembled into full length paired heavy and light chains using the guided de-novo assembler BASIC (Canzar S, et al. (2017) Bioinformatics 33:425-427). For each chain, the results of gene segment and CDR3 sequence IgBLAST v1.8.0 (Ye J, et al. (2013) *Nucleic Acids Res* 41: W34-40) assignment were parsed with Change-O (Gupta N T, et al. (2015) *Bioinformatics* 31:3356-3358) while a custom BLAST database (Camacho C, et al. (2009) *BMC Bioinformatics* 10:421) of IMGT (Lefranc M-P, et al. (2009) *Nucleic Acids Res.* 37:D1006-12) constant region sequences was used to determine heavy chain isotype and light chain type (lambda or kappa). Graph-tool (Peixoto T P. (2017), available at doi:10.6084/m9.figshare.1164194.v14) was used to draw clonal families, or "lineages", comprised of heavy chain sequences grouped by identical V and J gene assignment, identical amino acid CDR3 length, and an 80% CDR3 amino acid sequence similarity. The grouping was "greedy" in that for a sequence to be grouped, it needed to have 80% sequence similarity with only one other sequence in that clonal family. Assembly of T cell receptors followed an identical process except using the appropriate T cell sequence databases for each step. Invariant NKT cells were identified by TRAV10-TRAJ18 TRBV25-1 gene usage, while MATT cells were identified by TRAV1-2-TRAJ12/20/33 gene usage.

Mapping of DENV reads. The non-human reads were mapped to a serotype-specific consensus using loose parameters to optimize for yield. The mapping reads were then assembled using a reference-aware virus assembler (Yang X, et al. (2012) BMC Genomics 13:475), the assembly was completed manually, and all virus reads were remapped from the two relevant patients against their own consensus sequence.

Data availability. All sequencing reads are available as NCBI Gene Expression Omnibus (GEO) Submission No, GSEI 16672. Each fastq.gz, BAM, or tsv file often is named or contains references to experiment IDs rather than patient sample names: the conversion between the two is shown in Table 11A, and Table 11B below. Whenever a 10 digit numberic ID starts with an experiment ID and is followed by two more digits, the last 2 digits refer to the 384-well plate the cells were sorted into.

In situ RNA hybridization. Single molecule in situ hybridization probes and buffers were acquired from LGC Biosearch technologies and performed according to the manufacturer's instructions. 32 probes conjugated to fluorescein against positive strand and 29 probes conjugated to Fluo-rRed 610 against negative strand DENV2 16681 were designed to detect the viral RNA (see Supplementary File 2). For the B cell assays, PBMCs were isolated from a donor from the Stanford blood bank and B cells or naive B cells were isolated using the MACS B Cell Isolation Kit II, human (Milltenyi Biotech) or the Naive B Cell Isolation Kit II, human (Milltenyi Biotech), respectively. B cells were then incubated with DENV2 (strain 16681) for 48 hours. Positive and negative controls were performed on Human hepatoma (Huh7) cells, incubated with the same viral strain for 48 hours. After this time, 6 µl of cells were deposited onto a glass coverslip coated with poly-L-lysine, incubated for 5 minutes, fixed with 4% paraformaldehyde, washed, and hybridized for 4-16 hours with the probes. SlowFade™ Gold Antifade Mountant with DAPI was used as mounting liquid. Imaging was performed on a Leica DMI6000B microscope with a 63× oil immersion objective (NA 1.40).

B. Results

High-dimensional profiling of single cells from dengue virus infected patients. FACS was combined with viscRNA-Seq to profile the host and viral transcriptomes in peripheral mononuclear blood cells (PBMCs) collected early in the course of natural dengue infection in humans. Blood samples were derived from the Colombia cohort—four healthy control subjects and six DEW infected patients, two who experienced an uncomplicated disease course and four who subsequently progressed to SD (see Table 7).

TABLE 7

Columbia Cohort and Controls

| Subject | Diagnosis | Serotype | Viral Load |
|---|---|---|---|
| 3-013-1 | Healthy | N.A. | 0 |
| 3-027-1 | Healthy | N.A. | 0 |
| 3-018-1 | Healthy | N.A. | 0 |
| 3-006-1 | Healthy | N.A. | 0 |
| 1-008-1 | Dengue | 4 | $8 \times 10^3$ |
| 1-020-1 | Dengue | 1 | $1 \times 10^6$ |
| 1-013-1 | Severe | 4 | $9 \times 10^3$ |
| 1-026-1 | Severe | 3 | $9 \times 10^8$ |
| 1-010-1 | Severe | 3 | $6 \times 10^5$ |
| 1-036-1 | Severe | 3 | $5 \times 10^7$ |

All subjects were prospectively enrolled to a cohort that we established in Colombia ("Colombia cohort"). Subject information is shown in Table 8 and Tables 9A-9D. Disease severity was classified on-site using the criteria set forth in the World Health Organization 2009 Dengue: Guidelines for Diagnosis, Treatment, Prevention and Control. World Health Organization upon presentation and discharge. Patients were enrolled within 2-5 days after symptoms onset based on clinical presentation compatible with dengue or dengue with warning signs and positive NS1 antigen and/or anti-DENV IgM antibody. Notably, patients presenting with SD were excluded. Whole blood and serum samples were obtained upon presentation. qRT-PCR and serological assays confirmed the diagnosis of DENV infection and excluded other arboviral infections (including Zika and chikungunya). IgG avidity testing distinguished primary from secondary dengue (Table 8). PBMC samples were isolated, stored and shipped in liquid nitrogen.

TABLE 8

Demographic, clinical and laboratory characteristic of dengue patients whose samples were analysed in this study

| | | Healthy Controls (N = 4) | Dengue (N = 2) | Severe dengue (N = 4) |
|---|---|---|---|---|
| Age | Adult | 3 | 2 | 4 |
| | Child (<17 years) | 1 | 0 | 0 |
| Gender | Male | 2 | 0 | 0 |
| | Female | 2 | 2 | 4 |
| First sample day | mean (range) | — | 4.5 (4-5) | 3 (2-4) |
| Dengue diagnostics | Positive NS1 Ag | — | 2 | 4 |
| | Positive DENV IgM | — | 2 | 1 |
| Dengue exposure | Primary | — | 2 | 2 |
| | Secondary | — | 0 | 2 |
| Dengue serotype | DENV-1 | — | 1 | — |
| | DENV-2 | — | — | — |
| | DENV-3 | — | — | 3 |
| | DENV-4 | — | 1 | 1 |
| Clinical manifestations | Shock N (%) | — | 0 (0) | 3 (75) |
| | Plasma leakage N (%) | — | 0 (0) | 2 (50) |
| | Severe organ damage N (%) | — | 0 (0) | 4 (100) |
| | Bleeding N (%) | — | 0 (0) | 2 (50) |
| | Thrombocytopenia N (%) | — | 0 (0) | 3 (75) |
| | Hemoconcentration N (%) | — | 0 (0) | 0 (0) |

TABLE 9A

Dengue patient laboratory parameters.

| Patient No. | Age (years) | Gender | Days to Presentation | Admission Diagnosis | Discharge Diagnosis | Viral Load (copies/mL) | Dengue Exposure | Serotype | Plt Nadir $10^3/\mu L$ | Hct Peak (%) |
|---|---|---|---|---|---|---|---|---|---|---|
| 1-008 | 24 | F | 5 | D | D | 8.34 E3 | Primary | 4 | 216 | 39.4 |
| 1-010 | 17 | F | 4 | D + WS | SD | 6.47 E5 | Primary | 3 | 54 | 35.7 |
| 1-013 | 31 | F | 4 | D + WS | SD | 8.94 E3 | Secondary | 4 | 40 | 41.9 |
| 1-020 | 24 | F | 4 | D | D | 1.28 E6 | Primary | 1 | 117 | 44.3 |
| 1-026 | 23 | F | 2 | D | SD | 8.68 E8 | Secondary | 3 | 134 | 36.8 |
| 1-036 | 26 | F | 2 | D + WS | SD | 5.34 E7 | Primary | 3 | 88 | 48 |

Plt = Platelet;
Hct = Hematocrit.

TABLE 9B

Dengue patient laboratory parameters (continued).

| Patient No. | NS1 Ag | IgM (Duo) | IgG (Duo) | IgM (gold) | IgG (gold) | IgG Avidity (High > 0.6) |
|---|---|---|---|---|---|---|
| 1-008 | + | + | − | − | − | −0.006 |
| 1-010 | + | − | − | + | + | 0.43 |
| 1-013 | + | + | + | + | + | 0.98 |
| 1-020 | + | + | − | + | + | 0.47 |
| 1-026 | + | − | − | − | + | 0.89 |
| 1-036 | + | − | − | − | − | 0 |

TABLE 9C

Severe dengue criteria.

| Patient No. | Shock | Shock Criteria | Lowest MAP (mmHg) | Lowest Pulse Pressure (mmHg) | Vasoactive Support | Mechanical Ventilation | Hemorrhagic Manifestations |
|---|---|---|---|---|---|---|---|
| 1-010 | + | 1.4 | 44.3 | 25 | − | − | − |
| 1-013 | + | 4 | 62.6 | 19 | − | − | + |
| 1-026 | + | 4 | 63 | 35 | − | − | + |
| 1-036 | − | − | 78.6 | 22 | − | − | − |

Shock Criteria:
0 = None,
1 = Weak Pulse,
2 = Cold/Clammy Skin,
3 = Restlessness,
4 = Hypotension (<65 mmHg);
MAP = Mean arterial pressure

TABLE 9D

Severe dengue criteria (contined).

| Patient No. | Transfusion | Pulmonary Edema | AST Peak (UI/L) | Severe Organ Damage | Level of Care | Days From Fever Onset to ICU | Comorbidities, Co-infections, Pregnancy |
|---|---|---|---|---|---|---|---|
| 1-010 | − | − | 664 | + | ICU | 4 | |
| 1-013 | − | − | 332.4 | + | ICU | . | Post-partum: day 4 |
| 1-026 | − | + | 1356.5 | + | ICU | 5 | |
| 1-036 | − | − | 901.2 | + | No Ad | . | |

AST = Aspartate aminotransferase;
ICU = Intensive care unit;
Ad = Admission;

To sort multiple types of immune cells in patient PBMC samples and enable viscRNA-Seq with high specificity and throughput, two panels of antibodies against host cell surface markers were assembled as described above. The PBMC samples were split into several aliquots, immunostained, and sorted via. FACS into T cells, natural killer (NK) cells, B cells, monocytes, and dendritic (DC) cells (markers used listed in Table 10A; antibodies used listed in Table 10B; FACS data not shown),

TABLE 10A

Markers Used For Fluorescence Activated Cell Sorting (FACS)

| T/NK Markers | B/DC Markers | Monocyte Markers |
|---|---|---|
| CD235a− | CD235a− | CD235a− |
| CD19− | CD3− | CD3− |
| CD2+ | HLA-DR+ | CD19− |
| CD3+ or | CD19+ or | CD14+ |
| CD56+ | CD11c+ | CD11b+ or |
| | | CD66b+ |

TABLE 10B

Antibodies and dead cell stain used for Fluorescence Activated Cell Sorting (FACS)

| Ab | Color | Fluor | Source |
|---|---|---|---|
| dead | blue | Sytox | Zombie Violet ™ Fixable Viability Kit (BioLegend, San Diego, CA) |
| CD235a | violet | BV421 | BV421 Mouse Anti-Human CD235a, Clone GA-R2 (HIR2), Cat. No. 562938 (BD Biosciences, San Jose, CA) |
| CD3 | violet | BV421 | Brilliant Violet 421 ™ anti-human CD3 Antibody, Clone UCHT1 (BioLegend, San Diego, CA) |
| CD19 | violet | BV421 | Brilliant Violet 421 ™ anti-human CD19 Antibody, Clone HIB19 (BioLegend, San Diego, CA) |
| CD14 | violet | BV421 | Brilliant Violet 421 ™ anti-human CD14 Antibody, Clone M5E2 (BioLegend, San Diego, CA) |
| CD16 | violet | BV421 | Brilliant Violet 421 ™ anti-human CD16 Antibody, Clone B73.1 (BioLegend, San Diego, CA) |
| CD56 | violet | BV421 | Brilliant Violet 421 ™ anti-human CD56 (NCAM) Antibody, Clone 5.1H11 (BioLegend, San Diego, CA) |
| CD2 | green | FITC | FITC anti-human CD2 Antibody, Clone TS1/8 (BioLegend, San Diego, CA) |
| CD3 | red | APC | APC anti-human CD3 Antibody, Clone UCHT1 (BioLegend, San Diego, CA) |
| CD56 | IR | BV785 | Brilliant Violet 785 ™ anti-human CD56 (NCAM) Antibody, Clone 5.1H11 (BioLegend, San Diego, CA) |
| HLA-DR | green | FITC | FITC anti-human HLA-DR Antibody, Clone LN3 (BioLegend, San Diego, CA) |
| CD19 | red | APC | APC anti-human CD19 Antibody, Clone HIB19 (BioLegend, San Diego, CA) |
| CD20 | red | APC | APC anti-human CD20 Antibody, Clone 2H7 (BioLegend, San Diego, CA) |
| CD11c | IR | PE/Cy7 | PE/Cy7 anti-human CD11c Antibody, Clone Bu15 (BioLegend, San Diego, CA) |
| CD123 | IR | BV785 | Brilliant Violet 785 ™ anti-human CD123 Antibody, Clone 6H6 (BioLegend, San Diego, CA) |
| CD14 | green | FITC | FITC anti-human CD14 Antibody, Clone 63D3 (BioLegend, San Diego, CA) |
| CD16 | red | APC | APC anti-human CD16 Antibody, Clone B73.1 (BioLegend, San Diego, CA) |
| CD66b | IR | PE/Cy7 | PE/CY7 ANTI-HUMAN CD66B ANTIBODY, CLONE G10F5 (BIOLEGEND, SAN DIEGO, CA) |
| CD2 | red | APC | APC anti-human CD2 Antibody, Clone TS1/8 (BioLegend, San Diego, CA) |
| Axl | red | APC | Human Axl APC-conjugated Antibody, Claon 108724, Cat. No. FAB154A (R&D Systems, Minneapolis, MN) |

The viscRNA-Seq protocol was then followed, and each cell was sequenced at a depth of ~1 million reads on NextSeq 500 and NovaSeq (Illumina) instruments. To measure intracellular DENV RNA abundance, we conducted viscRNA-Seq using the previously reported pan-DENV capture oligo as described previously in Zanini, F. et al. (2018) eLIFE 7:e32942. The information provided by this approach on each individual cell included the cell type, immune activation state, infection state (whether and how much DEW RNA the cell contains), and sequence of the virus strain.

Figure 1B:
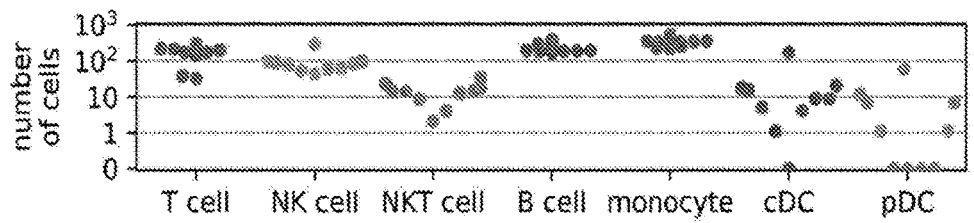
Figure 1C:
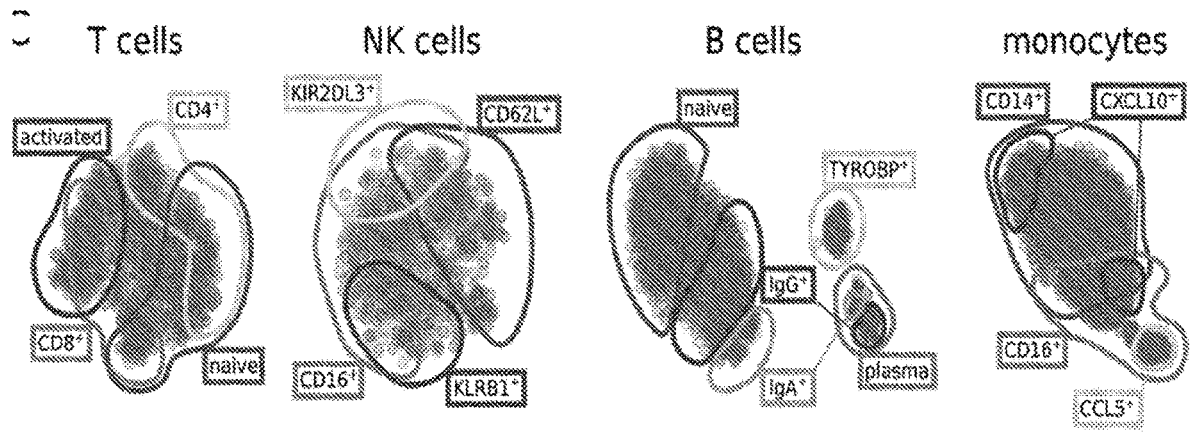

FACS-assisted viscRNA-Seq captures multiple cell types and activation states. Most human tissues including blood present a skewed composition of cell types. Unbiased cell capture, as routinely done in microfluidics protocols, produces detailed data on the most abundant cell populations, but fails to represent rare cell populations. To overcome this limitation, FACS was combined with a plate-based protocol to capture immune cells from samples containing less than 1,000,000 cells (because cells are sorted directly into single wells) with high sensitivity (as assessed by CD45 expression), and adequate representation of various cell populations (FIG. 1A) (Zanini F. & lishknn, E, (2018) Stanford University, available at github.com/iosonofabio/shknn; Carnevali P. (2018) ExpressionMatrix2, Chan Zuckerberg Initiative; available at github.com/chanzuckerberg/ExpressionMatrix2). In total, over 13,000 cells were sequenced, of which several hundred showed robust signal for DEN' RNA (FIG. 1A). Following quality filtering, tens to hundreds of cells were analyzed for most cell types of each sample, for a total of ~8,700 cells (FIG. 1B). Within each cell type, multiple distinct overlapping immune cell subtypes and cell states were well represented in the dataset (see FIG. 1C, Table 114, and Table 11B), For Table 11A and Table 11B, because fluorescent antibodies were used to enrich certain populations, these abundances do not directly reflect the fraction of cell types in the subjects' blood. These tables also contain experiment ID (used in the sequencing files) and diagnosis In particular, within B cells alone many naive, IgM/IGD double positive cells were profiled as well as isotype switched cells. Most B cells formed a continuum of differentiation, but two additional clusters were also identified: the first expressed markers of plasmablasts and plasma cells, whereas the second showed high expression of TYROBP, a transmembrane signalling protein that has been implicated in B cell proliferation.

TABLE 11A

Number of cells for each patient and cell subtype for B cells and T cells.

| | | | B cell | | | | | T cell | | |
|---|---|---|---|---|---|---|---|---|---|---|
| subject | exp ID | diagnosis | isonaive | isoswitched | naive | plasma | TYROBP+ | cytolytic | helper | killer |
| 3-013-1 | 10017011 | healthy | 168 | 27 | 116 | 1 | 2 | 40 | 32 | 80 |
| 3-027-1 | 10017012 | healthy | 143 | 42 | 85 | 6 | 2 | 90 | 42 | 75 |
| 1-008-1 | 10017013 | dengue | 168 | 21 | 110 | 9 | 6 | 66 | 57 | 41 |
| 1-013-1 | 10017014 | severe | 111 | 120 | 68 | 50 | 18 | 83 | 36 | 65 |
| 1-020-1 | 10017015 | dengue | 146 | 47 | 88 | 35 | 1 | 54 | 81 | 38 |
| 1-026-1 | 10017016 | severe | 266 | 119 | 154 | 11 | 8 | 109 | 74 | 81 |
| 3-018-1 | 10017017 | healthy | 151 | 37 | 112 | 4 | 3 | 88 | 35 | 93 |
| 3-006-1 | 10017018 | healthy | 271 | 27 | 126 | 13 | 91 | 33 | 25 | 25 |
| 1-010-1 | 10017021 | severe | 131 | 28 | 24 | 15 | 8 | 13 | 8 | 13 |
| 1-036-1 | 10017022 | severe | 236 | 60 | 69 | 4 | 68 | 10 | 8 | 8 |

TABLE 11B

Number of cells for each patient and cell subtype for NK cells and monocytes.

| | | NK cell | | | | | | monocytes | | |
|---|---|---|---|---|---|---|---|---|---|---|
| subject | diagnosis | CD16+ | CD56+ | CD57+ | CD62L+ | KIR2DL3+ | KLRB1+ | classical | double+ | nonclassical |
| 3-013-1 | healthy | 28 | 5 | 1 | 25 | 9 | 25 | 140 | 4 | 30 |
| 3-027-1 | healthy | 63 | 15 | 4 | 12 | 13 | 42 | 155 | 10 | 86 |
| 1-008-1 | dengue | 40 | 5 | 3 | 20 | 5 | 30 | 224 | 36 | 49 |
| 1-013-1 | severe | 38 | 6 | 9 | 26 | 6 | 25 | 234 | 47 | 47 |
| 1-020-1 | dengue | 56 | 21 | 4 | 49 | 13 | 28 | 147 | 17 | 26 |
| 1-026-1 | severe | 238 | 67 | 17 | 86 | 49 | 53 | 433 | 64 | 15 |
| 3-018-1 | healthy | 57 | 13 | 3 | 28 | 7 | 50 | 247 | 9 | 62 |
| 3-006-1 | healthy | 52 | 16 | 1 | 19 | 8 | 53 | 105 | 31 | 188 |
| 1-010-1 | severe | 7 | 6 | 1 | 10 | 3 | 10 | 40 | 114 | 53 |
| 1-036-1 | severe | 34 | 11 | 11 | 25 | 3 | 6 | 90 | 45 | 121 |

Figure 2A:
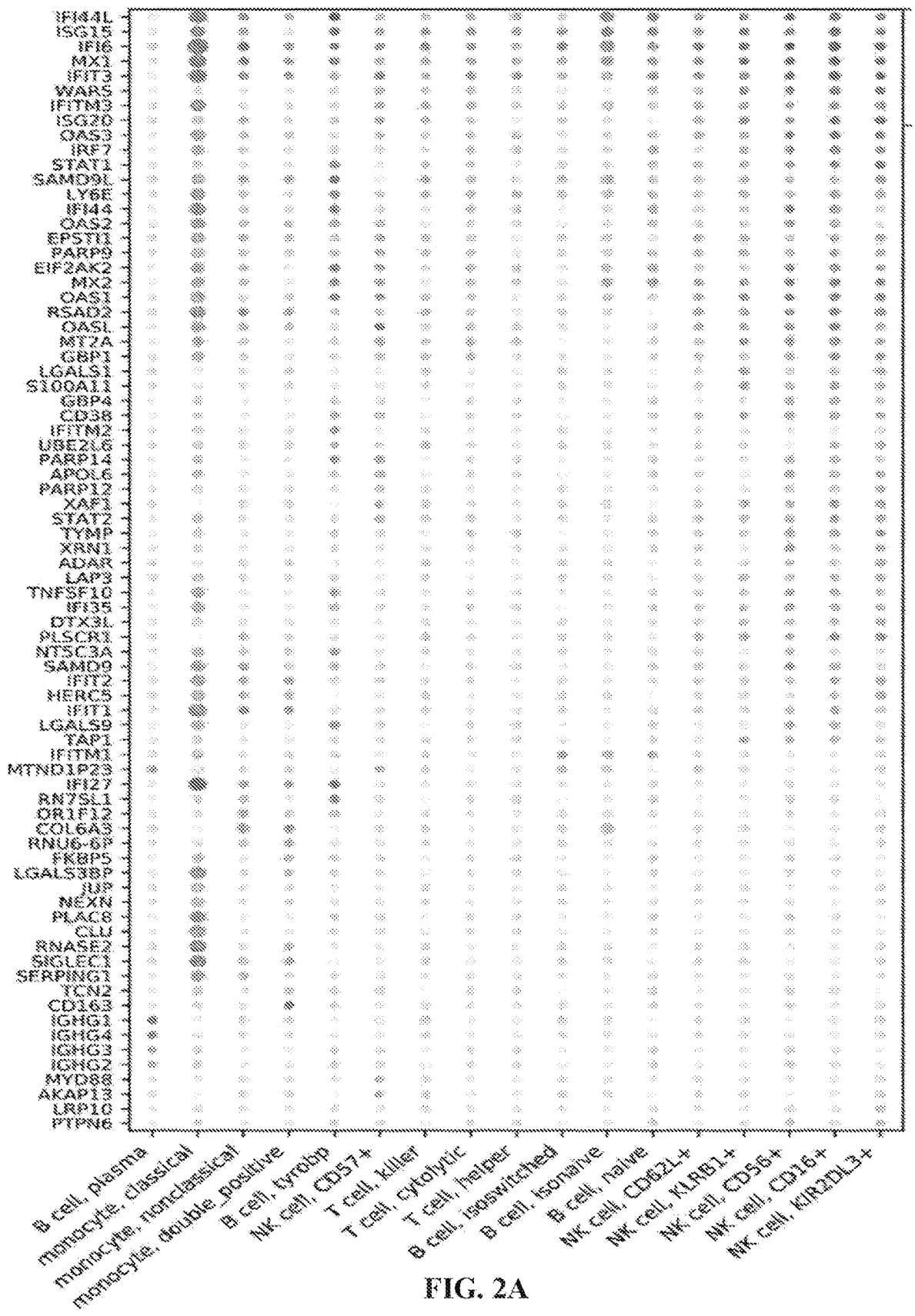
Figure 2E:
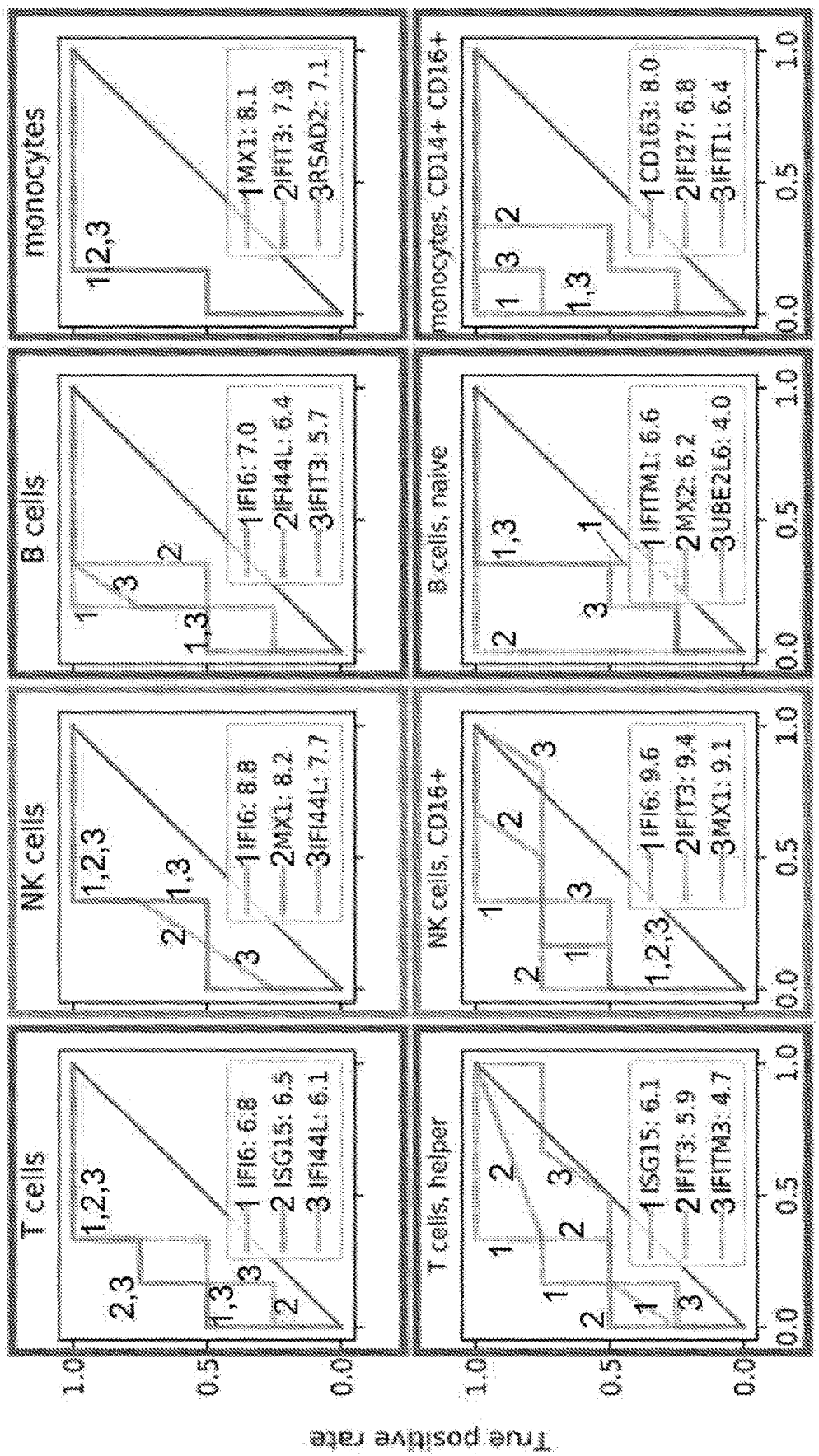

Profiling single cell gene expression identifies candidate predictive biomarkers of severe dengue infection. The host transcriptome responses in the various PBMC populations were profiled. As blood samples were obtained early in the course of dengue infection, this analysis was aimed at revealing alterations in gene expression that preceded the progression to SD. For each cell subtype and gene, the distribution of expression values was compared across the three categories of subjects: healthy control (H); uncomplicated dengue (D), and severe dengue (SD). To identify differentially expressed genes, a two-sample Kolmogorov-Smirnov test was used together with a computation of fold change in the averages across cells. Several genes whose expression was strongly upregulated early in the course of infection in subjects that subsequently progressed to SD were identified. Many of these genes belonged to the antiviral interferon response, yet they were upregulated in a cell type specific manner (FIG. 2A). Some genes were expressed in multiple cell types but were upregulated more strongly in specific cells from SD subjects (FIG. 2B); other genes were expressed essentially only during SD except in a few cell types (FIG. 2C); a few genes were expressed only in one cell type and only in subjects who subsequently developed SD (e.g. CD163 in monocytes, FIG. 2D). These results indicate that distinct cell populations respond differently to the same viral infection, confounding the performance of bulk assays, such as microarrays. Since this heterogeneity is not a hindrance but rather a resource within the single cell approach, the predictive potential of gene expression in specific cell types was explored. To do so, cells within the same patient and cell population were averaged and binary classification of severity at increasing thresholds of expression was tested, de facto simulating a pseudo-bulk assay that could be implemented in the clinic. A number of genes were identified in specific cell populations that showed great predictive power for distinguishing SD from other subjects, as assessed by receiver operating characteristic (ROC) curves (FIG. 2E). Two notable examples with optimal ROC performance (area under the curve=1) are MX2 in naive B lymphocytes and CD163 m double positive CD14+/CD16+ monocytes.

Figure 3A:
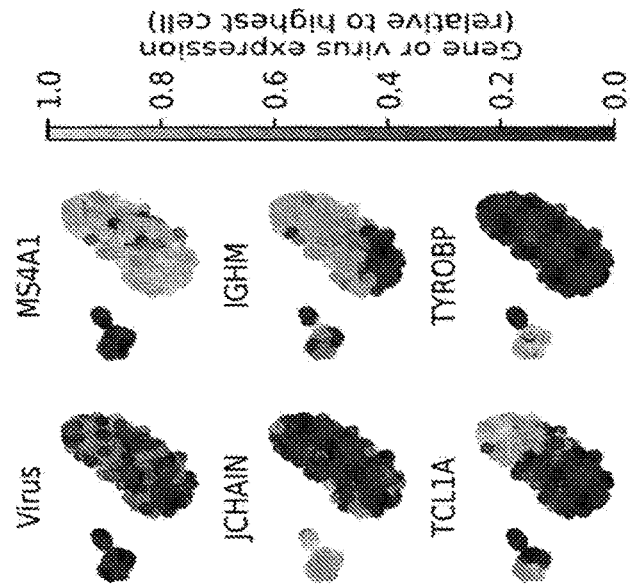
FIG. 3A-3H show Dengue virus in two severe dengue patients is mostly associated with naive B cells according to certain aspects of this disclosure.

Virus in severe dengue patients is primarily associated with naive B cells. To define the cell subtypes that are associated with DENV in the PBMC samples, cells with viral RNA reads were focused on. Viral reads were detected in two samples only (out of six dengue confirmed samples analyzed), both of which were derived from subjects who had high viral loads in their serum and that subsequently progressed to SD (samples 1-026-1 and 1-036-1, see Tables 9A-9D). In both samples, a small number of monocytes were associated with viral RNA. A weak upregulation of CD4, EXT1, GPR132, ZIMZ1, SLC27A3, MUCL1, SFPQ, NFIL3, NBPF9, GAB3, PSG2, and NBPF15 was observed in these virus-associated monocytes (data not shown). Downregulated genes were AC090498.1, PSME2P6, GADH, DLG1, MBNL1, EXOC6, CLEC12A, PTBP3, and SOD1 (data not shown). The majority of virus-associated cells were B lymphocytes (FIG. 3A). No viral reads were detected in other types of leukocytes. These findings are in line with a previous report based on bulk qPCR assays (Srikiatkhachorn A, et al. (2012) *PLoS One* 7:e51335). The fraction of uniquely mapped reads corresponding to viral RNA in those cells was heterogeneous but generally 1% or less, corresponding to several hundred reads per cell but much lower than was measured in cultured Huh7 cells as described by Zanini, F. et al. (2018) eLIFE 7:e32942.

Figure 3B:
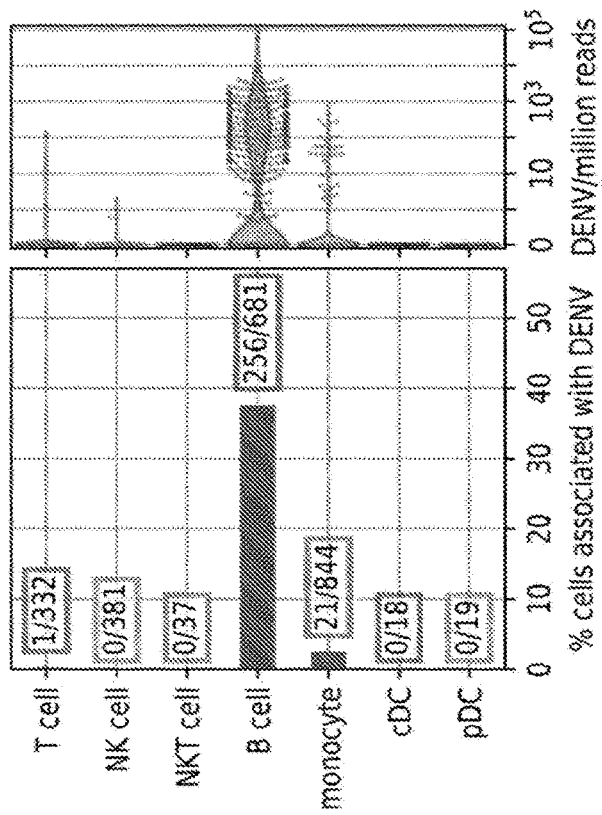
Figure 3C:
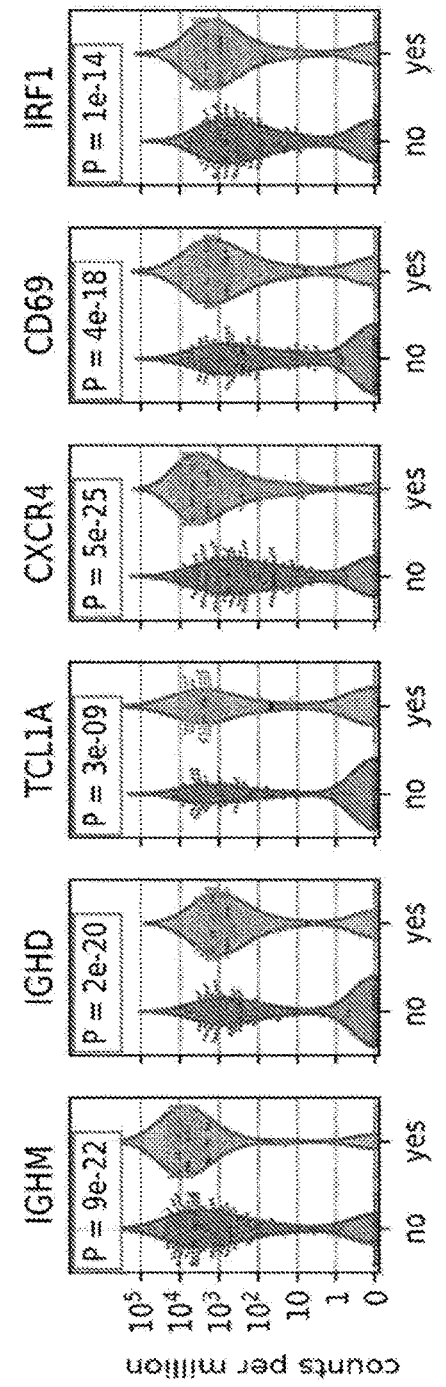
Figure 3D:
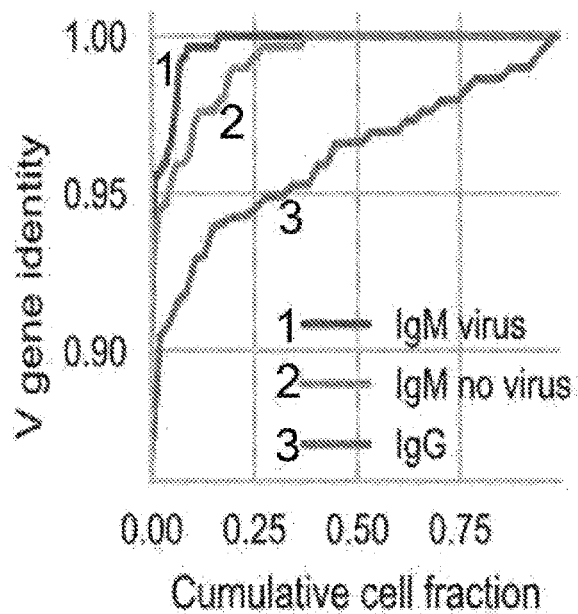

To determine whether a distinct subpopulation of B cells was specifically associated with DENV, the most upregulated genes in the virus-associated population versus other B cells from the same patients were identified. DENV-associated B cells were enriched but not exclusive to IgM/IGD isotypes as well as other markers of naive B lymphocytes, such as the transcription factor TCL1A. The surface receptors CD69, FCRL1, and CXCR4 that signal B cell activation and tissue-specific homing, and IRF1 that encodes an interferon related protein were also upregulated (FIG. 3B). A 2-dimensional embedding of the B cells via t-Distributed Stochastic Neighbor Embedding (tSNE) was identified from the two PBMC samples with detectable viral reads and measured no viral reads associated with cells belonging to the plasma cells or TYROBP$^+$ clusters (FIG. 3C). The whole B cell receptor (BCR) locus was then assembled de novo, and it was found that virus-associated, IgM B cells tended to have less hypermutations than other NM B cells from the same subjects (FIG. 3D). In contrast, V/J usage in heavy and light chains was not apparently different between virus-associated and bystander B cells in the same subjects (data not shown) Moreover, expression of a number of genes were found in this study to correlate with intracellular viral abundance in DENV-infected Huh7 cells and are known to participate in intracellular viral dynamics was not altered in the virus-associated B cells, raising the possibility that these cells are associated but not infected with DENV. A slight anticorrelation is in general expected due to dropout effects. Single molecule fluorescence in situ hybridization smFISH) was performed to detect positive and negative strand DENV RNA from naive B cells and monocytes from a healthy blood donor. No evidence was observed of either DENV strand in these B cells, unlike monocytes or control Huh7 cells (data not shown).

Figure 3E:
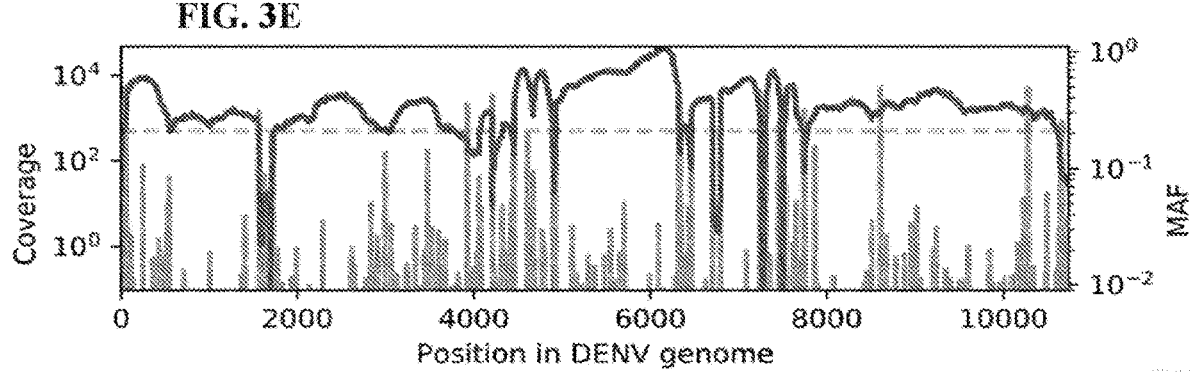
Figure 3F:
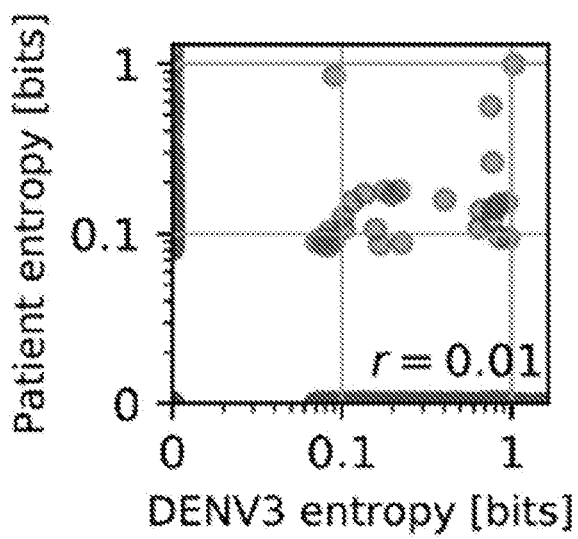
Figure 4A:
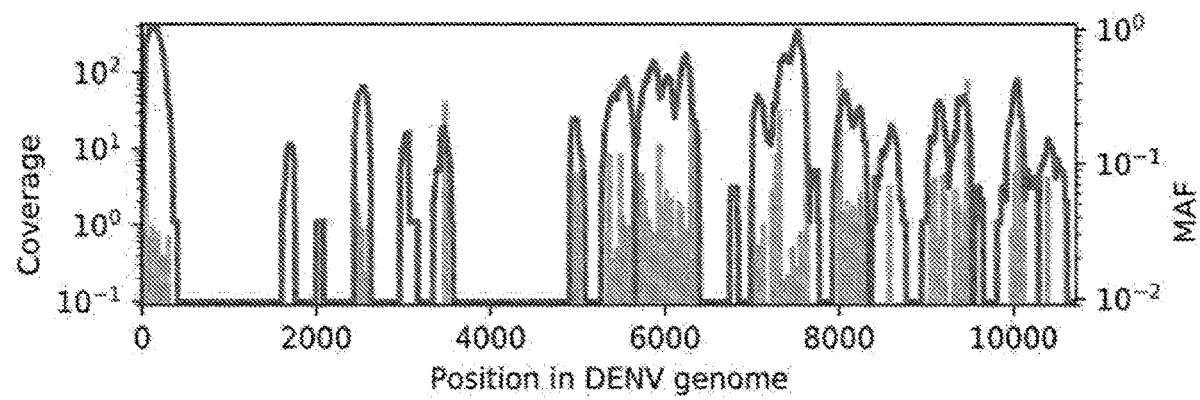
FIG. 4A shows coverage (upper line)) and minor allele frequencies (MAF, lower vertical lines) in the DENV genome for patient 1-036-1 according to some aspects of this disclosure
Figure 4B:
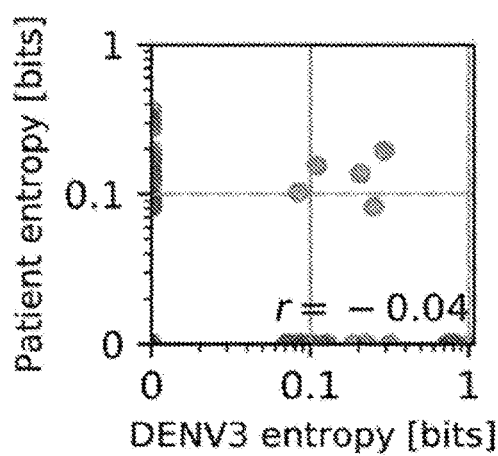
FIG. 4B shows comparison of intrapatient and cross-sectional allele frequencies for patient 1-036-1 according to some aspects of this disclosure. Total sequencing depth for this patient sample was much less than for patient 1-026-1.

In addition to counting the DENV reads, the reads were mapped in an iterative manner and ~300,000 viral reads were recovered from patient 1-026-1 and ~2,000 reads were recovered from patient 1-036-1. High coverage was obtained across the whole DENV genome and a third of the genome for these patients, respectively. The intrapatient population genomics showed a wide range of conservation levels, as determined by minor allele frequencies (FIG. 3E and FIG. 4A). Site-specific Shannon entropy restricted to positions with 200 or more virus reads did not correlate with cross-sectional entropy in DENV serotype 3 (FIG. 3F and FIG. 4B). This suggests that DENV genomic diversity within a single patient follows a distinct fitness landscape from DENV species as a whole, in agreement with previous evidence (as described in Parameswaran P, et al. (2012) *J Virol.* 86:8546-8558) and unlike other viruses such as HIV-1 (as described in Zanini F, et al. (2016) *Elife* 4: e11282).

Figure 3G:
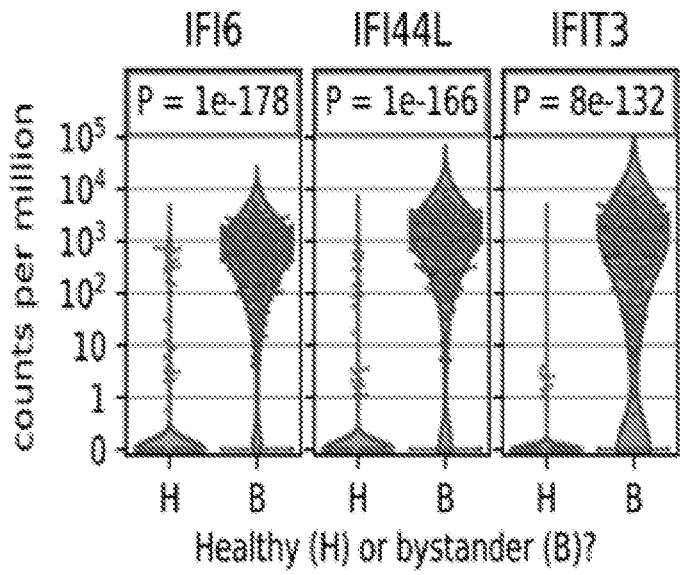
Figure 3H:
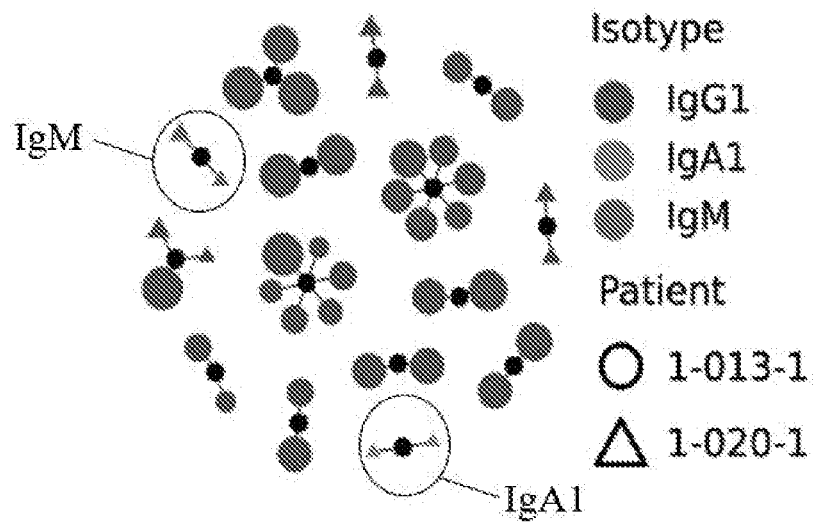

Hundreds of non DENV-associated B cells (bystanders) were recovered from samples containing DENV-associated cells. Differential gene expression was computed between these bystanders and B cells from healthy controls, and a strong antiviral response via interferon stimulated genes IFI6, IFI44L, and IFIT3 was identified (FIG. 3G). Moreover, it was considered whether the diversity of the immune repertoire (B and T cell receptors—BCR and TCR) could play a role in virus-cell association. Whereas assembled BCRs from patients with detected DENV-associated B cells scattered into small clones, the BCR repertoire of patients 1-013-1 and 1-020-1, who had no DENV-associated B cells, contained large clonal families ("lineages") comprised of multiple plasmablasts sharing similar antibody heavy chains, indicating a rapid and large clonal expansion in the B cell compartment (FIG. 3H). Clones were called based on only the α/γ chain or only the β/δ chain in preparing the lineages. These large clonal families all contained cells belonging to healthy, dengue, and severe dengue patients, thereby supporting their assignment as public clonotypes. The fact that such plasmablast expansions were captured simply as part of these patients' circulating B cell populations was surprising given the vast diversity of possible BCR rearrangements (see Georgiou G, et al. (2014) *Nat Biotechnol.* 32:158-168) and could be indicative of a more extensive plasmablast response and concurrent rise in neutralizing antibody titers known to occur in response to acute dengue infection (see Appanna R, et al. (2016) *EBiomedicine* 12:178-188). One clonal family had members belonging to both patients, while another featured two plasmablasts with nearly identical heavy chains, but distinct light chains. This raises the possibility of parallel somatic evolution (see Parameswaran P, et al. (2013) *Cell Host Microbe* 13: 691-700). Large public clones in the a and chains, independent of disease status, were identified while β and δ clones were found to be mostly private. Within the T cell compartment, clustering by TCRβ/δ CDR3s produced clonal families that were largely private to an individual, while clustering according to TCRα/γ CDR3s revealed known invariant T cell subsets, including invariant natural killer T cells (iNKT) and mucosal associated invariant T cells (MAIT), as well as public γ chain CDR3 sequences (e.g. ALWEYQELGK-KIKV (SEQ ID NO:342)) (data not shown) (see Ravens 5, et al. (2017) *Nat Immunol* 18:393-401).

Multiple genes, particularly interferon response genes, were upregulated in a cell-specific manner prior to progression to SD. The expression of MX2 in naive B cells and CD163 in CD14$^+$ CD16$^+$ monocytes was predictive of SD. The majority of DENV-associated cells in the blood of two patients who progressed to SD were naive IgM B cells expressing the CD69 and CXCR4 receptors and antiviral genes, followed by monocytes. Bystander uninfected B cells also demonstrated immune activation, and plasmablasts from two patients exhibited antibody lineages with convergently hypermutated heavy chain sequences. Lastly, assembly of the DENV genome revealed diversity at unexpected genomic sites. This study presents a multi-faceted molecular elucidation of natural dengue infection in humans and proposes biomarkers for prediction of SD, with implications for profiling any tissue and viral infection, and for the development of a dengue prognostic assay.

The heavy and light chain amino acid and nucleic acid sequences of the BCR repertoire of patients 1-013-1 and 1-020-1 (FIG. 3H) are set forth above in Table 1 and Table 2. Table 3 and Table 4 further summarize the specific CDR amino acid sequences, the grouped lineages, the isotype, and the V and J types for each of these antibodies. Amino acids that vary between antibodies in a specific lineage are bolded. Table 3 also identifies the median pairwise percent similarity between the CDR3 amino acid sequences of the heavy chain sequences in each lineage. All of these sequences represent exemplary antibodies within the context of this disclosure. Further study of these antibody sequences are described in the subsequent examples.

Example 2. Recombinant Antibody Production

DNA sequences for the antibodies identified from patients 1-013-1 and 1-020-1 were synthesized as gene fragments (GenScript Biotech Corp.) with at least 15 base pair overlaps matching the 5' signal sequence and 3' constant region in human IgG₁, kappa or lambda expression vectors. Vectors used were in-house constructs of Genbank LT615368.1, deposited by Tiller, T., et al. (2009) J. Immunol, Methods 350(1-2):183-193, Clones were generated based on the VDJ sequences set forth in Table 1 and Table 2. The flanking nucleotide sequence added to each of these nucleotide sequences are set forth below in Table 12. Certain antibody sequences were codon optimized prior to cloning using a *Homo sapiens* DNA codon optimization tool (Integrated DNA Technologies). The codon optimized sequences are set forth below in Table 13 and Table 14. Gibson assembly of the gene fragments was performed to prepare the coding sequences, and the coding sequences were cloned into the vectors. The clones were confirmed by sequencing. The clone DNA was transfected into 96-well blocks of 1 mL suspension 293 cells. Four days post-transfection, supernatants were assayed for antibody expression using an IgG ELISA.

Miniprep DNA (0.5 μg) for the MC and LC of each mAb was transfected into a 96-well, round bottom, deep well plate (VWR) containing 1 mL of 1.5×10⁶ suspension 293 cells (Expi293 System Kit, ThermoFisher). Cultures were grown in a Multitron shaker (INFORS HT) for four days.

TABLE 12

Flanking sequences adding to antibody sequences for cloning

| Antibody Type | 5' Flanking Sequence | 3' Flanking Sequence |
|---|---|---|
| Heavy chain | CTAGTAGCAAC TGCAACCGGT GTACATTCA (SEQ ID NO: 327) | CCTCCACCAA GGGCCCATCG GTCTTCCCCC TGGCAC (SEQ ID NO: 328) |
| Light chain-kappa | CTAGTAGCAA CTGCAACCGG TGTACATTCA (SEQ ID NO: 327) | GAACTGTGGCT GCACCATCTGT CTTCATCTTCC CGCCATCTGAT GAGCAGTTGAA ATCTGGAACTG CTAGCGTTGTG TGCCTGCTGAA TAAC (SEQ ID NO: 329) |
| Light chain-lambda | CTAGTAGCAAC TGCAACCGGT GTACATTCA (SEQ ID NO: 327) | GTCAGCCCAAG GCTGCCCCCTC GGTCAC (SEQ ID NO: 330) |

TABLE 13

Modified heavy chain sequences of antibodies for cloning and validation

| antibody id | Modified Nucleotide sequence | difference from patient sequence |
|---|---|---|
| 1001701405_M6 | SEQ ID NO: 331 CAGGTTCAGCTCGT GCAAAGTGGCGCGG AGGTGAAAAAACCT GGCAGCAGCGTCAA AGTTTCTTGTAAGG CCAGCGGTGGCACT TTTTCAAATTATGC ATTTAGTTGGGTGA GACAAGCACCAGGG CAGGGGCTGGAATG GATGGGGAGAATTA TCCCCATCTTTGGA ACACCCAAGTACGC GCAGAAATTCCAAG GCAGAGTAACAATA ACCAGAGACGAAAG CACGTCTACTGCGT ACATGGAACTGTCC AGCCTCCGCTCTGA GGATACTGCCGTAT ATTATTGCGCCAGA AGCCCTGGCATAG TTCAGGCTGGTTTC CTAGTGATTATTGG GGACAAGGCACCCT GGTGACCGTGTCTT CTG | Codon optimized |
| 1001701405_J9 | SEQ ID NO: 332 CAGGTCCAGCTGGT GCAGTCTGGGGCTG AGGTGAGGAAGCCT GGGTCCTCAGTGAA GGTCTCCTGCAAGA CTTCTGGAGGCTCC CTCAACAGTTATGG CATCAGTTGGGTGC GACAGGCCCCTGGA CAAGGGCTTGAGTG GATGGGAGGGATCA TCCCTTTCTTTGGT ACAGTTATCTATTC AGACAATTACCAGG GCAGAGCCTCGTTT TCCTCGGACGAATC TACGACCACAGCCT ACATGGAGCTGAGA AGCCTAAGATCTGA GGACACGGCCGTGT ATTACTGTGCGAGA TATTGTTATAGTGC CAGTTGTTATCACA ACTGGTTCGACCCC TGGGGCCAGGGAAC CCTGGTCACCGTCT CCACAG | Deletion of 42ⁿᵈ codon of sequence (deletion of Gly) |
| 1001701503_D8 | SEQ ID NO: 333 CAGCTGCAGCTACA GGAGTCGGGCCCAG GACTGGTGAAGCCT TCGGAGACCCTGTC CCTCACCTGCACTG TCTCTGGTGGCTCC ATCAGTAGGAGTAG TTACTTCTGGGGCT GGATCCGCCAGCCC CCAGGGAAGGGGCT GGAGTGGATTGGGA GTGTCTCTTATAGT GGGAGCACCTACTA CAACCCGTCCCTCA AGAGTCGAGTCAGC GTATCCGTAGACAC GTCCAGGAAGCAGT TCTCCCTGAAACTG ACGTCTGTGACCGC | Deletion of 34ᵗʰ codon of sequence (deletion of Thr; in CDR1) |

TABLE 13-continued

Modified heavy chain sequences of antibodies for cloning and validation

| antibody id | Modified Nucleotide sequence | difference from patient sequence |
|---|---|---|
| | CGCAGACACGGCTG TGTATTACTGTGCG AGACAGGACAGAAA CTGGTTCGACTCCT GGGGCCAGGGAACC CTGGTCACCGTCTC CTCAG | |
| 1001701403_P10 | SEQ ID NO: 334 CAAGTTCAGCTGCA AGAATCCGGGCCTG GCTTGGTCAAGCCT AGTGAGACACTGAG CCTTACCTGTACTG TTTCTGGGGATTCC ATCACGAGCTATTA TTGGAGTTGGATTA GGCAACCTCCCGGT CAAGGGCTCGAATG GATTGGCTACATAT ACTATAGCGGCGGT ACGAATTATAACCC TAGCTTGAAAAGCC GAGTTGTAATGTCT TTGGACACATCACG CAACCAGTTCTCCC TCAAACTGAACAGT CTTACCGCCGCAGA CACCGCTGTTTATT ATTGCGCCTCCGCT TTGAACTACTTCGA TTCTTCAGGGCCAG GTGGAGTAGCAATG GGAGGCGGATTCGA CTCATGGGGCCAAG GCGCACTCGTGACG GTCTCATCAG | Codon optimized |
| 1001701403_L2 | SEQ ID NO: 335 CAGGTACAACATCA GGAATCAGGTCCTG GGCTGGTAAAGCCG AGCGAAACCTTGTC ACTTACGTGTACGG TAAGCGGAGATTCT ATTAGCTCATACTA TTGGAACTGGATTA GACAGGCTCCTGGT AAGGGACTGGAATG GCTTGGGTATATTA ACTATAGCGGCAAC ACGGATTACAATAC CTCCCTGAAGAGTC GCGCCACTATTAGC CTCGATACTTCCAA GAACCAATTTTCAC TCAAATTGTCAAGT GTCACAACGGCGGA TACCGCCGTTTATT ACTGCGCCGGGGCG TTGTACTATTTTGA CTCTAGAGGGCCAG GCGGGGTAGCAATG GGTGGTGGCTTCGA CTCCTGGGGACAAG GAACGCTCGTGACG GTGTCCTCCG | Codon optimized |

TABLE 14

Modified light chain sequences of antibodies for cloning and validation

| antibody id | modified nucleotide sequence | difference from patient sequence |
|---|---|---|
| 1001701405_M6 | SEQ ID NO: 336 CAGTCTGTGCTTAC CCAACCCCCAAGCG TCTCTGGCGCTCCA GGACAACGGGTCAC AATTAGTTGCACCG GCGGCTCTTCAAAT ATCGGGGCAGGTTA CGATGTCCATTGGT ACCAGAAGCTGCCA GGTACCGCTCCTAA GCTCTTGATCTTCG GTAAGAACAATCGC CCTAGTGCGGTTCC CGACCGGTTTAGTG GTAGTAAGTCCGGG ACCTCTGCTTCACT CGCTATTACCGGGC TTAGGGCTGAGGAC GAGGCAGAATATTA CTGTCAGTCTTTCG ATTCTCTTAGCGGA TACGCAGTCTTTGG CGGTGGCACGCAGC TCACGGTCCTAG | Codon optimized |
| 1001701403_P10 | SEQ ID NO: 337 GATATGCAGATGAC GCAGTCTCCATCAT CTCTTTCAGCTTCC GTCGGTGATAGGGT TACCATTACTTGTA GAGCGTCACAGTCT ATTAGCACGTATTT GAATTGGTATCAGC AAAAGGCTGGTAAG GCCCCAAAATTGCT TATCTATGCTGCAT CATCATTGCAGTCC GGTGTACCGAGCAG GTTCAGCGGGTCAG GCAGCGGAACTGAT TTTACGCTGACCAT CTCCTCTCTTCAAC CTGAAGATTTTGCT ACATACTATTGTCA ACAGTCTTACAGTA CCCCCTTGTTCGGG CAAGGAACTAAGGT TGAAATTAAAC | Codon optimized |
| 1001701403_L2 | SEQ ID NO: 338 GATATACAGATGAC CCAGAGCCCTTCTT CCCTTTCTGCATCC GTAGGAGACCGAGT GACTATAACGTGTA GAGCCTCACAAAAC ATAAACAACTACCT CAATTGGTACCAGC AGAGACCAGGGAAG CCGCCAAACTTGCT TATTTACGCTGCGT CAACGCTTCAAGCG GGAGTCCCATCCCG ATTTTCTGGCAGGG GGTCCGGTACAGAC TTCACTCTTACAAT CTCAAGCCTTCAAC CAGAAGACTTCGCT ACTTACTACTGCCA GCAAAGCTATGGTT CACCATTGTTTGGT | Codon optimized |

TABLE 14 -continued

Modified light chain sequences of
antibodies for cloning and validation

| antibody id | modified nucleotide sequence | difference from patient sequence |
|---|---|---|
| | CAGGGGACAAAAGT AGAAATCAAGC | |

Example 3. Neutralization Assays

Sera was obtained from subjects 013-1 and 020-1 as identified in Example 1. Reporter virus particles (RVPs) generated by complementation of a GFP-expressing subgenomic West Nile virus (WNV) replicon with the structural genes of Dengue virus serotypes 1-4 (DENV1-4), Zika virus (ZIKV), or WNV were incubated with a 1:240 dilution of heat-inactivated sera for 1 hour at room temperature before addition of Raji cells that stably express DC-SIGN-R. After 2 days of incubation at 37° C., infection was scored as a percentage of GFP-positive cells by flow cytometry. Antibody-mediated neutralization of virus infectivity was measured as the percent reduction of GFP-positive cells in the presence versus absence of antibody. Table 15 below shows the percent neutralization of DENV1-4, ZIKV, and WNV RVPs by serum antibodies from patients 013-1 and 020-1.

TABLE 15

Serum ELISA testing against flavivirus antigens

| Subject | DENV1 | DENV2 | DENV3 | DENV4 | ZIKV | WNV |
|---|---|---|---|---|---|---|
| 013-1 | 100 | 100 | 100 | 97 | 85 | 34 |
| 020-1 | 50 | 84 | 60 | 28 | 24 | 5 |

IgG-containing supernatant (range of 3-3709 ng/ml, see Table 14, $4^{th}$ column) obtained following co-transfection of Expi293 cells with 33 out of the 38 paired heavy and light chain sequences from these subjects were tested for virus neutralizing activing as described in the prior paragraph. Neutralization was calculated as the percentage of reduction of infected cells observed in the presence versus absence of antibody. Monoclonal antibody C10(described by Dejnirattisai W., et al. (2015) Nat Immunol. 16(2):170-177) and monoclonal antibody E16 (described by Oliphant T, et al. (2005) Nat Med 11(5):522-530) were used as positive controls for neutralization of DENV and WNV, respectively. The data from this experiment is shown in Table 16 below.

Monoclonal antibodies with at least 50% neutralizing activity will be scaled up for production, quantified by ELISA, and re-tested in the neutralization assay using ten serial five-fold dilutions (starting at 10 μg/ml). Antibody dose-response neutralization curves will be analyzed by non-linear regression (GraphPad Prism v 6.0 g, GraphPad Software Inc.) to calculate the concentration of antibody required to inhibit infection by 50% (IC50).

Example 4. ELISA to Quantify IgG in Expi293 Supernatants

Plates (96 well, Nunc Maxisorb, VWR) were coated overnight with anti-Human IgG, Fcγ (Jackson Immunoresearch) at 2 μg/ml in PBS, pH7.2. The next day the plate was washed 3×300 μl PBST and blocked for 1 hour in 1% BSA/PBS. A human IgG (Jackson Immunoresearch) standard curve was prepared in ⅓ dilutions starting from 100 ng/mL, in assay diluent (0.5% BSA/PBS/0.05% Tween-20). Supernatants from Expi293 cells expressing the patient antibodies as described in Example 2 were diluted in assay diluent between ⅕ and 1/500. Both standards and samples were allowed to bind for 2 hours, washed 6×300 μl PBST and a 1/5000 cocktail of anti-human kappa-HRP and lambda-HRP antibodies (SouthernBiotech) added for 1 hour in assay diluent. After 6×300 ul PBST washes, the plate was developed with TMB (KPL). The data for this experiment is shown in Table 16 (fourth column from left).

TABLE 16

Neutralization Assay Results

| Patient | Clonal family | mAb | IgG (ng/ml) | Binding DENV2 rE* | Binding DV2 RVP* | Neut DENV1 | Neut DENV2 | Neut DENV3 | Neut DENV4 | Neut ZIKV | Neut WNV |
|---|---|---|---|---|---|---|---|---|---|---|---|
| 1-013-1 | 32 | 1001701405_P4 | 362 | 1.1 | 1.9 | $51^2$ | −250 | −41 | −18 | 16 | $33^1$ |
| 1-013-1 | | 1001701403_I13 | | | | | | | | | |
| 1-020-1 | 127 | 1001701503_I7 | 2170 | 2.4 | 1.9 | −25 | $69^2$ | 16 | 8 | −2 | $60^2$ |
| 1-013-1 | 186 | 1001701403_C4 | 792 | 1.1 | 1.1 | $57^2$ | 17 | $48^1$ | −55 | −2 | −22 |
| 1-013-1 | | 1001701403_J2 | 15 | 1.1 | 1.1 | −94 | −72 | −191 | −59 | −24 | −36 |
| 1-013-1 | | 1001701405_N2 | 1163 | 1 | 1 | $79^3$ | −17 | −53 | −61 | −23 | −15 |
| 1-020-1 | 201 | 1001701503_L8 | 2384 | 1.1 | 2.1 | $64^2$ | 14 | $36^1$ | $27^1$ | −16 | −10 |
| 1-020-1 | | 1001701503_H1 | 40 | 1.1 | 1.3 | $72^2$ | −40 | −22 | −55 | −25 | −21 |
| 1-013-1 | 215 | 1001701405_M6 | 1056 | 1 | 1.1 | −113 | −43 | −48 | −41 | −27 | −43 |
| 1-013-1 | | 1001701403_H3 | 2884 | 3.5 | 2 | $33^1$ | $40^1$ | $46^1$ | $60^2$ | 10 | 17 |
| 1-013-1 | 243 | 1001701405_J8 | 64 | 1 | 1.1 | $69^2$ | −46 | −29 | −49 | −32 | −73 |
| 1-013-1 | | 1001701405_J9 | 1238 | 1 | 1.3 | $87^3$ | $89^3$ | $96^4$ | $90^3$ | −27 | −47 |
| 1-013-1 | 248 | 1001701403_J3 | 54 | 1.1 | 1.2 | $72^2$ | −69 | −1 | −25 | −66 | −57 |
| 1-013-1 | | 1001701403_P4 | 362 | 1.1 | 1.9 | $51^2$ | −250 | −41 | −18 | 16 | $33^1$ |
| 1-013-1 | 254 | 1001701403_M11 | 1930 | 1.1 | 1.3 | $94^4$ | −68 | −23 | −42 | 3 | 20 |
| 1-013-1 | | 1001701403_M4 | 1367 | 1.1 | 1.3 | $100^4$ | −52 | −62 | −31 | 6 | 13 |
| 1-013-1 | | 1001701405_L3 | 3709 | 1.1 | 1.1 | $100^4$ | −12 | −23 | −8 | 5 | −18 |
| 1-013-1 | | 1001701405_K11 | 2167 | 1.1 | 1.1 | $96^4$ | −99 | −34 | −26 | −2 | −7 |
| 1-013-1 | | 1001701403_O4 | 1053 | 1.1 | 1 | $96^4$ | −102 | −28 | 2 | −2 | −2 |
| 1-013-1 | 746 | 1001701405_I11 | 891 | 3.2 | 1.8 | $53^2$ | $47^1$ | 15 | $41^1$ | −13 | 15 |
| 1-013-1 | | 1001701405_C1 | 882 | 3.2 | 1.8 | $56^2$ | $41^1$ | 22 | $37^1$ | −7 | 12 |
| 1-013-1 | | 1001701405_G5 | | | | | | | | | |
| 1-013-1 | | 1001701403_P2 | 48 | 0.4 | 0.3 | $100^4$ | $100^4$ | $40^1$ | $69^2$ | $62^2$ | $100^4$ |
| 1-013-1 | | 1001701403_A7 | 278 | 1.1 | 1.1 | $46^1$ | −73 | −24 | −52 | −10 | −59 |

TABLE 16-continued

Neutralization Assay Results

| Patient | Clonal family | mAb | IgG (ng/ml) | Binding DENV2 rE* | Binding DV2 RVP* | Neut DENV1 | Neut DENV2 | Neut DENV3 | Neut DENV4 | Neut ZIKV | Neut WNV |
|---|---|---|---|---|---|---|---|---|---|---|---|
| 1-013-1 | | 1001701405_L9 | | | | | | | | | |
| 1-013-1 | 755 | 1001701405_E9 | 784 | 1.1 | 1.8 | 33[1] | 1 | 15 | −7 | −13 | −28 |
| 1-013-1 | | 1001701403_I8 | | | | | | | | | |
| 1-020-1 | 962 | 1001701503_E1 | 764 | 1.1 | 1 | −58 | −61 | −38 | −29 | −16 | −67 |
| 1-020-1 | | 1001701503_F10 | 267 | 1.1 | 1.1 | 90[3] | −27 | −1 | −30 | −24 | −43 |
| 1-013-1 | 1152 | 1001701405_N8 | 1093 | 1.1 | 1.1 | 90[3] | −53 | 3 | −52 | −62 | −62 |
| 1-013-1 | | 1001701403_F4 | 3 | 3.6 | 2 | 57[2] | 57[2] | 20 | 69[2] | 22 | 28[1] |
| 1-020-1 | 1227 | 1001701503_K2 | 489 | 2.1 | 1.9 | 19 | 53[2] | −31 | −38 | 1 | 57[2] |
| 1-020-1 | | 1001701503_A5 | 1011 | 1 | 1.1 | −97 | −20 | −43 | −28 | 5 | −3 |
| 1-020-1 | 1255 | 1001701503_B10 | 2595 | 1.2 | 2 | 41[1] | −57 | 24 | 22 | 18 | −13 |
| 1-013-1 | | 1001701403_M1 | 1724 | 1.1 | 1.9 | −27 | −5 | −16 | 4 | −7 | −29 |
| 1-020-1 | | 1001701503_D8 | 1759 | 1.5 | 1.9 | 11 | 18 | −41 | −32 | 7 | −62 |
| 1-013-1 | 1353 | 1001701403_P10 | 1935 | 1.1 | 1.9 | 0 | 55[2] | 15 | 12 | −8 | −23 |
| 1-013-1 | | 1001701403_L2 | 2598 | 1.1 | 1.9 | 6 | 54[2] | 48[1] | 9 | −10 | −18 |
| 2B7 or C10 | | DENV cross-reactive mAb | 1000 | 0.9 | 1.9 | 52[2] | 66[2] | −95 | 98[4] | 99[4] | −195 |
| h3H5 | | DENV2-specific mAb | 1000 | 5.3 | 3.2 | nd | nd | nd | nd | nd | nd |
| untransfected | | | nd | 1.1 | 0.9 | 0 | 0 | 0 | 0 | 0 | 0 |
| blank | | | nd | 0.9 | 1.1 | 0 | 0 | 0 | 0 | 0 | 0 |
| CR4354 or E16 | | WNV-specific mAb | 1000 | 1 | 1 | −303 | −327 | −415 | −177 | −38 | 99[4] |

Figure 5:
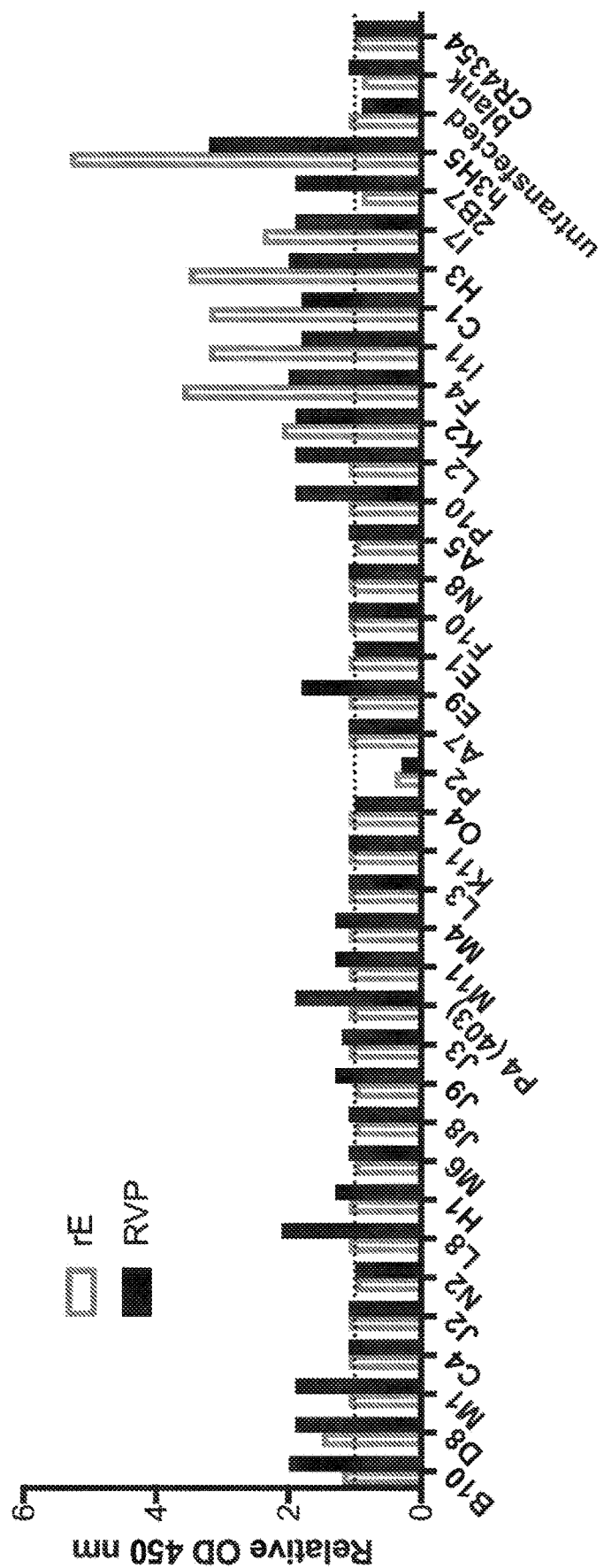
FIG. 5 shows ELISA analysis of the patient-derived antibodies according to certain aspects of this disclosure. Thirty three of 38 mAbs that were successfully cloned were tested by ELBA for binding to recombinant DENV2 monomeric E protein (rE) and DENV2 virus particles (RVP). Shown are the OD450 nm values summarized as fold change over the average of negative controls: untransfected cell supernatant (untransfected), blocking buffer only (blank), and IgG1 isotype control (CR4354). For each antibody, the left data plot is rE, and the right data plot is RVP.

Percent neutralization:
1: 25-50%;
2: 51-75%;
3: 76-90%;
4: >90%;
nd: not determined Example 5. ELISA to Detect Antigen-Specific Antibodies To immobilize RVPs, high-binding 96-well plates (Corning) were coated with 3 of an anti-flavivirus E protein mouse monoclonal antibody 4G2 (Novus Biologicals) in 100 PBS at 4° C. overnight. Plates were washed six times in wash buffer (PBS containing 0.05% Tween 20) followed by incubation with 100 μl blocking buffer (1% BSA in PBS). Next, DENV2 RVPs as described in Example 3 was added in 100 μl blocking buffer. One microgram of DENV2 recombinant E protein (Native Antigen) was immobilized directly on the plate in 100 ul PBS overnight at 4° C.). Plates were then incubated for 1 hour at room temperature and washed six times with wash buffer. Human mAbs from subjects 013-1 or 020-1 as described in Example 2 were diluted in blocking buffer (100 μl; 2 μg/ml) and added to the plates and incubated for 1 hour at room temperature. Positive controls were monoclonal antibody 2B7 (described by Dejnirattisai W., et al. (2015) Nat Immunol. 16(2):170-177), which binds only to RVP, and mouse monoclonal antibody 3H5-1 (described by Henchal E A, et al. (1982) Am J Trop Med Hyg 31(4):830-836), which binds to both rE and RVP, WNV-specific mAb CR4354 (described by Kaufmann B, et al. (2010) Proc Natl Acad Sci USA 107(44):18950-189:5:5) was used as an isotype control antibody. After washing the plates again with wash buffer, 100 μl of HRP-conjugated mouse anti-human IgG (Thermo Scientific) or HRP-conjugated goat anti-mouse IgG (Thermo Scientific) diluted 1:1000 in blocking buffer was added to plates and incubated for 1 hour at room temperature. 1-Step™ Ultra TMB-ELISA substrate (Thermo Scientific) was added to the plates (100 μl/well) and incubated for six minutes at room temperature in the dark. The reaction was stopped by the addition of 100 μl 1N hydrocholoric acid (Fisher), and the optical density at a wavelength of 450 nm was determined (Spectramax i3, Molecular Devices). The data from this experiment is shown in FIG. 5.

Example 6. Binding Profile of Purified IgGs

Figure 6A:
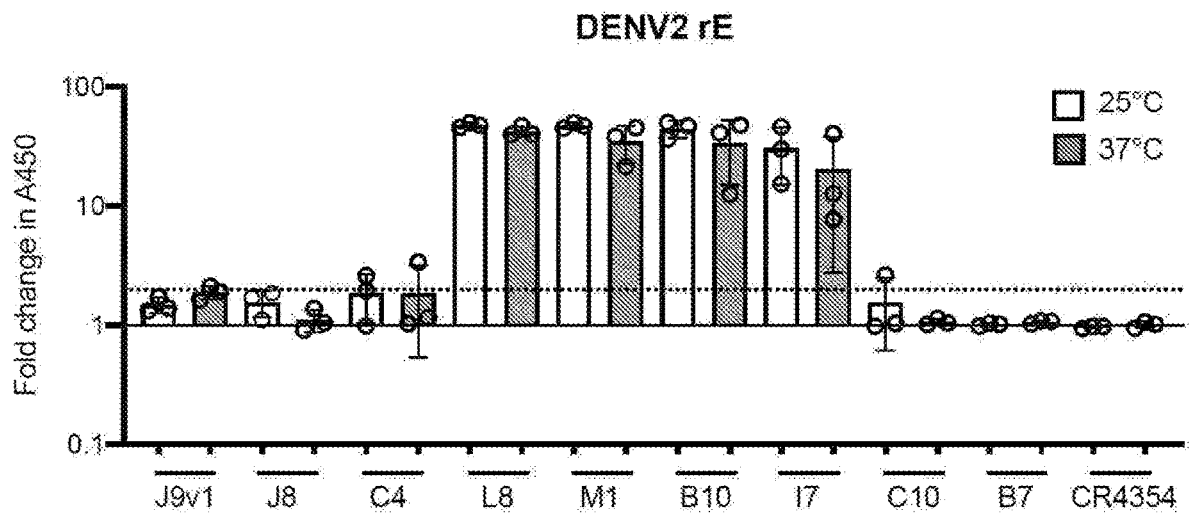
FIGS. 6A-6B show antibody reactiveness to DENV2 according to certain aspects of this disclosure. The indicated monoclonal antibodies on the x-axis were tested for binding to DENV2 rE (FIG. 6A) or DENV2 RVP (FIG. 6B) by ELISA. DENV-reactive antibodies C10 and B7 were included as positive controls for binding to RVPs, while WNV-specific antibody CR4354 was used as a negative control. Bar graphs indicate the mean fold change in absorbance values at 450 nm (A450) relative to those obtained in the absence of primary antibody obtained from three independent experiments indicated by circles. Error bars represent the standard deviation.
Figure 6B:
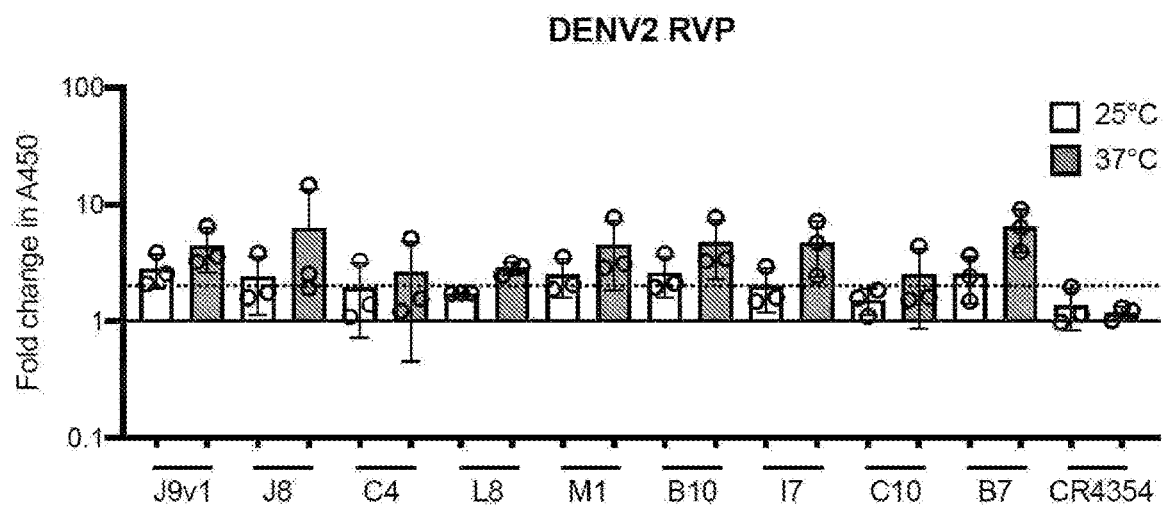

Production of six antibodies (J9, C4, B10, L8, M1, I7) was scaled up by transfection of 5-50 ml ExpiCHO cells (Invitrogen), followed by IgG purification over a Protein A column (MabSelect SuRe, GE Healthcare). These antibodies were selected based on their ability to neutralize >50% of infection by at least four of the six viruses tested in Table 16. Consistent with the pilot screen using crude IgG-containing supernatant (Example 5, FIG. 5), B10, L8, M1, I7 were found to bind to both DENV2 soluble recombinant E (rE) protein and RVPs, while J9 bound to RVPs only. No binding of C4 was detected to either rE or RVPs, despite performing the ELISA under two different temperature conditions (25° C. or 37° C.). These data are summarized in FIGS. 6A-6B.

Example 7. Neutralization Potency of IgGs

Dose-response neutralization assays as described in Example 3 were performed to obtain IC50 values, which represent the antibody concentration at which 50% of virus infection is inhibited. As controls, we included previously described anti-flavivirus broadly neutralizing antibodies EDE1 C10 and EDE2 B7 (described by Dejnirattisai W., et al. (2015) Nat Immunol. 16(2):170-177) and the WNV-specific mAb CR4354 (described by Kaufmann B, et al. (2010) Proc Natl Acad Sci USA 107(44):18950-18955). The results are summarized in Table 17. Despite undetectable binding to DENV2 by ELISA (FIGS. 6A-6B), antibody C4 neutralized all four serotypes of DENV (DENV1-4), although with low potency against DENV4. J9 displayed the highest potency, neutralizing DENV1-4 with an average IC50 of 23 ng/ml. Although, unlike the EDE1 C10, J9 did not neutralize ZIKV, it inhibited some DENV serotypes with up to approximately 60-fold greater potency.

TABLE 17

Neutralization potency of purified IgGs
IG50 (ng/mL)

|       | J9  | C4   | B10 | M1   | L8   | I7   | EDE1 C10 | EDE2 2B7 | CR4354 |
|-------|-----|------|-----|------|------|------|----------|----------|--------|
| DENV1 | 6   | 69   | 757 | 1091 | 360  | 1751 | 352      | 91       | na     |
| DENV2 | 30  | 262  | 929 | 937  | 177  | 1142 | 171      | 64       | na     |
| DENV3 | 15  | 36   | 499 | 2156 | 292  | 1771 | 753      | 45       | na     |
| DENV4 | 39  | 1624 | 698 | 900  | 2454 | na   | 38       | 206      | na     |
| ZIKV  | na  | na   | na  | na   | na   | na   | 38       | na       | na     |
| WNV   | na  | na   | na  | na   | na   | 620  | na       | na       | 7      |

Example 8. Impact of Heavy Chain Modification on J9 Neutralizing Activity

Figure 7:
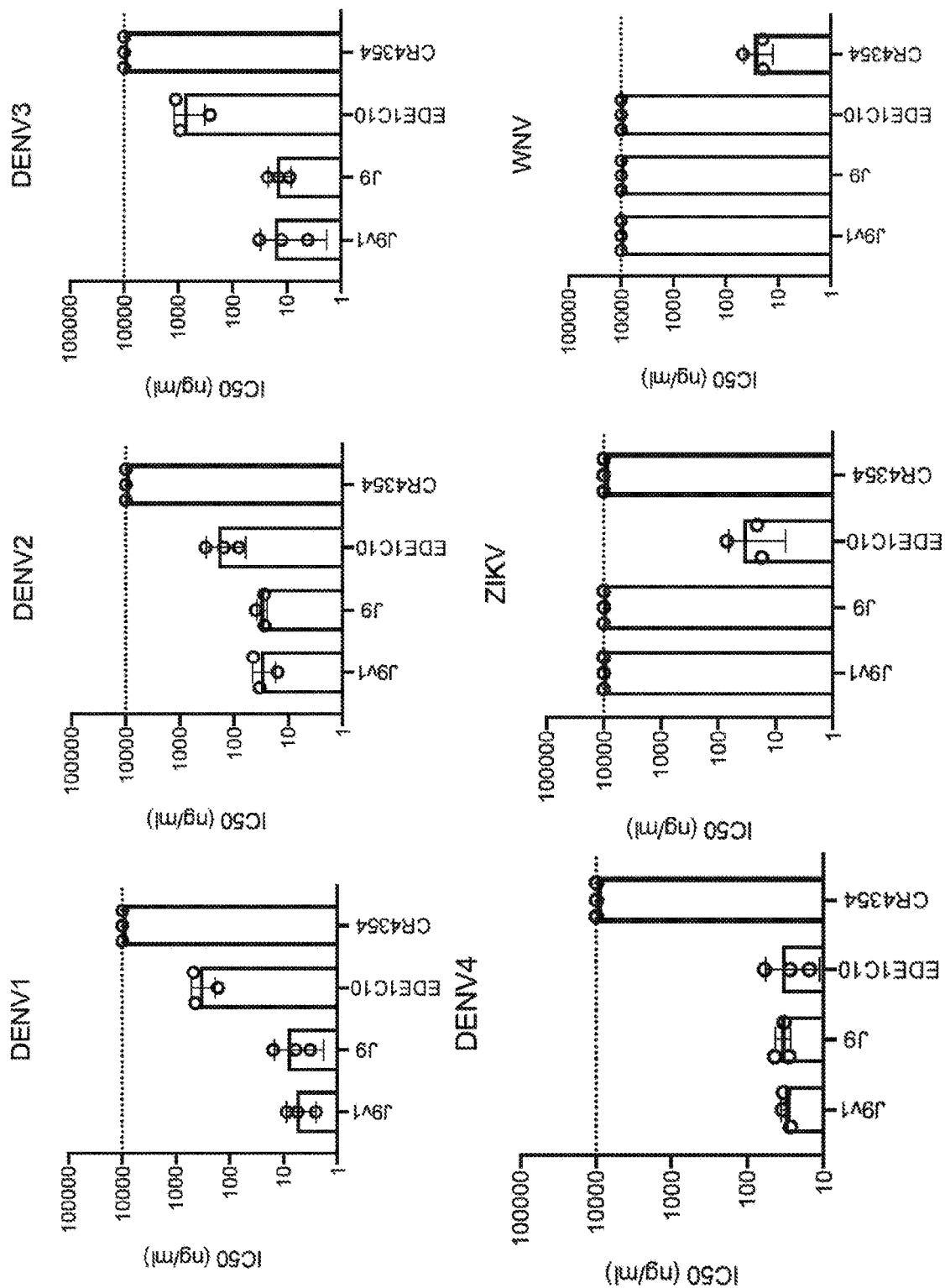
FIG. 7 shows a comparison of mean IC50 values of the J9v1 and J9 against DENV1, DENV2, DENV3, DENV4, ZIKV, and WNV according to certain aspects of this disclosure. Results were obtained from three independent experiments; represented by circles. DENV- and ZIKV-reactive antibody EDE1C10 and WNV-specific antibody CR4354 were used as controls. Error bars indicate the standard deviation. The dotted horizontal line in each graph shows that >50% of viruses remained infectious at the highest antibody concentration tested (10 µg/ml).
Figure 8A:
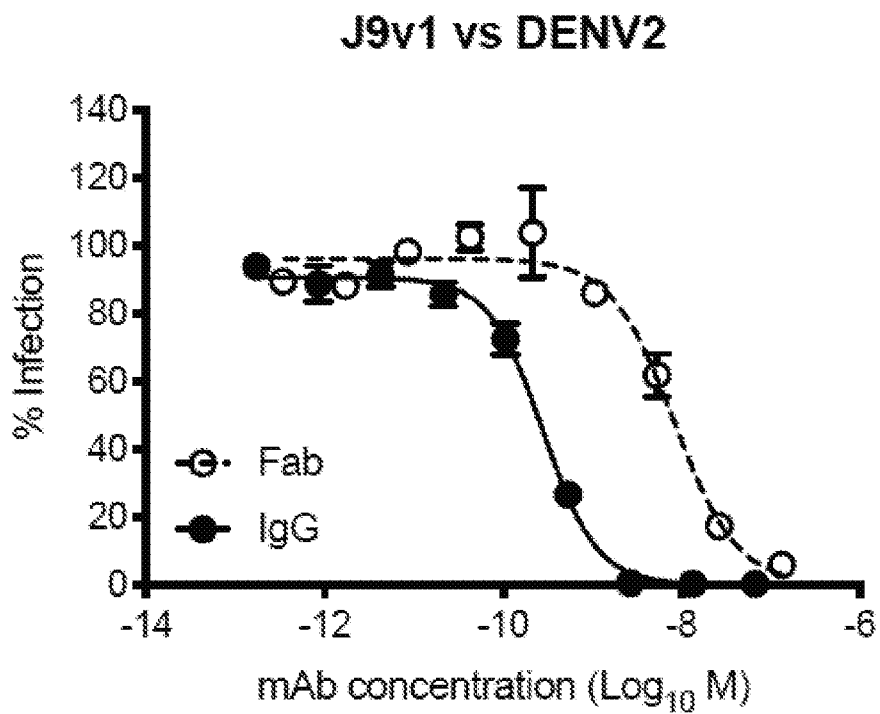
FIGS. 8A-8C show representative dose-response neutralization profiles of J9v1, C4, and EDE1C10, respectively, against DENV2 according to certain aspects of this disclosure. Data is shown for the IgG (solid line) and for the Fab fragment (dotted line). Error bars indicate the range of infectivity obtained from two technical replicates.
Figure 8B:
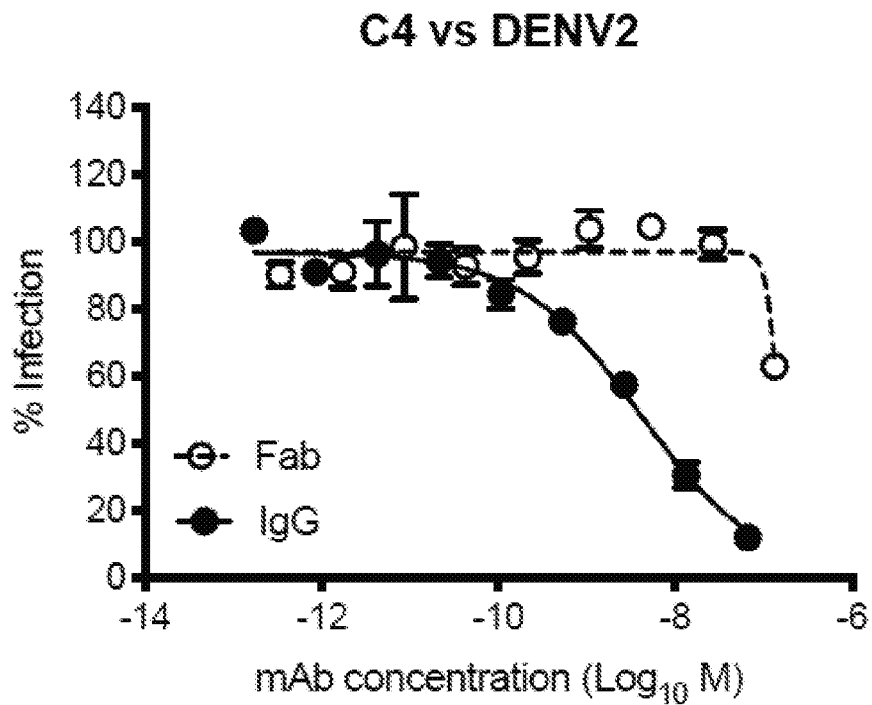
Figure 8C:
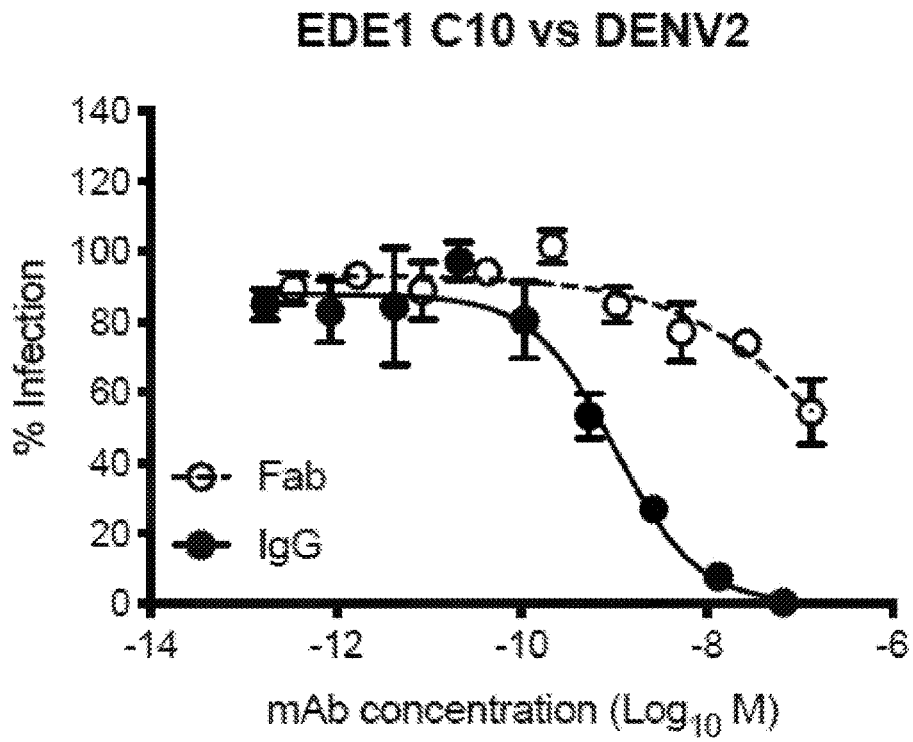
Figure 8D:
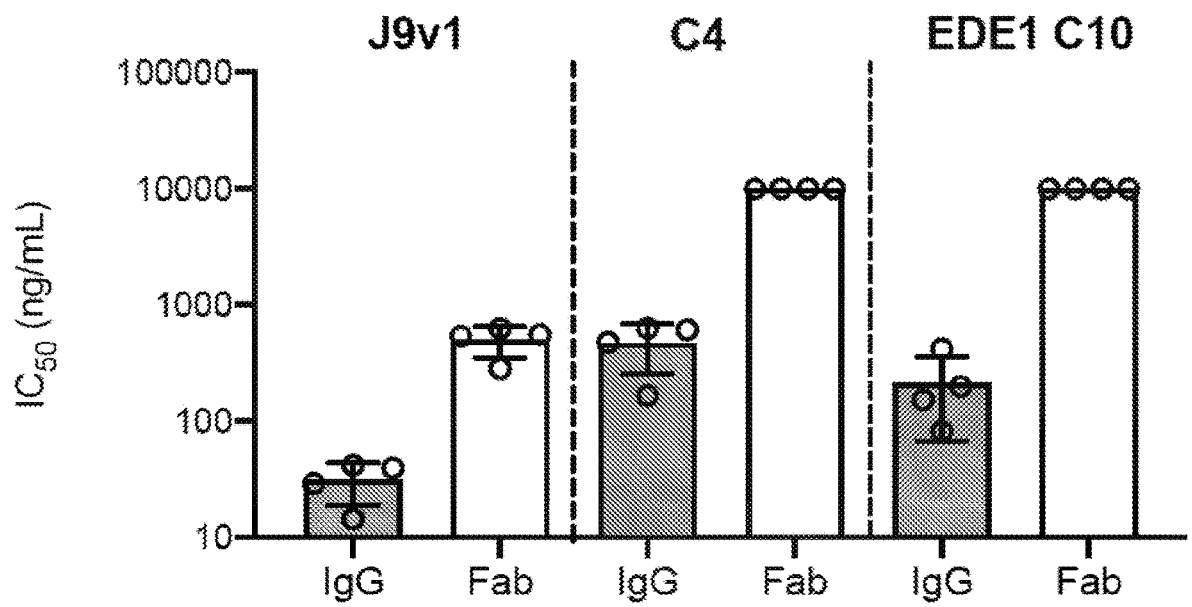
FIG. 8D shows a summary of the mean 1050 values from four independent experiments according to aspects of this disclosure. Error bars indicate the standard deviation.

As shown in Table 13, the modified J9 heavy chain DNA sequence used for recombinant antibody production (SEQ ID NO:332) included a deletion of a glycine residue present in the native amino acid sequence. A new gene fragment that included the native glycine residue in the heavy chain sequence (SEQ ID NO:50) was synthesized for recombinant IgG production with the corresponding light chain using similar methods as those described in Example 2. The IgG encoding the native heavy chain sequence is referred to in the following examples as J9v1. As shown in FIG. 7, J9 and J9v1 displayed similar breadth and potency in their neutralizing activity against DENV1-4. The amino acid residue sequences of J9v1. VH (SEQ ID NO:442) and J9 VH (SEQ ID NO:442) are shown below with the deleted Glycine reside underlined.

| J9v1 | AEVRKPGSSVKVSCKTSGGSLNSYGISWVRQA<br>PGGQGLEWMGGIIPFFGTVIYSDNYQGRASFS<br>SDESTTTAYMELRSLRSEDTAVYYCARYCYSA<br>SCYHNWFDPWGQGTLVTVST<br>(SEQ ID NO: 440) |
|---|---|
| J9 (G42 deletion) | AEVRKPGSSVKVSCKTSGGSLNSYGISWVRQA<br>PGQGLEWMGGHPFFGTVIYSDNYQGRASFSSD<br>ESTTTAYMELRSLRSEDTAVYYCARYCYSASC<br>YHNWFDPWGQGTLVTVST<br>(SEQ ID NO: 442) |

Example 9. Neutralization Potency of Fabs

To determine whether J9v1 requires bivalent binding for potent neutralization, Fab fragments from IgG (Pierce Fab Preparation Kit, Thermo Scientific) were generated and purified and tested in neutralization assays at 2× molar concentration relative to IgG. Despite a reduction in neutralization potency relative to IgG, J9v1 Fab was still able to neutralize DENV2 completely. In contrast Fab fragments of C4 and EDE1 C10, for which a large proportion of viruses remained infectious at the highest concentration tested (6.7 μg/ml for J9v1, EDE1 C10, EDE2 B7; 20 μg/ml for C4). These results are shown in FIGS. 8A-8D.

Example 10. Potential for Antibody-Dependent Enhancement In Vitro

Figure 9A:
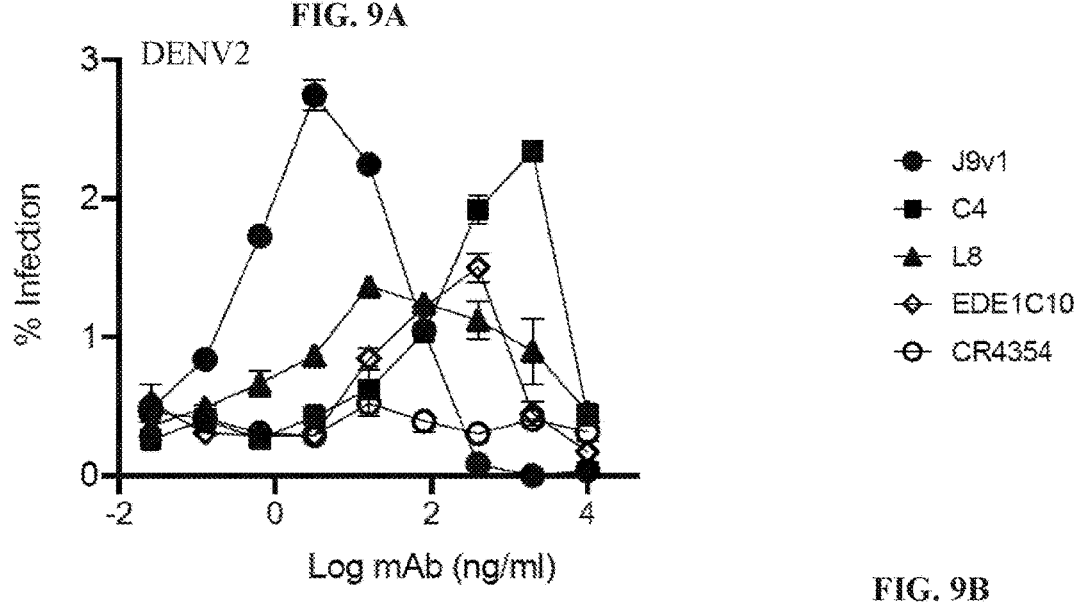
FIGS. 9A-9C show representative dose-response antibody-dependent enhancement of infection with DENV2, ZIKV, and WNV, respectively, according to certain aspects of this disclosure. Error bars indicate the range of infectivity obtained from two technical replicates.
Figure 9B:
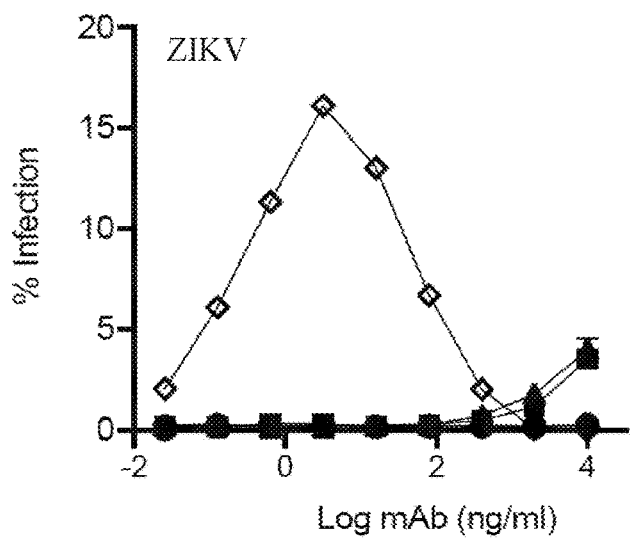
Figure 9C:
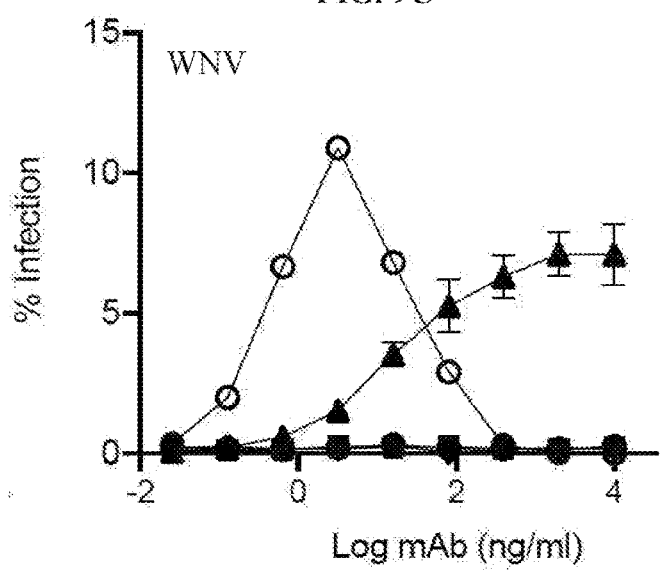
Figures 9D, 9E, 9F:
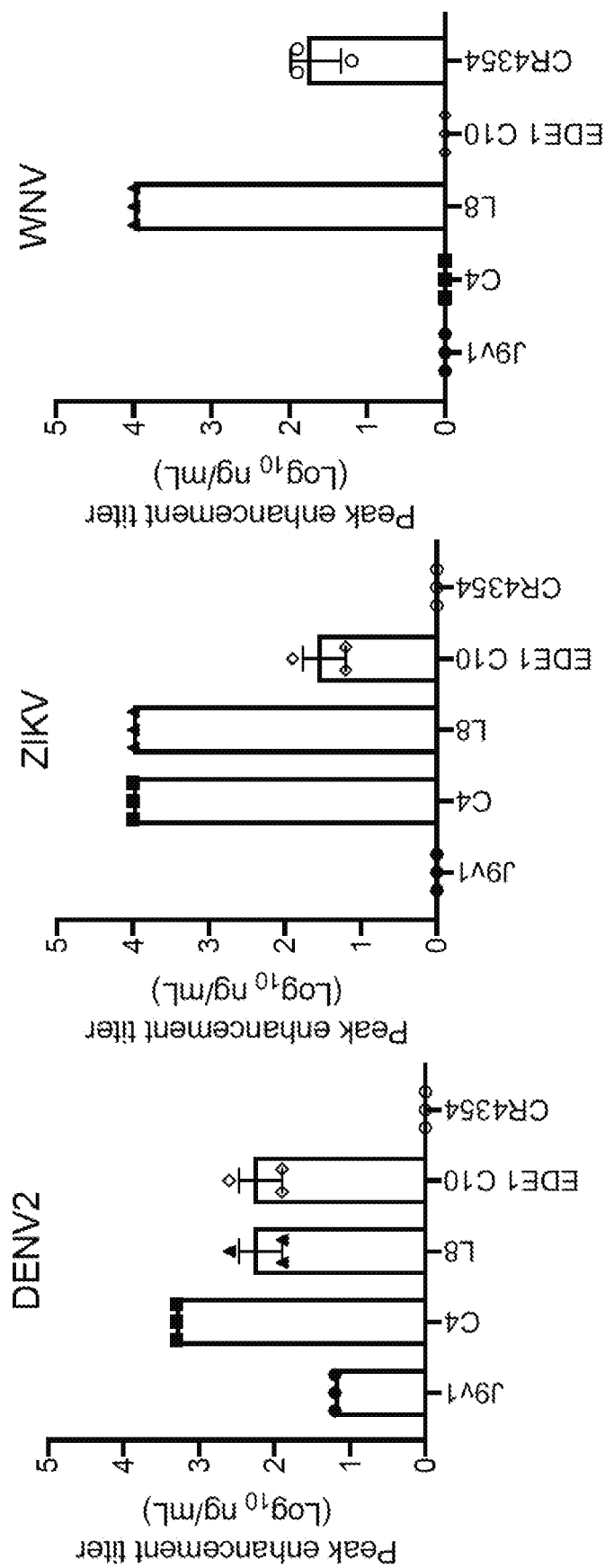
FIGS. 9D-9F show the calculated mean peak antibody titers for enhancement of DENV2, ZIKV, and WNV, respectively, from three independent experiments according to aspects of this disclosure. Error bars indicate the standard deviation.

In vitro, sub-neutralizing concentrations of antibodies can facilitate entry into host cells expressing Fc gamma receptor (FcγR). This process, termed antibody-dependent enhancement (ADE), has been implicated in pathogenesis as the risk of severe disease following secondary DENV infection is highest within a range of intermediate concentrations of pre-existing DENV-specific antibodies, beyond which protection. ADE potential of the antibodies was measured in K562 cells, which express FcγR and are poorly permissive for infection in the absence of antibodies, making them a useful system in which to study ADE. The experiment setup is similar to the neutralization assay described in Example 3, except that K562, not Raji-DCSIGNR, cells were used. For each antibody tested (J9v1, C4, L8, and controls EDE1. C10 and CR4354), the peak enhancement titer was calculated, which is the concentration at which the highest level of ADE of DENV2, ZIKV, or WNV was observed. Consistent with its high neutralization potency. J9v1 displayed the lowest peak enhancement titer (10 ng/ml) against DENV2, beyond which neutralization was observed (FIG. 9A and FIG. 9D). At high antibody concentrations, C4 and L8, modestly enhanced ZIKV infection (FIG. 9B and FIG. 9E). L8 also mediated ADE of WNV (FIG. 9C and FIG. 9F) with no neutralization observed even at the highest antibody concentration tested (10 μg/ml). Thus, despite DENV-specific neutralizing activity, C4 and L8 displayed binding cross-reactivity against other flaviviruses. In contrast, J9v1 did not enhance ZIKV or WNV infection, suggesting an inability to bind these flaviviruses. Overall, these results suggest that the high neutralization potency of J9v1 limits its potential for ADE to a narrow range of low antibody concentrations, beyond which neutralization is observed.

Example 11. Effect of Virus Particle Maturation on Neutralizing Activity

Although cleavage of prM, a chaperone protein for the envelope (E) glycoproteins from the virus particle surface is a required step in the flavivirus life cycle, infectious particles produced in vitro are often heterogeneous with respect to their prM content. A recent study showed that DENV isolated directly from plasma of acutely infected individuals displayed increased prM cleavage efficiency and were less sensitive to neutralization than DE' passaged in cell lines (Raut, R. et al., 2019, Proc. Natl. Acad. Sci USA 116(1): 227-232), suggesting that the ability to neutralize mature DENV particles lacking prM is important for antibody-mediated protection against circulating viruses.

Figure 10A:
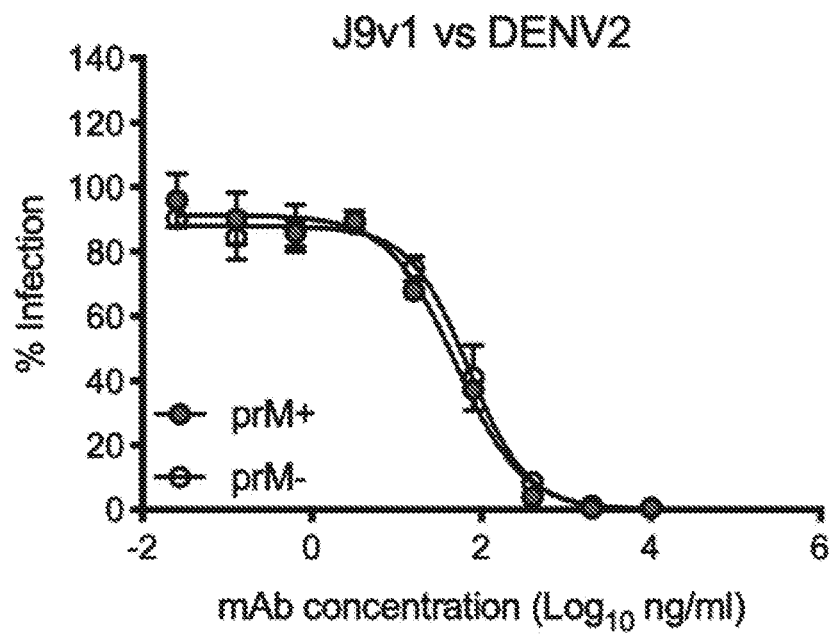
FIG. 10A-10D show dose-response neutralization profile of antibodies J9v1, C4, EDE1C10, and mE60, respectively, against DENV2 produced using standard methods (prM+) or in the presence of overexpressed human furin (prM−) according to certain aspects of this disclosure. Error bars indicate the range of infectivity obtained from two technical replicates.
Figure 10B:
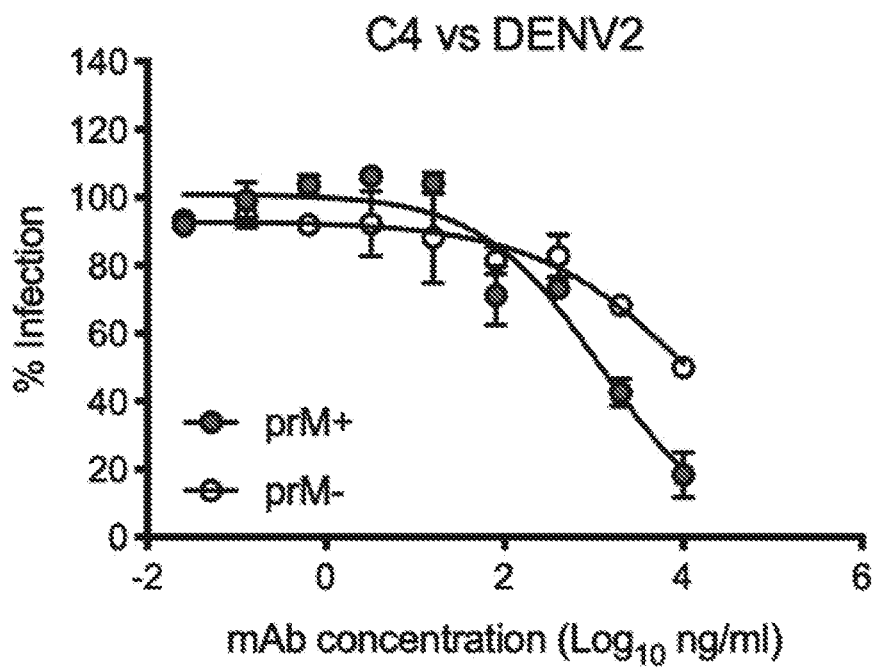
Figure 10C:
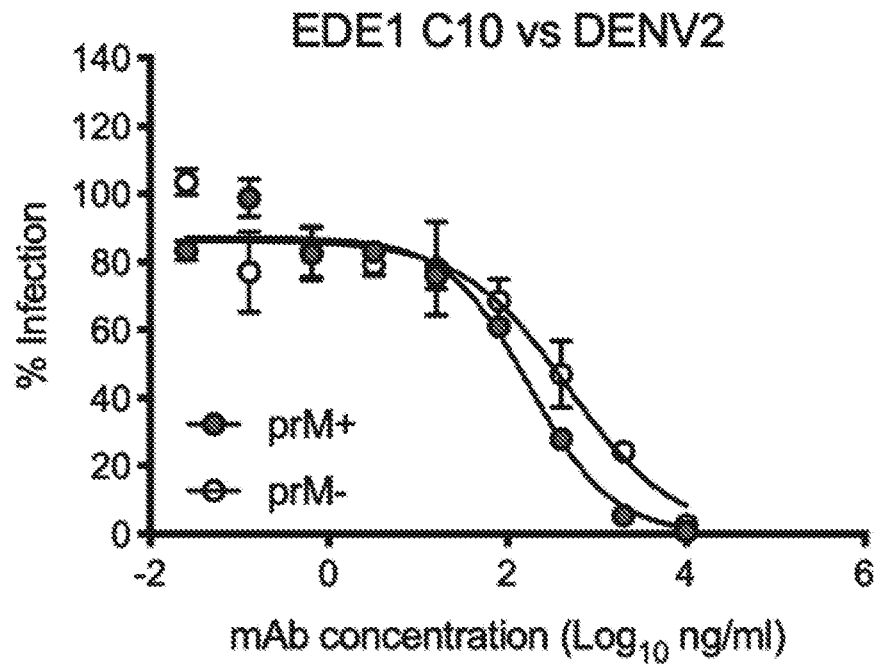
Figure 10D:
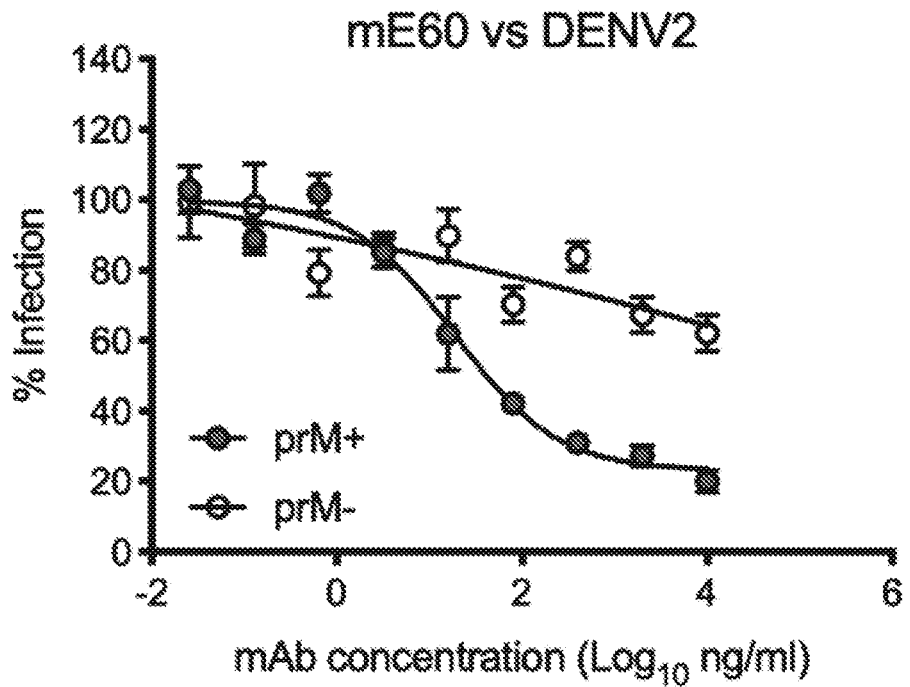
Figure 10E:
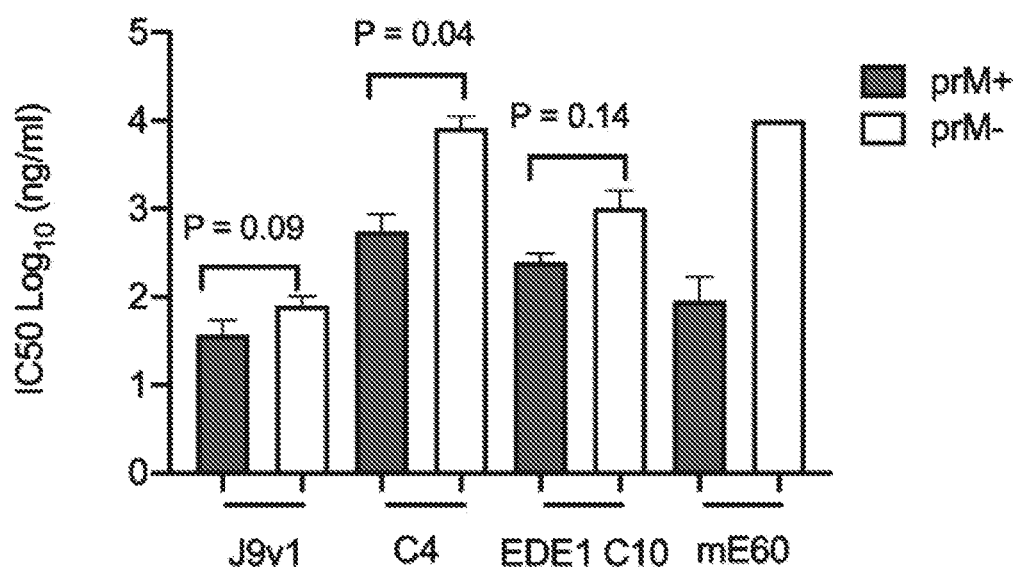
FIG. 10E shows a comparison of mean IC50 values obtained from three independent experiments according to certain aspects of this disclosure. Indicated P values were obtained from paired t-tests. For mE60, 50% neutralization was not observed at the highest antibody concentration tested (10 µg/ml).

The ability of J9v1, C4, and control antibodies EDE1 C10 and mouse monoclonal antibody E60 (Oliphant, T. et al., 2006, J. Virol. 80(24):12149-59) to neutralize DENV2 produced using standard methods (prM+) or in the presence of overexpressed human furin (prM−), which increases prM cleavage efficiency, was compared. As previously shown, E60 did not efficiently neutralize prM− DENV2 (FIG. 10D and FIG. 10E), Similarly, increased prM cleavage efficiency reduced C4 neutralization potency (FIG. 10B and FIG. 10E), resulting in a large proportion of viruses that remained infectious at the highest concentration tested (10 μg/ml). In contrast, virion maturation state had minimal effects on the neutralization potency of J9v1 (FIG. 10A and FIG. 10E) and EDE1 C10 (FIG. 10C and FIG. 10E).

Example 12. Mechanism of Neutralization

It was investigated whether J9v1 and C4 could inhibit infectivity after virus attachment to cells, which is a characteristic of many potently neutralizing antibodies against flaviviruses. Neutralization assays as described in Example 3 were performed with a few modifications. Specifically, antibodies were incubated with virus either before (pre-) or after (post-) the addition of Raji-DCSIGNR cells at 4° C. Following wash steps in cold media to remove unbound virus, cells were incubated for 48 h at 37° C. and infection measured by flow cytometry as described in Example 3.

Figure 11A:
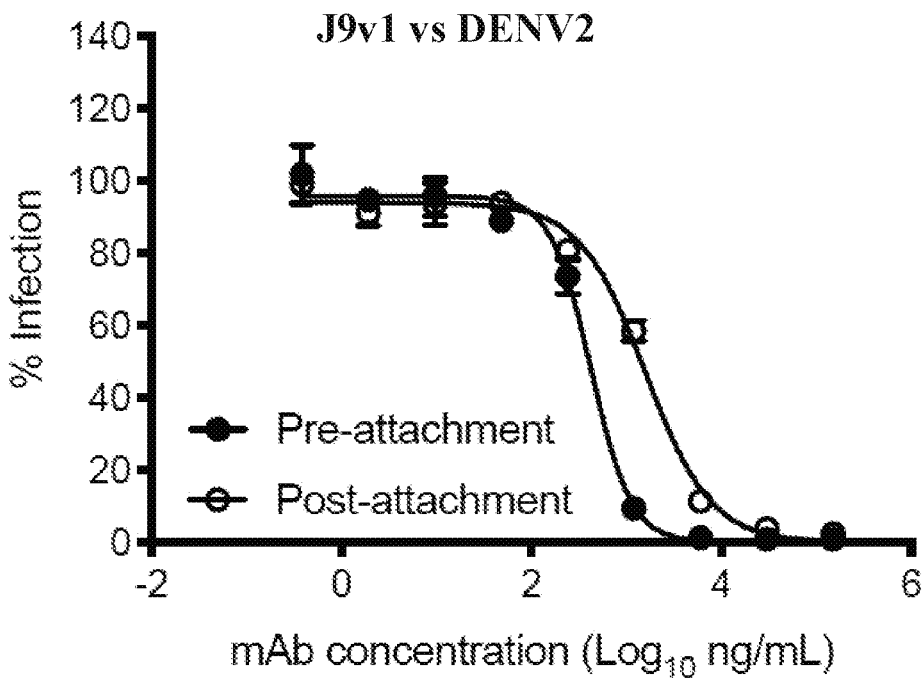
FIG. 11A-11D show dose-response neutralization profile of antibodies J9v1, C4, EDE1C10, and m3H51, respectively, obtained either pre- or post-DENV2 attachment to Raji-DCSIGNR cells according to certain aspects of this disclosure. Error bars indicate the range of infectivity obtained from two technical replicates. Data are representative of three independent experiments.
Figure 11B:
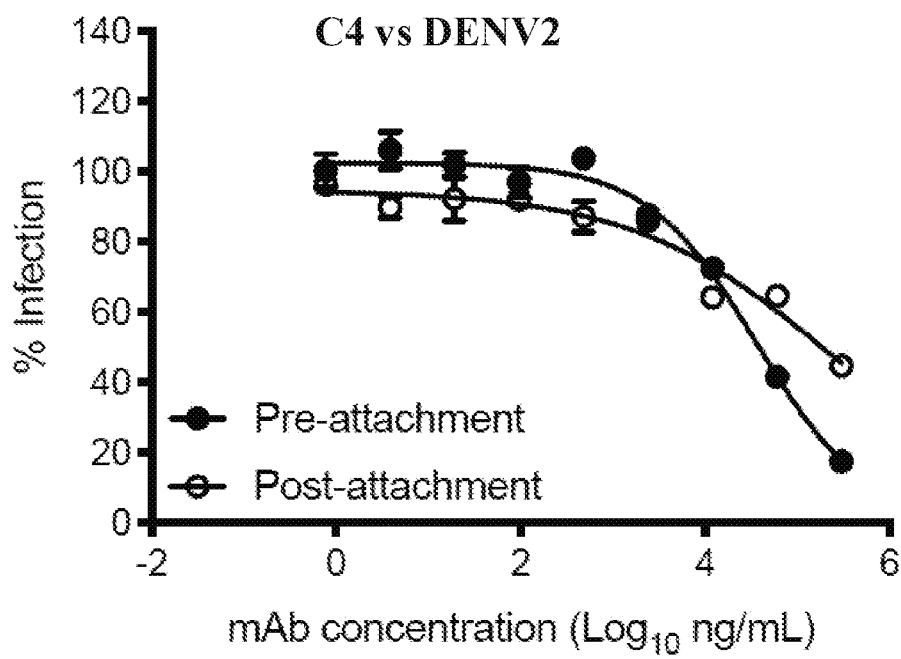
Figure 11C:
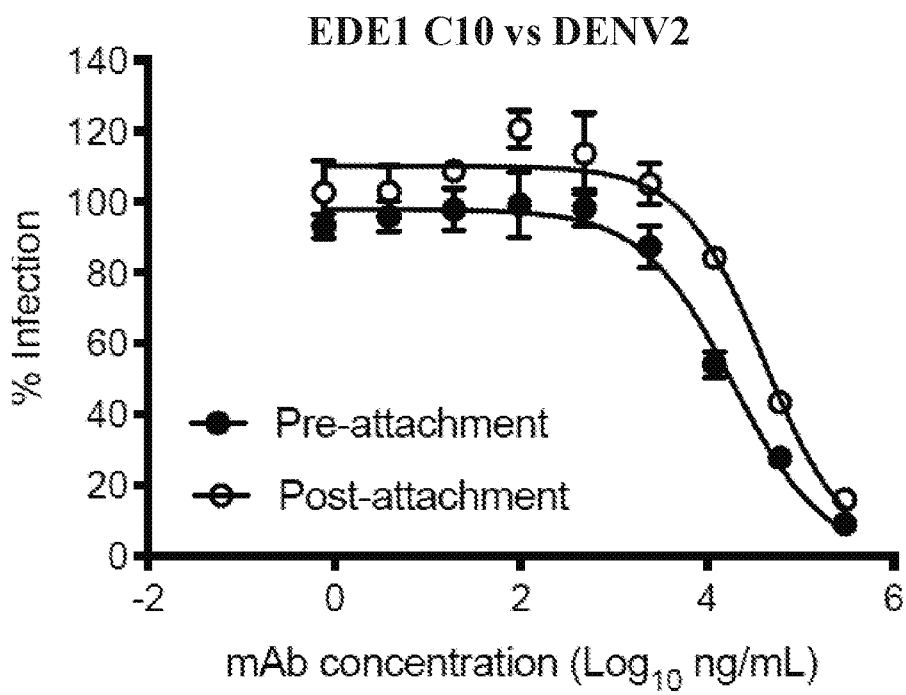
Figure 11D:
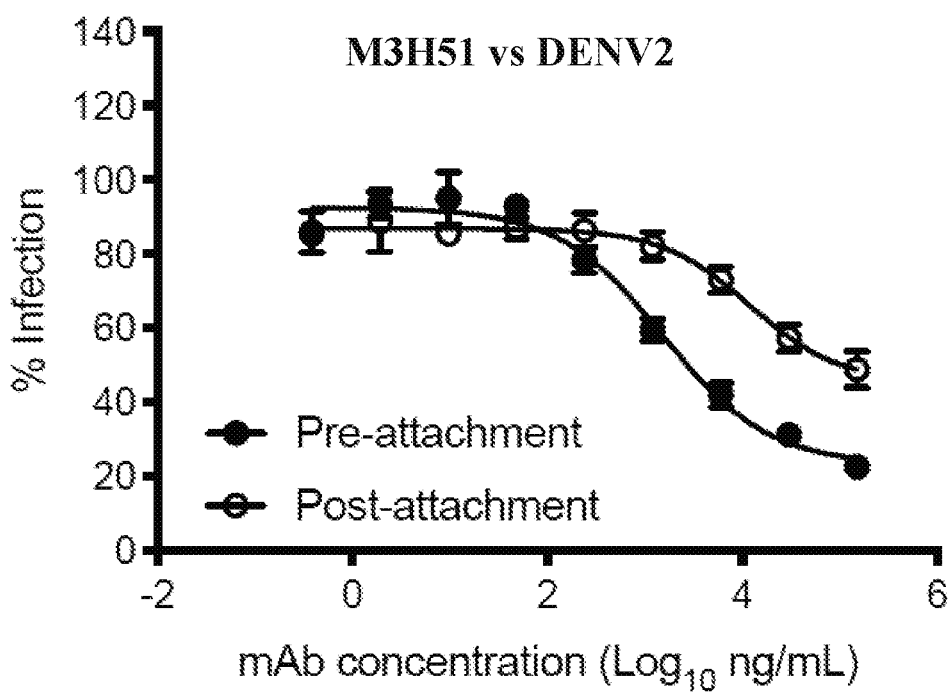

As observed with the control mouse mAb m3H5-1 (Henchal, E. A., et al., 1982, Amer. J. Trop. Med. Hyg. 31(4):830-836), when added after virus attachment to cells, C4 failed to inhibit 40-50% of infection at the highest concentration tested (300 μg/mL) (FIG. 11B and FIG. 11D). In contrast, J9v1 (FIG. 11A) and EDE1 C10 (FIG. 11C) potently neutralized DENV2 infection in both pre- and post-attachment neutralization assays.

Example 13. Lineage Analysis of J9 Clonal Family

To gain insight into the in vivo development of the bNAb J9 and J8 clones, PBMCs from sample 1-013-02 (the next sample timepoint of the donor from which J9 and J8 mAbs were identified in plasmablasts) were used to perform next generation sequencing of the B cell receptor (BCR) repertoire. The PBMCs were also polyclonally stimulated to increase the percentage of antigen specific sequences (Waltari et al., 2019, Frontiers in Immunology, Vol. 10, June 25, Article 1452) and both analyses were focused on the heavy chain repertoires, which are sufficient to identify clonal relationships (Zhou & Kleinstein, 2019, bioRxiv, doi.org/10.1101/665760; pre-print of article; available online Jun. 18, 2019).

A. Materials and Methods

Preparation of Growth-Arrested Feeder Cells, Human fibroblast cell line MRC-5 (CCL-171) was obtained from ATCC (Manassas, VA) and grown in B cell growth media containing Corning® DMEM [+] 4.5 g/L glucose, sodium pyruvate [−] L-glutamine (VWR International, Radnor, PA), 1×Pen/Strep/Glu and 10% ultralow IgG HI-FBS (Thermo Fisher Scientific, Waltham, MA), to 80% confluence before being treated for 4 h with 5 μg/ml mitomycin C (Tocris, R&D Systems). Monolayers of growth arrested cells were washed 3 times with PBS, harvested with trypsin, neutralized with growth media, washed 1× in growth media and finally cryopreserved using 10% DMSO, 30% HI-FBS in growth media.

Preparation of PBMCs for BCR Repertoire Analysis. The day before PBMCs were thawed, $1.2 \times 10^6$ feeder cells were seeded in a T25 flask (VWR) in 4 ml of B cell growth media and cultured overnight in a humidified 37° C. 5% $CO_2$ incubator. PBMCs were quickly thawed at 37° C., washed 1× in 10 ml of growth media, and divided in half. One half was resuspended in 4 ml of 2×B cell growth media containing 2×ITS from 100× Insulin, Transferrin, Selenium (Thermo Fisher Scientific), 20 ng/ml 2 ng/ml IL-2. King/ml 10 ng/ml IL-6 (R&D Systems, Minneapolis, MN) and 4 μg/ml CpG (ODN 2006-G5, InvivoGen, San Diego, CA). The 4 ml of PBMCs were then added to the T25 flask with 4 ml of conditioned feeder cell media. The final 8 ml cell culture was allowed to grow for 5 days at 37° C., 5% $CO_2$ in a humidified incubator. At day 5 the cells were pelleted at 350×g for 5 min, resuspended and lysed in Qiagen RLT buffer with beta-mercaptoethanol for 10 min, frozen on dry ice, and transferred to −80° C. storage until RNA purification. The second half of PBMCs were immediately lysed in RLT buffer without further processing.

BCR Primer Design and Pool Preparation. Dry oligos of desalted purity (IDT) were reconstituted at 100 μM in Qiagen EB and stored in aliquots at −80° C. The oligos are shown in Table 18 and contain sufficient random base pairs to act as unique molecular identifiers (UMIs) for every mRNA transcript present in a sample. LAM are added in variations of 8 or 12 nucleotide stretches to offset the high level of sequence similarity and lower Illumina sequencing accuracy in Ig amplicons at the 3' and 5' ends (see table footnotes). A pool of IgH RT primers was made by mixing 10 μl of each primer from the individual 100 μM stocks (100 μl final volume). Separately 10 μl of each of lambda RT primers were mixed from individual 100 μM stocks (20 μl final volume). Next, a 10 μM, 5:1 molar mix of Ig heavy: lambda chain RT primers was made using 16.7 μl RT primer pool and 3.3 μl lambda RT primer pool, in a final 180 μl of Qiagen EB. The same procedure and molar ratio were repeated in the preparation of the IgH (n=12): lambda (n=16) forward primers. Kappa RT and forward primer pools were prepared by mixing 10 μl of each kappa RT (n=2) primer or kappa forward (n=8) primer from the individual 100 μM stocks and then diluting the mix to 10 μM final.

TABLE 18

| Amplicon Primers. | |
|---|---|
| IgH_constant RT primer pool[1] | |
| RT_IgA_08N | TGACTGGAGTTCAGACGTGTGCTCTTCCGATCT(N)(N)(N)(N)(N)(N)(N)(N)GGGGAAGAAGCCCTGGAC (SEQ ID NO: 343) |
| RT_IgA_12N | TGACTGGAGTTCAGACGTGTGCTCTTCCGATCT(N)(N)(N)(N)(N)(N)(N)(N)(N)(N)(N)(N)GGGGAAGAAGCCCTGGAC (SEQ ID NO: 344) |
| RT_IgG_08N | TGACTGGAGTTCAGACGTGTGCTCTTCCGATCT(N)(N)(N)(N)(N)(N)(N)(N)GGGAAGTAGTCCTTGACCA (SEQ ID NO:345) |
| RT_IgG_12N | TGACTGGAGTTCAGACGTGTGCTCTTCCGATCT(N)(N)(N)(N)(N)(N)(N)(N)(N)(N)(N)(N)GGAAGTAGTCCTTGACCA (SEQ ID NO: 346) |

TABLE 18-continued

Amplicon Primers.

| | |
|---|---|
| RT_IgM_long_8N | TGACTGGAGTTCAGACGTGTGCTCTTCCGATCT(N)(N)(N)(N)(N)(N)(N((N)GAAGGAAGT CCTGTGCGAG (SEQ ID NO: 347) |
| RT_IgM_long_12N | TGACTGGAGTTCAGACGTGTGCTCTTCCGATCTN(N)(N)(N)(N)(N)(NXN)(N)(N)(N)(N) (N)GAAGGAAGTCCTGTGCGAG (SEQ ID NO: 348) |
| RT_IgE_long_8N | TGACTGGAGTTCAGACGTGTGCTCTTCCGATCT(N)(N)(N)(N)(N)(N)(N)AAGTAGCCC GTGGCCAGG (SEQ ID NO: 349) |
| RT_IgE_long_12N | TGACTGGAGTTCAGACGTGTGCTCTTCCGATCT(N)(N)(N)(N)(N)(N)(N)(N)(N)(N)(N)A AGTAGCCCGTGGCCAGG (SEQ ID NO: 350) |
| RT_IgD_long_8N | TGACTGGAGTTCAGACGTGTGCTCTTCCGATCT(N)(N)(N)(N)(N)(N}(N)TGGGTGGTAC CCAGTTATCAA (SEQ ID NO: 351) |
| RT_IgD_long_12N | TGACTGGAGTTCAGACGTGTGCTCTTCCGATCT(N}(N)(N)(N)(N)(N)(N}(N)(N)(N)(N)(N)T GGGTGGTACCCAGTTATCAA (SEQ ID NO: 352) |

LC_constant RT primer pool[1]

| | |
|---|---|
| kappa.rev_08N | TGACTGGAGTTCAGACGTGTGCTCTTCCGATCT(N)(N)(N)(N)(N)(N)(N)(N)AGTTCCAGAT TTCAACTGCTCATCAGAT (SEQ ID NO: 353) |
| kappa.rev_12N | TGACTGGAGTTCAGACGTGTGCTCTTCCGATCT(N)(N)(N)(N)(N)(N)(N)(N)(N)(N)(N)(N)A GTTCCAGATTTCAACTGCTCATCAGAT (SEQ ID NO: 354) |
| lambda.rev_08N | TGACTGGAGTTCAGACGTGTGCTCTTCCGATCT(N)(N)(N)(N)(N)(N)(N)(N)GAGGGCGGG AACAGAGTGAC (SEQ ID NO: 355) |
| lambda.rev_12N | TGACTGGAGTTCAGACGTGTGCTCTTCCGATCT(N)(N)(N)(N)(N)(N)(N)(N)(N)(N)(N)G AGGGCGGGAACAGAGTGAC (SEQ ID NO: 356) |

IgH_V forward primer pool[1]

| | |
|---|---|
| IGH.forP1_08N | ACACTCTTTCCCTACACGACGCTCTTCCGATCT(N)(N)(N)(N)(N)(N)(N)(N)SCAGCTGGTG CAGTCTGG (SEQ ID NO: 357) |
| IGH.forP1_12N | ACACTCTTTCCCTACACGACGCTCTTCCGATCT(N)(N)(N)(N)(N)(N)(N)(N)(N)(N)(N)(N)SC AGCTGGTGCAGTCTGG (SEQ ID NO: 358) |
| IGH.forP135_08N | ACACTCTTTCCCTACACGACGCTCTTCCGATCT(N)(N)(N)(N)(N)(N)(N)(N)GTGCAGCTGG TGGAGTCTG (SEQ ID NO: 359) |
| IGH.forP135_12N | ACACTCITTCCCTACACGACGCTCTTCCGATCT(N)(N)(N)(N)(N)(N)(N)(N)(N)(N)(N)(N)GT GCAGCTGGTGGAGTCTG (SEQ ID NO: 360) |
| IGH.forP2_08N | ACACTCITTCCCTACACGACGCTCTTCCGATCT(N)(N)(N)(N)(N)(N)(N)(N)TCACCTTGAA GGAGTCTGG (SEQ ID NO: 361) |
| IGH.forP2_12N | ACACTCTTTCCCTACACGACGCTCTTCCGATCT(N)(N)(N)(N)(N)(N)(N)(N)(N)(N)(N)(N)TC ACCTTGAAGGAGTCTGG (SEQ ID NO: 362) |
| IGH.forP4.1_08N | ACACTCTTTCCCTACACGACGCTCTTCCGATCT(N)(N)(N)(N)(N)(N)(N)(N)TGCAGCTGCA GGAGTCG (SEQ ID NO: 363) |
| IGH.forP4.1_12N | ACACTCTTTCCCTACACGACGCTCTTCCGATCT(N)(N)(N)(N)(N)(N)(N)(N)(N)(N)(N)(N)TG CAGCTGCAGGAGTCG (SEQ 1D NO: 364) |
| IGH.forP4.2_08N | ACACTCTTTCCCTACACGACGCTCTTCCGATCT(N)(N)(N)(N)(N)(N)(N)(N)GTGCAGCTAC AGCAGTGG (SEQ ID NO: 365) |
| IGH.forP4.2_12N | ACACTCTTTCCTACACGACGCTCTTCCGATCT(N)(N)(N)(N)(N)(N)(N)(N)(N)(N)(N)(N)GT GCAGCTACAGCAGTGG (SEQ ID NO: 366) |
| IGH.forP6_08N | ACACTCTTTCCCTACACGACGCTCTTCCGATCT(N)(N)(N)(N)(N)(N)(N)(N)GTACAGCTGC AGCAGTCA (SEQ ID NO: 367) |
| IGH.forP6_12N | ACACTCTTTCCCTACACGACGCTCTTCCGATCT(N)(N)(N)(N)(N)(N)(N)(N)(N)(N)(N)(N) GTACAGCTGCAGCAGTCA (SEQ ID NO: 368) |

LC_V forward primer pool[1]

| | |
|---|---|
| Vka_08N | ACACTCTTTCCCTACACGACGCTCTTCCGATCT(N)(N)(N)(N)(N)(N)(N)(N)GACATCCRGD TGACCCAGTCTCC (SEQ ID N0.369) |
| Vka_12N | ACACTCTTTCCCTACACGACGCTCTTCCGATCT(N)(N)(N)(N)(N)(N)(N)(N)(N)(N)(N)(N)GA CATCCRGDTGACCCAGTCTCC (SEQ ID NO: 370) |

TABLE 18-continued

Amplicon Primers.

| | |
|---|---|
| VKb_08N | ACACTCTTTCCCTACACGACGCTCTTCCGATCT(N)(N)(N)(N)(N)(N)(N)(N)GAAATTGTRW TGACRCAGTCTCC (SEQ ID NO: 371) |
| VKb_12N | ACACTCTTTCCCTACACGACGCTCTTCCGATCT(N)(N)(N)(N)(N)(N)(N)(N)(N)(N)(N)(N)GA AATTGTRWTGACRCAGTCTCC (SEQ ID NO: 372) |
| VKc_08N | ACACTCTTTCCCTACACGACGCTCTTCCGATCT(N)(N)(N)(N)(N)(N)(N)(N)GATATTGTGM TGACBCAGWCTCC (SEQ ID NO: 373) |
| VKc_12N | ACACTCTTTCCCTACACGACGCTCTTCCGATCT(N)(N)(N)(N)(N)(N)(N)(N)(N)(N)(N)(N)GA TATTGTGMTGACBCAGWCTCC (SEQ ID NO: 374) |
| VKd_08N | ACACTCTTTCCCTACACGACGCTCTTCCGATCT(N)(N)(N)(N)(N)(N)(N)(N)GAAACGACAC TCACGCAGTCTC (SEQ ID NO: 375) |
| VKd_12N | ACACTCTTTCCCTACACGACGCTCTTCCGATCT(N)(N)(N)(N)(N)(N)(N)(N)(N)(N)(N)(N)GA AACGACACTCACGCAGTCTC (SEQ ID NO: 376) |
| Vla_08N | ACACTCTTTCCCTACACGACGCTCTTCCGATCT(N)(N)(N)(N)(N)(N)(N)(N)CAGTCTGTSB TGACGCAGCCGCC (SEQ ID NO: 377) |
| Vla_12N | ACACTCTTTCCCTACACGACGCTCTTCCGATCT(N)(N)(N)(N)(N)(N)(N)(N)(N)(N)(N)(N)CA GTCTGTSBTGACGCAGCCGCC (SEQ ID NO: 378) |
| VLb_08N | ACACTCTTTCCCTACACGACGCTCTTCCGATCT(N)(N)(N)(N)(NXN)(N)CN)TCCTATGWGC TGACWCAGCCAC (SEQ ID NO: 379) |
| VLb_12N | ACACTCTTTCCCTACACGACGCTCTTCCGATCT(N)(N)(N)(N)(N)(N)(N)(N)(N)(N)(N)(N)TC CTATGWGCTGACWCAGCCAC (SEQ ID NO: 380) |
| VLc_08N | ACACTCTTTCCCTACACGACGCTCTTCCGATCT(N)(N)(N)(N)(N)(N)(N)(N)TCCTATGAGC TGAYRCAGCYACC(SEQ ID NO: 381) |
| VLc_12N | ACACTCTTTCCCTACACGACGCTCTTCCGATCT(N)(N)(N)(N)(N)(N)(N)(N)(N)(N)(N)(N)TC CTATGAGCTGAYTCAGCYACC (SEQ ID NO: 382) |
| VLd_08N | ACACTCTTTCCCTACACGACGCTCTTCCGATCT(N)(N)(N)(N)(N)(N)(N)(N)CAGCCTGTGC TGACTCARYC (SEQ ID NO: 383) |
| VLd_12N | ACACTCTTTCCCTACACGACGCTCTTCCGATCT(N)(N)(N)(N)(N)(N)(N)(N)(N)(N)(N)(N)CA GCCTGTGCTGACTCARYC (SEQ ID NO: 384) |
| Vle_08N | ACACTCTTTCCCTACACGACGCTCTTCCGATCT(N)(N)(N)(N)(N)(N)(N)(N)CAGDCTGTGG TGACYCAGGAGCC (SEQ ID NO: 385) |
| Vle_12N | ACACTCTTTCCCTACACGACGCTCTTCCGATCT(N)(N)(N)(N)(N)(N)(N)(N)(N)(N)(N)(N)CA GDCTGTGGTGACYCAGGAGCC (SEQ ID NO: 386) |
| VLf_08N | ACACTCTTTCCCTACACGACGCTCTTCCGATCT(N)(N)(N)(N)(N)(N)(M)(N)CAGCCWGKG CTGACTCAGCCMCC (SEQ ID NO: 387) |
| VLf_12N | ACACTCTTTCCCTACACGACGCTCTTCCGATCT(N)(N)(N)(N)(N)(N)(N)(N)(N)(N)(N)(N)CA GCCWGKGCTGACTCAGCCMCC (SEQ ID NO: 388) |
| VLg_08N | ACACTCTTTCCCTACACGACGCTCTTCCGATCT(N)(N)(N)(N)(N)(N)(N)(N)TCCTCTGAGC TGASTCAGGASCC (SEQ ID NO: 389) |
| VLg_12N | ACACTCTTTCCCTACACGACGCTCTTCCGATCT(N)(N)(N)(N)(N)(N)(N)(N)(N)(N)(N)(N)TC CTCTGAGCTGASTCAGGASCC (SEQ ID NO: 390) |
| VLh_08N | ACACTCTTTCCCTACACGACGCTCTTCCGATCT(N)(N)(N)(N)(N)(N)(N)(N)CAGTCTGYYC TGAYTCAGCCT (SEQ ID NO: 391) |
| VLh_12N | ACACTCTTTCCCTACACGACGCTCTTCCGATCT(N)(N)(N)(N)(N)(N)(N)(N)(N)(N)(N)(N)CA GTCTGYYCTGAYTCAGCCT (SEQ ID NO: 392) |
| Vli_08N | ACACTCTTTCCCTACACGAC:GCTCTTCCGATCT(N)(N)(N)(N)(N)(N)(N)(N)AATTTTATGC TGACTCAGCCCC (SEQ ID NO: 393) |
| Vli_12N | ACACTCTTTCCCTACACGACGCTCTTCCGATCT(N)(N)(N)(N)(N)(N)(N)(N)(N)(N)(N)(N)AA TTTTATGCTGACTCAGCCCC (SEQ ID NO: 394) |

TABLE 18-continued

Amplicon Primers.

Illumina sample index primers[2]

| | |
|---|---|
| PE1_A6 | AATGATACGGCGACCACCGAGATCTACACCGGTTAAAACACTCTTTCCCTACACGACG<br>CTCTTCCGATCT (SEQ ID NO: 395) |
| PE2_A6 | CAAGCAGAAGACGGCATACGAGATAAATTGGCGTGACTGGAGTTCAGACGTGTGCTCT<br>TCCGATCT(SEQ ID NO: 396) |
| PE1_A12 | AATGATACGGCGACCACCGAGATCTACACGAACATAAACACTCTTTCCCTACACGACG<br>CTCTTCCGATCT(SEQ ID NO: 397) |
| PE2_A12 | CAAGCAGAAGACGGCATACGAGATAATACAAGGTGACTGGAGTTCAGACGTGTGCTCT<br>TCCGATCT (SEQ ID NO: 308) |
| PE1_A4 | AATGATACGGCGACCACCGAGATCTACACACTGGTAAACACTCTTTCCCTACACGACG<br>CTCTTCCGATCT (SEQ ID NO: 399) |
| PE2_A4 | CAAGCAGAAGACGGCATACGAGATAATGGTCAGTGACTGGAGTTCAGACGTGTGCTCT<br>TCCGATCT (SEQ ID NO: 400) |

[1]The 5' end of the primers correspond to adapter sequences for PE indexing, the middle 8 or 12 Ns for random barcode UMIs (unique molecular identifiers), followed by gene-specific sequences (constant domain reverse or framework 1 region forward). Primer design was based on primers used in Vollmers et al. 2013, Proc. Natl Acad. Sci. USA 110 (33) 13463-13468 and Waltari et al. 2019. At each N position, oligos were synthesized using a 25/25/25/25 mix of each nucleotide.
[2]See Illumina® Sequencing: Multiplexed Sequencing with the Illumina Genome Analyzer System, Illumina, Pub. No. 770-2008-011, Dec. 2,2008 (e.g., A1 does not multiplex well with A2 and A3 when the sample number is less than 5).

BCR Amplicon Preparation. Total RNA yields from the PBMC and stimulated PBMCs were determined by absorbance at 260 nm on the NanoDrop™ One (Thermo Fisher Scientific). An input of 100 ng total RNA was used for first strand cDNA synthesis with gene-specific reverse transcription (RT) primers directed to the constant regions. The RT primers for IgG, IgM, IgA and lambda were pooled, whereas the kappa RT was done in a separate reaction. Light chain kappa RT was carried out in separate reactions because the transcript abundance and amplification efficiency tended to out-compete heavy and lambda chains in multiplexed reactions. Primers are shown in Table 18. One hundred nanograms total RNA was added on ice to 10 µM of pooled RI primers for HC/lambda or kappa chain (primer pools as described above and in Table 18) and 1 mM of dNTP in a 10 µl final volume, allowed to anneal for 3 min at 72° C., and returned to ice. First strand reverse transcription was performed using SuperScript III RT (200 U/µl, Thermo Fisher Scientific). To the 10 µl annealed sample, on ice, 4 µl of 5× Superscript RT buffer, 1 µl 0.1M dithiothreitol, 1 µl Superase-IN (20 U/µl, Thermo Fisher), and of RNase free water were added, to give a final volume of 20 µl. cDNA was made in a thermocycler for 1 hour at 50° C., 5 min 85° C., 4° C. hold, Second-strand cDNA was synthesized using Phusion High Fidelity Polymerase (Thermo Fisher). To the 20 µl first strand cDNA, 10 µl of 5× Phusion buffer, 1 µl of 10 mM dNTPs, 0.5 µl Phusion Taq, 1.5 µl DMSO, 7 µl of RNase free water, and 10 µl of the 10 µM pool of forward primers (as described above and shown in Table 18), were added, to give a final volume of 50 µl. Samples were incubated at 98° C. for 4 min, 52° C. for 1 min, 72° C. for 5 min and 4° C. hold. Double-stranded cDNA was transferred to a low retention DNase-free 1.5 ml Eppendorf tube and purified two times using Agencourt® AMPure® XP beads (Beckman Coulter, Brea, CA), at a volume ratio of 1:1, and eluted in 25 µl of Qiagen EB buffer. Double-stranded cDNA was PCR amplified with Platinum DNA Polymerase High Fidelity (5 U/µl HiFi Taq, Thermo Fisher). To the 25 µl of eluted second strand cDNA, 5 µl of 10×HiFi Taq buffer, 2 µl of 50 mM MgSO4, 1 µl 10 mM dNTPs, 0.2 HiFi Taq, 1 µl each of two PE primers completing Illumina adapter sequences (Table 18) and 14.8 µl of water, were added, to give a final volume of 50 µl. Samples were run at 94° C. for 2 min, 27 cycles of 94° C. for 30 sec, 65° C. for 30 sec, and 68° C. for 2 min, followed by 68° C. for 7 min and 4° C. hold. Final libraries were run on 2% E-Gel™ EX agarose gels (Thermo Fisher Scientific) and bands extracted with Quantum Prep Freeze N' Squeeze™ DNA Extraction Spin Columns (BioRad, Hercules, CA). After one clean-up with 1:1 Agencourt® AMPure® XP beads, amplicons were eluted in 25-35 µl Qiagen EB. An aliquot was diluted to 5-500 µg/µl and 2 µl quantified on the Agilent Fragment Analyzer Automated CE System using the DNF-474 High Sensitivity, 1 bp-6000 bp, NGS Fragment Analysis Kit (Advanced Analytical Technologies, Agilent Technologies, Santa Clara, CA), according to the manufacturer's instructions. Pairs of samples (PBMC and stimulated PBMC amplicons) were sequenced together using different Illumina barcodes to demultiplex after sequencing, Amplicon mixtures corresponding to 10:1 ratios of heavy chain+lambda:kappa were submitted for 300 forward×250 reverse sequencing with MiSeq v3 kits (Illumina) at the Chan Zuckerberg Biohub Genomics Center, Addition of 15-20% v/v PhiX Control Library was added to increase sequence diversity and overall sequencing performance. Each MiSeq run resulted in 7.5-20 million paired raw reads, which was reduced to 0.5-3.5 million unique Ig sequences after processing. All MiSeq data was deposited in the NCBI Sequence Read Archive (SRA) database under accession PRJNA524904.

BCR Repertoire Data Analysis Pipeline, After completion of MiSeq sequencing, antibody repertoires were analyzed using methods based on the Immcantation pipeline. An overview of BCR sequencing analysis and practical considerations included in the Immcantation pipeline, are reviewed in Yaari, G. and Kleinstein, S. H., 2015, Genome Medicine, Vo. 7, Article 121 (doi: 10.1186/s13073-015-0243-2). This pipeline, available at immcantation.readthedocs.io, continues to be updated as the field advances, and is composed of multiple software packages: pRESTO, Change-O, SHazaM, TIgGER, and Alakazam. Because the Immcantation pipeline can be run using Docker containers, a cloud-based workflow was created incorporating Reflow (available at github.com/grailbio/reflow) that allowed for seamless processing of the constituent Immcantation software packages. The workflow is available at Github (github.com/czbiohub/bcell_pipeline). Some key characteristics of this new workflow include the use of unique molecular identifiers (UMIs) at both 5' and 3' ends of the Ig sequences, the collapse of sequences with identical UMIs, the use of the IgBLAST algorithm (Ye, J. et al., 2013, *Nucleic Acids Research* 41 (Web Server Issue): W34-W40, pub. online May 11, 2013) to calculate general Ig characteristics of each sequence, and the determination of clonal families by first calculating a clonal threshold nucleotide distance via a nearest-neighbor algorithm and then collapsing sequences based on this threshold (Gupta, N. T. et al., 2017, J. Immunology 198(6):2489-2499). We ran the initial steps using the pRESTO script (presto-abseq.sh at bitbucket.org/kleinstein/immcantation/src/97a70949607b6671a182a84d5052b705d1677891/pipelines/?at=default) with variations that are included in the Github repository for this work. Given that sample and amplicon preparation included UMIs of varying lengths at both 5' and 3' ends to improve sequencing quality, code to standardize the UNIT length for subsequent steps (8 bp at each end) was included. The script first removes reads with average Q scores less than 20, and then annotates the reads based on 5' or 3' amplicon primers. All reads with identical UMIs are then collapsed, with consensus sequences created and UMI numbers annotated into the sequence name. This is followed by assembly of 5' and 3' paired-ends, at which point the UMIs at both ends are combined to create a 16 bp signature per cDNA transcript, also annotated into the sequence name. In the next step, the constant regions are re-analyzed for each paired read, and isotype and subtype annotated into the sequence name. The final pRESTO steps include collapsing of identical BCR sequences of the same isotype followed by filtering to only include BCR sequences that were found in 2 or more representative reads per UMI, to avoid including sequences that vary only due to sequencing error. The workflow continues with subsequent Immcantation packages, using the following scripts without changes at the website above: Change-0 IgBLAST (changed-igblast.sh), which calculates Ig repertoire characteristics, TigGER (tigger-genotype.R), which estimates novel V-gene alleles, SHazaM (shazam-threshold.R), which determines the optimal threshold for delineating clonal families, and Change-O Clone (changeo-clone.sh) that groups the sequences into clonal families. Lastly, a series of R scripts based on Alakazam were used to visualize results (scripts available at the Github page for this work). This workflow includes both heavy and light chain reads, and all outputs include both sequences, but without knowledge of pairing. As such, analysis was focused only on the more diverse heavy chain results. In addition to the Immcantation procedure of optimizing the clonal threshold value during each analysis (using SHazaM), a second strategy to identify mAb matches to clonal families in the repertoire was used. For these comparisons, all unique heavy chain sequences (i.e. not only those with 2 or more UMIs) were included, the mAb sequences appended, and a constant 12% threshold value in Change-0 was applied to delineate clonal families.

B. Results

Figure 12A:
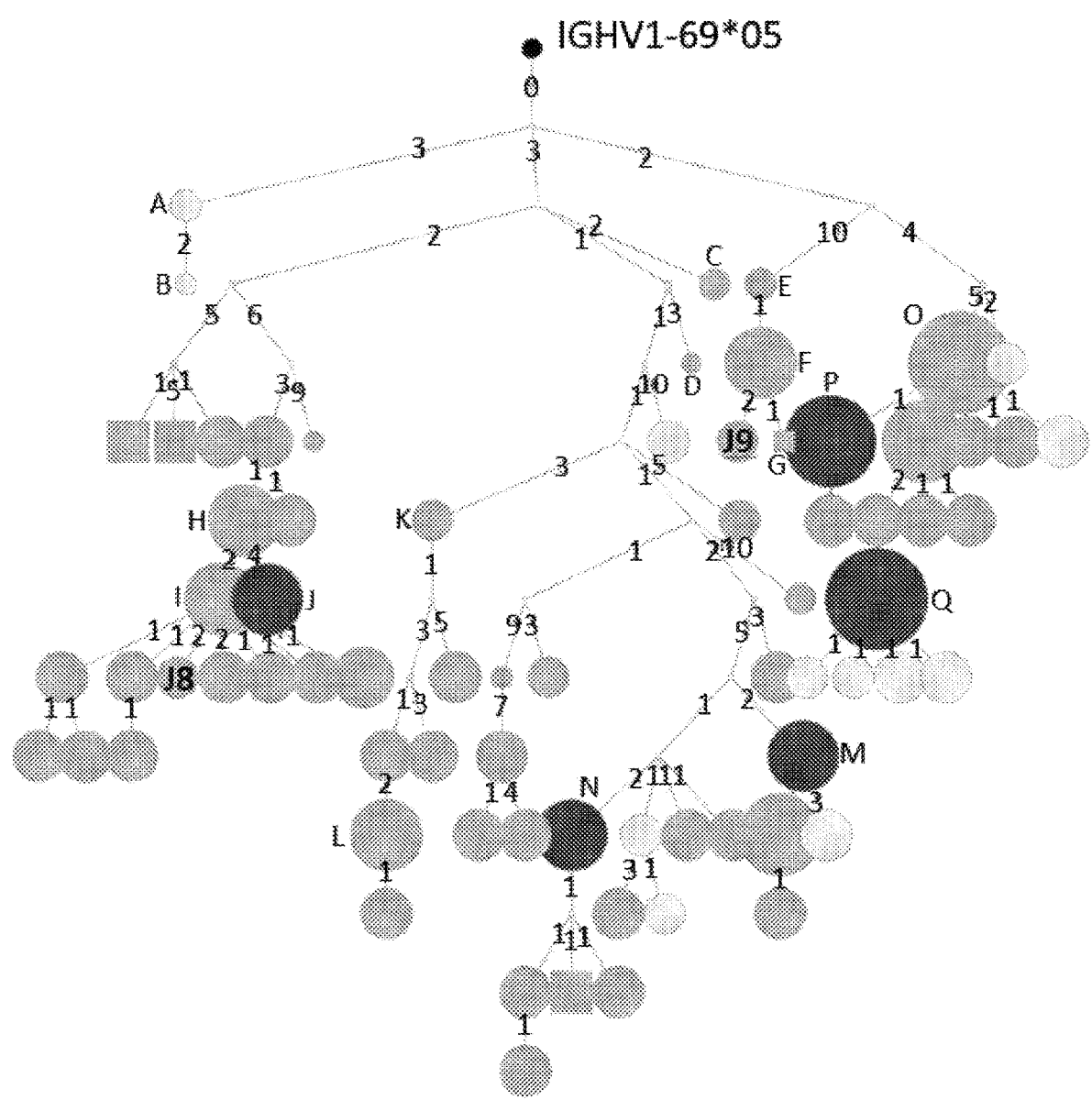
FIG. 12A shows a parsimony-based network construction of heavy chain sequences clonally related to J8 & J9 VH at the nucleotide level according to certain aspects of this disclosure. Sequences derived from PBMC are shown in the lightest gray, stimulated-PBMC in medium gray, and dark gray corresponds to clones identified in both sample conditions. IgG and IgA isotype clones are depicted by circles and squares, respectively, and the size of the shape correlates to the number of sequencing reads with unique molecular identifiers. The numbers along lines of the lineage represent the nucleotide changes from the founding IGVH1-69*05 germline. The letters correspond to sequences provided at the nucleotide and amino acid level in Tables 19A-19B.

In the repertoire of sample 1-013-02, a total of 43,758 BCR sequences related to the variable heavy chain (VH) of J9 and J8 were identified. Nine and fourteen clones with a 100% match at the nucleotide level to J9 and J8 in the stimulated PBMC repertoire were identified, respectively. A parsimony-based network construction of the heavy chain sequences clonally related to J8 & J9 VH at the nucleotide level is shown in FIG. 12A. Sequences were limited to 118 that met 3 criteria: 1) highest numbers of unique molecular identifier (UMI) counts (>35 in PBMC repertoire and >150 in stimulated PBMC repertoire IgG sequences and >15 in IgA sequences), 2) <5% somatic hypermutation, and 3) 97% identity to J9 or J8 sequences. The J9 and J8 lineage derived from a founder clone using a VDJ recombination of IGHV1-69 with IGHD2-2 and MEW with no CDRH3 insertions or deletions. The majority of clones were of the $IgG_1$ subtype, with no IgM identified having a UMI count >2 and only a small percentage of IgA (1.8% of stimulated PBMC relatives; FIG. 12A, squares). The numbers along lines of the lineage represent the nucleotide changes from the founding IGVH1-69*05 germline. Sequences obtained from the PBMC repertoire are shown in the lightest gray and the greater number obtained from the antigen-enriched stimulated PBMC repertoire, are shown in gray. Sequences found in both sample conditions are shown in dark gray. The relative size of the circles correlates to the number of reads for the sequence, which in turn is thought to correlate to the number of B cells present in the sample, with larger circles representing more abundant clones. These abundant clones, the founder clone and a consensus sequence derived from the 43,758 clonotypes are listed by nucleotide and amino acid sequence in Tables 19A-19B. Regarding Table 19A, forward primers used for NGS do not cover the first 24 nucleotides (8 amino acids) in VH framework 1. Many positions indicate a selection pressure preference for a particular size, charge, or hydrophobicity as shown in Table 20. The framework 2 glycine insertion of J9v1 was removed in a recombinant mAb variant (J9) and shown to not be necessary for function as shown in Example 8. Variant VH sequences would preferably retain the identity of the invariable amino acid residues identified in Table 20 so as to reduce likelihood of impact on function.

Overall, the repertoire showed a rapid expansion of class switched $IgG_1$ with numerous point nucleotide (nt) mutations from germline, strongly suggesting both J9 (28 nt) and J8 (27 nt) plasmablasts derived from memory B cells from a prior infection. Less mutated IgG clones A (3 nt), B (5 nt), and C (5 nt) close to the top of the tree of the acute phase repertoire could represent antibodies derived from a de novo immune response, or from less mutated memory clones. Several VH mutations occur towards the top of the lineage tree including CDR-H2 I53F, CDR-H3 T99A/P and D100cH (FIG. 12A, clones labeled A, B and C), and are retained throughout the continued somatic hypermutation (SH v1) of the VH, and therefore may be required for activity. An amino acid alignment of the founder, J9 and J8 VH sequences is shown in FIG. 12B (full sequences listed in Table 21A; founder CDR sequences listed in Table 21B), The three residues that are predicted to be key for improving or initiating the founder clone's binding to DENV are in bold. The numbering used in Table 20 and FIG. 12B follows the Kabat system (Kabat E. A. et al, 1991, *Sequences of Proteins Immunological Interest*, Fifth Edition. NIH Publication No. 91-3242) and the CDRs are defined using a combination of residues defined by Chothia C. and Lesk M., 1987, J Mol Biol. 196: 901-917 and Kabat (1991).

TABLE 19A

J8 and J9 Clonally-Related Heavy Chain Nucleotide Sequences

| Clone | VH nucleotide sequence |
|---|---|
| founder | GCTGAGGTGAAGAAGCCTGGGTCCTCGGTGAAGGTCTCCTGCAAGGCTTCTGGAGGCACCTTCAGCAGCTATGCTATCAGC<br>TGGGTGCGACAGGCCCCTGGACAAGGGCTTGAGTGGATGGGAGGGATCATCCCTATCTTTGGTACAGCAAACTACGCACA<br>GAAGTTCCAGGGCAGAGTCACGATTACCACGGACGAATCCACGAGCACAGCCTACATGGAGCTGAGCAGCCTGAGATCTG<br>AGGACACGGCCGTGTATTACTGTGCGAGATATTGTAGTAGTACCAGCTGCTATCACAACTGGTTCGACCCCTGGGGCCAGG<br>GAACCCTGGTCACCGTCTCCTCA (SEQ ID NO: 401) |
| A | GCTGAGGTGAAGAAGCCTGGGTCCTCAGTGAAGGTCTCCTGCAAGGCTTCTGGAGGCACCTTCAGCAGCTATGCTATCAGC<br>TGGGTGCGACAGGCCCCTGGACAAGGGCTTGAGTGGATGGGAGGGATCATCCCTATCTTTGGTACAGCAAACTACGCACA<br>GAAGTTCCAGGGCAGAGTCACGATTACCACGGACGAATCCACGAGCACAGCCTACATGGAGCTGAGCAGCCTGAGATCTG<br>AGGACACGGCCGTGTATTACTGTGCGAGATACTGTTACAGTGCCAGTTGTTATCACAACTGGTTCGACCCCTGGGGCCAGG<br>GAACGCTGGTCACCGTCTCCTCA (SEQ ID NO: 402) |
| B | GCTGAGGTGAAGAAGCCTGGGTCCTCGGTGAAGGTCTCCTGCAAGGCTTCTGGAGGCACCTTCAGCAGCTATGCTATCAGC<br>TGGGTGCGACAGGCCCCTGGACAAGGGCTTGAGTGGATGGGAGGGATCATCCCTATCTTTGGTACAGCAAACTACGCACA<br>GAAGTTCCAGGGCAGAGTCACGATTACCGCGGACAAATCCACGAGCACAGCCTACATGGAGCTGAGCAGCCTGAGATCTG<br>AGGACACGGCCGTGTATTACTGTGCGAGATACTGTTACAGTGCCAGTTGTTATCACAACTGGTTCGACCCCTGGGGCCAGG<br>GAACGCTGGTCACCGTCTCCTCA (SEQ ID NO: 403) |
| C | GCTGAGGTGAAGAAGCCTGGGTCCTCAGTGAAGGTCTCCTGCAAGGCTTCTGGAGGCACCTTCAGCAGCTATGCTATCAGC<br>TGGGTGCGACAGGCCCCTGGACAAGGGCTTGAGTGGATGGGAGGGATCATCCCTTTCTTTGGTACAAGAGACCACGCACA<br>GAACTTCCAGGGCAGAGTCACGATTACCACGGACGAATCCACGAGCACAGCCTACATGGAGCTGAGCAGCCTGAGATCTG<br>AGGACACGGCCGTCTATTACTGTGCGAGATATTGTAGTAGTCCCAGTTGTTATCACAACTGGTTCGACCCCTGGGGCCAGG<br>GAACCCTGGTCACCGTCTCCTCA (SEQ ID NO: 404) |
| D | GCTGAGGTGAAGAAGCCTGGGTCCTCGGTGAAGGTCTCCTGCAAGGCTTCTGGAGGCACCTTCAGCAGCTATGCTATCAGC<br>TGGGTGCGACAGGCCCCTGGACAAGGGCTTGAGTGGATGGGAGGGATCATCCCTATCTTTGGTACAGCAAACTACGCACA<br>GAAGTTCCAGGGCAGAGTCACGATTACCGCGGACAAATCCACGAGCACAGCCTACATGGAGCTGAGCAGCCTGAGATCTG<br>AGGACACGGCCGTGTATTACTGTGCGAGATATTGTAGTAGTGCCAGTTGCTATCACAACTGGTTCGACCCCTGGGGCCAGG<br>GAACCCTGGTCACCGTCTCCTCA (SEQ ID NO: 405) |
| E | GCTGAGGTGAGGAAGCCTGGGTCCTCAGTGAAGGTCTCCTGCAAGATTTCTGGAGGCTCCCTCAACAGTTATGGCATCAGC<br>TGGGTGCGACAGGCCCCTGGTGGACAAGGGCTTGAGTGGATGGGAGGGATCATCCCTTTCTTTGGTACAGTTATCTATTCA<br>GACAATTACCAGGACAGAGTCTCGTTTTCCTCGGACGAATCTACGACCACAGCCTACATGGAGCTGAGAAGCCTAAGATCT<br>GAGGACACGGCCGTGTATTACTGTGCGAGATATTGTTATAGTGCCAGTTGTTATCACAACTGGTTCGACCCCTGGGGCCAG<br>GGAACCCTGGTCACCGTCTCCTCA (SEQ ID NO: 406) |
| F | GCTGAGGTGAGGAAGCCTGGGTCCTCAGTGAAGGTCTCCTGCAAGATTTCTGGAGGCTCCCTCAACAGTTATGGCATCAGC<br>TGGGTGCGACAGGCCCCTGGTGGACAAGGGCTTGAGTGGATGGGAGGGATCATCCCTTTCTTTGGTACAGTTATCTATTCA<br>GACAATTACCAGGACAGAGTCTCGTTTTCCTCGGACGAATCTACGACCACAGCCTACATGGAGCTGAGAAGCCTAAGATCT<br>GAGGACACGGCCGTGTATTACTGTGCGAGATATTGTTATAGTGCCAGTTGTTATCACAACTGGTTCGACCCCTGGGGCCAG<br>GGAACCCTGGTCACCGTCTCCACA (SEQ ID NO: 407) |
| G | GCTGAGGTGAGGAAGCCTGGGTCCTCAGTGAAGGTCTCCTGCAAGATTTCTGGAGGCTCCCTCAACAGTTATGGCATCAGC<br>TGGGTGCGACAGGCCCCTGGTGGACAAGGGCTTGAGTGGATGGGAGGGATCATCCCTTTCTTTGGTACAGTTATCTATTCA<br>GACAATTACCAGGACAGAGTCTCGTTTTCCTCGGACGAATCTACGACCACAGCCTACATGGAGCTGAGAAGCCTAAGATCT<br>GAGGACACGGCCGTGTATTACTGTGCGAGGTATTGTTATAGTGCCAGTTGTTATCACAACTGGTTCGACCCCTGGGGCCAG<br>GGAACCCTGGTCACCGTCTCCACA (SEQ ID NO: 408) |
| H | GCTGAGGTGAAGAAGCCTGGGTCCTCAGTTAAGGTCTCCTGCAAGGCTTCTGGAGGCACCTTCAGCAGCAATTCTGTCACC<br>TGGGTGCGACAGGCCCCTGGACACGGGCTTGAGTGGATGGGAACAATCGTCCCTTTCTTTGGTACAAGACACTCCGCAGAC<br>AACTTTCAGGGCAGAGTCACGATCACCACGGACGAATCCACGACCACAGTGTACATGGAGCTGAGCAGCCTGAGATCTGA<br>CGACACGGCCGTGTATTACTGTGCGAGATCTTGTGAGAGTCCCAGTTGTTACCACAACTGGTTCGACCCCTGGGGCCAGGG<br>AACCCTGGTCACCGTCACCTCA (SEQ ID NO: 409) |
| I | GCTGAGGTGAAGAAGCCTGGGTCCTCAGTGAAGGTCTCCTGCAAGGCTTCTGGAGGCACCTTCAGCAGCAATTCTGTCAC<br>TGGGTGCGGCAGGCCCCTGGACACGGGCTTGAGTGGATGGGAACAATCATCCCTTTCTTTGGTACAAGACACTACGCAGA<br>CAACTTTCAGGGCAGAGTCACGATCACCACGGACGAATCCACGACCACAGTGTACATGGAGCTGAGCAGCCTGAGATCTG<br>ACGACACGGCCGTGTATTACTGTGCGCGATCTTGTGAGAGTCCCAGTTGTTACCACAACTGGTTCGACCCCTGGGGCCAG<br>GAACCCTGGTCACCGTCACCTCA (SEQ ID NO: 410) |
| J | GCTGAGGTGAAGAAGCCTGGGTCCTCAGTGAAGGTCTCCTGCAAGGCTTCTGGAGGCACCTTCAGCAGCAATTCTGTCACC<br>TGGGTGCGGCAGGCCCCTGGACACGGGCTTGAGTGGATGGGAACAATCATCCCTTTCTTTGGTACAAGACACTACGCAGA<br>CAACTTTCAGGACAGAGTCACGATCACCACGGACGAATCCACGACCACAGTGTATATGGAACTGAGCAGCCTGAGATCTG<br>ACGACACGGCCCTGTATTACTGTGCGAGATCTTGTGAGAGTCCCAGTTGTTACCACAACTGGTTCGACCCCTGGGGCCAGG<br>GAACCCTGGTCACCGTCACCTCA(SEQ ID NO: 411) |
| K | GCTGAGGTGAAGAAGCCTGGGTCCTCAGTGAAGGTCTCCTGCAAGGCTTCTGGAGGCACCTTCAGCAACTATGCTATCAGC<br>TGGGTGCGACAGGCCCCTGGACAAGGGCTTGAGTGGATGGGAGGGGTCACCCCTTTCTTTGGTACGAGAAACTACGCAGA<br>CATGTTCCAGGGCAGAGTCACGATTACCACGGACGAATCCACGAGCACAGTCTACATGGAGCTGAGCAGCCTGAGATCTG<br>AGGACACGGCCGTCTATTATTGTGCGAGATATTGTAGTAGTCCCAGCTGCTATCACAAGTGGTTCGACCCCTGGGGCCAGG<br>GAACCCTGGTCACCGTCTCCTCA (SEQ ID NO: 412) |
| L | GCTGAGGTGAAGAAGCCTGGGTCCTCAGTGAAGGTCTCCTGCAAGGCTTCTGGAGGCACCTTCAACAACTATGCCATCAGC<br>TGGGTGCGACAGGCCCCTGGACAAGGGCTTGAGTGGATGGGAGGGGTCACCCCTTTCTTTGGTACGAGAAACTACGCCGA<br>CATGTTCCAGGACAGAATCACGATTACCACGGACGAATCCACGACCACAGTCTACATGGAACTGAGCAGCCTGAGATCTG |

TABLE 19A-continued

J8 and J9 Clonally-Related Heavy Chain Nucleotide Sequences

| Clone | VH nucleotide sequence |
|---|---|
|  | AAGACACGGCCGTCTATTATTGTGCGAGATACTGTAGTAATCCCAGCTGCTATCACAAGTGGTTCGACCCCTGGGGCCAGG GAACCCTGGTCACCGTCTCCTCA((SEQ ID NO: 413) |
| M | GCTGAGGTGAAGAAGCCTGGGTCCTCAGTGAAGGTCTCCTGCAAGCCTTCTGGAGGCACCTTCAGCCGTAGTTATGGTCTC GCGTGGGTGCGGCAGGCCCCTGGACAAGGGCTTGAGTGGATGGAGGGATCATCCCGTTCTTTGGTACAAGAAACTACGC AGACGACTTCCAGGACAGAATCACGCTTACGACGGACGAAACCACGACCACAGCCTACATGGAGCTGAGCAGCCTGAGAT CTGAGGACACGGCCGTGTATTACTGTGCGAGATATTGTAGTAGTGCCAGTTGCTATCACAACTGGTTCGACCCCTGGGGCC AGGGAACCCTGGTCACCGTCTCCTCA (SEQ ID NO: 414) |
| N | GCTGAGGTGAAGAAGCCTGGGTCCTCAGTTAAGGTCTCCTGCAAGCCTTCTGGAGGCACCTTCAGCGGTAGTTATGGTCTC GCGTGGGTGCGGCAGGCCCCTGGACAAGGGCTTGAGTGGATGGGAGGGATCATCCCTTTCTTTGGGACAAGAAACTACGC AGACGACTTCCAGGACAGAGTCACACTAACCACGGACGAAACCACGACCACAGCCTACATGGAGCTGAGCAGCCTGAGAT CTGAGGACACGGCCGTCTATTACTGTGCGAGATATTGTAGTAGTGCCAGTTGCTATCACAACTGGTTCGACCCCTGGGGCC AGGGAACCCTGGTCACCGTCTCCTCA (SEQ ID NO: 415) |
| O | GCTGAGGTGAAGAAGCCTGGGTCCTCAGTGAAGGTCTCCTGCAGGGCTTCTGGAGGCCCCTTCAATAGCTATGGTATCACC TGGGTGCGACAGGCCCCTGGACAAGGGCTTGAGTGGATGGGAGGGATCAGCCCCTTTCTTTGGGACACGAAACTACGCAGA GAGGTTCCAAGACAGACTCACGATTACCACGGACGAATCCACGACCGCAGCCTACATGGAGCTGCAGCCTGACATCTG ACGACACGGCCGTCTATTACTGTGCGAGATATTGTTACAGTGCCAGTTGTTATCACAACTGGTTCGACCCCTGGGGCCAGG GAACCCTGGTCACCGTCTCCTCA (SEQ ID NO: 416) |
| P | GCTGAGGTGAAGAAGCCTGGGTCCTCAGTGAAGGTCTCCTGCAGGGCTTCTGGAGGCCCCTTCAATAGCTATGGTATCACC TGGGTGCGACAGGCCCCTGGACAAGGGCTTGAGTGGATGGGAGGGATCAGCCCTTTCTTTGGTACACGAAACTACGCAGA GAGGTTCCAAGACAGACTCACGATTAGCACGGACGAATCCACGACCGCAGCCTACATGGAGCTGCGCAGCCTGACATCTG ACGACACGGCCGTCTATTACTGTGCGAGATATTGTTACAGTGCCAGTTGTTATCACAACTGGTTCGACCCCTGGGGCCAGG GAACCCTGGTCACCGTCTCCTCA (SEQ ID NO: 417) |
| Q | GCTGAGGTGAAGAAGCCTGGGTCCTCAGTGAAGGTCTCCTGCAGGGCTTCTGGAGGCCCCTTCAATAGTTATGGTATCACC TGGGTGCGACAGGCCCCTGGACAAGGGCTTGAGTGGATGGGAGGGATCAGCCCTTTCTTTGGGACACGAAACTACGCAGA GAGGTTCCAAGACAGACTCACGATTACCACGGACGAGTCTACGACCGCAGCCTACATGGAGCTGCGCAGCCTGACATCTG ACGACACGGCCGTCTATTACTGTGCGAGATACTGTTACAGTGCCAGTTGTTATCACAACTGGTTCGACCCCTGGGGCCAGG GAACGCTGGTCACCGTCTCCTCA (SEQ ID NO: 418) |
| consensus | GCTGAGGTGAAGAAGCCTGGGTCCTCAGTGAAGGTCTCCTGCAAGGCTTCTGGAGGCACCTTCAGCAGCTATGGTATCACC TGGGTGCGACAGGCCCCTGGACAAGGGCTTGAGTGGATGGGAGGGATCATCCCTTTCTTTGGTACAAGAAACTACGCAGA CAACTTCCAGGACAGAGTCACGATTACCACGGACGAATCCACGACCACAGCCTACATGGAGCTGAGCAGCCTGAGATCTG ACGACACGGCCGTGTATTACTGTGCGAGATATTGTAGTAGTGCCAGTTGTTATCACAACTGGTTCGACCCCTGGGGCCAGG GAACCCTGGTCACCGTCTCCTCA (SEQ ID NO: 419) |

TABLE 19B

J8 and J9 Clonally-Related Heavy Chain Amino Acid Sequences

| Clone | VH amino acid sequence |
|---|---|
| founder | AEVKKPGSSVKVSCKASGGTFSSYA ISWVRQAPGQGLEWMGGIIPIFGTA NYAQKFQGRVTITTDESTSTAYMEL SSLRSEDTAVYYCARYCSSTSCYDN WFDPWGQGTLVTVSS (SEQ ID NO: 420) |
| A | AEVKKPGSSVKVSCKASGGTFSSYA ISWVRQAPGQGLEWMGGIIPIFGTA NYAQKFQGRVTITTDESTSTAYMEL SSLRSEDTAVYYCARYCYSASCYHN WFDPWGQGTLVTVSS (SEQ ID NO: 421) |
| B | AEVKKPGSSVKVSCKASGGTFSSYA ISWVRQAPGQGLEWMGGIIPIFGTA NYAQKFQGRVTITADKSTSTAYMEL SSLRSEDTAVYYCARYCYSASCYHN WFDPWGQGTLVTVSS (SEQ ID NO: 422) |
| C | AEVKKPGSSVKVSCKASGGTFSSYA ISWVRQAPGQGLEWMGGIIPFFGTR DHAQNFQGRVTITTDESTSTAYMEL SSLRSEDTAVYYCARYCSSPSCYHN WFDPWGQGTLVTVSS (SEQ ID NO: 423) |
| D | AEVKKPGSSVKVSCKASGGTFSSYA ISWVRQAPGQGLEWMGGIIPIFGTA NYAQKFQGRVTITADKSTSTAYMEL SSLRSEDTAVYYCARYCSSASCYHN WFDPWGQGTLVTVSS (SEQ ID NO: 424) |
| E | AEVRKPGSSVKVSCKISGGSLNSYG ISWVRQAPGGQGLEWMGGIIPFFGT VIYSDNYQDRVSFSSDESTTTAYME LRSLRSEDTAVYYCARYCYSASCYH NWFDPWGQGTLVTVSS (SEQ ID NO: 425) |
| F | AEVRKPGSSVKVSCKISGGSLNSYG ISWVRQAPGGQGLEWMGGIIPFFGT VIYSDNYQDRVSFSSDESTTTAYME LRSLRSEDTAVYYCARYCYSASCYH NWFDPWGQGTLVTVST (SEQ ID NO: 426) |
| G | AEVRKPGSSVKVSCKISGGSLNSYG ISWVRQAPGGQGLEWMGGIIPFFGT VIYSDNYQDRVSFSSDESTTTAYME |

TABLE 19B-continued

J8 and J9 Clonally-Related Heavy Chain Amino Acid Sequences

| Clone | VH amino acid sequence |
|---|---|
|  | LRSLRSEDTAVYYCARYCYSASCYH<br>NWFDPWGQGTLVTVST<br>(SEQ ID NO: 427) |
| H | AEVKKPGSSVKVSCKASGGTFSSNS<br>VTWVRQAPGHGLEWMGTIVPFFGTR<br>HSADNFQGRVTITTDESTTTVYMEL<br>SSLRSDDTAVYYCARSCESPSCYHN<br>WFDPWGQGTLVTVTS<br>(SEQ ID NO: 428) |
| I | AEVKKPGSSVKVSCKASGGTFSSNS<br>VTWVRQAPGHGLEWMGTIIPFFGTR<br>HYADNFQGRVTITTDESTTTVYME<br>LSSLRSDDTAVYYCARSCESPSCY<br>HNWFDPWGQGTLVTVTS<br>(SEQ ID NO: 429) |
| J | AEVKKPGSSVKVSCKASGGTFSSNS<br>VTWVRQAPGHGLEWMGTIIPFFGTR<br>HYADNFQDRVTITTDESTTTVYMEL<br>SSLRSDDTALYYCARSCESPSCYHN<br>WFDPWGQGTLVTVTS<br>(SEQ ID NO: 430) |
| K | AEVKKPGSSVKVSCKASGGTFSNYA<br>ISWVRQAPGQGLEWMGGVTPFFGTR<br>NYADMFQGRVTITTDESTSTVYMEL<br>SSLRSDTAVYYCARYCSSPSCYHK<br>WFDPWGQGTLVTVSS<br>(SEQ ID NO: 431) |
| L | AEVKKPGSSVKVSCKASGGTFNNYA<br>ISWVRQAPGQGLEWMGGVTPFFGTR<br>NYADMFQDRITITTDESTTTVYMEL<br>SSLRSEDTAVYYCARYCSNPSCYHK<br>WFDPWGQGTLVTVSS<br>(SEQ ID NO: 432) |
| M | AEVKKPGSSVKVSCKPSGGTFSGSY<br>GLAWVRQAPGQGLEWMGGIIPFFGT<br>RNYADDFQDRITLTTDETTTTAYME<br>LSSLRSEDTAVYYCARYCSSASCYH<br>NWFDPWGQGTLVTVSS<br>(SEQ ID NO: 433) |
| N | AEVKKPGSSVKVSCKPSGGTFSGSY<br>GLAWVRQAPGQGLEWMGGIIPFFGT<br>RNYADDFQDRVTLTTDETTTTAYME<br>LSSLRSEDTAVYYCARYCSSASCYH<br>NWFDPWGQGTLVTVSS<br>(SEQ ID NO: 434) |
| O | AEVKKPGSSVKVSCRASGGPFNSYG<br>ITWVRQAPGQGLEWMGGISPFFGTR<br>NYAERFQDRLTITTDESTTAAYMEL<br>RSLTSDDTAVYYCARYCYSASCYHN<br>WFDPWGQGTLVTVSS<br>(SEQ ID NO: 435) |
| P | AEVKKPGSSVKVSCRASGGPFNSYG<br>ITWVRQAPGQGLEWMGGISPFFGTR<br>NYAERFQDRLTISTDESTTAAYMEL<br>RSLTSDDTAVYYCARYCYSASCYHN<br>WFDPWGQGTLVTVSS<br>(SEQ ID NO: 436) |
| Q | AEVKKPGSSVKVSCRASGGPFNSYG<br>ITWVRQAPGQGLEWMGGISPSFGTR<br>NYAERFQDRLTITTDESTTAAYMEL<br>RSLTSDDTAVYYCARYCYSASCYHN<br>WFDPWGQGTLVTVSS<br>(SEQ ID NO: 437) |
| consensus | AEVKKPGSSVKVSCKASGGTFSSYG<br>ITWRQAPGQGLEWMGGIIPFFGTRN<br>YADNFQDRVTITTDESTTTAYMELS<br>SLRSDDTAVYYCARYCSSASCYHNW<br>FDPWGQGTLVTVSS<br>(SEQ ID NO: 438) |

TABLE 20

Variable and invariable amino acid usage in the VH region of the J9/J8 mAb clonal fam

| VH region | Variable positions | Invariable CDR positions |
|---|---|---|
| Framework 1 | K12R, K23R, A24T/I/P | — |
| CDR-H1 | T28S/P, F29L, S30N, S31N/G, S32insertion, Y33N, A34G/S, I35V/L, S35aT/A | G26, G27 |
| Framework 2 | G42insertionG, Q43H | — |
| CDR-H2 | G50T, I51V, I52V/T/S, I53F/S, A57R/V, N58D/I/H, Y59H/S, A60S, Q61D/E, K62N/M/D/R, F63Y, G65D | W47, M48, G49, P52a, F54, G55, T56 |
| Framework 3 | V67A/I/L, V68 T/S, I69F/V/L, T70S, T71A/S, E73K S74T, S76T, T77A, A78V, S82aR, E85R, V89L | — |
| CDR-H3 | Y95S, S97Y/E, S98N, T99A/P, N100dK | S100, C100a, Y100b, D100cH, W100e, F100f, D101, P102 |
| Framework 4 | S112T, S113T | — |

TABLE 21A

VH amino acid sequences aligned in FIG. 12B

| | |
|---|---|
| Founder VDJ | QVQLVQSGAEVKKPGSSVKVSCKASGGTF<br>SSYAISWVRQAPGQGLEWMGGUPIFGTAN<br>YAQKFQGRVTITTDESTSTAYMELSSLRS<br>EDTAVYYCARYCSSTSCYDNWFDPWGQGT<br>LVTVSS (SEQ ID NO: 439) |
| J9 mAb v1 | AEWKPGSSVKVSCKTSGGSLNSYGISWVR<br>QAPGQGLEWMGGIIPFFGTATYSDNYQG<br>RASFSSDESTTTAYMELRSLRSEDTAVYY<br>CARYCYSASCYHNWFDPWGQGTLVTVST<br>(SEQ ID NO: 440) |
| J8 mAb | AEVKKPGSSVKVSCKASGGTFSSNSVTWV<br>RQAPGHGLEWMGGIIPFFGTRHYADNFQG<br>RVTVTTDESTTTVYMELSSLRSDDTAVYY<br>CARSCESPSCYHNWFDPWGQGTLVTVTS<br>(SEQ ID NO: 441) |

TABLE 21B

Founder VH CDR sequences

| | |
|---|---|
| CDRH1 | GGITSSYAIS<br>(SEQ ID NO: 443) |
| CDRH2 | WNIGGIIPIFGTANYAQKFQG<br>(SEQ ID NO: 444) |
| CDRH3 | ARYCSSTSCYDNWFDP<br>(SEQ ID NO: 445) |

Clonotypes conforming to the J8/J9 lineage derived from deep sequencing 1-013-02 PBMC were also found in the same donor's convalescent PBMC sample (1-013-03; 227 sequences) and a second donor's acute and convalescent PBMC samples (1-(20-02 and 1-020-03; 36 and 3 sequences, respectively) from the same cohort of Colombian DENV patients. In addition, 82 clonotypes of J8 and J9 were identified by in silico analysis of sequences from a different cohort DENV patients from Nicaragua (subjects 289, 311, 320, 517 and 524) deposited in the Observed Antibody Space resource (antibodymap.org) by Parameswara P. et al. (Convergent antibody signatures in human dengue. *Cell Host Microbe* 13(6): 691-700). These sequences are expressly excluded from the embodiments described in this disclosure. The J9/J8 clonotypes were members of hundreds of thousands of VII sequences from the Nicaraguan cohort deposited but were not identified as convergent among subjects.

The light chains of both J9 and J8 used the same founder germline IGKV3-11 and IGKJ2 genes with identical CDR lengths (but include different 6nt insertions in CDRL3), and SHM (10 nt and 3nt, respectively) with only one mutation in common (CDRL2 position T56S). Immunoglobulin heavy and light chains assemble into a single BCR protein for binding and selection by antigen, therefore the LC sequences are expected to contribute uniquely to the activities of the J8 and J9 mAbs. However, as the NGS data does not include VH/VL pairing, relationships between the sequenced VII and VL repertoires cannot be assigned. It is expected that the VII founder sequence and the J8 and J9 VH sequences will function with LC other than those identified in the studies described in this disclosure. From the BCR repertoire analysis, the number of VL sequences are more than 100-fold fewer than HC sequences using 0.18/9 LC/HC sequence constraints.

Example 14. Broadly Neutralizing Antibodies from Divergent Lineages

Figure 13:
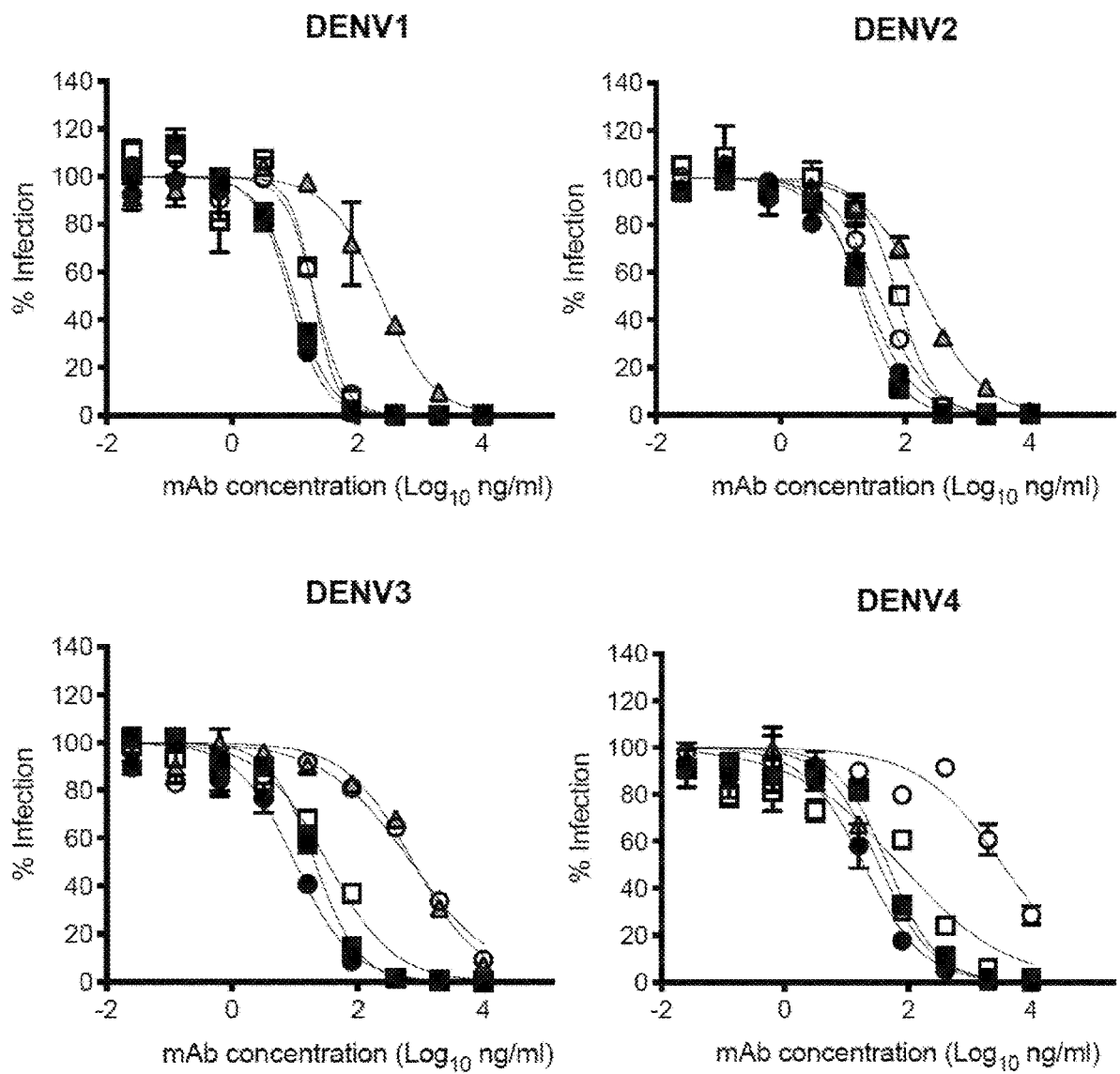
FIG. 13 shows neutralization profiles of J9v1, J8, J9v1 heavy chain paired with J8 light chain (J9v1HC_J8LC), J8 heavy chain paired with J9 light chain (J8HC_J9LC) and control antibody EDE1C10 against DENV1-4, ZIKV and WNV according to certain aspects of this disclosure. Error bars indicate the range of infectivity obtained from two technical replicates. Dose-response curves are representative of two independent experiments.
Figure 13:
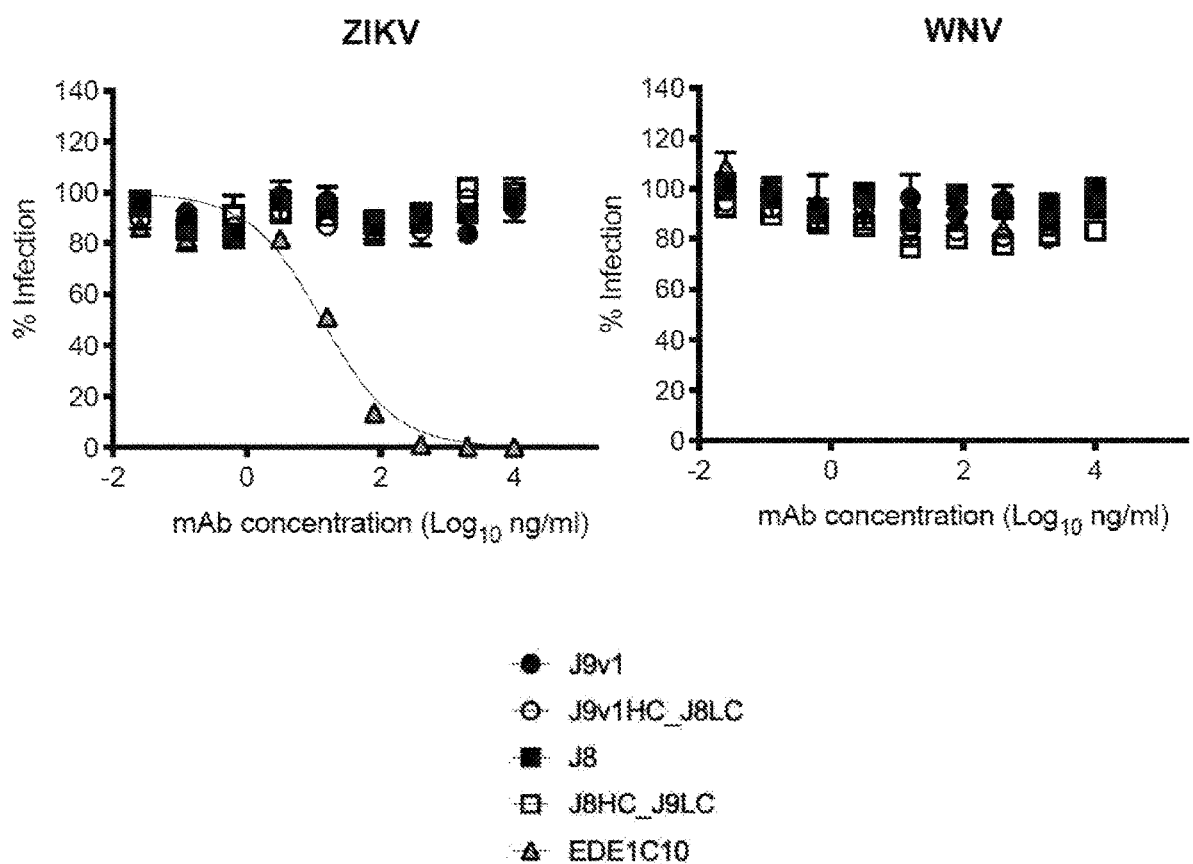

Although no neutralizing activity was detected for J8 in the initial screen with crude IgG-containing supernatant (see Table 16), the lineage analysis described in Example 13 revealed that this antibody belonged to a clonally expanded family of extensively matured antibodies, suggesting antigen-selection. Therefore, J8 IgG was expressed and purified and re-tested in neutralization assays along with J9v1 and EDE1 C10 as controls. As shown in FIG. 13, J8 displayed similarly broad and potent neutralizing activity against DENV1-4 as J9v1, indicating that multiple maturation pathways within this lineage led to broadly neutralizing antibodies. Indeed, chimeric IgG expressing J9v1 heavy chain with J8 light chain and vice versa displayed similar neutralizing activity against DENV1 and DENV2. However, chimeric IgG expressing J9v1 heavy chain with J8 light chain displayed less potent neutralization of DENV 3 and DENV4, suggesting that the light chain contributed to the neutralizing activity of J9v1 against these viruses.

Disclosed are materials, compositions, and ingredients that can be used for, can be used in conjunction with or can be used in preparation for the disclosed embodiments. These and other materials are disclosed herein, and it is understood that when combinations, subsets, interactions, groups, etc. of these materials are disclosed that while specific reference of each various individual and collective combinations and permutations of these compositions may not be explicitly disclosed, each is specifically contemplated and described herein. For example, if a method is disclosed and discussed, and a number of modifications that can be made to a number of molecules included in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties. The following description provides further non-limiting examples of the disclosed compositions and methods.

What is claimed is:

1. A synthetic antibody or antigen binding portion thereof comprising:
    (a) a heavy chain variable region comprising
        (i) a CDRH1 comprising SEQ ID NO:164
        (ii) a CDRH2 comprising SEQ ID NO:199; and
        (iii) a CDRH3 comprising SEQ ID NO:232; and
    (b) a light chain variable region comprising
        (i) a CDRL1 comprising SEQ ID NO:266;
        (ii) a CDRL2 comprising SEQ ID NOs: 291; and
        (iii) a CDRL3 comprising SEQ ID NO:308
    or
    (c) a heavy chain variable region comprising
        (i) a CDRH1 comprising SEQ ID NO:163;
        (ii) a CDRH2 comprising SEQ ID NO:198; and
        (iii) a CDRH3 comprising SEQ ID NO:231; and
    (d) a light chain variable region comprising
        (i) a CDRL1 comprising SEQ ID NO:265;
        (ii) a CDRL2 comprising SEQ ID NOs: 291; and
        (iii) a CDRL3 comprising SEQ ID NO:307,
    wherein the synthetic antibody or the antigen binding portion thereof is a Fab fragment, a F(ab')2 fragment, a monovalent fragment consisting of the VL, VH, CL and CH1 domains, a bivalent fragment comprising two Fab fragments linked by a disulfide bridge, an Fv fragment consisting of VL and VH domains of a single arm of an antibody, a single chain antibody Fv (scFv), or a diabody.

2. The synthetic antibody or the antigen binding portion thereof of claim 1, comprising (a) and (b).

3. The synthetic antibody or the antigen binding portion thereof of claim 1, comprising (c) and (d).

4. A pharmaceutical preparation comprising:
    a pharmaceutically acceptable carrier; and
    the synthetic antibody or the antigen binding portion thereof of claim 1.

5. A diagnostic preparation comprising:
    a pharmaceutically acceptable carrier; and
    the synthetic antibody or the antigen binding portion thereof of claim 1.

6. A method for treatment of dengue virus disease, comprising administering to a subject a therapeutically effective amount of the pharmaceutical preparation of claim 4.

7. A method for the diagnosis of dengue virus disease, comprising:
    administering to a subject an effective amount of the diagnostic preparation of claim 5; and,
    detecting in the subject binding of the synthetic antibody or the antigen binding portion thereof as a determination of presence of the dengue virus disease.

8. A method of detecting presence of dengue virus in a biological sample, comprising:
    contacting the biological sample with the diagnostic preparation of claim 5, and
    detecting in the biological sample an amount of binding of the synthetic antibody or the antigen binding portion thereof as a determination of presence of the dengue virus.

9. A method for treatment of dengue virus disease, comprising administering to a subject a therapeutically effective amount of a composition comprising a pharmaceutically acceptable carrier, and a synthetic antibody or antigen binding portion thereof comprising one or both of
    (1) a heavy chain variable region comprising
        (i) a CDRH1 comprising SEQ ID NO:164;
        (ii) a CDRH2 comprising SEQ ID NO:199; and
        (iii) a CDRH3 comprising SEQ ID NO:232; and
    a light chain variable region comprising
        (i) a CDRL1 comprising SEQ ID NO:266;
        (ii) a CDRL2 comprising SEQ ID NOs: 291; and
        (iii) a CDRL3 comprising SEQ ID NO:308; or
    (2) a heavy chain variable region comprising
        (i) a CDRH1 comprising SEQ ID NO:163;
        (ii) a CDRH2 comprising SEQ ID NO:198; and
        (iii) a CDRH3 comprising SEQ ID NO:231; and
    a light chain variable region comprising
        (i) a CDRL1 comprising SEQ ID NO:265;
        (ii) a CDRL2 comprising SEQ ID NOs: 291; and
        (iii) a CDRL3 comprising SEQ ID NO:307.

10. A method for diagnosis of dengue virus disease comprising:
    administering to a subject an effective amount of the of a composition comprising a synthetic antibody or antigen binding portion thereof comprising one or both of one or both of
    (1) a heavy chain variable region comprising
        (i) a CDRH1 comprising SEQ ID NO:164;
        (ii) a CDRH2 comprising SEQ ID NO:199; and
        (iii) a CDRH3 comprising SEQ ID NO:232; and
    a light chain variable region comprising
        (i) a CDRL1 comprising SEQ ID NO:266;
        (ii) a CDRL2 comprising SEQ ID NOs: 291; and
        (iii) a CDRL3 comprising SEQ ID NO:308; or
    (2) a heavy chain variable region comprising
        (i) a CDRH1 comprising SEQ ID NO:163;
        (ii) a CDRH2 comprising SEQ ID NO:198; and
        (iii) a CDRH3 comprising SEQ ID NO:231; and
    a light chain variable region comprising
        (i) a CDRL1 comprising SEQ ID NO:265;
        (ii) a CDRL2 comprising SEQ ID NOs: 291; and
        (iii) a CDRL3 comprising SEQ ID NO:307; and,
    detecting in the subject binding of the synthetic antibody or the antigen binding portion thereof as a determination of presence of the dengue virus disease.

11. A method of detecting presence of dengue virus in a biological sample comprising:
  contacting the biological sample with a composition comprising a synthetic antibody or antigen binding portion thereof comprising one or both of
  (1) a heavy chain variable region comprising
    (i) a CDRH1 comprising SEQ ID NO:164;
    (ii) a CDRH2 comprising SEQ ID NO:199; and
    (iii) a CDRH3 comprising SEQ ID NO:232; and
  a light chain variable region comprising
    (i) a CDRL1 comprising SEQ ID NO:266;
    (ii) a CDRL2 comprising SEQ ID NOs: 291; and
    (iii) a CDRL3 comprising SEQ ID NO:308; or
  (2) a heavy chain variable region comprising
    (i) a CDRH1 comprising SEQ ID NO:163;
    (ii) a CDRH2 comprising SEQ ID NO:198; and
    (iii) a CDRH3 comprising SEQ ID NO:231; and
  a light chain variable region comprising
    (i) a CDRL1 comprising SEQ ID NO:265;
    (ii) a CDRL2 comprising SEQ ID NOs: 291; and
    (iii) a CDRL3 comprising SEQ ID NO:307; and,
  detecting in the biological sample an amount of binding of the synthetic antibody or the antigen binding portion thereof as a determination of presence of the dengue virus.

* * * * *

UNITED STATES PATENT AND TRADEMARK OFFICE
CERTIFICATE OF CORRECTION

| | |
|---|---|
| PATENT NO. | : 12,161,890 B2 |
| APPLICATION NO. | : 17/265704 |
| DATED | : December 10, 2024 |
| INVENTOR(S) | : Fabio Zanini et al. |

Page 1 of 1

It is certified that error appears in the above-identified patent and that said Letters Patent is hereby corrected as shown below:

In the Claims

In Column 353, Line 19:
In Claim 1, delete "NO:164" and
Insert -- NO:164; --.

In Column 353, Line 61:
In Claim 7, delete "for the" and
Insert -- for --.

In Column 354, Line 45:
In Claim 10, delete "of the of a" and
Insert -- of a --.

Signed and Sealed this
Eighteenth Day of February, 2025

Coke Morgan Stewart
*Acting Director of the United States Patent and Trademark Office*

SEQUENCE LISTING

```
<160> NUMBER OF SEQ ID NOS: 446

<210> SEQ ID NO 1
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Val Gln Ser Gly Ala Glu Val Lys Lys Pro Gly Ala
1               5                   10                  15

Ser Val Lys Val Ser Cys Arg Ala Ser Gly Asn Ser Phe Ser Gly Tyr
            20                  25                  30

Gly Ile Ser Trp Val Arg Gln Ala Pro Gly Gln Gly Leu Glu Trp Met
        35                  40                  45

Gly Trp Leu Thr Pro Tyr Thr Asp Asn Arg Lys Tyr Ala Glu Asp Leu
```

```
                    50                  55                  60
Gln Gly Arg Val Thr Met Thr Ile Asp Thr Ser Thr Arg Thr Ala Tyr
 65                  70                  75                  80

Met Glu Leu Arg Ser Leu Arg Ser Asp Asp Thr Ala Phe Tyr Tyr Cys
                 85                  90                  95

Ala Thr Gly Gly Pro Asn Phe Trp Ser Gly His Asn Trp Leu Asp Pro
            100                 105                 110

Trp Gly Gln Gly Thr Leu Val Thr Val Ser Ser
            115                 120
```

<210> SEQ ID NO 2
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Gln Val Gln Leu Val Gln Ser Gly Ala Glu Val Lys Lys Pro Gly Ala
  1               5                  10                  15

Ser Val Lys Val Ser Cys Met Ala Ser Gly His Thr Phe Ser Gly Tyr
                 20                  25                  30

Gly Ile Ser Trp Val Arg Gln Ala Pro Gly Gln Gly Leu Glu Trp Met
             35                  40                  45

Gly Trp Ser Thr Pro Tyr Thr Gly Lys Ile Glu Tyr Ala Glu Lys Phe
         50                  55                  60

Gln Gly Arg Val Thr Met Thr Ile Asp Thr Ser Thr Gly Thr Ala Tyr
 65                  70                  75                  80

Met Glu Leu Arg Ser Leu Arg Ser Asp Asp Thr Ala Phe Tyr Tyr Cys
                 85                  90                  95

Ala Thr Gly Gly Pro Asn Phe Trp Ser Gly His Asn Trp Leu Asp Pro
            100                 105                 110

Trp Gly Gln Gly Thr Leu Val Thr Val Ser Ser
            115                 120
```

<210> SEQ ID NO 3
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Gln Val Gln Leu Val Gln Ser Gly Ala Glu Val Lys Lys Pro Gly Ala
  1               5                  10                  15

Thr Val Lys Val Ser Cys Lys Ala Ser Gly Tyr Thr Phe Thr Ser Phe
                 20                  25                  30

Ala Val Asn Trp Val Arg Gln Ala Pro Gly Gln Ser Phe Glu Trp Met
             35                  40                  45

Gly Trp Ile Asn Ile Gly Ser Gly Asn Thr Lys Tyr Ser Gln Lys Phe
         50                  55                  60

Gln Gly Arg Val Thr Ile Thr Gly Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ala Leu Phe Gly Leu Val Ala Val Ala Ser Pro Phe Asp Asn
```

```
                    100                 105                 110
Trp Gly Gln Gly Thr Leu Val Thr Val Ser Ser
            115                 120

<210> SEQ ID NO 4
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Ala Gln Leu Val Gln Ser Gly Ala Glu Val Lys Lys Pro Gly Ser
1               5                   10                  15

Ser Val Lys Leu Ser Cys Lys Ala Ser Gly Gly Thr Phe Thr Ser Tyr
            20                  25                  30

Ala Ile Asn Trp Val Arg Gln Ala Pro Gly Gln Gly Leu Glu Trp Met
        35                  40                  45

Gly Glu Ile Asn Val Ile Phe Gly Ser Thr Lys Tyr Ala Gln Lys Phe
    50                  55                  60

His Gly Arg Val Thr Ile Ala Thr Asp Glu Ser Thr Gly Thr Val Tyr
65                  70                  75                  80

Met Glu Leu Arg Thr Leu Arg Leu Asp Asp Thr Gly Val Tyr Tyr Cys
                85                  90                  95

Ala Arg Ala Asp Glu Met Ala Thr Ala Gln Gly Phe Tyr Ala Phe Asp
            100                 105                 110

Ile Trp Gly Gln Gly Thr Met Val Thr Val Ser Ser
            115                 120

<210> SEQ ID NO 5
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Ala Gln Leu Val Gln Ser Gly Ala Glu Val Lys Lys Pro Gly Ser
1               5                   10                  15

Ser Val Lys Val Ser Cys Lys Ala Ser Gly Gly Ser Phe Thr Ser Tyr
            20                  25                  30

Gly Val Asp Trp Val Arg Gln Ala Pro Gly Gln Gly Leu Glu Trp Met
        35                  40                  45

Gly Gly Ile Asn Val Val Phe Gly Ser Val Lys Tyr Ala Gln Lys Phe
    50                  55                  60

Gln Gly Arg Val Thr Ile Thr Lys Asp Asp Ser Arg Thr Thr Val Tyr
65                  70                  75                  80

Met Glu Val Arg Ser Leu Arg Ser Glu Asp Thr Ala Met Tyr Tyr Cys
                85                  90                  95

Ala Arg Ala Asp Glu Met Ala Thr Ile Glu Gly Phe Tyr Ala Phe Asp
            100                 105                 110

Ile Trp Gly Gln Gly Thr Met Ile Thr Val Ser Ser
            115                 120

<210> SEQ ID NO 6
<211> LENGTH: 124
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 6

Gln Ala Gln Leu Val Gln Ser Gly Ala Glu Val Lys Lys Pro Gly Ser
1               5                   10                  15

Ser Val Lys Val Ser Cys Lys Ala Ser Gly Gly Thr Phe Thr Ser Tyr
            20                  25                  30

Gly Ile Asp Trp Val Arg Gln Ala Pro Gly Gln Gly Leu Glu Trp Val
        35                  40                  45

Gly Gly Ile Asn Pro Ile Phe Gly Ser Thr Lys Tyr Pro Gln Lys Phe
    50                  55                  60

Gln Gly Arg Val Thr Val Ser Thr Asp Glu Ser Thr Ser Thr Ala Tyr
65                  70                  75                  80

Met Glu Leu Arg Ser Leu Arg Ser Glu Asp Thr Ala Met Tyr Tyr Cys
                85                  90                  95

Ala Arg Ala Asp Glu Met Ala Thr Thr Gly Gly Phe Tyr Ala Phe Asp
            100                 105                 110

Ile Trp Gly Gln Gly Thr Met Val Thr Val Ser Ser
        115                 120

<210> SEQ ID NO 7
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val His Leu Val Gln Ser Gly Ala Glu Val Lys Lys Pro Gly Ser
1               5                   10                  15

Ser Val Lys Val Ser Cys Lys Ser Gly Gly Thr Phe Thr Asn Tyr
            20                  25                  30

Pro Ile Thr Trp Val Arg Gln Ala Pro Gly Gln Gly Leu Glu Trp Met
        35                  40                  45

Gly Gly Ile Leu Pro Ile Leu Asp Thr Ala Asn Tyr Ala Gln Glu Phe
    50                  55                  60

Gln Gly Arg Val Thr Ile Thr Ala Asp Glu Ser Thr Ser Thr Ala Tyr
65                  70                  75                  80

Met Glu Leu Ser Asn Leu Arg Ser Glu Asp Thr Ala Val Tyr Tyr Cys
                85                  90                  95

Ala Arg Val Tyr Phe Asp Ser Gly Gly Tyr Phe Asp Ser Trp Gly Gln
            100                 105                 110

Gly Thr Leu Val Thr Val Ser Ser
        115                 120

<210> SEQ ID NO 8
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Val His Leu Val Gln Ser Gly Ala Glu Val Lys Lys Pro Gly Ser
1               5                   10                  15
```

-continued

Ser Val Lys Val Ser Cys Lys Thr Ser Gly Gly Thr Phe Thr Lys Tyr
            20                  25                  30

Pro Ile Thr Trp Val Arg Gln Ala Pro Gly Gln Gly Leu Glu Trp Met
            35                  40                  45

Gly Gly Ile Leu Pro Ile Leu Asp Thr Ala Asn Tyr Ala Gln Glu Phe
    50                  55                  60

Gln Gly Arg Val Thr Ile Thr Ala Asp Glu Ser Thr Ser Thr Ala Tyr
65                  70                  75                  80

Met Glu Leu Ser Asn Leu Arg Ser Glu Asp Thr Ala Val Tyr Tyr Cys
                85                  90                  95

Ala Arg Val Tyr Tyr Asp Ser Gly Gly Tyr Phe Asp Ser Trp Gly Gln
            100                 105                 110

Gly Thr Leu Val Thr Val Ser Ser
            115                 120

<210> SEQ ID NO 9
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Phe Ser Trp Val Arg Gln Ala Pro Gly Gln Gly Leu Glu Trp Met
            35                  40                  45

Gly Arg Ile Ile Pro Ile Phe Gly Thr Pro Lys Tyr Ala Gln Lys Phe
    50                  55                  60

Gln Gly Arg Val Thr Ile Thr Arg Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Pro Trp His Ser Ser Gly Trp Phe Pro Ser Asp Tyr Trp
            100                 105                 110

Gly Gln Gly Thr Leu Val Thr Val Ser Ser
            115                 120

<210> SEQ ID NO 10
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Val Gln Leu Val Gln Ser Gly Ala Glu Leu Lys Lys Pro Gly Ser
1               5                   10                  15

Ser Val Lys Val Ser Cys Lys Ser Ser Gly Gly Thr Phe Arg Asn Tyr
            20                  25                  30

Ser Phe Ser Trp Val Arg Gln Ala Pro Gly Gln Gly Leu Glu Trp Met
            35                  40                  45

Gly Arg Ser Ile Pro Ile Phe Gly Thr Ala Lys Tyr Ala Gln Lys Phe
    50                  55                  60

Gln Gly Arg Val Thr Ile Thr Thr Asp Glu Ser Thr Ser Thr Ala Tyr
65                  70                  75                  80

Met Asp Leu Ser Ser Leu Arg Ser Glu Asp Thr Ala Val Tyr Tyr Cys
                85                  90                  95

Ala Arg Ser Pro Trp His Asn Ser Gly Trp Phe Pro Leu Asp Ser Trp
            100                 105                 110

Gly Gln Gly Thr Leu Val Thr Val Ser Ser
        115                 120

<210> SEQ ID NO 11
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Asn
            20                  25                  30

Ser Val Thr Trp Val Arg Gln Ala Pro Gly His Gly Leu Glu Trp Met
        35                  40                  45

Gly Thr Ile Ile Pro Phe Phe Gly Thr Arg His Tyr Ala Asp Asn Phe
    50                  55                  60

Gln Gly Arg Val Thr Val Thr Asp Glu Ser Thr Thr Thr Val Tyr
65                  70                  75                  80

Met Glu Leu Ser Ser Leu Arg Ser Asp Asp Thr Ala Val Tyr Tyr Cys
                85                  90                  95

Ala Arg Ser Cys Glu Ser Pro Ser Cys Tyr His Asn Trp Phe Asp Pro
            100                 105                 110

Trp Gly Gln Gly Thr Leu Val Thr Val Thr Ser
        115                 120

<210> SEQ ID NO 12
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Val Gln Ser Gly Ala Glu Val Arg Lys Pro Gly Ser
1               5                   10                  15

Ser Val Lys Val Ser Cys Lys Thr Ser Gly Gly Ser Leu Asn Ser Tyr
            20                  25                  30

Gly Ile Ser Trp Val Arg Gln Ala Pro Gly Gln Gly Leu Glu Trp
        35                  40                  45

Met Gly Gly Ile Ile Pro Phe Phe Gly Thr Val Ile Tyr Ser Asp Asn
    50                  55                  60

Tyr Gln Gly Arg Ala Ser Phe Ser Asp Glu Ser Thr Thr Thr Ala
65                  70                  75                  80

Tyr Met Glu Leu Arg Ser Leu Arg Ser Glu Asp Thr Ala Val Tyr Tyr
                85                  90                  95

Cys Ala Arg Tyr Cys Tyr Ser Ala Ser Cys Tyr His Asn Trp Phe Asp
            100                 105                 110

```
Pro Trp Gly Gln Gly Thr Leu Val Thr Val Ser Thr
        115                 120

<210> SEQ ID NO 13
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Val Gln Ser Gly Ala Glu Val Lys Lys Pro Gly Ser
1               5                   10                  15

Ser Val Lys Val Ser Cys Glu Ala Ser Gly Val Ser Leu Ser Ser Tyr
            20                  25                  30

Gly Ile Ser Trp Val Arg Gln Ala Pro Gly Arg Gly Leu Glu Trp Met
        35                  40                  45

Gly Gly Ile Ile Pro Phe Phe Gly Thr Arg Asn Tyr Ala His Asp Phe
    50                  55                  60

Glu Gly Arg Leu Thr Ile Thr Thr Asp Glu Ser Thr Arg Thr Val Tyr
65                  70                  75                  80

Met Glu Leu Ser Ser Leu Arg Ser Glu Asp Thr Ala Val Tyr Tyr Cys
                85                  90                  95

Ala Arg Arg Asn Ala Lys Gly Gly Tyr Ser Gly Gly Asn Trp Phe Asp
            100                 105                 110

Pro Trp Gly Gln Gly Thr Pro Val Thr Val Ser Ser
        115                 120

<210> SEQ ID NO 14
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Val Gln Ser Gly Ala Glu Val Lys Lys Pro Gly Ser
1               5                   10                  15

Ser Val Arg Val Ser Cys Thr Ala Ser Gly Gly Thr Phe Ser Ser Leu
            20                  25                  30

Ala Ile Ser Trp Val Arg Gln Ala Pro Gly Gln Gly Leu Glu Trp Met
        35                  40                  45

Gly Gly Leu Ile Pro Val Phe Gly Ile Pro Asn Tyr Ala Glu Asp Phe
    50                  55                  60

Gln Gly Arg Val Thr Ile Thr Ala Asp Glu Ser Thr Arg Thr Ala Tyr
65                  70                  75                  80

Met Asp Leu Ser Ser Leu Ser Ala Asp Thr Ala Val Tyr Tyr Cys
                85                  90                  95

Ala Arg Arg Ser Gly Lys Gly Gly Tyr Ser Gly Gly Asn Trp Phe Asp
            100                 105                 110

Pro Trp Gly Gln Gly Thr Leu Val Thr Val Ser Ser
        115                 120

<210> SEQ ID NO 15
<211> LENGTH: 127
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 15

Gln Val Gln Leu Val Gln Ser Gly Ser Glu Val Lys Lys Pro Gly Ser
1               5                   10                  15

Ser Val Arg Val Ser Cys Arg Ala Ser Gly Gly Thr Phe Asn Ser Leu
            20                  25                  30

Pro Ile Ser Trp Leu Arg Gln Ala Pro Gly Gln Gly Pro Glu Trp Met
        35                  40                  45

Gly Arg Ile Ile Pro Phe Phe Ala Thr Pro Thr Tyr Ala Glu Lys Phe
50                  55                  60

Gln Gly Arg Val Thr Ile Thr Ala Asp Glu Ser Thr Ala Thr Ala Tyr
65                  70                  75                  80

Met Glu Leu Ser Asn Leu Arg Ser Asp Asp Thr Ala Val Tyr Tyr Cys
                85                  90                  95

Ala Arg Asp Leu Asn Phe Tyr Asp Ser Ser Gly Tyr His Phe Ala Arg
            100                 105                 110

Trp Phe Asp Pro Trp Gly Gln Gly Thr Leu Val Thr Val Ser Ser
        115                 120                 125

<210> SEQ ID NO 16
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Gln Leu Val Gln Ser Gly Ala Glu Val Lys Lys Pro Gly Ser
1               5                   10                  15

Ser Val Lys Val Ser Cys Thr Thr Ser Gly Gly Thr Leu Ser Ser Tyr
            20                  25                  30

Pro Ile Ser Trp Val Arg Gln Ala Pro Gly Gln Gly Leu Glu Trp Met
        35                  40                  45

Gly Arg Ile Thr Pro Phe Phe Gly Thr Thr Asn Tyr Ala Glu Gln Phe
50                  55                  60

Gln Gly Arg Ile Thr Ile Thr Thr Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Val His Tyr Ser Asp Ser Ser Gly Tyr His Phe Gly Arg
            100                 105                 110

Trp Phe Asp Pro Trp Gly Gln Gly Thr Leu Val Thr Val Ser Ser
        115                 120                 125

<210> SEQ ID NO 17
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Val Gln Ser Gly Ser Glu Val Lys Lys Pro Gly Ser
1               5                   10                  15
```

```
Ser Val Arg Val Ser Cys Arg Ala Ser Gly Thr Phe Ser Ser Leu
            20                  25                  30

Ala Ile Ser Trp Val Arg Gln Ala Pro Gly Gln Gly Pro Glu Trp Met
            35                  40                  45

Gly Arg Ile Ile Pro Phe Phe Ala Thr Pro Ser Tyr Ala Glu Asn Phe
 50                  55                  60

Gln Gly Arg Val Thr Ile Thr Ala Asp Glu Ser Thr Ser Thr Ala Tyr
 65                  70                  75                  80

Met Glu Leu Ser Asn Leu Arg Ser Asp Asp Thr Ala Val Tyr Tyr Cys
                85                  90                  95

Ala Arg Asp Leu Asn Phe Tyr Asp Ser Ser Gly Tyr His Phe Ala Arg
            100                 105                 110

Trp Phe Asp Pro Trp Gly Gln Gly Thr Leu Val Thr Val Ser Ser
            115                 120                 125

<210> SEQ ID NO 18
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Val Gln Leu Val Gln Ser Gly Ala Glu Val Lys Lys Pro Gly Ser
 1               5                  10                  15

Ser Val Lys Val Ser Cys Lys Val Ser Gly Thr Phe Ser Ser Ser
            20                  25                  30

Pro Ile Ser Trp Val Arg Gln Ala Pro Gly Gln Gly Phe Glu Trp Met
            35                  40                  45

Gly Arg Ile Ile Pro Phe Phe Gly Ser Pro Ser Tyr Ala Glu Gln Phe
 50                  55                  60

Gln Asp Arg Val Thr Ile Thr Thr Asp Glu Ser Thr Thr Thr Ala Tyr
 65                  70                  75                  80

Met Glu Leu Arg Ser Leu Arg Ser Glu Asp Thr Ala Val Tyr Tyr Cys
                85                  90                  95

Ala Arg Asp Val Asn Tyr Tyr Asp Ser Ser Gly Tyr His Phe Gly Arg
            100                 105                 110

Trp Phe Asp Pro Trp Gly Gln Gly Thr Leu Val Thr Val Ser Ser
            115                 120                 125

<210> SEQ ID NO 19
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Val Gln Ser Gly Ala Glu Val Lys Lys Pro Gly Ser
 1               5                  10                  15

Ser Val Lys Val Ser Cys Lys Val Ser Gly Gly Thr Phe Ser Ser Ser
            20                  25                  30

Pro Ile Ser Trp Val Arg Gln Ala Pro Gly Gln Gly Phe Glu Trp Met
            35                  40                  45

Gly Arg Ile Ile Pro Phe Phe Gly Ser Pro Thr Tyr Ala Glu Gln Phe
 50                  55                  60
```

Gln Gly Arg Val Thr Ile Thr Thr Asp Glu Ser Thr Ser Thr Ala Tyr
65                  70                  75                  80

Met Glu Leu Ser Ser Leu Arg Ser Ala Asp Thr Ala Val Tyr Tyr Cys
                85                  90                  95

Ala Arg Asp Val Asn Tyr Tyr Asp Ser Ser Gly Tyr His Phe Gly Arg
            100                 105                 110

Trp Phe Asp Pro Trp Gly Gln Gly Thr Leu Val Thr Val Ser Ser
        115                 120                 125

<210> SEQ ID NO 20
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Pro Phe Ser Gly Tyr
            20                  25                  30

Ala Met His Trp Val Arg Gln Ala Pro Gly Lys Gly Leu Glu Trp Val
        35                  40                  45

Ala Phe Ile Ser Tyr Asp Gly Ser Asp Lys Tyr Tyr Ala Asp Ser Val
    50                  55                  60

Lys Gly Arg Phe Thr Ile Ser Arg Asp Asn Ser Glu Asn Thr Leu His
65                  70                  75                  80

Leu Gln Met Asn Ser Leu Arg Ala Glu Asp Thr Ala Val Tyr Tyr Cys
                85                  90                  95

Ala Lys Asn Tyr Gly Ser Gly Ser Leu Asn Trp Phe Asp Ala Trp Gly
            100                 105                 110

Gln Gly Thr Leu Val Thr Val Ser Ser
        115                 120

<210> SEQ ID NO 21
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Pro Phe Arg Ser Tyr
            20                  25                  30

Ala Met His Trp Val Arg Gln Ala Pro Gly Lys Gly Leu Glu Trp Val
        35                  40                  45

Ala Phe Ile Ser Tyr Asp Gly Thr Asn Thr Tyr Tyr Ala Asp Ser Val
    50                  55                  60

Lys Gly Pro Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Tyr Gly Ser Gly Ser Gln Asn Trp Phe Asp Ser Trp Gly
            100                 105                 110

Gln Gly Thr Leu Val Thr Val Ser Ser
        115                 120

<210> SEQ ID NO 22
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Val Arg Leu Val Glu Ser Gly Gly Val Val Gln Pro Gly Arg
1               5                   10                  15

Ser Leu Arg Leu Ser Cys Ala Gly Ser Gly Phe Ser Phe Ser Thr Tyr
                20                  25                  30

Ala Met His Trp Val Arg Gln Ala Pro Gly Lys Gly Leu Glu Trp Val
            35                  40                  45

Ala Leu Ile Tyr Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Phe Cys
                85                  90                  95

Ala Lys Asn Tyr Gly Ser Gly Ser Leu Asn Trp Tyr Asp Ala Trp Gly
            100                 105                 110

Gln Gly Thr Leu Val Ile Val Ser Ser
        115                 120

<210> SEQ ID NO 23
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Asn Tyr
                20                  25                  30

Ala Leu His Trp Val Arg Gln Ala Pro Gly Lys Gly Leu Glu Trp Val
            35                  40                  45

Ala Leu Ile Tyr Tyr Asp Gly Ser Arg Lys Tyr Tyr Ala Asp Ser Val
        50                  55                  60

Lys Gly Arg Phe Thr Ile Ser Arg Asp Asn Ser Lys Asn Thr Leu His
65                  70                  75                  80

Leu Gln Met Asn Ser Val Arg Val Glu Asp Thr Ala Val Tyr Tyr Cys
                85                  90                  95

Ala Lys Asn Tyr Gly Ser Gly Thr Leu Asn Trp Phe Asp Ala Trp Gly
            100                 105                 110

Gln Gly Thr Leu Val Thr Val Ser Ser
        115                 120

<210> SEQ ID NO 24
<211> LENGTH: 121
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 24

Gln Val Gln Leu Val Glu Ser Gly Gly Gly Val Val Gln Pro Gly Arg
1               5                   10                  15

Ser Leu Arg Leu Ser Cys Val Gly Ser Glu Phe Pro Phe Lys Ala Tyr
            20                  25                  30

Ala Met His Trp Val Arg Gln Ala Pro Gly Lys Gly Leu Glu Trp Val
        35                  40                  45

Ala Phe Ile Ser Tyr Asp Gly Ser Asn Thr Tyr Ala Asp Ser Val
    50                  55                  60

Lys Gly Arg Phe Ser Leu Ser Arg Asp Asn Ser Lys Asn Thr Leu Tyr
65                  70                  75                  80

Leu Asp Met Asn Pro Leu Arg Pro Glu Asp Thr Ala Val Tyr Tyr Cys
                85                  90                  95

Ala Lys Asn Tyr Gly Ser Gly Ser Leu Asn Trp Phe Asp Ser Trp Gly
            100                 105                 110

Gln Gly Thr Leu Leu Thr Val Ser Ala
        115                 120

<210> SEQ ID NO 25
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Val Glu Ser Gly Gly Gly Val Val Arg Pro Gly Arg
1               5                   10                  15

Ser Leu Arg Val Ser Cys Ala Ala Ser Gly Phe Thr Phe Ser Asn Phe
            20                  25                  30

Ala Met His Trp Val Arg Gln Ala Pro Gly Lys Gly Leu Glu Trp Val
        35                  40                  45

Ala Leu Ile Tyr Tyr Asp Gly Ser Asn Lys Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Pro Asp Asp Thr Ala Val Tyr Tyr Cys
                85                  90                  95

Ala Lys Asn Tyr Gly Ser Gly Thr Leu Asn Trp Phe Asp Ser Trp Gly
            100                 105                 110

Gln Gly Thr Leu Val Thr Val Ser Ser
        115                 120

<210> SEQ ID NO 26
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Val Gln Leu Val Glu Ser Gly Gly Gly Val Val Gln Pro Gly Arg
1               5                   10                  15

Ser Leu Thr Leu Ser Cys Ala Asp Ser Gly Phe Thr Phe Thr Thr Asp

```
                20                  25                  30

Ala Met His Trp Val Arg Gln Ala Pro Gly Lys Gly Leu Glu Trp Val
        35                  40                  45

Ala Val Ile Ser Tyr Asp Gly Thr Glu Lys Tyr Tyr Gly Asp Ser Val
    50                  55                  60

Glu Gly Arg Phe Thr Ile Ser Arg Asp Asn Ser Lys Asn Thr Leu Phe
65                  70                  75                  80

Leu Gln Met Ser Asp Leu Arg Pro Arg Asp Ser Ala Val Tyr Phe Cys
                85                  90                  95

Ala Arg Glu Gly Thr Tyr Ser Gly Ile Val Thr Gly Gln Ser Gln Ser
            100                 105                 110

Pro Ser Ser Tyr Met Asp Val Trp Gly Lys Gly Thr Thr Val Ile Val
        115                 120                 125

Ser Ser
    130

<210> SEQ ID NO 27
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Val Gln Leu Val Glu Ser Gly Gly Gly Val Val Gln Pro Gly Arg
1               5                   10                  15

Ser Leu Arg Leu Ser Cys Ala Asp Ser Gly Phe Thr Phe Arg Thr Asp
            20                  25                  30

Ala Met His Trp Val Arg Gln Ala Pro Gly Lys Gly Leu Glu Trp Val
        35                  40                  45

Ala Val Ile Ser Tyr Asp Gly Ser Glu Lys Tyr Tyr Gly Asp Ser Val
    50                  55                  60

Glu Gly Arg Phe Thr Ile Ser Arg Asp Asn Ser Lys Asn Thr Leu Phe
65                  70                  75                  80

Leu Gln Met Asn Ala Leu Arg Pro Gly Asp Thr Ala Val Tyr Phe Cys
                85                  90                  95

Ala Arg Glu Gly Thr Tyr Ser Gly Ile Val Thr Gly Gln Ser Gln Ser
            100                 105                 110

Pro Ser Ser Tyr Met Ala Val Trp Gly Lys Gly Thr Thr Val Ile Val
        115                 120                 125

Ser Ser
    130

<210> SEQ ID NO 28
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Val Gln Leu Val Glu Ser Gly Gly Gly Leu Val Pro Pro Gly Gly
1               5                   10                  15

Ser Leu Arg Leu Ser Cys Ala Ala Ser Gly Phe Thr Phe Asp Ser Tyr
            20                  25                  30

Trp Met Ser Trp Val Arg Gln Ala Pro Gly Lys Gly Leu Glu Trp Val
```

```
                35                  40                  45
Ala Asn Ile Lys Leu Asp Gly Ser Glu Lys Cys Tyr Val Asp Ser Val
         50                  55                  60

Lys Gly Arg Phe Thr Ile Ser Arg Asp Asn Ala Lys Asn Ser Leu Phe
 65                  70                  75                  80

Leu Gln Met Asn Ser Leu Arg Ala Glu Asp Thr Ala Val Tyr Tyr Cys
                 85                  90                  95

Ala Arg Val Ala Ser His Pro Ser Leu Phe Ser Pro Tyr Tyr Phe Asp
            100                 105                 110

Tyr Trp Gly Gln Gly Thr Leu Val Thr Val Ser Ser
            115                 120

<210> SEQ ID NO 29
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Val Gln Leu Val Glu Ser Gly Gly Gly Leu Val Pro Pro Gly Gly
 1               5                  10                  15

Ser Leu Lys Val Ser Cys Ala Ala Ser Gly Phe Thr Phe Asp Asn Tyr
                 20                  25                  30

Trp Met Ser Trp Val Arg Gln Ala Pro Gly Lys Gly Leu Glu Trp Val
             35                  40                  45

Ala Asn Ile Lys Leu Asp Gly Ser Glu Lys Cys Tyr Val Asp Ser Val
         50                  55                  60

Lys Gly Arg Phe Thr Ile Ser Arg Asp Asn Ala Arg Asn Ser Leu Phe
 65                  70                  75                  80

Leu Gln Met Asn Ser Leu Arg Ala Glu Asp Thr Ala Val Tyr Tyr Cys
                 85                  90                  95

Ala Arg Val Ala Ser His Pro Thr Leu Phe Ser Pro Tyr Tyr Phe Asp
            100                 105                 110

Tyr Trp Gly Gln Gly Thr Leu Val Thr Val Ser Ser
            115                 120

<210> SEQ ID NO 30
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gln Val Gln Leu Gln Gln Trp Gly Ala Gly Leu Leu Lys Pro Ser Glu
 1               5                  10                  15

Thr Leu Ser Leu Thr Cys Gly Val Ser Asp Gly Pro Leu Ile Gly Tyr
                 20                  25                  30

Tyr Trp Ala Trp Ile Arg Gln Thr Pro Gly Lys Gly Leu Glu Trp Ile
             35                  40                  45

Gly Glu Ile Thr His Ser Gly Asn Thr Asn Tyr Asn Pro Ser Leu Glu
         50                  55                  60

Ser Arg Val Thr Ile Ser Val Asp Thr Ser Lys Asn Gln Phe Ser Leu
 65                  70                  75                  80

Lys Val Asn Ser Val Thr Ala Ala Asp Thr Ala Val Tyr Tyr Cys Ala
```

```
                    85                  90                  95
Arg Gly Pro Gly Gly Thr Ser Thr Ser Cys Tyr Arg Cys Trp Phe Asp
                100                 105                 110

Pro Trp Gly Gln Gly Thr Leu Val Thr Val Ser Ser
            115                 120

<210> SEQ ID NO 31
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gln Val Gln Leu Gln Gln Trp Gly Ala Gly Leu Leu Lys Pro Ser Glu
1               5                   10                  15

Thr Leu Ser Leu Thr Cys Ala Val His Gly Gly Pro Leu Ile Gly Trp
                20                  25                  30

Tyr Trp Ser Trp Ile Arg Gln Thr Pro Glu Lys Gly Leu Glu Trp Ile
            35                  40                  45

Gly Glu Ile Thr His Ser Gly Ser Thr Asn Tyr Asn Pro Ser Leu Lys
        50                  55                  60

Ser Arg Val Thr Ile Ser Val Asp Thr Ser Lys Asn His Phe Ser Leu
65                  70                  75                  80

Lys Leu Thr Ser Val Thr Ala Ala Asp Thr Ala Val Tyr Tyr Cys Ala
                85                  90                  95

Arg Gly Pro Gly Gly Thr Ser Thr Ser Cys Tyr Gln Cys Trp Phe Asp
                100                 105                 110

Pro Trp Gly Gln Gly Thr Leu Val Thr Val Ser Ser
            115                 120

<210> SEQ ID NO 32
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Ser Tyr Tyr Trp Gly Trp Ile Arg Gln Pro Pro Gly Lys Gly Leu Glu
            35                  40                  45

Trp Ile Gly Ser Leu Tyr Tyr Ser Gly Ser Thr Tyr Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Tyr Ser Val Thr Ala Ala Asp Thr Ala Val Tyr Tyr
                85                  90                  95

Cys Ala Gly Gln Asp Tyr Ser Gly Thr Tyr Tyr Asp Tyr Phe Asp Tyr
            100                 105                 110

Trp Gly Gln Gly Ala Leu Val Thr Val Ser Ser
        115                 120
```

```
<210> SEQ ID NO 33
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Met Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Gly Gln Asp Tyr Ser Gly Thr Tyr Tyr Asp Tyr Phe Asn Tyr
            100                 105                 110

Trp Gly Gln Gly Thr Leu Val Thr Val Ser Ser
        115                 120

<210> SEQ ID NO 34
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Asn Thr Arg
            20                  25                  30

Ser Tyr Tyr Trp Gly Trp Ile Arg Gln Pro Pro Gly Lys Gly Leu Glu
        35                  40                  45

Trp Ile Gly Ser Ile Phe Tyr Thr Gly Ser Thr Tyr Tyr Asn Pro Ser
    50                  55                  60

Leu Lys Ser Arg Val Thr Ile Ser Val Asp Thr Ser Asn Asn Gln Phe
65                  70                  75                  80

Ser Leu Arg Leu Ser Ser Val Thr Ala Ala Asp Thr Ala Val Tyr Tyr
                85                  90                  95

Cys Ala Arg Gln Asp Arg Asn Trp Phe Asp Ser Trp Gly Gln Gly Thr
            100                 105                 110

Leu Val Thr Val Ser Ser
        115

<210> SEQ ID NO 35
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35
```

```
Gln Leu Gln Leu Gln Glu Ser Gly Pro Gly Leu Val Lys Pro Ser Ala
1               5                   10                  15

Thr Leu Ser Leu Thr Cys Thr Val Ser Arg Gly Ser Ile Ser Thr Asn
            20                  25                  30

Asp His Ser Trp Gly Trp Ile Arg Gln Pro Pro Gly Lys Gly Leu Glu
        35                  40                  45

Trp Val Gly Ser Leu His His Ser Gly Asn Thr Tyr Tyr Asn Pro Ser
50                      55                  60

Leu Lys Ser Arg Leu Thr Ile Ser Leu Asp Thr Ser Glu Thr Gln Phe
65                  70                  75                  80

Ser Leu Asn Leu Ser Ser Val Thr Ala Ala Asp Thr Ala Val Tyr Tyr
                85                  90                  95

Cys Val Arg Gln Asn Arg Asn Trp Phe Asp Ser Trp Gly Gln Gly Thr
            100                 105                 110

Leu Val Ser Val Ser Ser
            115

<210> SEQ ID NO 36
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Arg Ser
            20                  25                  30

Ser Thr Tyr Phe Trp Gly Trp Ile Arg Gln Pro Pro Gly Lys Gly Leu
        35                  40                  45

Glu Trp Ile Gly Ser Val Ser Tyr Ser Gly Ser Thr Tyr Tyr Asn Pro
50                      55                  60

Ser Leu Lys Ser Arg Val Ser Val Ser Val Asp Thr Ser Arg Lys Gln
65                  70                  75                  80

Phe Ser Leu Lys Leu Thr Ser Val Thr Ala Ala Asp Thr Ala Val Tyr
                85                  90                  95

Tyr Cys Ala Arg Gln Asp Arg Asn Trp Phe Asp Ser Trp Gly Gln Gly
            100                 105                 110

Thr Leu Val Thr Val Ser Ser
            115

<210> SEQ ID NO 37
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Thr Ser Tyr
            20                  25                  30

Tyr Trp Ser Trp Ile Arg Gln Pro Pro Gly Gln Gly Leu Glu Trp Ile
        35                  40                  45
```

-continued

Gly Tyr Ile Tyr Tyr Ser Gly Gly Thr Asn Tyr Asn Pro Ser Leu Lys
            50                  55                  60

Ser Arg Val Val Met Ser Leu Asp Thr Ser Arg Asn Gln Phe Ser Leu
 65                  70                  75                  80

Lys Leu Asn Ser Leu Thr Ala Ala Asp Thr Ala Val Tyr Tyr Cys Ala
                85                  90                  95

Ser Ala Leu Asn Tyr Phe Asp Ser Ser Gly Pro Gly Gly Val Ala Met
            100                 105                 110

Gly Gly Gly Phe Asp Ser Trp Gly Gln Gly Ala Leu Val Thr Val Ser
        115                 120                 125

Ser

<210> SEQ ID NO 38
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gln Val Gln His Gln Glu Ser Gly Pro Gly Leu Val Lys Pro Ser Glu
 1               5                  10                  15

Thr Leu Ser Leu Thr Cys Thr Val Ser Gly Asp Ser Ile Ser Ser Tyr
            20                  25                  30

Tyr Trp Asn Trp Ile Arg Gln Ala Pro Gly Lys Gly Leu Glu Trp Leu
        35                  40                  45

Gly Tyr Ile Asn Tyr Ser Gly Asn Thr Asp Tyr Asn Thr Ser Leu Lys
            50                  55                  60

Ser Arg Ala Thr Ile Ser Leu Asp Thr Ser Lys Asn Gln Phe Ser Leu
 65                  70                  75                  80

Lys Leu Ser Ser Val Thr Thr Ala Asp Thr Ala Val Tyr Tyr Cys Ala
                85                  90                  95

Gly Ala Leu Tyr Tyr Phe Asp Ser Arg Gly Pro Gly Gly Val Ala Met
            100                 105                 110

Gly Gly Gly Phe Asp Ser Trp Gly Gln Gly Thr Leu Val Thr Val Ser
        115                 120                 125

Ser

<210> SEQ ID NO 39
<211> LENGTH: 370
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
caggttcagc tggtgcagtc tggtgctgag gtgaagaagc tggggcctc agtgaaggtc      60 tcctgcaggg cttctggtaa cagcttttcc ggctatggta tcagctgggt gcgacaggcc    120
cctggacaag gcttgagtg gatggggtgg ctcacccctt acactgataa cagaaagtat    180
gcagaggacc tccagggcag agtcaccatg accatagaca catccacgag gacggcctac    240
atggagctga ggagcctgag atctgacgac acggcctttt attactgtgc gacgggggga    300 ccaaatttt ggagtggcca caactggctc gaccccctggg gccagggaac cctggtcacc    360
gtctcctcag                                                            370

<210> SEQ ID NO 40
<211> LENGTH: 370
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
caggttcagc tggtgcagtc tggagctgag gtgaagaagc ctggggcctc agtgaaggtc      60
tcctgcatgg cttctggtca cacctttagc ggctatggta tcagctgggt gcgacaggcc     120
cctggacaag ggcttgagtg gatgggatgg agcaccccctt acactggaaa gatagagtat     180
gcagagaaat tccagggcag agtcaccatg accatagaca catccacggg gacggcctac     240
atggagctga ggagcctgag atctgacgac acggcctttt attactgtgc gacgggggga     300 ccaaatttt ggagtggcca caattggctc gaccccctggg ccagggaac cctggtcacc     360 gtctcctcag                                                            370

<210> SEQ ID NO 41
<211> LENGTH: 370
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
caggtccagc ttgtgcagtc tggggctgag gtgaagaagc ctggggccac agtgaaggtt      60
tcctgcaagg cttctggata caccttcacg agttttgctg tgaactgggt gcgccaggcc     120
cccggacaaa gttttgagtg gatgggatgg atcaacattg gcagtggtaa cacaaaatat     180
tcacagaagt tccagggcag agtcaccatt accggggaca catccgcgag cacagcgtac     240
atggaactga gcagcctgag atctgaagac acggctgtat attactgtgc gagagcactg     300
tttgggttgg tggcagttgc ttcacctttt gacaactggg gccagggaac cctggtcacc     360
gtctcctcag                                                            370

<210> SEQ ID NO 42
<211> LENGTH: 373
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
caggcccagc tggtgcagtc tggggctgag gtgaagaagc ctgggtcttc agtgaagctt      60
tcctgcaagg cttctggagg cacctccacc agctatgcta tcaactgggt gcgacaggcc     120
cctggacaag ggcttgagtg gatggagag atcaacgtaa ttttggttc aacaaaatac      180 gcacagaagt tccacggcag agtcactatt gccacggacg aatccacggg cacagtctac     240
atggaactga gaactctaag acttgacgac acgggcgtgt attactgtgc gagagcggac     300
gagatggcca cagctcaagg attctatgct tttgatatct ggggccaagg gacaatggtc     360
accgtctctt cag                                                        373

<210> SEQ ID NO 43
<211> LENGTH: 373

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
caggcccagc tggtgcagtc tggggctgag gtgaagaagc ctgggtcctc agtgaaagtc      60
tcctgcaagg cttctggagg cagcttcacc agttatggtg tcgactgggt gcgacaggcc     120
cctggacaag ggcttgagtg gatgggtggg ataaatgttg tctttggctc agtaaaatac     180
gcacagaagt tccagggcag agtcacgatc accaaggacg attccaggac tacagtctac     240
atggaggtga ggagcctgag atctgaggac acggccatgt attactgtgc gagagcggac     300
gagatggcta caattgaagg gttctatgca tttgatatct ggggccaagg gacaatgatc     360
accgtctcct cag                                                        373

<210> SEQ ID NO 44
<211> LENGTH: 373
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
caggcccagt tggtgcagtc tggggctgag gtgaagaagc ctgggtcctc agtgaaggtc      60
tcctgcaagg cttctggagg cacgttcacc agctatggga tcgactgggt gcgacaggcc     120
cctggacagg ggcttgagtg ggtgggggg atcaaccccca tctttggttc gacaaagtac     180
ccacagaagt ttcaaggcag agtcacggtt agcacggacg aatccacgag cacagcctac     240
atggagttga gaagcctgag atctgaggac acggccatgt attactgtgc gagagcggac     300
gagatggcta caactggagg cttctatgct tttgatatct ggggccaggg gacaatggtc     360
accgtctcct cag                                                        373

<210> SEQ ID NO 45
<211> LENGTH: 361
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
caggtgcacc tggtgcagtc tggggctgag gtgaagaagc ctgggtcctc ggtgaaggtc      60
tcctgcaaga cttctggagg caccttcacc aactatccta tcacctgggt gcgacaggcc     120
cctggacaag ggcttgagtg gatgggaggg atcctcccta tccttgatac agctaactac     180
gcacaggagt tccagggcag agtcacgatt accgcggacg aatccacgag cacagcctac     240
atggagctga gcaacctgag atctgaggac acggccgtgt attactgtgc gagagtttac     300
tttgatagtg gtggttattt tgactcctgg ggccagggaa ccctggtcac cgtctcctca     360
g                                                                     361

<210> SEQ ID NO 46
<211> LENGTH: 361
<212> TYPE: DNA
<213> ORGANISM: Artificial Sequence
<220> FEATURE:
<223> OTHER INFORMATION: Description of Artificial Sequence: Synthetic -continued polynucleotide

<400> SEQUENCE: 46
caggtgcacc tggtgcagtc tggggctgag gtgaagaagc ctgggtcctc ggtgaaggtc      60
tcctgcaaga cttctggagg caccttcacc aagtatccta tcacctgggt gcgacaggcc     120
cctggacaag ggcttgagtg gatgggaggg atcctcccta tccttgatac agctaactac     180
gcacaggagt tccagggcag agtcacgatt accgcggacg aatccacgag cacagcctac     240
atggagctga gcaacctgag atctgaggac acggccgtgt attactgtgc gagagtttac     300
tatgatagtg gtggttattt tgactcctgg ggccagggaa ccctggtcac cgtctcctca     360
g                                                                    361

<210> SEQ ID NO 47
<211> LENGTH: 367
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
caggtccagc tggtgcagtc tggggctgag gtgaagaagc ctgggtcctc ggtgaaggtc      60
tcctgcaagg cttctggagg caccttcagc aactatgctt tcagctgggt gcgacaggcc     120
cctggacaag ggcttgagtg gatgggaagg atcatccctta tctttggtac accaaagtac     180
gcccagaagt tccagggcag agtcacgatt accaggacg aatccacgag cacagcctac      240
atggagctga gcagcctgag atcggaggac acggccgtgt attactgtgc gagaagcccc     300
tggcacagca gtggctggtt cccttctgac tactggggcc agggaaccct ggtcaccgtc     360
tcctcag                                                              367

<210> SEQ ID NO 48
<211> LENGTH: 367
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
caggtccagc tggtgcagtc tggggctgag ttgaagaagc ctgggtcctc ggtgaaggtc      60
tcctgcaagt cttctggagg caccttcagg aactacagtt tcagctgggt gcgacaggcc     120
cctggacaag ggcttgagtg gatgggaagg agtatcccta tctttggtac agcaaaatac     180
gcacagaagt tccagggcag agtcacgatt actacggacg aatccacgag cacagcctac     240
atggacttga gcagcctaag atctgaggac acggccgtgt attactgtgc gagaagcccc     300
tggcataaca gtggctggtt cccttcttgac tcctggggcc agggaaccct ggtcaccgtc    360
tcctcag                                                              367

<210> SEQ ID NO 49
<211> LENGTH: 370
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49

```
caggtccaac tggtgcaatc tggggctgag gtgaagaagc ctgggtcctc agtgaaggtc    60
tcctgcaagg cttctggagg caccttcagc agcaattctg tcacctgggt gcggcaggcc   120
cctggacacg ggcttgagtg gatgggaaca atcatccctt tctttggtac aagacactac   180
gcagacaact tcagggcag agtcacagtc accacgacg aatccacgac cacggtgtac    240
atggagctga gcagcctgag atctgacgac acggccgtgt attactgtgc gcgatcttgt   300
gagagtccca gttgttacca caactggttc gaccctggg gccagggaac cctggtcacc   360
gtcacctcag                                                           370

<210> SEQ ID NO 50
<211> LENGTH: 373
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
caggtccagc tggtgcagtc tggggctgag gtgaggaagc ctgggtcctc agtgaaggtc    60
tcctgcaaga cttctggagg ctccctcaac agttatggca tcagttgggt gcgacaggcc   120
cctggtggac aagggcttga gtggatggga gggatcatcc ctttctttgg tacagttatc   180
tattcagaca attaccaggg cagagcctcg ttttcctcgg acgaatctac gaccacagcc   240
tacatggagc tgagaagcct aagatctgag gacacggccg tgtattactg tgcgagatat   300
tgttatagtg ccagttgtta tcacaactgg ttcgacccct ggggccaggg aaccctggtc   360
accgtctcca cag                                                       373

<210> SEQ ID NO 51
<211> LENGTH: 373
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
caggtccagc tggtgcagtc tggggctgag gtgaagaagc ctgggtcctc agtgaaggtc    60
tcctgcgagg cctctggagt cagcctcagc agctatggta tcagctgggt gcgacaggcc   120
cctggacggg gccttgagtg gatgggaggg atcatccctt tctttggaac aagaaactac   180
gcacatgact tcgagggccg actcacgatt accacggacg aatctacgcg cacagtatat   240
atggagctga gtagcctgag atctgaggac acggccgtgt attattgtgc gaggagaaac   300
gcgaaggggg gttattccgg agggaactgg ttcgaccct ggggccaggg aaccccggtc    360
accgtctcct cag                                                       373

<210> SEQ ID NO 52
<211> LENGTH: 373
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
caggtccagc tggtgcagtc tggggctgag gtgaagaagc ctgggtcctc agtgagggtc    60
tcctgcacgg cttctggagg caccttcagt agtcttgcca tcagctgggt gcggcaggcc   120
```

```
cctggacaag gccttgagtg gatgggaggg ctcatccctg tctttggtat accaaactac    180
gcagaggact tccagggcag agtcacgatt accgcggacg aatccacgag acggcctac     240 atggacctga gcagcctgag cgctgacgac acggccgtgt attactgtgc gaggagaagt    300 gggaagggg gttattccgg agggaactgg ttcgacccct ggggccaggg aaccctggtc     360
accgtctcct cag                                                       373
```

<210> SEQ ID NO 53
<211> LENGTH: 382
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53

```
caggtccagc tggtccagtc tgggtctgag gtgaagaagc ctgggtcctc ggtgagggtc     60
tcctgcaggg cttctggagg caccttcaac agtttgccta tcagctggct gcgacaggcc    120
cctggacaag ggcctgagtg gatgggaagg atcatccctt tctttgcgac accaacgtac    180
gcagagaagt tccagggcag agtcaccatt accgcggacg aatccacggc cacagcctac    240
atggagctga gcaacctgag atccgacgac acggccgtat attactgtgc gagagatcta    300
aatttttatg atagtagtgg ttatcacttc gcgcggtggt tcgacccctg gggccaggga    360
accctggtca ccgtctcctc ag                                             382
```

<210> SEQ ID NO 54
<211> LENGTH: 382
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54

```
caggtccagt tggtgcagtc tggggctgag gtgaagaagc ctgggtcctc ggtgaaggtc     60
tcctgcacga cttccggagg caccctcagc agttatccta tcagctgggt gcgacaggcc    120
cctggacaag ggcttgagtg gatgggaagg atcactcctt tctttggtac aacaaactac    180
gcagagcagt tccagggcag aatcacgatc accacggacg aatccacgag cacggcatat    240
atggagctga gcagcctgag atctgaggac acggccgtct attactgtgc gagagatgtc    300
cactactcag atagtagtgg ttatcacttc gggcggtggt tcgacccctg gggccaggga    360
actctggtca ccgtctcctc ag                                             382
```

<210> SEQ ID NO 55
<211> LENGTH: 382
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55

```
caggtccagc tggtccagtc tgggtctgag gtgaagaagc ctgggtcctc ggtgagggtc     60
tcctgcaggg cttctggagg caccttcagc agcttggcta tcagctgggt gcgacaggcc    120
cctggacaag ggcctgagtg gatgggaagg atcatccctt tctttgctac accaagctac    180
gcagagaact tccagggcag agtcacgatt accgcggacg aatccacgag cacagcctac    240
```

```
atggagctga gcaacctgag atctgacgac acggccgtgt attactgtgc gagagatcta       300
aatttctatg atagtagtgg ttatcacttc gcgcggtggt tcgacccctg gggccaggga       360
accctggtca ccgtctcctc ag                                                382

<210> SEQ ID NO 56
<211> LENGTH: 382
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
caggtccagc tagtgcagtc tggggctgag gtgaagaagc ctgggtcctc ggtgaaggtc       60
tcctgcaagg tttctggagg caccttcagc agctctccta tcagctgggt tcgacaggcc      120
cctggacaag ggtttgagtg gatgggaagg atcatccctt tctttggttc accaagctac      180
gcagagcagt tccaggacag agtcacaatt accacgacg aatccacgac tacagcctac       240
atggagctgc gcagcctgag atctgaggac acggccgtgt attactgtgc gagagatgtt      300
aattattacg atagtagtgg ttatcacttc gggcggtggt tcgacccctg gggccaggga      360
accctggtca ccgtctcctc ag                                                382

<210> SEQ ID NO 57
<211> LENGTH: 382
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
caggtccagc tagtgcagtc tggggctgag gtgaagaagc ctgggtcgtc ggtaaaggtc       60
tcctgcaagg tttctggagg caccttcagc agctctccta tcagctgggt tcgacaggcc      120
cctggacaag ggtttgagtg gatgggaagg atcatccctt tttttggttc accaacctac      180
gcagagcagt tccagggcag agtcacaatc accacggacg aatctacgag tacagcctac      240
atggagctga gcagcctgag atctgcggac acggccgtct attactgtgc gagagatgtt      300
aattattacg atagtagtgg ttatcacttc gggcggtggt tcgacccctg gggccaggga      360
accctggtca ccgtctcctc ag                                                382

<210> SEQ ID NO 58
<211> LENGTH: 364
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
caggtgcagc tggtggagtc tgggggaggc gtggtccagc ctgggaggtc cctgagactc       60
tcctgtgcag cctctggatt ccccttcagt ggctatgcta tgcactgggt ccgccaggct      120
ccaggcaagg gctggagtg gtggcttt atatcatatg atggaagcga taaatactac        180
gcagactccg tgaagggccg attcaccatc tccagagaca attccgaaaa cacgttgcat      240
ctgcaaatga acagcctgag agctgaggac acggctgtgt attactgtgc gaagaactat      300
ggttcgggga gtttgaactg gttcgacgcc tggggccagg gaaccctggt caccgtctcc      360
```

```
tcag                                                           364

<210> SEQ ID NO 59
<211> LENGTH: 364
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
caggtgcagc tggtggagtc tgggggaggc gtggtccagc ctggggggtc cctgagactc    60
tcctgtgcag cctctggatt ccccttcagg agctatgcta tgcactgggt ccgccaggct   120
ccaggcaagg ggctggagtg ggtggctttc atatcatatg atggaaccaa tacatactac   180
gcagactccg tgaagggccc attcaccatc tccagagaca attccaagaa cacgctgtac   240
ctgcaaatga acagcctcag agctgaggac acggctgttt attactgtgc gaagaattat   300
ggttcgggga gccagaactg gttcgattcc tggggccagg gaaccctggt caccgtctcc   360
tcag                                                           364

<210> SEQ ID NO 60
<211> LENGTH: 364
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
caggtgcggc tggtggagtc tggggagggc gtggtccagc ctgggaggtc cctgagactc    60
tcctgtgcag gctctggatt ctccttcagt acctatgcta tgcactgggt ccgccaggct   120
ccaggcaagg ggctggagtg ggtggcactt atatactatg atggaagcaa taaatactac   180
gcggactctg tgaagggccg attcaccatc tccagagaca attccaagaa tacggtgtat   240
ttgcaaatga acagcctgag acctgaggac acggctgtgt atttctgtgc gaagaactat   300
ggttcgggga gtttgaactg gtacgacgcc tggggccagg gaaccctggt catcgtttcc   360
tcag                                                           364

<210> SEQ ID NO 61
<211> LENGTH: 364
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
caggtgcaac tggtggagtc tgggggaggc gtggtccagc ctgggaggtc cctgagactc    60
tcctgtgcag cctctggatt caccttcagt aactatgctc tgcactgggt ccgccaggct   120
ccaggcaagg ggctcgagtg ggtggcactt atatactatg atggaagcag gaaatactat   180
gcagactccg tgaagggccg attcaccatc tccagagaca attccaagaa cacgctccat   240
ctgcaaatga acagcgtgag agttgaggac acggctgtct attactgtgc gaagaactat   300
ggttcgggga ccttgaactg gttcgacgcc tggggccagg gaaccctggt caccgtctcc   360
tcag                                                           364

<210> SEQ ID NO 62
```

<211> LENGTH: 364
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 62
caggtgcaac ttgtggagtc tgggggaggc gtggtccagc ctggaggtc cctgagactc     60 tcctgtgtag gctctgaatt cccccttcaag gcctatgcta tgcactgggt ccgccaggct    120
ccaggcaagg gcctggagtg ggtggcattt atatcatatg atggatccaa tacatattat    180
gcagactccg tgaagggccg attcagcctc tccaggaca attcgaagaa cacccctgtat    240 ctagacatga accccctgag acctgaagac acggctgtgt attattgtgc gaagaattac    300
ggttcgggga gtttgaattg gttcgactct tggggccagg ggaccctgct caccgtctcc    360
gcag                                                                  364

<210> SEQ ID NO 63
<211> LENGTH: 364
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 63
caggtgcaac tggtggagtc tgggggaggc gtggtccggc ctggaggtc cctgcgagtc     60 tcctgtgcag cctctggatt caccttcagt aattttgcaa tgcactgggt ccgccaggct    120
ccaggcaagg ggctggagtg ggtggcactt atatattatg atggaagcaa taaatattac    180
gcagactccg tgaggggccg attcaccatc tccagagaca attccaagaa cacactgtat    240
ctgcaaatga acagcctgag acctgacgac acggctgtgt attactgtgc gaaaaactac    300
ggttcgggga ctttgaattg gttcgactcc tggggccagg gaaccctggt caccgtctcc    360
tcag                                                                  364

<210> SEQ ID NO 64
<211> LENGTH: 391
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 64
caggtgcagc tggtggagtc tgggggaggc gtggtccagc ctggaggtc cctgacactc     60 tcctgtgcag actctggatt caccttcaca accgatgcta tgcactgggt ccgtcaggct    120
ccaggcaagg ggctggagtg ggtggccgtc atatcatatg atggaaccga gaatactat    180 ggagactccg tggagggccg attcaccatc tccagagaca attccaagaa cacgctgttt    240
ctgcaaatga gcgacctgag acctagggac tcggctgtgt atttctgtgc gagagaggga    300
acctacagtg gaattgtgac tggccaatcc caatccccct cttcatacat ggacgtctgg    360
ggcaaaggga ctacggtcat cgtctcctca g                                   391

<210> SEQ ID NO 65
<211> LENGTH: 391
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 65

```
caggtgcagt tggtggagtc tgggggaggc gtggtccagc ctggagggtc cctgagactc    60
tcctgtgcag attctggatt caccttcaga accgacgcta tgcactgggt ccgtcaggcc   120
ccaggcaagg ggctggagtg ggtggccgtc atatcatatg atggatccga gaaatattat   180
ggagactccg tgagggccg attcaccatc tccagagaca attccaagaa tacgctgttt   240
ctgcaaatga acgccctgag acctggggac acggctgtgt atttctgtgc gagagaggga   300
acctacagtg gaattgtgac tggccaatcc caatcgccct cctcatacat ggccgtctgg   360
ggcaaaggga ctacggtcat cgtctcctca g                                  391
```

<210> SEQ ID NO 66
<211> LENGTH: 373
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66

```
gaggtgcagc tggtggagtc tgggggaggc ttggtcccgc ctggggggtc cctgagactc    60
tcctgtgcag cctctggatt cacctttgat agttattgga tgagctgggt ccgccaggct   120
ccagggaagg ggctggagtg ggtggccaac ataaagctag atggaagtga gaatgctat    180
gtggactctg tgaagggccg attcaccatc tccagagaca cgccaagaa ctcactgttt   240
ctgcaaatga acagcctgag agccgaggac acggctgtct attactgtgc gagagtcgct   300
agtcacccaa gcttgttttc accctactac tttgactact ggggccaggg aaccctggtc   360
accgtctcct cag                                                      373
```

<210> SEQ ID NO 67
<211> LENGTH: 373
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67

```
gaggtgcagc tggtggagtc tgggggaggc ttggtcccgc ctggggggtc cctaaaagtc    60
tcctgtgcag cctctggatt cacctttgac aactattgga tgagctgggt ccgccaggct   120
ccagggaagg ggctggagtg ggtggccaac ataaagctag atggaagtga gaatgctat    180
gtggactctg tgaagggccg attcaccatc tccagagaca cgccaggaa ctcactgttt   240
ctgcaaatga acagcctgag agccgaggac acggctgtct attactgtgc gagagtcgct   300
agtcacccaa ctttgttttc accctactac tttgactact ggggccaggg aaccctggtc   360
actgtctcct cag                                                      373
```

<210> SEQ ID NO 68
<211> LENGTH: 373
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68

```
caggtgcagc tgcaacagtg gggcgcagga ctgttgaagc cttcggagac cttgtccctc    60
acctgcggtg tctctgatgg gcccctcatt ggttactact gggcctggat ccgccagacc   120
ccagggaagg ggctggagtg gattgggag atcactcata gtggaaacac caactacaac   180
ccgtccctcg agagtcgagt caccatttcc gttgacacgt ccaagaacca gttctccctg   240
aaggtgaact ctgttaccgc cgcggacacg gctgtctatt attgtgcgag aggccccggg   300
gggactagca ccagttgtta taggtgttgg ttcgacccct ggggccaggg aaccctggtc   360
accgtctcct cag                                                      373

<210> SEQ ID NO 69
<211> LENGTH: 373
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69
caggtgcagc tacagcaatg gggcgcagga ctgttgaagc cttcggagac cctgtccctc    60
acctgcgctg tccatggtgg gcccttgatt ggttggtact ggagctggat ccgccagacc   120
ccagagaagg ggctggagtg gattgggaa atcactcata gtggaagcac caactacaac   180
ccgtccctca agagtcgagt caccatatca gtagacacgt ccaagaacca cttctccctc   240
aagctgacgt ctgtgaccgc cgcggacacg gctgtgtatt actgtgcgag ggccccggg   300 ggcacaagta ccagctgcta tcaatgttgg ttcgacccct ggggccaggg aaccctggtc   360
accgtctcct cag                                                      373

<210> SEQ ID NO 70
<211> LENGTH: 370
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70
caggtgcagc tgcaggagtc gggcccagga ctggtgaagc cttcggagac cctgtcactc    60
acctgcactg tctctggtgg ctccatcagc agtagtagtt attactgggg ctggatccgc   120
cagcccccag gaaggggct ggagtggatt gggagtctct attatagtgg gagcacctac   180
tacaacccgt ccctcaagag tcgagtcacc atatccgtag acacgtccaa gaaccagttc   240
tccctgaagc tgtactctgt gaccgccgca gacacggctg tgtattactg tgcgggacag   300
gactatagtg ggacttacta tgactacttt gactactggg gccagggagc cctggtcacc   360
gtctcctcag                                                          370

<210> SEQ ID NO 71
<211> LENGTH: 370
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
caggtgcagc tgcaggagtc gggcccagga ctggtgaagc cttcggagac cctgtcactc    60
acctgcactg tctctggtgg ctccatcagc agtagtagtt attactgggg ctggatccgc   120
```

```
cagcccccag ggaagggct  ggagtggatt  gggagtatgt  attatagtgg  gagcacctac      180
tacaacccgt ccctcaagag  tcgagtcacc  atatccgtag  acacgtccaa  gaaccagttc      240
tccctgaagc tgagctctgt  gaccgccgca  gacacggctg  tgtattactg  tgcgggacag      300
gactatagtg ggacttacta  tgactacttt  aactactggg  gccagggaac  cctggtcacc      360
gtctcctcag                                                                  370
```

```
<210> SEQ ID NO 72
<211> LENGTH: 355
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72
cagctgcagc tgcaggagtc  gggcccagga  ctggtgaagc  cttcggagac  cctgtccctc       60
acctgcactg tctctggtgg  ctccatcaac  actaggagtt  actactgggg  ctggatccgc      120
cagcctccag ggaagggct   ggagtggatt  gggagtatct  tttatactgg  gagcacctac      180
tacaacccgt ccctcaagag  tcgagtcacc  atatccgtag  acacgtccaa  caaccagttc      240
tccctgaggc tgagctctgt  gaccgccgca  gacacggctg  tgtattactg  tgcgagacag      300
gacagaaact ggttcgactc  ctggggccag  ggaaccctgg  tcaccgtctc  ctcag           355
```

```
<210> SEQ ID NO 73
<211> LENGTH: 355
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
caactgcagc tgcaggagtc  gggcccagga  ctagtgaagc  cttcggcgac  cctgtccctc       60
acctgcactg tctctcgtgg  ctccatcagc  actaatgatc  attcttgggg  ctggatccgc      120
cagcccccag ggaagggact  ggagtgggtt  ggcagtcttc  atcattctgg  gaacacctac      180
tacaacccgt ccctcaagag  tcggctcacc  atatcactcg  acacgtccga  gacccagttc      240
tccctgaacc tgagctctgt  gaccgccgcg  gacacggccg  tctattattg  tgtgagacag      300
aatcggaact ggttcgactc  ctggggccag  ggaaccctgg  tcagcgtctc  gtcag           355
```

```
<210> SEQ ID NO 74
<211> LENGTH: 358
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74
cagctgcagc tacaggagtc  gggcccagga  ctggtgaagc  cttcggagac  cctgtccctc       60
acctgcactg tctctggtgg  ctccatcagt  aggagtagta  cttacttctg  gggctggatc      120
cgccagcccc agggaaggg   gctggagtgg  attgggagtg  tctcttatag  tgggagcacc      180
tactacaacc cgtccctcaa  gagtcgagtc  agcgtatccg  tagacacgtc  caggaagcag      240
ttctccctga aactgacgtc  tgtgaccgcc  gcagacacgg  ctgtgtatta  ctgtgcgaga      300
caggacagaa actggttcga  ctcctggggc  cagggaaccc  tggtcaccgt  ctcctcag        358
```

<210> SEQ ID NO 75
<211> LENGTH: 388
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75
caggtgcagc tgcaggagtc gggcccagga ctggtgaagc cttcggagac cctgtccctc        60
acctgcactg tctctggtga ctccatcact agttactact ggagttggat caggcagccc       120
ccagggcagg gactggagtg gattggctat atctattaca gtgggggcac caactacaac       180
ccctccctca gagtcgagt cgtcatgtca ctggacacgt cgaggaatca gttctccctg        240
aagctgaact ctctgaccgc tgcggacacg gccgtgtatt attgtgcgag cgccttgaat       300
tattttgata gtagtggccc cggtggcgtc gcgatggggg ggggatttga ctcctggggc       360
cagggagccc tggtcaccgt ctcctcag                                          388

<210> SEQ ID NO 76
<211> LENGTH: 388
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76
caggtgcagc atcaggagtc gggcccaggc ctggtgaagc cttcggagac cctgtccctc        60
acctgcactg tctctggtga ctccatcagt agttactact ggaactggat ccggcaggcc       120
ccagggaagg gactggagtg gcttgggtat ataaattaca gtgggaacac cgactacaac       180
acctccctca gagtcgagc taccatatca ctagacacgt cgaagaacca gttctccctg        240
aaactgagct ccgtgaccac tgcggatacg gccgtctatt actgtgcggg cgccttgtat       300
tactttgata gtcgtggccc cggtggcgtc gcgatggggg ggggtttga ctcctggggc        360 cagggaaccc tggtcaccgt ctcctcag                                          388

<210> SEQ ID NO 77
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Val Pro Lys Leu
            35                  40                  45

Met Ile Tyr Asp Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Arg Ser
                85                  90                  95

```
Ser Thr Leu Leu Phe Gly Gly Gly Thr Lys Leu Thr Val Leu
            100                 105                 110

<210> SEQ ID NO 78
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Phe Asp Val Asn Asn Arg Pro Ser Gly Val Ser Thr Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Thr Ser Phe Thr Lys Ser
                85                  90                  95

Thr Thr Leu Leu Phe Gly Gly Gly Thr Lys Leu Thr Val Leu
            100                 105                 110

<210> SEQ ID NO 79
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ala Gly Tyr
            20                  25                  30

Leu Asn Trp Tyr Gln Gln Lys Pro Gly Lys Ala Pro Glu Leu Leu Ile
        35                  40                  45

Tyr Ser Ala Ser Thr Leu Gln Ser Gly Phe Pro Ser Arg Phe Asn Gly
    50                  55                  60

His Gly Ser Gly Thr Asp Phe Thr Leu Thr Ile Thr Ser Leu Gln Pro
65                  70                  75                  80

Glu Asp Phe Ala Thr Tyr Tyr Cys Gln Gln Ser Phe Arg Thr Pro Thr
                85                  90                  95

Thr Phe Gly Gly Gly Thr Arg Val Glu Ile Lys
            100                 105

<210> SEQ ID NO 80
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80
```

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Thr Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Arg Gly Val Pro Ser Arg Phe Ser Gly
50                  55                  60

Ser Gly Ser Glu Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Trp Thr
                85                  90                  95

Phe Gly Gln Gly Thr Lys Val Glu Ile Lys
                100                 105

<210> SEQ ID NO 81
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Asp Ile Gln Met Thr Gln Ser Pro Ser Thr Leu Ser Ala Ser Val Gly
1               5                   10                  15

Asp Ser Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Arg Gly Val Pro Ser Arg Phe Ser Gly
50                  55                  60

Ser Gly Ser Gly Thr Glu Phe Thr Leu Thr Ile Asp Ser Leu Gln Pro
65                  70                  75                  80

Asp Asp Phe Ala Thr Tyr Tyr Cys Gln Gln Tyr Asn Thr Tyr Trp Thr
                85                  90                  95

Phe Gly Gln Gly Thr Lys Val Glu Ile Lys
                100                 105

<210> SEQ ID NO 82
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Val Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Arg Leu Glu Ser Gly Val Pro Ser Arg Phe Ser Gly
50                  55                  60

Ser Gly Ser Glu Thr Glu Phe Thr Leu Thr Ile Ser Ser Leu Gln Pro
65                  70                  75                  80
```

Asp Asp Phe Ala Thr Tyr Tyr Cys Gln Gln Tyr Asn Ser Tyr Trp Thr
                85                  90                  95

Phe Gly Gln Gly Thr Lys Val Glu Ile Lys
            100                 105

<210> SEQ ID NO 83
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Tyr Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly His Val Val Phe Gly Gly Gly Thr Lys Leu Thr Val Leu
            100                 105                 110

<210> SEQ ID NO 84
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Tyr Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly His Val Ile Phe Gly Gly Gly Thr Lys Val Thr Val Leu
            100                 105                 110

<210> SEQ ID NO 85
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 85

Gln Ser Val Leu Thr Gln Pro Pro Ser Val Ser Gly Ala Pro Gly Gln
1               5                   10                  15

Arg Val Thr Ile Ser Cys Thr Gly Gly Ser Ser Asn Ile Gly Ala Gly
            20                  25                  30

Tyr Asp Val His Trp Tyr Gln Lys Leu Pro Gly Thr Ala Pro Lys Leu
        35                  40                  45

Leu Ile Phe Gly Lys Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Arg Ala Glu Asp Glu Ala Glu Tyr Tyr Cys Gln Ser Phe Asp Ser Leu
                85                  90                  95

Ser Gly Tyr Ala Val Phe Gly Gly Gly Thr Gln Leu Thr Val Leu
            100                 105                 110

<210> SEQ ID NO 86
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Asp Ile Gln Met Thr Gln Ser Pro Ser Thr Leu Pro Ala Ser Val Gly
1               5                   10                  15

Asp Arg Val Thr Ile Thr Cys Arg Ala Ser Gln Ser Ile Asp Ser Trp
            20                  25                  30

Leu Ala Trp Phe Gln Gln Lys Pro Gly Lys Ala Pro Lys Leu Leu Ile
        35                  40                  45

Ser Lys Ala Ser Thr Leu Glu Asn Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Ser Tyr Ser Pro
                85                  90                  95

Trp Thr Phe Gly Gln Gly Thr Lys Val Glu Ile Lys
            100                 105

<210> SEQ ID NO 87
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Ser Gly Ile Pro Ala Arg Phe Ser Gly
    50                  55                  60

Ser Gly Ser Gly Thr Asp Phe Thr Leu Thr Ile Ser Ser Leu Glu Pro

```
                65                  70                  75                  80
Glu Asp Phe Ala Val Tyr Tyr Cys Gln His Arg Ser Asn Trp Pro Pro
                        85                  90                  95
Arg Val Tyr Thr Phe Gly Gln Gly Thr Lys Leu Glu Ile Lys
                100                 105                 110
```

<210> SEQ ID NO 88
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

```
Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Gly Ser Ser
                20                  25                  30

Leu Ala Trp Tyr Gln Gln Lys Pro Gly Gln Ala Pro Arg Leu Leu Ile
            35                  40                  45

Tyr Asp Ala Ser Lys Arg Ala Ser Gly Phe Pro Ala Arg Phe Ser Gly
50                  55                  60

Ser Gly Ser Gly Thr Asp Phe Thr Leu Thr Ile Ser Ser Leu Glu Pro
65                  70                  75                  80

Gly Asp Phe Ala Val Tyr Tyr Cys Gln Gln Arg Ser Ser Trp Pro Pro
                85                  90                  95

Tyr Met Tyr Thr Phe Gly Gln Gly Thr Lys Leu Glu Ile Lys
                100                 105                 110
```

<210> SEQ ID NO 89
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

```
Gln Ser Ala Leu Thr Gln Pro Ala Ser Val Ser Gly Ser Pro Gly Gln
1               5                   10                  15

Ser Ile Thr Ile Ala Cys Thr Gly Thr Ser Ser Asp Val Gly Gly Tyr
                20                  25                  30

Asn Phe Val Ser Trp Tyr Gln Gln His Pro Gly Glu Ala Pro Arg Leu
            35                  40                  45

Leu Ile Phe Asp Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Phe Cys Ser Ser Tyr Thr Ser Arg
                85                  90                  95

Ser Ser Arg Thr Tyr Val Phe Gly Thr Gly Thr Arg Val Thr Val Leu
                100                 105                 110
```

<210> SEQ ID NO 90
<211> LENGTH: 112
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 90

Gln Ser Ala Leu Thr Gln Pro Ala Ser Val Ser Gly Ser Pro Gly Gln
1               5                   10                  15

Ser Ile Thr Ile Ser Cys Thr Gly Ser Ser Ser Asp Val Gly Gly Tyr
            20                  25                  30

Asn Tyr Val Ser Trp Tyr Gln Gln His Pro Gly Lys Ala Pro Lys Leu
        35                  40                  45

Leu Ile Phe Asp Val Ser Asn Arg Pro Ser Gly Val Ser Asn Arg Phe
    50                  55                  60

Ser Gly Ser Lys Ser Asn Thr Ala Ser Leu Thr Ile Ser Gly Leu
65                  70                  75                  80

Gln Ala Glu Asp Glu Ala Asp Tyr Tyr Cys Ser Ser Tyr Thr Ala Arg
                85                  90                  95

Thr Ser Arg Thr Tyr Val Phe Gly Ser Gly Thr Lys Val Thr Val Leu
            100                 105                 110

<210> SEQ ID NO 91
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Glu Lys Val Met Thr Gln Ser Pro Ala Ser Leu Ser Val Ser Pro Gly
1               5                   10                  15

Glu Arg Ala Thr Phe Ser Cys Arg Ala Ser Gln Ser Val Asn Asn Asn
            20                  25                  30

Leu Ala Trp Tyr Gln Gln Lys Pro Gly Gln Ala Pro Arg Leu Leu Ile
        35                  40                  45

Tyr Gly Ala Ser Ser Arg Val Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Thr Phe Gly Gln Gly Thr Lys Leu Asp Ile Lys
            100                 105

<210> SEQ ID NO 92
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Gly Asn Asn
            20                  25                  30

Leu Val Trp Tyr Gln Gln Lys Pro Gly Gln Ala Pro Arg Leu Leu Ile
        35                  40                  45

Tyr Gly Ala Ser Thr Arg Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Cys Tyr Asn Trp Pro Pro
                85                  90                  95

Thr Phe Gly Gln Gly Thr Asn Leu Glu Ile Lys
            100                 105

<210> SEQ ID NO 93
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Glu Lys Val Met Thr Gln Ser Pro Ala Thr Leu Ser Val Ser Pro Gly
1               5                   10                  15

Glu Arg Ala Thr Phe Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Asn Arg Val Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asp Asn Trp Pro Pro
                85                  90                  95

Thr Phe Gly Gln Gly Thr Lys Leu Asp Ile Lys
            100                 105

<210> SEQ ID NO 94
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Ser Asn
            20                  25                  30

Leu Val Trp Tyr Gln Gln Lys Pro Gly Gln Ala Pro Arg Leu Leu Ile
        35                  40                  45

Tyr Arg Ala Ser Thr Arg Val Thr Gly Ile Pro Ala Arg Phe Ser Gly
    50                  55                  60

Ser Gly Ser Gly Thr Glu Phe Thr Leu Thr Ile Ser Ser Leu Leu Ser
65                  70                  75                  80

Glu Asp Phe Ala Ile Tyr Tyr Cys Gln Gln Phe Tyr Asn Trp Pro Pro
                85                  90                  95

Thr Phe Gly Gln Gly Thr Lys Leu Glu Ile Lys
            100                 105

<210> SEQ ID NO 95
<211> LENGTH: 107
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 95

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Ser Asn
            20                  25                  30

Leu Val Trp Tyr Gln Gln Lys Pro Gly Gln Ala Pro Arg Leu Leu Ile
        35                  40                  45

Tyr Arg Ala Ser Thr Arg Val Thr Gly Ile Pro Ala Arg Phe Ser Gly
50                  55                  60

Ser Gly Ser Gly Thr Glu Phe Thr Leu Thr Ile Ser Ser Leu Leu Ser
65                  70                  75                  80

Glu Asp Phe Ala Val Tyr Tyr Cys Gln Gln Phe Tyr Asn Trp Pro Pro
                85                  90                  95

Thr Phe Gly Gln Gly Thr Lys Leu Glu Ile Lys
            100                 105

<210> SEQ ID NO 96
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Gly Ser Asn
            20                  25                  30

Leu Ala Trp Tyr Gln Gln Lys Pro Gly Gln Thr Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Trp Trp Thr
                85                  90                  95

Phe Gly Leu Gly Thr Lys Val Glu Ile Lys
            100                 105

<210> SEQ ID NO 97
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Glu Ile Val Val Thr Gln Ser Pro Ala Thr Leu Ser Val Ser Leu Gly
1               5                   10                  15

Glu Arg Ala Thr Leu Ser Cys Arg Ala Ser Gln Asn Ile Gly Ser Asn
            20                  25                  30

Leu Ala Trp Tyr Gln Gln Lys Pro Gly Gln Ala Pro Arg Leu Leu Ile
        35                  40                  45
```

```
Tyr Gly Ala Ser Thr Arg Ala Thr Gly Thr Pro Ala Arg Phe Ser Gly
    50                  55                  60

Ser Gly Ser Glu Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Trp Thr
                85                  90                  95

Phe Gly Gln Gly Thr Lys Val Glu Ile Lys
                100                 105

<210> SEQ ID NO 98
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Glu Val Val Thr Gln Ser Pro Ala Thr Leu Ser Val Ser Pro Gly
1               5                   10                  15

Glu Arg Ala Thr Leu Ser Cys Arg Ala Ser Gln Ser Val Gly Ser Asn
                20                  25                  30

Leu Ala Trp Tyr Gln Gln Lys Pro Gly Gln Ala Pro Arg Leu Leu Leu
            35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Leu Trp Thr
                85                  90                  95

Phe Gly Gln Gly Thr Lys Val Glu Ile Lys
                100                 105

<210> SEQ ID NO 99
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Gly Ser Asn
                20                  25                  30

Leu Ala Trp Tyr Gln Gln Lys Pro Gly Gln Ala Pro Thr Leu Leu Ile
            35                  40                  45

Tyr Ala Ala Ser Thr Arg Ala Thr Gly Ile Pro Ala Arg Phe Ser Gly
    50                  55                  60

Ser Gly Ser Trp Thr Glu Phe Asn Leu Thr Ile Asn Ser Leu Gln Ser
65                  70                  75                  80

Glu Asp Phe Ala Val Tyr Tyr Cys Gln Gln Tyr Asn Asn Trp Trp Thr
                85                  90                  95

Phe Gly Gln Gly Thr Lys Val Glu Ile Lys
                100                 105

<210> SEQ ID NO 100
<211> LENGTH: 106
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Glu Ile Val Met Thr Gln Ser Pro Val Thr Val Ser Val Ser Pro Gly
1               5                   10                  15

Glu Arg Ala Thr Leu Ser Cys Arg Val Ser Gln Ser Val Gly Ser Asn
            20                  25                  30

Leu Ala Trp Tyr Gln Gln Lys Pro Gly Gln Ala Pro Arg Leu Leu Ile
        35                  40                  45

Tyr Ala Ala Ser Thr Arg Ala Thr Gly Val Pro Ala Arg Phe Ser Gly
    50                  55                  60

Ser Lys Ser Gly Thr Glu Phe Thr Leu Thr Ile Ser Ser Leu Gln Pro
65                  70                  75                  80

Glu Asp Leu Ala Val Tyr Tyr Cys Gln Gln Tyr Asn Asn Trp Trp Thr
                85                  90                  95

Phe Gly Gln Gly Thr Lys Val Glu Ile Lys
            100                 105

<210> SEQ ID NO 101
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Glu Ile Val Met Thr Gln Ser Pro Ala Thr Leu Ser Val Ser Pro Gly
1               5                   10                  15

Glu Arg Pro Thr Leu Ser Cys Arg Ala Ser Gln Asn Ile Gly Arg Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Val Pro Ala Arg Phe Ser Gly
    50                  55                  60

Ser Gly Ser Glu Thr Glu Phe Asn Leu Thr Ile Asn Ser Leu Gln Ser
65                  70                  75                  80

Glu Asp Leu Ala Val Tyr Tyr Cys Gln Gln Tyr Asn Asn Trp Trp Thr
                85                  90                  95

Phe Gly Gln Gly Thr Lys Val Glu Ile Lys
            100                 105

<210> SEQ ID NO 102
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Gln Ser Val Leu Thr Gln Pro Pro Ser Val Ser Gly Ala Pro Gly Gln
1               5                   10                  15

Arg Val Thr Ile Ser Cys Thr Gly Thr Ser Ser Asn Ile Gly Ala Gly
            20                  25                  30

Tyr Asp Val His Trp Tyr Gln Gln Phe Pro Gly Lys Ala Pro Lys Leu

```
                   35                  40                  45

Leu Ile Phe Gly Asn Asn Arg Pro Ser Gly Val Pro Asp Arg Phe
     50                  55                  60

Ser Gly Ser Lys Ser Gly Thr Ser Ala Ser Leu Ala Ile Thr Gly Leu
 65                  70                  75                  80

Gln Ala Glu Asp Ala Asp Tyr Tyr Cys Gln Ser Tyr Asp Asn Ser
                 85                  90                  95

Leu Lys Ala Val Phe Gly Gly Gly Thr Arg Leu Thr Val Leu
                100                 105                 110

<210> SEQ ID NO 103
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Gln Ser Val Leu Thr Gln Pro Pro Ser Val Ser Gly Ala Pro Gly Gln
 1               5                  10                  15

Arg Ile Thr Ile Ser Cys Thr Gly Thr Ser Ser Asn Leu Gly Ala Gly
                 20                  25                  30

Phe Asp Val His Trp Tyr Gln Gln Leu Pro Gly Lys Ala Pro Glu Leu
             35                  40                  45

Leu Ile Phe Gly Asn Asn Arg Pro Ser Gly Val Pro Asp Arg Phe
     50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Asn Ser
                 85                  90                  95

Leu Lys Ala Val Phe Gly Gly Gly Thr Arg Leu Thr Val Leu
                100                 105                 110

<210> SEQ ID NO 104
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Gln Thr Val Val Thr Gln Glu Pro Ser Phe Ser Val Ser Pro Gly Gly
 1               5                  10                  15

Thr Val Thr Leu Thr Cys Gly Leu Ser Ser Gly Ser Val Ser Thr Thr
                 20                  25                  30

His Tyr Pro Ser Trp Tyr Gln Arg Thr Pro Gly Gln Ala Pro Arg Thr
             35                  40                  45

Leu Ile Tyr Thr Thr Asn Thr Arg Ser Ser Gly Val Pro Asp Arg Phe
     50                  55                  60

Ser Gly Ser Ile Leu Gly Asn Lys Ala Ala Leu Thr Ile Thr Gly Ala
 65                  70                  75                  80

Gln Ala Asp Asp Glu Ser Asp Tyr Tyr Cys Val Leu Tyr Met Gly Arg
                 85                  90                  95

Gly Ile Ser Val Phe Gly Gly Gly Thr Lys Leu Thr Val Leu
                100                 105                 110
```

```
<210> SEQ ID NO 105
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Ile Thr
            20                  25                  30

His Tyr Pro Ser Trp Tyr Arg Gln Thr Pro Gly Gln Ala Pro Arg Thr
        35                  40                  45

Leu Ile Tyr Thr Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Val Leu Tyr Met Gly Arg
                85                  90                  95

Gly Ile Ser Val Phe Gly Gly Gly Thr Lys Leu Thr Val Leu
            100                 105                 110

<210> SEQ ID NO 106
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Phe Val Ser Trp Tyr Gln His His Pro Gly Asn Ala Pro Lys Leu
        35                  40                  45

Leu Ile Tyr Gly Val Thr Asp Arg Pro Ser Gly Val Ser Lys Arg Phe
    50                  55                  60

Ser Gly Ser Arg Ser Gly Asn Thr Ala Ser Leu Thr Ile Ser Gly Leu
65                  70                  75                  80

Gln Ser Glu Asp Glu Ala Asp Tyr Tyr Cys Ser Ser Tyr Thr Thr Phe
                85                  90                  95

Ile Thr Arg Gly Trp Ile Phe Gly Gly Gly Thr Arg Leu Thr Val Leu
            100                 105                 110

<210> SEQ ID NO 107
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30
```

```
Asn Phe Val Ser Trp Tyr Gln Gln Pro Gly Lys Ala Pro Lys Leu
            35                  40                  45

Ile Ile Tyr Asp Val Ser Asn Arg Pro Ser Gly Val Ser Asp Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ala Ser
                 85                  90                  95

Ser Thr Arg Asn Phe Val Phe Gly Thr Gly Thr Gln Val Thr Val Leu
            100                 105                 110

<210> SEQ ID NO 108
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Asp Ile Gln Met Thr Gln Ser Pro Ser Thr Leu Ser Ala Ser Val Gly
 1               5                   10                  15

Asp Arg Val Thr Ile Thr Cys Arg Ala Ser Gln Ser Phe Ser Thr Trp
             20                  25                  30

Leu Ala Trp Tyr Gln Gln Lys Pro Gly Lys Ala Pro Lys Leu Leu Ile
         35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asp Thr Tyr Ser Thr
                 85                  90                  95

Phe Gly Gln Gly Thr Lys Val Glu Val Lys
            100                 105

<210> SEQ ID NO 109
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Asp Ile Gln Met Thr Gln Ser Pro Ser Thr Leu Ser Ala Ser Val Gly
 1               5                   10                  15

Asp Arg Val Thr Ile Thr Cys Arg Ala Ser Gln Ser Phe Ser Ser Trp
             20                  25                  30

Leu Ala Trp Tyr Gln Gln Lys Pro Gly Lys Ala Pro Lys Leu Leu Ile
         35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asp Thr Tyr Ser Thr
                 85                  90                  95

Phe Gly Gln Gly Thr Lys Val Glu Val Lys
            100                 105
```

```
<210> SEQ ID NO 110
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Asp Ile Gln Leu Thr Gln Ser Pro Ser Phe Leu Ser Ala Ser Val Arg
1               5                   10                  15

Asp Arg Val Thr Ile Thr Cys Arg Ala Ser Gln Gly Ile Ser Thr Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Leu Ser Asn Tyr Leu Phe
                85                  90                  95

Thr Phe Gly Pro Gly Thr Lys Val Asp Ile Lys
            100                 105

<210> SEQ ID NO 111
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Thr Tyr
            20                  25                  30

Leu Ala Trp Tyr Gln Gln Lys Pro Gly Lys Ala Pro Lys Leu Leu Ile
        35                  40                  45

Tyr Asp Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Asn Tyr Val Phe
                85                  90                  95

Thr Phe Gly Pro Gly Thr Lys Val Asp Ile Lys
            100                 105

<210> SEQ ID NO 112
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Asp Val Gln Leu Thr Gln Ser Pro Ser Phe Leu Ser Ala Ser Val Gly
1               5                   10                  15
```

His Arg Val Thr Ile Thr Cys Arg Ala Ser Gln Gly Ile Ser Thr Tyr
                20                  25                  30

Leu Ala Trp Tyr Gln Gln Lys Pro Gly Lys Ala Pro Lys Leu Leu Ile
            35                  40                  45

Tyr Asp Ala Ser Thr Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Ser Ser Tyr Val Phe
                85                  90                  95

Thr Phe Gly Pro Gly Thr Lys Val Asp Ile Lys
                100                 105

<210> SEQ ID NO 113
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Asp Met Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Tyr
                20                  25                  30

Leu Asn Trp Tyr Gln Gln Lys Ala Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Phe Gly Gln Gly Thr Lys Val Glu Ile Lys
                100                 105

<210> SEQ ID NO 114
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Asn Asn Tyr
                20                  25                  30

Leu Asn Trp Tyr Gln Gln Arg Pro Gly Lys Pro Pro Asn Leu Leu Ile
            35                  40                  45

Tyr Ala Ala Ser Thr Leu Gln Ala Gly Val Pro Ser Arg Phe Ser Gly
 50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Gly Ser Pro Leu
                85                  90                  95

Phe Gly Gln Gly Thr Lys Val Glu Ile Lys
            100                 105

<210> SEQ ID NO 115
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 115

```
cagtctgccc tgactcagcc tgcctccgtg tctgggtctc ctggacagtc gatcaccatc    60
tcctgcactg gaaccagcag tgacgttggt ggttataact atgtctcctg gtaccaacaa   120
cacccaggca agtccccaa actcatgatt tatgatgtca gtaatcggcc ctcaggggtt    180
tctaatcgct tctctggctc caagtctggc aacacggcct ccctgaccat ctctgggctc   240
caggctgagg acgaggctga ttattactgc agctcatata aaggagcag cacctcctc    300 ttcggcggag ggaccaagct gaccgtccta g                                  331
```

<210> SEQ ID NO 116
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 116

```
cagtctgccc tgactcagcc tgcctccgtg tctgggtctc ctggacagtc gatcaccatc    60
tcctgcactg gaaccagcag tgacgttggt ggttataact atgtctcctg gtaccaacaa   120
cacccaggca agccccccaa actcatgatt tttgatgtca ataatcggcc ctcaggggtt   180
tctactcgct tctctggctc caagtctggc aacacggcct ccctgaccat ctctgggctc   240
caggctgagg acgaggctga ttattactgc acctcattta caagagcac cactctccta   300 tttggcggag ggaccaagct gaccgtccta g                                  331
```

<210> SEQ ID NO 117
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 117

```
gacatccaga tgacccagtc tccatcctcc ctgtctgcat ctgtaggaga cagagtcacc    60
atcacttgcc gggccagcca gagcattgcc ggctatttaa attggtatca gcagaaacca   120
ggaaaagccc ctgagctcct gatctactct gcatccactt tgcaaagtgg attcccttca   180
aggttcaatg gccatggatc tgggacagat ttcactctca ccatcaccag tctgcaacct   240
gaggattttg caacttacta ctgtcaacag agtttcagaa ccccaccac tttcggcgga   300 gggaccaggg tggagatcaa ac                                            322
```

<210> SEQ ID NO 118
<211> LENGTH: 319
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 118

```
gacatccaga tgacccagtc tccttccacc ctgtctgcat ctgtaggaga cagagtcacc   60
atcacttgcc gggccagtca gagtattggt acctggttgg cctggtatca gcagaaacca  120
gggaaagccc ctaaactcct gatctataag gcgtccagtt tagaaagggg ggtcccatca  180
aggttcagcg gcagtggatc tgagacagaa ttcactctca ccatcagcag cctgcagcct  240
gatgattttg caacttatta ctgccaacag tataatagtt attggacgtt cggccagggg  300
accaaggtgg aaatcaaac                                               319
```

<210> SEQ ID NO 119
<211> LENGTH: 319
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 119

```
gacatccaga tgacccagtc tccttccacc ctgtctgcat ctgtaggaga cagcgtcacc   60
atcacttgcc gggccagtca gagtattagt agttggttgg cctggtatca gcagaaacca  120
gggaaagccc ctaagctcct gatctataag gcgtctagtt tagaaagagg ggtcccatca  180
aggttcagcg gcagtggatc tgggacagaa ttcactctca ccatcgacag cctgcagcct  240
gatgattttg caacttatta ctgccaacaa tataatactt attggacgtt cggccaaggg  300
accaaggtgg aaatcaaac                                               319
```

<210> SEQ ID NO 120
<211> LENGTH: 319
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 120

```
gacatccaga tgacccagtc tccttccacc ctgtctgcat ctgtaggaga cagagtcacc   60
atcacttgcc gggccagtca gagtgttagt tcctggttgg cctggtatca gcagaaacca  120
gggaaagccc ctaaactcct gatctataag gcgtctcgtt tagaaagtgg ggtcccatca  180
aggttcagcg gcagtggatc tgagacagaa ttcactctca ccatcagcag cctgcagcct  240
gatgattttg caacttatta ctgccaacag tataatagtt attggacgtt cggccagggg  300
accaaggtgg aaatcaaac                                               319
```

<210> SEQ ID NO 121
<211> LENGTH: 337
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 121

```
cagtctgtgc tgacgcagcc gccctcagtg tctggggccc cagggcagag ggtcaccatc   60
tcctgcactg ggagcagctc caacatcggg gcaggttatg atgtacactg gtaccagcaa  120
cttccaggaa cagccccaaa actcctcatc tatggttaca gcaatcggcc ctcaggggtc  180
```
cctgaccgat tctctggctc caagtctggc acctcagcct ccctggccat cactgggctc    240
caggctgagg atgaggctga ttattactgc cagtcctatg acagcagcct gagtggtcat    300
gtggtattcg gcggagggac caagctgacc gtcctag                              337

<210> SEQ ID NO 122
<211> LENGTH: 337
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 122
cagtctgtgc tgacgcagcc gccctcagtg tctggggccc cagggcagag ggtcaccatc    60
tcctgcactg ggagcagctc caacatcggg gcaggttatg atgtacactg gtaccagcaa    120
cttccaggaa cagcccccaa actcctcatc tatggttaca gcaatcggcc ctcaggggtc    180
cctgaccgat tctctggctc caagtctggc acctcagcct ccctggccat cactgggctc    240
caggctgagg atgaggctga ttattactgc cagtcctatg acagcagcct gagtggtcat    300
gtgatattcg gcggagggac caaggtgacc gtcctag                              337

<210> SEQ ID NO 123
<211> LENGTH: 334
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 123
cagtctgtgc tgacgcagcc gccctcagtg tctggggccc cagggcagag ggtcaccatc    60
tcctgcactg ggggcagctc caacatcggg gcgggttatg atgtacactg gtaccagaag    120
cttccaggaa cagcccccaa actcctcatc tttggtaaga acaatcgacc ctcaggggtc    180
cctgaccgat tctctggctc gaagtctggc acctcagcct ccctggccat cactgggctc    240
cgggctgagg atgaggctga gtattactgc cagtcctttg acagcctgag tggctatgct    300
gtgttcggag gaggcaccca actgaccgtc ctcg                                 334

<210> SEQ ID NO 124
<211> LENGTH: 325
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 124
gacatccaga tgacccagtc tccttccacc ctgcctgcat ctgtaggaga cagagtcacc    60
atcacttgcc gggccagtca gagtattgat agctggttgg cctggtttca gcagaaacca    120
gggaaagccc ctaagcttct gatctctaag gcgtctacct tagaaaatgg ggtcccatca    180
aggttcagcg gcagtggatc tgggacagaa ttcactctca ccatcagcag cctgcagcct    240
gatgattttg caacttatta ctgccaacag tatagtagtt attctccgtg gacgttcggc    300
caagggacca aggtggaaat caaac                                           325

<210> SEQ ID NO 125
<211> LENGTH: 331
<212> TYPE: DNA

<213> ORGANISM: Artificial Sequence
<220> FEATURE:
<223> OTHER INFORMATION: Description of Artificial Sequence: Synthetic
      polynucleotide

<400> SEQUENCE: 125
gatattgtgt tgacacagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggcctctgg catcccagcc   180
agattcagtg gcagtgggtc tgggacagac ttcactctca ccatcagcag cctagagcct   240
gaagattttg cagtttatta ctgtcagcac cgtagcaact ggcctccccg ggtgtacact   300
tttggccagg ggaccaagct ggagatcaaa c                                   331

<210> SEQ ID NO 126
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 126
gacattgtgt tgacacagtc tccagccacc ctgtctttgt ctccagggga aagagccacc    60
ctctcctgca gggccagtca gagtgttggc agttccttgg cctggtacca acagaaacct   120
ggccaggctc ccagactcct catctatgat gcatccaaga gggcctctgg cttcccagcc   180
aggttcagtg gcagtgggtc tgggacagac ttcactctca ccatcagcag cctagagcct   240
ggagattttg cagtttatta ctgtcagcag cgtagcagct ggcctccata catgtacact   300
tttggccagg ggaccaagct ggagatcaaa c                                   331

<210> SEQ ID NO 127
<211> LENGTH: 337
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 127
cagtctgccc tgactcagcc tgcctccgtg tctgggtctc ctggacagtc gatcaccatc    60
gcctgcactg gaaccagcag tgacgtcggt ggttataact ttgtctcctg gtatcaacaa   120
cacccaggca agcccccag  acttctcatt tttgatgtca gtaatcggcc ctcaggggtc   180
tctaatcgct tctctggctc caagtctggc aacacggcct ccctgaccat ctccggactt   240
caggctgagg acgaggctga ttattttgc  agctcataca caagtcgcag ctcccggact   300
tacgtcttcg gaactgggac cagggtcacc gtcctag                             337

<210> SEQ ID NO 128
<211> LENGTH: 337
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 128
cagtctgccc tgactcagcc tgcctccgtg tctgggtcgc ctggacagtc gatcaccatc    60
tcctgcactg gaagcagcag tgacgttggt ggttataact atgtctcctg gtaccagcaa   120

```
cacccaggca aagcccccaa actcctgatt tttgatgtca gtaatcggcc ctcaggggtt    180
tctaatcgct tctctggctc caagtctagc aacacggcct ccctgaccat ctctgggctc    240
caggctgagg acgaggctga ttattactgc agctcatata cagccaggac ctcccggact    300
tatgtcttcg gaagtgggac caaggtcacc gtcctag                             337
```

<210> SEQ ID NO 129
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 129

```
gaaaaagtga tgacgcagtc tccagccagc ctgtctgtgt ctccagggga aagagccacc     60
ttctcctgca gggccagtca gagtgtcaac aacaacttag cctggtacca gcaaaaacct    120
ggccaggctc ccaggctcct catctatggt gcgtcctcca gggtcactgg tatcccagcc    180
aggttcagtg gcagtgggtc tgggacagag ttcactctca ccatcagcag cctgcagtct    240
gaagattttg cagtttatta ctgtcagcag tataataact ggcctccgac ttttggccag    300
gggaccaagc tggatatcaa ac                                             322
```

<210> SEQ ID NO 130
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 130

```
gaaatagtga tgacgcagtc tccagccacc ctgtctgtgt ctccagggga aagagccacc     60
ctctcctgca gggccagtca gagtgttggc aacaacttag tctggtacca gcagaaacct    120
gggcaggctc ccaggctcct catctatggt gcatccacca ggaccactgg tatcccagcc    180
aggttcagtg gcagtgggtc tgggacagag ttcactctca ccatcagcag cctgcagtct    240
gaagattttg cagtttatta ctgtcagcag tgttataact ggcctccgac ttttggccag    300
gggaccaacc tggagatcaa ac                                             322
```

<210> SEQ ID NO 131
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 131

```
gaaaaagtga tgacgcagtc tccagccacc ctgtctgtgt ctccagggga aagagccacc     60
ttctcctgca gggccagtca gagtgtcagc agcaacttag cctggtacca gcagaagcct    120
ggccaggctc ccaggctcct catctatggt gcatccaaca gggtcactgg tatcccagcc    180
aggttcagtg gcagtgggtc tgggacagag ttcactctca ccatcagcag cctgcagtct    240
gaagattttg cagtttatta ctgtcagcag tatgataact ggcctccgac ttttggccag    300
gggaccaagc tggatatcaa ac                                             322
```

<210> SEQ ID NO 132
<211> LENGTH: 322
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 132

```
gaaatagtga tgacgcagtc tccagccacc ctgtctgtgt ctccagggga aagagccacc    60
ctctcctgca gggccagtca gagtattagc agcaacttag tctggtacca gcagaaacct   120
ggccaggctc ccaggctcct catctatcgt gcatccacca gggtcactgg tatcccagcc   180
aggttcagtg gcagtgggtc tgggacagag ttcactctca ccatcagcag cctgctgtct   240
gaagattttg caatttatta ctgtcagcag ttttataact ggcctccgac ttttggccag   300
gggaccaagc tggaaatcaa ac                                            322
```

<210> SEQ ID NO 133
<211> LENGTH: 322
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 133

```
gaaatagtga tgacgcagtc tccagccacc ctgtctgtgt ctccagggga aagagccacc    60
ctctcctgca gggccagtca gagtattagc agcaacttag tctggtacca gcagaaacct   120
ggccaggctc ccaggctcct catctatcgt gcatccacca gggtcactgg tatcccagcc   180
aggttcagtg gcagtgggtc tgggacagag ttcactctca ccatcagcag cctgctgtct   240
gaagattttg cagtttatta ctgtcagcag ttttataact ggcctccgac ttttggccag   300
gggaccaagc tggaaatcaa ac                                            322
```

<210> SEQ ID NO 134
<211> LENGTH: 319
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 134

```
gaaatagtga tgacgcagtc tccagccacc ctgtctgtgt ctccagggga aagagccacc    60
ctctcctgca gggccagtca gagtgttggc agcaacttag cctggtacca gcagaaacct   120
ggccagactc ccaggctcct catctatggt gcctccacca gggccactgg tatcccagcc   180
aggttcagtg gcagtgggtc tgggacagac ttcactctca ccatcagcag cctgcagtct   240
gaggattttg cagtttatta ctgtcagcag tataataact ggtggacgtt cggcctaggg   300
accaaggtgg aaatcaaac                                                319
```

<210> SEQ ID NO 135
<211> LENGTH: 319
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 135

```
gaaatagtgg tgacgcagtc tccagccacc ctgtctgtgt ctctggggga aagagccacc    60
ctctcctgca gggccagtca gaacattggc agcaacttag cctggtacca gcagaaacct   120
ggccaggctc ccaggctcct catctacggt gcatccacca gggccactgg taccccagcc   180
aggttcagtg gcagtgggtc tgagacagag ttcactctca ccatcagcag cctgcagtct   240
gaggattttg cagtttatta ctgtcagcag tataataact ggtggacgtt cggccaaggg   300
accaaggtgg aaatcaaac                                                 319
```

<210> SEQ ID NO 136
<211> LENGTH: 319
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 136

```
gaagtagtgg tgacgcagtc tccagccacc ctgtctgtgt ctccagggga aagagccacc    60
ctctcctgca gggccagtca gagtgttggc agcaacttag cctggtacca gcagaaacct   120
ggccaggctc ccaggctcct cctctatggt gcatccacca gggccactgg tatcccagcc   180
aggttcagtg gcagtgggtc tgggacagag ttcactctca ccatcagcag cctgcagtct   240
gaagattttg cagtttatta ctgtcagcag tataataact tgtggacgtt cggccaaggg   300
accaaggtgg aaatcaaac                                                 319
```

<210> SEQ ID NO 137
<211> LENGTH: 319
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 137

```
gaaatagtga tgacgcagtc tccagccacc ctgtctgtgt ctccagggga aagagccacc    60
ctctcctgca gggccagtca gagtattggc agcaacttag cctggtacca acagaaacct   120
ggccaggctc ccacgctcct catctatgct gcgtccacca gggccactgg tatcccggcc   180
aggttcagtg gcagtgggtc ttggacagag ttcaatctca ccatcaacag cctgcagtct   240
gaagattttg cagtttatta ctgtcagcaa tataataact ggtggacgtt cggccaaggg   300
accaaggtgg aaatcaaac                                                 319
```

<210> SEQ ID NO 138
<211> LENGTH: 319
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 138

```
gaaatagtga tgacgcagtc tccagtcacc gtgtctgtgt ctccagggga aagagccacc    60
ctctcgtgca gggtcagtca gagtgttggc agcaacttag cctggtacca gcagaaacct   120
ggccaggctc ccaggcttct catctatgct gcatccacca gggccactgg tgtcccagcc   180
aggttcagtg gcagtaagtc tgggacagag ttcactctca ccatcagcag cctgcagcct   240
gaagatttag cagtttatta ctgtcagcag tataataact ggtggacgtt cggccaaggg   300
```

```
accaaggtgg aaatcaaac                                            319

<210> SEQ ID NO 139
<211> LENGTH: 319
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 139
gagatagtga tgacgcagtc tccagccacc ctgtctgtgt ctccagggga aagacccacc   60
ctctcctgca gggccagtca gaatattggc aggaacttag cctggtacca gcagaaacct  120
ggccaggctc ccaggctcct catctatggt gcatccacca gggccactgg tgtcccagcc  180
aggttcagtg gcagtgggtc tgagacagag ttcaatctca caatcaacag cctgcagtct  240
gaagatcttg cagtttatta ctgtcagcag tataataact ggtggacgtt cggccaaggg  300
accaaggtgg aaatcaaac                                              319

<210> SEQ ID NO 140
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 140
cagtctgtgc tgacgcagcc gccctcagtg tctggggccc cagggcagag ggtcaccatc   60
tcctgcactg ggaccagctc caacatcggg gcaggttatg atgttcactg gtaccagcag  120
tttccaggaa aagccccccaa actcctcatc tttgggaaca acaaccggcc ctcaggggtc  180
cctgaccgat tctctggctc caagtctggc acctcagcct ccctggccat cactgggctc  240
caggctgagg atgacgctga ttattactgc cagtcctatg acaacagcct gaaggcggta  300
ttcggcggag ggaccaggct gaccgtccta g                                331

<210> SEQ ID NO 141
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 141
cagtctgtgc tgacgcagcc gccctcagtg tctggggccc cagggcagag gatcaccatc   60
tcctgcactg ggaccagctc caacctcggg gcaggttttg atgttcactg gtatcagcag  120
cttccaggaa aagccccccga actcctcatc tttgggaaca acaaccggcc ctcaggggtc  180
cctgaccgat tctctggctc caagtctggc acctcagcct ccctggccat cactgggctc  240
caggctgagg atgaggctga ttattactgc cagtcctatg acaacagcct gaaggcggta  300
ttcggcggag ggaccaggct gaccgtccta g                                331

<210> SEQ ID NO 142
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 142

```
cagactgtgg tgacccagga gccatcgttc tcagtgtccc ctggagggac agtcacactc      60
acttgtggct tgagctctgg ctcagtctct actactcact accccagctg gtaccagcgg     120
accccaggcc aggctccacg cacgctcatc tacaccacaa acactcgctc ttctggggtc     180
cctgatcgct tctctggctc catcctaggg aacaaagctg ccctcaccat cacggggggcc    240 caggcagatg atgaatctga ttattactgt gtgctgtata tgggtcgtgg catttcggtg     300
ttcggcggag ggaccaagct gaccgtccta g                                    331
```

<210> SEQ ID NO 143
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 143

```
cagactgtgg tgacccagga gccatcgttc tcagtgtccc ctggagggac agtcacactc      60
acttgtggct tgagctctgg ctcagtctct attactcact accccagctg gtatcggcag     120
accccaggcc aggctccacg cacgctcatc tacaccacaa acactcgctc ttctggggtc     180
cctgatcgct tctctggctc catcctaggg aacaaagctg ccctcaccat cacggggggcc    240 caggcagatg atgaatctga ttattactgt gtgctgtata tgggtcgtgg catttcggtg     300
tttggcggag ggaccaagct gaccgtccta g                                    331
```

<210> SEQ ID NO 144
<211> LENGTH: 337
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 144

```
cagtctgccc tgactcagcc tgcctccgtg tctgggtctc ctggacagtc gatcaccatc      60
tcctgcactg gaaccagcag tgacgttggt ggttataact ttgtctcctg gtaccaacac     120
cacccaggca acgcccccaa actcctgatt tatggtgtca ctgatcggcc ctcagggggtc    180 tctaaacgat tctcaggttc caggtctggc aacacggcct ccctgaccat ctctgggctc     240
cagtctgagg acgaggctga ttattactgc agctcatata caaccttcat cacccgcggt    300
tggattttcg gcggagggac cagactgacc gtcctag                              337
```

<210> SEQ ID NO 145
<211> LENGTH: 337
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 145

```
cagtctgccc tgactcagcc tgcctccgtg tctgggtctc ctggacagtc gatcacgatc      60
tcctgcactg gaaccagcag tgacgttggt ggttataact ttgtctcctg gtaccaacaa     120
cagccaggca aagcccccaa actcatcatt tatgatgtca gtaatcggcc ctcaggggtt    180
tctgatcgct tctctggctc caagtctggc aacacggcct ccctgaccat ctctgggctc     240
```

<210> SEQ ID NO 146
<211> LENGTH: 319
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 146

```
gacatccaga tgacccagtc tccttccacc ctgtctgcat ctgtaggaga cagagtcacc    60
atcacttgcc gggccagtca gagttttagt acttggttgg cctggtatca gcagaaacca   120
gggaaagccc ctaagctcct gatctataag gcgtctagtt tagaaagtgg ggtcccatca   180
aggttcagcg gcagtggatc tgggacagaa ttcactctca ccatcagcag cctgcagcct   240
gatgattttg caacttatta ctgccaacag tatgatactt attcgacgtt cggccaaggg   300
accaaggtgg aagtcaaac                                                319
```

<210> SEQ ID NO 147
<211> LENGTH: 319
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 147

```
gacatccaga tgacccagtc tccttccacc ctgtctgcat ctgtaggaga cagagtcacc    60
atcacttgcc gggccagtca gagttttagt agttggttgg cctggtatca gcagaaacca   120
gggaaagccc ctaagctcct gatctataag gcgtctagtt tagaaagtgg ggtcccatca   180
aggttcagcg gcagtggatc tgggacagaa ttcactctca ccatcagcag cctgcagcct   240
gatgattttg caacttatta ctgccaacag tatgatactt attcgacgtt cggccaaggg   300
accaaggtgg aagtcaaac                                                319
```

<210> SEQ ID NO 148
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 148

```
gacatccagt tgacccagtc tccatccttc ctgtctgcat ctgtgagaga cagagtcacc    60
atcacttgcc gggccagtca gggcattagc acttatttag cctggtatca gcaaaaacca   120
gggaaagccc ctaagctcct gatctatgct gcatccactt tgcaaagtgg ggtcccatca   180
aggttcagcg gcagtggatc tgggacagac ttcactctca caatcagcag cctgcagcct   240
gaagattttg caacttatta ctgtcaacac cttagtaatt acctgttcac tttcggccct   300
gggaccaaag tggatatcaa ac                                            322
```

<210> SEQ ID NO 149
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 149
gacatccagt tgacccagtc tccatccttc ctgtctgcat ctgtaggaga cagagtcacc      60
atcacttgcc gggccagtca gggcattagc acttatttag cctggtatca gcaaaaacca     120
gggaaagccc ctaagctcct gatctatgat gcatccactt tgcaaagtgg ggtcccatca     180
aggttcagcg gcagtggatc tgggacagaa ttcactctca caatcagcag cctgcagcct     240
gaagattttg caacttatta ctgtcaacag cttaataatt acgttttcac tttcggccct     300
gggaccaaag tggatatcaa ac                                              322

<210> SEQ ID NO 150
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 150
gacgtccagt tgacccagtc tccatccttc ctgtctgcat ctgtaggaca cagagtcacc      60
atcacttgcc gggccagtca gggcattagc acttatttag cctggtatca gcaaaagcca     120
gggaaagccc ctaagctcct gatctatgat gcatccactt tgcaaagtgg ggtcccatca     180
aggttcagcg gcagtggatc tgggacagaa ttcactctca caatcagcag cctgcagcct     240
gaagattttg caacttatta ctgtcaacag cttagtagtt acgtattcac tttcggccct     300
gggaccaaag tggatatcaa ac                                              322

<210> SEQ ID NO 151
<211> LENGTH: 319
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 151
gacatgcaga tgacccagtc tccatcctcc ctgtctgcat ctgtaggaga cagagtcacc      60
atcacttgcc gggcaagtca gagcattagc acctatttaa attggtatca gcagaaagca     120
gggaaagccc ctaaactcct gatctatgct gcatcaagtt tgcaaagtgg ggtcccatca     180
cggttcagtg gcagtggatc tgggacagat ttcactctca ccatcagcag tctgcaacct     240
gaagattttg caacttacta ctgtcaacag agttacagta cccccctgtt cggccaaggg     300
accaaggtgg aaatcaaac                                                  319

<210> SEQ ID NO 152
<211> LENGTH: 319
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 152
gacatccaga tgacccagtc tccatcctcc ctgtctgcat ctgtaggaga cagggtcacc      60
atcacttgcc gggcaagcca gaacattaac aactatttaa attggtatca acagagacca     120

```
gggaaacccc ctaacctcct gatctatgct gcatctactt tgcaagctgg ggtcccatca    180
aggttcagtg gccgtggatc tgggacagat ttcactctca ccatcagcag tctgcaacct    240
gaagattttg ctacttacta ctgtcagcaa agttacggta gtcccctgtt cggccaaggg    300
accaaggtgg aaatcaaac                                                 319
```

```
<210> SEQ ID NO 153
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Gly Asn Ser Phe Ser Gly Tyr Gly
1               5

<210> SEQ ID NO 154
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Gly His Thr Phe Ser Gly Tyr Gly
1               5

<210> SEQ ID NO 155
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Gly Tyr Thr Phe Thr Ser Phe Ala
1               5

<210> SEQ ID NO 156
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Gly Gly Thr Phe Thr Ser Tyr Ala
1               5

<210> SEQ ID NO 157
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Gly Gly Ser Phe Thr Ser Tyr Gly
1               5
```

```
<210> SEQ ID NO 158
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Gly Gly Thr Phe Thr Ser Tyr Gly
1               5

<210> SEQ ID NO 159
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Gly Gly Thr Phe Thr Asn Tyr Pro
1               5

<210> SEQ ID NO 160
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Gly Gly Thr Phe Thr Lys Tyr Pro
1               5

<210> SEQ ID NO 161
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Gly Gly Thr Phe Ser Asn Tyr Ala
1               5

<210> SEQ ID NO 162
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Gly Gly Thr Phe Arg Asn Tyr Ser
1               5

<210> SEQ ID NO 163
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163
```

```
Gly Gly Thr Phe Ser Ser Asn Ser
1               5

<210> SEQ ID NO 164
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Gly Gly Ser Leu Asn Ser Tyr Gly
1               5

<210> SEQ ID NO 165
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Gly Val Ser Leu Ser Ser Tyr Gly
1               5

<210> SEQ ID NO 166
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Gly Gly Thr Phe Ser Ser Leu Ala
1               5

<210> SEQ ID NO 167
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Gly Gly Thr Phe Asn Ser Leu Pro
1               5

<210> SEQ ID NO 168
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Gly Gly Thr Leu Ser Ser Tyr Pro
1               5

<210> SEQ ID NO 169
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 169

Gly Gly Thr Phe Ser Ser Leu Ala
1               5

<210> SEQ ID NO 170
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Gly Gly Thr Phe Ser Ser Ser Pro
1               5

<210> SEQ ID NO 171
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Gly Phe Pro Phe Ser Gly Tyr Ala
1               5

<210> SEQ ID NO 172
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Gly Phe Pro Phe Arg Ser Tyr Ala
1               5

<210> SEQ ID NO 173
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Gly Phe Ser Phe Ser Thr Tyr Ala
1               5

<210> SEQ ID NO 174
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Gly Phe Thr Phe Ser Asn Tyr Ala
1               5
```

<210> SEQ ID NO 175
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Glu Phe Pro Phe Lys Ala Tyr Ala
1               5

<210> SEQ ID NO 176
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Gly Phe Thr Phe Ser Asn Phe Ala
1               5

<210> SEQ ID NO 177
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Gly Phe Thr Phe Thr Thr Asp Ala
1               5

<210> SEQ ID NO 178
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Gly Phe Thr Phe Arg Thr Asp Ala
1               5

<210> SEQ ID NO 179
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Gly Phe Thr Phe Asp Ser Tyr Trp
1               5

<210> SEQ ID NO 180
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 180

Gly Phe Thr Phe Asp Asn Tyr Trp
1               5

<210> SEQ ID NO 181
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Asp Gly Pro Leu Ile Gly Tyr Tyr
1               5

<210> SEQ ID NO 182
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Gly Gly Pro Leu Ile Gly Trp Tyr
1               5

<210> SEQ ID NO 183
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Gly Gly Ser Ile Ser Ser Ser Ser Tyr Tyr
1               5                   10

<210> SEQ ID NO 184
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Gly Gly Ser Ile Asn Thr Arg Ser Tyr Tyr
1               5                   10

<210> SEQ ID NO 185
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Arg Gly Ser Ile Ser Thr Asn Asp His Ser
1               5                   10

<210> SEQ ID NO 186
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 186

Gly Gly Ser Ile Ser Arg Ser Ser Thr Tyr Phe
1               5                   10

<210> SEQ ID NO 187
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Gly Asp Ser Ile Thr Ser Tyr Tyr
1               5

<210> SEQ ID NO 188
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Gly Asp Ser Ile Ser Ser Tyr Tyr
1               5

<210> SEQ ID NO 189
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Leu Thr Pro Tyr Thr Asp Asn Arg
1               5

<210> SEQ ID NO 190
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Ser Thr Pro Tyr Thr Gly Lys Ile
1               5

<210> SEQ ID NO 191
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Ile Asn Ile Gly Ser Gly Asn Thr
1               5
```

```
<210> SEQ ID NO 192
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Ile Asn Val Ile Phe Gly Ser Thr
1               5

<210> SEQ ID NO 193
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Ile Asn Val Val Phe Gly Ser Val
1               5

<210> SEQ ID NO 194
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Ile Asn Pro Ile Phe Gly Ser Thr
1               5

<210> SEQ ID NO 195
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Ile Leu Pro Ile Leu Asp Thr Ala
1               5

<210> SEQ ID NO 196
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Ile Ile Pro Ile Phe Gly Thr Pro
1               5

<210> SEQ ID NO 197
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 197

Ser Ile Pro Ile Phe Gly Thr Ala
1               5

<210> SEQ ID NO 198
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Ile Ile Pro Phe Phe Gly Thr Arg
1               5

<210> SEQ ID NO 199
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Ile Ile Pro Phe Phe Gly Thr Val
1               5

<210> SEQ ID NO 200
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Ile Ile Pro Phe Phe Gly Thr Arg
1               5

<210> SEQ ID NO 201
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Leu Ile Pro Val Phe Gly Ile Pro
1               5

<210> SEQ ID NO 202
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Ile Ile Pro Phe Phe Ala Thr Pro
1               5

<210> SEQ ID NO 203
<211> LENGTH: 8

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Ile Thr Pro Phe Phe Gly Thr Thr
1               5

<210> SEQ ID NO 204
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Ile Ile Pro Phe Phe Gly Ser Pro
1               5

<210> SEQ ID NO 205
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Ile Ser Tyr Asp Gly Ser Asp Lys
1               5

<210> SEQ ID NO 206
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Ile Ser Tyr Asp Gly Thr Asn Thr
1               5

<210> SEQ ID NO 207
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Ile Tyr Tyr Asp Gly Ser Asn Lys
1               5

<210> SEQ ID NO 208
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Ile Tyr Tyr Asp Gly Ser Arg Lys
```

```
<210> SEQ ID NO 209
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Ile Ser Tyr Asp Gly Ser Asn Thr
1               5

<210> SEQ ID NO 210
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Ile Ser Tyr Asp Gly Thr Glu Lys
1               5

<210> SEQ ID NO 211
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Ile Ser Tyr Asp Gly Ser Glu Lys
1               5

<210> SEQ ID NO 212
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Ile Lys Leu Asp Gly Ser Glu Lys
1               5

<210> SEQ ID NO 213
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Ile Thr His Ser Gly Asn Thr
1               5

<210> SEQ ID NO 214
<211> LENGTH: 7
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 214

Ile Thr His Ser Gly Ser Thr
1               5

<210> SEQ ID NO 215
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Leu Tyr Tyr Ser Gly Ser Thr
1               5

<210> SEQ ID NO 216
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Met Tyr Tyr Ser Gly Ser Thr
1               5

<210> SEQ ID NO 217
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Ile Phe Tyr Thr Gly Ser Thr
1               5

<210> SEQ ID NO 218
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Leu His His Ser Gly Asn Thr
1               5

<210> SEQ ID NO 219
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Val Ser Tyr Ser Gly Ser Thr
1               5

<210> SEQ ID NO 220

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Ile Tyr Tyr Ser Gly Gly Thr
1               5

<210> SEQ ID NO 221
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Ile Asn Tyr Ser Gly Asn Thr
1               5

<210> SEQ ID NO 222
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Ala Thr Gly Gly Pro Asn Phe Trp Ser Gly His Asn Trp Leu Asp Pro
1               5                   10                  15

<210> SEQ ID NO 223
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Ala Arg Ala Leu Phe Gly Leu Val Ala Val Ala Ser Pro Phe Asp Asn
1               5                   10                  15

<210> SEQ ID NO 224
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Ala Arg Ala Asp Glu Met Ala Thr Ala Gln Gly Phe Tyr Ala Phe Asp
1               5                   10                  15

Ile

<210> SEQ ID NO 225
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 225

Ala Arg Ala Asp Glu Met Ala Thr Ile Glu Gly Phe Tyr Ala Phe Asp
1               5                   10                  15

Ile

<210> SEQ ID NO 226
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Ala Arg Ala Asp Glu Met Ala Thr Thr Gly Gly Phe Tyr Ala Phe Asp
1               5                   10                  15

Ile

<210> SEQ ID NO 227
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Ala Arg Val Tyr Phe Asp Ser Gly Gly Tyr Phe Asp Ser
1               5                   10

<210> SEQ ID NO 228
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Ala Arg Val Tyr Tyr Asp Ser Gly Gly Tyr Phe Asp Ser
1               5                   10

<210> SEQ ID NO 229
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Ala Arg Ser Pro Trp His Ser Ser Gly Trp Phe Pro Ser Asp Tyr
1               5                   10                  15

<210> SEQ ID NO 230
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Ala Arg Ser Pro Trp His Asn Ser Gly Trp Phe Pro Leu Asp Ser
1               5                   10                  15
```

```
<210> SEQ ID NO 231
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Ala Arg Ser Cys Glu Ser Pro Ser Cys Tyr His Asn Trp Phe Asp Pro
1               5                   10                  15

<210> SEQ ID NO 232
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Ala Arg Tyr Cys Tyr Ser Ala Ser Cys Tyr His Asn Trp Phe Asp Pro
1               5                   10                  15

<210> SEQ ID NO 233
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Ala Arg Arg Asn Ala Lys Gly Gly Tyr Ser Gly Gly Asn Trp Phe Asp
1               5                   10                  15

Pro

<210> SEQ ID NO 234
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Ala Arg Arg Ser Gly Lys Gly Gly Tyr Ser Gly Gly Asn Trp Phe Asp
1               5                   10                  15

Pro

<210> SEQ ID NO 235
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Ala Arg Asp Leu Asn Phe Tyr Asp Ser Ser Gly Tyr His Phe Ala Arg
1               5                   10                  15

Trp Phe Asp Pro
            20

<210> SEQ ID NO 236
```

```
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Ala Arg Asp Val His Tyr Ser Asp Ser Ser Gly Tyr His Phe Gly Arg
1               5                   10                  15

Trp Phe Asp Pro
            20

<210> SEQ ID NO 237
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Ala Arg Asp Leu Asn Phe Tyr Asp Ser Ser Gly Tyr His Phe Ala Arg
1               5                   10                  15

Trp Phe Asp Pro
            20

<210> SEQ ID NO 238
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Ala Arg Asp Val Asn Tyr Tyr Asp Ser Ser Gly Tyr His Phe Gly Arg
1               5                   10                  15

Trp Phe Asp Pro
            20

<210> SEQ ID NO 239
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Ala Lys Asn Tyr Gly Ser Gly Ser Leu Asn Trp Phe Asp Ala
1               5                   10

<210> SEQ ID NO 240
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Ala Lys Asn Tyr Gly Ser Gly Ser Gln Asn Trp Phe Asp Ser
1               5                   10

<210> SEQ ID NO 241
```

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Ala Lys Asn Tyr Gly Ser Gly Ser Leu Asn Trp Tyr Asp Ala
1               5                   10

<210> SEQ ID NO 242
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Ala Lys Asn Tyr Gly Ser Gly Thr Leu Asn Trp Phe Asp Ala
1               5                   10

<210> SEQ ID NO 243
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Ala Lys Asn Tyr Gly Ser Gly Ser Leu Asn Trp Phe Asp Ser
1               5                   10

<210> SEQ ID NO 244
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Ala Lys Asn Tyr Gly Ser Gly Thr Leu Asn Trp Phe Asp Ser
1               5                   10

<210> SEQ ID NO 245
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Ala Arg Glu Gly Thr Tyr Ser Gly Ile Val Thr Gly Gln Ser Gln Ser
1               5                   10                  15

Pro Ser Ser Tyr Met Asp Val
            20

<210> SEQ ID NO 246
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 246

Ala Arg Glu Gly Thr Tyr Ser Gly Ile Val Thr Gly Gln Ser Gln Ser
1               5                   10                  15

Pro Ser Ser Tyr Met Ala Val
            20

<210> SEQ ID NO 247
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Ala Arg Val Ala Ser His Pro Ser Leu Phe Ser Pro Tyr Tyr Phe Asp
1               5                   10                  15

Tyr

<210> SEQ ID NO 248
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Ala Arg Val Ala Ser His Pro Thr Leu Phe Ser Pro Tyr Tyr Phe Asp
1               5                   10                  15

Tyr

<210> SEQ ID NO 249
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Ala Arg Gly Pro Gly Gly Thr Ser Thr Ser Cys Tyr Arg Cys Trp Phe
1               5                   10                  15

Asp Pro

<210> SEQ ID NO 250
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Ala Arg Gly Pro Gly Gly Thr Ser Thr Ser Cys Tyr Gln Cys Trp Phe
1               5                   10                  15

Asp Pro

<210> SEQ ID NO 251
<211> LENGTH: 15
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 251

Ala Gly Gln Asp Tyr Ser Gly Thr Tyr Tyr Asp Tyr Phe Asp Tyr
1               5                   10                  15

<210> SEQ ID NO 252
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Ala Gly Gln Asp Tyr Ser Gly Thr Tyr Tyr Asp Tyr Phe Asn Tyr
1               5                   10                  15

<210> SEQ ID NO 253
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Ala Arg Gln Asp Arg Asn Trp Phe Asp Ser
1               5                   10

<210> SEQ ID NO 254
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Val Arg Gln Asn Arg Asn Trp Phe Asp Ser
1               5                   10

<210> SEQ ID NO 255
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Ala Ser Ala Leu Asn Tyr Phe Asp Ser Ser Gly Pro Gly Gly Val Ala
1               5                   10                  15

Met Gly Gly Gly Phe Asp Ser
            20

<210> SEQ ID NO 256
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Ala Gly Ala Leu Tyr Tyr Phe Asp Ser Arg Gly Pro Gly Gly Val Ala

```
1               5               10              15
Met Gly Gly Gly Phe Asp Ser
            20

<210> SEQ ID NO 257
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Ser Ser Asp Val Gly Gly Tyr Asn Tyr
1               5

<210> SEQ ID NO 258
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Gln Ser Ile Ala Gly Tyr
1               5

<210> SEQ ID NO 259
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Gln Ser Ile Gly Thr Trp
1               5

<210> SEQ ID NO 260
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Gln Ser Ile Ser Ser Trp
1               5

<210> SEQ ID NO 261
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Gln Ser Val Ser Ser Trp
1               5

<210> SEQ ID NO 262
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 262

Ser Ser Asn Ile Gly Ala Gly Tyr Asp
1               5

<210> SEQ ID NO 263
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Ser Ser Asn Ile Gly Ala Gly Tyr Asp
1               5

<210> SEQ ID NO 264
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Gln Ser Ile Asp Ser Trp
1               5

<210> SEQ ID NO 265
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Gln Ser Val Ser Ser Tyr
1               5

<210> SEQ ID NO 266
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Gln Ser Val Gly Ser Ser
1               5

<210> SEQ ID NO 267
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Ser Ser Asp Val Gly Gly Tyr Asn Phe
1               5
```

```
<210> SEQ ID NO 268
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Gln Ser Val Asn Asn Asn
1               5

<210> SEQ ID NO 269
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Gln Ser Val Gly Asn Asn
1               5

<210> SEQ ID NO 270
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Gln Ser Val Ser Ser Asn
1               5

<210> SEQ ID NO 271
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Gln Ser Ile Ser Ser Asn
1               5

<210> SEQ ID NO 272
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Gln Ser Val Gly Ser Asn
1               5

<210> SEQ ID NO 273
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 273

Gln Asn Ile Gly Ser Asn
1               5

<210> SEQ ID NO 274
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Gln Asn Ile Gly Arg Asn
1               5

<210> SEQ ID NO 275
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Ser Ser Asn Ile Gly Ala Gly Tyr Asp
1               5

<210> SEQ ID NO 276
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Ser Ser Asn Leu Gly Ala Gly Phe Asp
1               5

<210> SEQ ID NO 277
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Ser Gly Ser Val Ser Thr Thr His Tyr
1               5

<210> SEQ ID NO 278
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Ser Gly Ser Val Ser Ile Thr His Tyr
1               5

<210> SEQ ID NO 279
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Ser Ser Asp Val Gly Gly Tyr Asn Phe
1               5

<210> SEQ ID NO 280
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Gln Ser Phe Ser Thr Trp
1               5

<210> SEQ ID NO 281
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Gln Ser Phe Ser Ser Trp
1               5

<210> SEQ ID NO 282
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Gln Gly Ile Ser Thr Tyr
1               5

<210> SEQ ID NO 283
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Gln Ser Ile Ser Thr Tyr
1               5

<210> SEQ ID NO 284
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Gln Asn Ile Asn Asn Tyr
```

```
1               5
```

<210> SEQ ID NO 285
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Asp Val Ser
1

<210> SEQ ID NO 286
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Asp Val Asn
1

<210> SEQ ID NO 287
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Ser Ala Ser
1

<210> SEQ ID NO 288
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Lys Ala Ser
1

<210> SEQ ID NO 289
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Gly Tyr Ser
1

<210> SEQ ID NO 290
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 290

Gly Lys Asn
1

<210> SEQ ID NO 291
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Asp Ala Ser
1

<210> SEQ ID NO 292
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Gly Ala Ser
1

<210> SEQ ID NO 293
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Arg Ala Ser
1

<210> SEQ ID NO 294
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Ala Ala Ser
1

<210> SEQ ID NO 295
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Gly Asn Asn
1

<210> SEQ ID NO 296

```
<210> SEQ ID NO 296
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Thr Thr Asn
1

<210> SEQ ID NO 297
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Gly Val Thr
1

<210> SEQ ID NO 298
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Ser Ser Tyr Thr Arg Ser Ser Thr Leu Leu
1               5                   10

<210> SEQ ID NO 299
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Thr Ser Phe Thr Lys Ser Thr Thr Leu Leu
1               5                   10

<210> SEQ ID NO 300
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Gln Gln Ser Phe Arg Thr Pro Thr Thr
1               5

<210> SEQ ID NO 301
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301
```

```
Gln Gln Tyr Asn Ser Tyr Trp Thr
1               5

<210> SEQ ID NO 302
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Gln Gln Tyr Asn Thr Tyr Trp Thr
1               5

<210> SEQ ID NO 303
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Gln Ser Tyr Asp Ser Ser Leu Ser Gly His Val Val
1               5                   10

<210> SEQ ID NO 304
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Gln Ser Tyr Asp Ser Ser Leu Ser Gly His Val Ile
1               5                   10

<210> SEQ ID NO 305
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Gln Ser Phe Asp Ser Leu Ser Gly Tyr Ala Val
1               5                   10

<210> SEQ ID NO 306
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Gln Gln Tyr Ser Ser Tyr Ser Pro Trp Thr
1               5                   10

<210> SEQ ID NO 307
<211> LENGTH: 12
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 307

Gln His Arg Ser Asn Trp Pro Pro Arg Val Tyr Thr
1               5                   10

<210> SEQ ID NO 308
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Gln Gln Arg Ser Ser Trp Pro Pro Tyr Met Tyr Thr
1               5                   10

<210> SEQ ID NO 309
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Ser Ser Tyr Thr Ser Arg Ser Ser Arg Thr Tyr Val
1               5                   10

<210> SEQ ID NO 310
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Ser Ser Tyr Thr Ala Arg Thr Ser Arg Thr Tyr Val
1               5                   10

<210> SEQ ID NO 311
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Gln Gln Tyr Asn Asn Trp Pro Pro Thr
1               5

<210> SEQ ID NO 312
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Gln Gln Cys Tyr Asn Trp Pro Pro Thr
1               5
```

```
<210> SEQ ID NO 313
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Gln Gln Tyr Asp Asn Trp Pro Pro Thr
1               5

<210> SEQ ID NO 314
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Gln Gln Phe Tyr Asn Trp Pro Pro Thr
1               5

<210> SEQ ID NO 315
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Gln Gln Tyr Asn Asn Trp Trp Thr
1               5

<210> SEQ ID NO 316
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Gln Gln Tyr Asn Asn Leu Trp Thr
1               5

<210> SEQ ID NO 317
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Gln Ser Tyr Asp Asn Ser Leu Lys Ala Val
1               5                   10

<210> SEQ ID NO 318
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318
```

Val Leu Tyr Met Gly Arg Gly Ile Ser Val
1               5                   10

<210> SEQ ID NO 319
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Ser Ser Tyr Thr Thr Phe Ile Thr Arg Gly Trp Ile
1               5                   10

<210> SEQ ID NO 320
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Ser Ser Tyr Thr Ala Ser Ser Thr Arg Asn Phe Val
1               5                   10

<210> SEQ ID NO 321
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Gln Gln Tyr Asp Thr Tyr Ser Thr
1               5

<210> SEQ ID NO 322
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Gln His Leu Ser Asn Tyr Leu Phe Thr
1               5

<210> SEQ ID NO 323
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Gln Gln Leu Asn Asn Tyr Val Phe Thr
1               5

<210> SEQ ID NO 324
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 324

Gln Gln Leu Ser Ser Tyr Val Phe Thr
1               5

<210> SEQ ID NO 325
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

Gln Gln Ser Tyr Ser Thr Pro Leu
1               5

<210> SEQ ID NO 326
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Gln Gln Ser Tyr Gly Ser Pro Leu
1               5

<210> SEQ ID NO 327
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327
ctagtagcaa ctgcaaccgg tgtacattca                                      30

<210> SEQ ID NO 328
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328
cctccaccaa gggcccatcg gtcttccccc tggcac                               36

<210> SEQ ID NO 329
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 329
gaactgtggc tgcaccatct gtcttcatct tcccgccatc tgatgagcag ttgaaatctg     60
gaactgctag cgttgtgtgc ctgctgaata ac                                   92
```

```
<210> SEQ ID NO 330
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 330
gtcagcccaa ggctgccccc tcggtcac                                           28

<210> SEQ ID NO 331
<211> LENGTH: 367
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 331
caggttcagc tcgtgcaaag tggcgcggag gtgaaaaaac ctggcagcag cgtcaaagtt        60
tcttgtaagg ccagcggtgg cacttttttca aattatgcat ttagttgggt gagacaagca     120
ccagggcagg gctggaatg gatggggaga attatcccca tctttggaac acccaagtac       180
gcgcagaaat tccaaggcag agtaacaata accagagacg aaagcacgtc tactgcgtac     240
atggaactgt ccagcctccg ctctgaggat actgccgtat attattgcgc cagaagcccc     300
tggcatagtt caggctggtt tcctagtgat tattggggac aaggcaccct ggtgaccgtg     360
tcttctg                                                                367

<210> SEQ ID NO 332
<211> LENGTH: 370
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 332
caggtccagc tggtgcagtc tggggctgag gtgaggaagc ctgggtcctc agtgaaggtc        60
tcctgcaaga cttctggagg ctccctcaac agttatgcca tcagttgggt gcgacaggcc     120
cctggacaag gcttgagtg gatgggaggg atcatccctt tctttggtac agttatctat       180
tcagacaatt accagggcag agcctcgttt tcctcggacg aatctacgac cacagcctac     240
atggagctga gaagcctaag atctgaggac acggccgtgt attactgtgc gagatatttgt   300 tatagtgcca gttgttatca caactggttc gaccctgggg ccagggaac cctggtcacc      360 gtctccacag                                                             370

<210> SEQ ID NO 333
<211> LENGTH: 355
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 333
cagctgcagc tacaggagtc gggcccagga ctggtgaagc cttcggagac cctgtccctc        60
acctgcactg tctctggtgg ctccatcagt aggagtagtt acttctgggg ctggatccgc     120
cagcccccag ggaaggggct ggagtggatt gggagtgtct cttatagtgg gagcacctac     180
```

```
tacaacccgt ccctcaagag tcgagtcagc gtatccgtag acacgtccag gaagcagttc    240
tccctgaaac tgacgtctgt gaccgccgca gacacggctg tgtattactg tgcgagacag    300
gacagaaact ggttcgactc ctggggccag ggaaccctgg tcaccgtctc ctcag         355
```

<210> SEQ ID NO 334
<211> LENGTH: 388
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 334

```
caagttcagc tgcaagaatc cgggcctggc ttggtcaagc ctagtgagac actgagcctt     60
acctgtactg tttctgggga ttccatcacg agctattatt ggagttggat taggcaacct    120
cccggtcaag ggctcgaatg gattggctac atatactata gcggcggtac gaattataac    180
cctagcttga aaagccgagt tgtaatgtct ttggacacat cacgcaacca gttctccctc    240
aaactgaaca gtcttaccgc cgcagacacc gctgtttatt attgcgcctc cgctttgaac    300
tacttcgatt cttcagggcc aggtggagta gcaatgggag gcggattcga ctcatggggc    360
caaggcgcac tcgtgacggt ctcatcag                                       388
```

<210> SEQ ID NO 335
<211> LENGTH: 388
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 335

```
caggtacaac atcaggaatc aggtcctggg ctggtaaagc cgagcgaaac cttgtcactt     60
acgtgtacgg taagcggaga ttctattagc tcatactatt ggaactggat tagacaggct    120
cctggtaagg gactggaatg gcttgggtat attaactata gcggcaacac ggattacaat    180
acctccctga gagtcgcgc cactattagc ctcgatactt ccaagaacca attttcactc     240
aaattgtcaa gtgtcacaac ggcggatacc gccgtttatt actgcgccgg ggcgttgtac    300
tattttgact ctagagggcc aggcggggta gcaatgggtg gtggcttcga ctcctgggga    360
caaggaacgc tcgtgacggt gtcctccg                                       388
```

<210> SEQ ID NO 336
<211> LENGTH: 334
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 336

```
cagtctgtgc ttacccaacc cccaagcgtc tctggcgctc caggacaacg ggtcacaatt     60
agttgcaccg gcggctcttc aaatatcggg gcaggttacg atgtccattg gtaccagaag    120
ctgccaggta ccgctcctaa gctcttgatc ttcgtaagaa caatcgccc tagtgggtt     180 cccgaccggt ttagtggtag taagtccggg acctctgctt cactcgctat taccgggctt    240
agggctgagg acgaggcaga atattactgt cagtctttcg attctcttag cggatacgca    300
gtctttggcg gtggcacgca gctcacggtc ctag                                334
```

<210> SEQ ID NO 337
<211> LENGTH: 319
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 337
gatatgcaga tgacgcagtc tccatcatct ctttcagctt ccgtcggtga tagggttacc      60
attacttgta gagcgtcaca gtctattagc acgtatttga attggtatca gcaaaaggct     120
ggtaaggccc caaaattgct tatctatgct gcatcatcat tgcagtccgg tgtaccgagc     180
aggttcagcg ggtcaggcag cggaactgat tttacgctga ccatctcctc tcttcaacct     240
gaagattttg ctacatacta ttgtcaacag tcttacagta cccccttgtt cgggcaagga     300
actaaggttg aaattaaac                                                  319

<210> SEQ ID NO 338
<211> LENGTH: 319
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 338
gatatacaga tgacccagag cccttcttcc ctttctgcat ccgtaggaga ccgagtgact      60
ataacgtgta gagcctcaca aaacataaac aactacctca attggtacca gcagagacca    120
ggcaagccgc caaacttgct tatttacgct gcgtcaacgc ttcaagcggg agtcccatcc    180
cgattttctg cagggggtc cggtacagac ttcactctta caatctcaag ccttcaacca    240
gaagacttcg ctacttacta ctgccagcaa agctatggtt caccattgtt tggtcagggg    300
acaaaagtag aaatcaagc                                                  319

<210> SEQ ID NO 339
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Asp Tyr Lys Asp Asp Asp Asp Lys
1               5

<210> SEQ ID NO 340
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 340

His His His His His His
1               5

<210> SEQ ID NO 341
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 341

Tyr Pro Tyr Asp Val Pro Asp Tyr Ala
1               5

<210> SEQ ID NO 342
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

Ala Leu Trp Glu Val Gln Glu Leu Gly Lys Lys Ile Lys Val
1               5                   10

<210> SEQ ID NO 343
<211> LENGTH: 59
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(41)
<223> OTHER INFORMATION: a, c, t, g, unknown or other

<400> SEQUENCE: 343
tgactggagt tcagacgtgt gctcttccga tctnnnnnnn ngggaagaa gccctggac     59

<210> SEQ ID NO 344
<211> LENGTH: 63
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(45)
<223> OTHER INFORMATION: a, c, t, g, unknown or other

<400> SEQUENCE: 344
tgactggagt tcagacgtgt gctcttccga tctnnnnnnn nnnnggggga agaagccctg     60
gac                                                                  63

<210> SEQ ID NO 345
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(41)
<223> OTHER INFORMATION: a, c, t, g, unknown or other

<400> SEQUENCE: 345
tgactggagt tcagacgtgt gctcttccga tctnnnnnnn ngggaagtag tccttgacca     60

<210> SEQ ID NO 346
<211> LENGTH: 64
```

<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(45)
<223> OTHER INFORMATION: a, c, t, g, unknown or other

<400> SEQUENCE: 346
tgactggagt tcagacgtgt gctcttccga tctnnnnnnn nnnngggaa gtagtccttg    60 acca                                                                64

<210> SEQ ID NO 347
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(41)
<223> OTHER INFORMATION: a, c, t, g, unknown or other

<400> SEQUENCE: 347
tgactggagt tcagacgtgt gctcttccga tctnnnnnnn ngaaggaagt cctgtgcgag    60

<210> SEQ ID NO 348
<211> LENGTH: 66
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(47)
<223> OTHER INFORMATION: a, c, t, g, unknown or other

<400> SEQUENCE: 348
tgactggagt tcagacgtgt gctcttccga tctnnnnnnn nnnnnnngaa ggaagtcctg    60
tgcgag                                                              66

<210> SEQ ID NO 349
<211> LENGTH: 59
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(41)
<223> OTHER INFORMATION: a, c, t, g, unknown or other

<400> SEQUENCE: 349
tgactggagt tcagacgtgt gctcttccga tctnnnnnnn naagtagccc gtggccagg    59

<210> SEQ ID NO 350
<211> LENGTH: 63
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base

```
<222> LOCATION: (34)..(45)
<223> OTHER INFORMATION: a, c, t, g, unknown or other

<400> SEQUENCE: 350
tgactggagt tcagacgtgt gctcttccga tctnnnnnnn nnnnaagta gcccgtggcc    60 agg                                                                 63

<210> SEQ ID NO 351
<211> LENGTH: 62
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(41)
<223> OTHER INFORMATION: a, c, t, g, unknown or other

<400> SEQUENCE: 351
tgactggagt tcagacgtgt gctcttccga tctnnnnnnn ntgggtggta cccagttatc    60
aa                                                                  62

<210> SEQ ID NO 352
<211> LENGTH: 66
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(45)
<223> OTHER INFORMATION: a, c, t, g, unknown or other

<400> SEQUENCE: 352
tgactggagt tcagacgtgt gctcttccga tctnnnnnnn nnnntgggt ggtacccagt     60 tatcaa                                                              66

<210> SEQ ID NO 353
<211> LENGTH: 69
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(41)
<223> OTHER INFORMATION: a, c, t, g, unknown or other

<400> SEQUENCE: 353
tgactggagt tcagacgtgt gctcttccga tctnnnnnnn nagttccaga tttcaactgc    60
tcatcagat                                                           69

<210> SEQ ID NO 354
<211> LENGTH: 73
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(45)
<223> OTHER INFORMATION: a, c, t, g, unknown or other
```

<400> SEQUENCE: 354
tgactggagt tcagacgtgt gctcttccga tctnnnnnnn nnnnnagttc cagatttcaa    60
ctgctcatca gat    73

<210> SEQ ID NO 355
<211> LENGTH: 61
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(41)
<223> OTHER INFORMATION: a, c, t, g, unknown or other

<400> SEQUENCE: 355
tgactggagt tcagacgtgt gctcttccga tctnnnnnnn ngagggcggg aacagagtga    60
c    61

<210> SEQ ID NO 356
<211> LENGTH: 65
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(45)
<223> OTHER INFORMATION: a, c, t, g, unknown or other

<400> SEQUENCE: 356
tgactggagt tcagacgtgt gctcttccga tctnnnnnnn nnnnngaggg cgggaacaga    60
gtgac    65

<210> SEQ ID NO 357
<211> LENGTH: 59
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(41)
<223> OTHER INFORMATION: a, c, t, g, unknown or other

<400> SEQUENCE: 357
acactctttc cctacacgac gctcttccga tctnnnnnnn nscagctggt gcagtctgg    59

<210> SEQ ID NO 358
<211> LENGTH: 63
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(45)
<223> OTHER INFORMATION: a, c, t, g, unknown or other

<400> SEQUENCE: 358
acactctttc cctacacgac gctcttccga tctnnnnnnn nnnnnscagc tggtgcagtc    60
tgg    63

<210> SEQ ID NO 359
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(41)
<223> OTHER INFORMATION: a, c, t, g, unknown or other

<400> SEQUENCE: 359
acactctttc cctacacgac gctcttccga tctnnnnnnnn ngtgcagctg gtggagtctg    60

<210> SEQ ID NO 360
<211> LENGTH: 64
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(45)
<223> OTHER INFORMATION: a, c, t, g, unknown or other

<400> SEQUENCE: 360
acactctttc cctacacgac gctcttccga tctnnnnnnnn nnnngtgca gctggtggag    60 tctg                                                                64

<210> SEQ ID NO 361
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(41)
<223> OTHER INFORMATION: a, c, t, g, unknown or other

<400> SEQUENCE: 361
acactctttc cctacacgac gctcttccga tctnnnnnnnn ntcaccttga aggagtctgg    60

<210> SEQ ID NO 362
<211> LENGTH: 64
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(45)
<223> OTHER INFORMATION: a, c, t, g, unknown or other

<400> SEQUENCE: 362
acactctttc cctacacgac gctcttccga tctnnnnnnnn nnnnntcacc ttgaaggagt    60
ctgg                                                                64

<210> SEQ ID NO 363
<211> LENGTH: 58
<212> TYPE: DNA
<213> ORGANISM: Artificial Sequence
<220> FEATURE:

<223> OTHER INFORMATION: Description of Artificial Sequence: Synthetic
      primer
<220> FEATURE:
<221> NAME/KEY: modified_base
<222> LOCATION: (34)..(41)
<223> OTHER INFORMATION: a, c, t, g, unknown or other

<400> SEQUENCE: 363
acactctttc cctacacgac gctcttccga tctnnnnnnnn ntgcagctgc aggagtcg        58

<210> SEQ ID NO 364
<211> LENGTH: 62
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(45)
<223> OTHER INFORMATION: a, c, t, g, unknown or other

<400> SEQUENCE: 364
acactctttc cctacacgac gctcttccga tctnnnnnnnn nnnntgcag ctgcaggagt        60 cg                                                                      62

<210> SEQ ID NO 365
<211> LENGTH: 59
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(41)
<223> OTHER INFORMATION: a, c, t, g, unknown or other

<400> SEQUENCE: 365
acactctttc cctacacgac gctcttccga tctnnnnnnnn ngtgcagcta cagcagtgg       59

<210> SEQ ID NO 366
<211> LENGTH: 63
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(45)
<223> OTHER INFORMATION: a, c, t, g, unknown or other

<400> SEQUENCE: 366
acactctttc cctacacgac gctcttccga tctnnnnnnnn nnnngtgca gctacagcag       60 tgg                                                                     63

<210> SEQ ID NO 367
<211> LENGTH: 59
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(41)
<223> OTHER INFORMATION: a, c, t, g, unknown or other -continued

<400> SEQUENCE: 367
acactctttc cctacacgac gctcttccga tctnnnnnnn ngtacagctg cagcagtca    59

<210> SEQ ID NO 368
<211> LENGTH: 63
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(45)
<223> OTHER INFORMATION: a, c, t, g, unknown or other

<400> SEQUENCE: 368
acactctttc cctacacgac gctcttccga tctnnnnnnn nnnnngtaca gctgcagcag    60
tca    63

<210> SEQ ID NO 369
<211> LENGTH: 64
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(41)
<223> OTHER INFORMATION: a, c, t, g, unknown or other

<400> SEQUENCE: 369
acactctttc cctacacgac gctcttccga tctnnnnnnn ngacatccrg dtgacccagt    60
ctcc    64

<210> SEQ ID NO 370
<211> LENGTH: 68
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(45)
<223> OTHER INFORMATION: a, c, t, g, unknown or other

<400> SEQUENCE: 370
acactctttc cctacacgac gctcttccga tctnnnnnnn nnnnngacat ccrgdtgacc    60
cagtctcc    68

<210> SEQ ID NO 371
<211> LENGTH: 64
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(41)
<223> OTHER INFORMATION: a, c, t, g, unknown or other

<400> SEQUENCE: 371
acactctttc cctacacgac gctcttccga tctnnnnnnn ngaaattgtr wtgacrcagt    60
ctcc    64

```
<210> SEQ ID NO 372
<211> LENGTH: 68
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(45)
<223> OTHER INFORMATION: a, c, t, g, unknown or other

<400> SEQUENCE: 372
acactctttc cctacacgac gctcttccga tctnnnnnnn nnnnngaaat tgtrwtgacr     60
cagtctcc                                                              68

<210> SEQ ID NO 373
<211> LENGTH: 64
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(41)
<223> OTHER INFORMATION: a, c, t, g, unknown or other

<400> SEQUENCE: 373
acactctttc cctacacgac gctcttccga tctnnnnnnn ngatattgtg mtgacbcagw     60
ctcc                                                                  64

<210> SEQ ID NO 374
<211> LENGTH: 68
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(45)
<223> OTHER INFORMATION: a, c, t, g, unknown or other

<400> SEQUENCE: 374
acactctttc cctacacgac gctcttccga tctnnnnnnn nnnnngatat tgtgmtgacb     60 cagwctcc                                                              68

<210> SEQ ID NO 375
<211> LENGTH: 63
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(41)
<223> OTHER INFORMATION: a, c, t, g, unknown or other

<400> SEQUENCE: 375
acactctttc cctacacgac gctcttccga tctnnnnnnn ngaaacgaca ctcacgcagt     60
ctc                                                                   63

<210> SEQ ID NO 376
```

```
<211> LENGTH: 67
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(45)
<223> OTHER INFORMATION: a, c, t, g, unknown or other

<400> SEQUENCE: 376
acactctttc cctacacgac gctcttccga tctnnnnnnn nnnnngaaac gacactcacg      60
cagtctc                                                               67

<210> SEQ ID NO 377
<211> LENGTH: 64
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(41)
<223> OTHER INFORMATION: a, c, t, g, unknown or other

<400> SEQUENCE: 377
acactctttc cctacacgac gctcttccga tctnnnnnnn ncagtctgts btgacgcagc      60
cgcc                                                                  64

<210> SEQ ID NO 378
<211> LENGTH: 68
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(45)
<223> OTHER INFORMATION: a, c, t, g, unknown or other

<400> SEQUENCE: 378
acactctttc cctacacgac gctcttccga tctnnnnnnn nnnnncagtc tgtsbtgacg      60
cagccgcc                                                              68

<210> SEQ ID NO 379
<211> LENGTH: 63
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(41)
<223> OTHER INFORMATION: a, c, t, g, unknown or other

<400> SEQUENCE: 379
acactctttc cctacacgac gctcttccga tctnnnnnnn ntcctatgwg ctgacwcagc      60
cac                                                                   63

<210> SEQ ID NO 380
<211> LENGTH: 67
<212> TYPE: DNA
<213> ORGANISM: Artificial Sequence
```

<220> FEATURE:
<223> OTHER INFORMATION: Description of Artificial Sequence: Synthetic
      primer
<220> FEATURE:
<221> NAME/KEY: modified_base
<222> LOCATION: (34)..(45)
<223> OTHER INFORMATION: a, c, t, g, unknown or other

<400> SEQUENCE: 380
acactctttc cctacacgac gctcttccga tctnnnnnnn nnnntccta tgwgctgacw    60 cagccac                                                             67

<210> SEQ ID NO 381
<211> LENGTH: 64
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(41)
<223> OTHER INFORMATION: a, c, t, g, unknown or other

<400> SEQUENCE: 381
acactctttc cctacacgac gctcttccga tctnnnnnnn ntcctatgag ctgayrcagc    60 yacc                                                                64

<210> SEQ ID NO 382
<211> LENGTH: 68
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(45)
<223> OTHER INFORMATION: a, c, t, g, unknown or other

<400> SEQUENCE: 382
acactctttc cctacacgac gctcttccga tctnnnnnnn nnnntccta tgagctgayr    60 cagcyacc                                                            68

<210> SEQ ID NO 383
<211> LENGTH: 61
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(41)
<223> OTHER INFORMATION: a, c, t, g, unknown or other

<400> SEQUENCE: 383
acactctttc cctacacgac gctcttccga tctnnnnnnn ncagcctgtg ctgactcary    60
c                                                                   61

<210> SEQ ID NO 384
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

```
<220> FEATURE:
<221> NAME/KEY: modified_base
<222> LOCATION: (34)..(45)
<223> OTHER INFORMATION: a, c, t, g, unknown or other

<400> SEQUENCE: 384
acactctttc cctacacgac gctcttccga tctnnnnnnn nnnnncagcc tgtgctgact    60 caryc                                                                65

<210> SEQ ID NO 385
<211> LENGTH: 64
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(41)
<223> OTHER INFORMATION: a, c, t, g, unknown or other

<400> SEQUENCE: 385
acactctttc cctacacgac gctcttccga tctnnnnnnn ncagdctgtg gtgacycagg    60
agcc                                                                 64

<210> SEQ ID NO 386
<211> LENGTH: 68
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(45)
<223> OTHER INFORMATION: a, c, t, g, unknown or other

<400> SEQUENCE: 386
acactctttc cctacacgac gctcttccga tctnnnnnnn nnnnncagdc tgtggtgacy    60
caggagcc                                                             68

<210> SEQ ID NO 387
<211> LENGTH: 64
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(41)
<223> OTHER INFORMATION: a, c, t, g, unknown or other

<400> SEQUENCE: 387
acactctttc cctacacgac gctcttccga tctnnnnnnn ncagccwgkg ctgactcagc    60 cmcc                                                                 64

<210> SEQ ID NO 388
<211> LENGTH: 68
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(45)
```

<223> OTHER INFORMATION: a, c, t, g, unknown or other

<400> SEQUENCE: 388
acactctttc cctacacgac gctcttccga tctnnnnnnn nnnnncagcc wgkgctgact    60 cagccmcc    68

<210> SEQ ID NO 389
<211> LENGTH: 64
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(41)
<223> OTHER INFORMATION: a, c, t, g, unknown or other

<400> SEQUENCE: 389
acactctttc cctacacgac gctcttccga tctnnnnnnn ntcctctgag ctgastcagg    60 ascc    64

<210> SEQ ID NO 390
<211> LENGTH: 68
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(45)
<223> OTHER INFORMATION: a, c, t, g, unknown or other

<400> SEQUENCE: 390
acactctttc cctacacgac gctcttccga tctnnnnnnn nnnntcctc tgagctgast    60 caggascc    68

<210> SEQ ID NO 391
<211> LENGTH: 62
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(41)
<223> OTHER INFORMATION: a, c, t, g, unknown or other

<400> SEQUENCE: 391
acactctttc cctacacgac gctcttccga tctnnnnnnn ncagtctgyy ctgaytcagc    60
ct    62

<210> SEQ ID NO 392
<211> LENGTH: 66
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(45)
<223> OTHER INFORMATION: a, c, t, g, unknown or other

<400> SEQUENCE: 392

```
acactctttc cctacacgac gctcttccga tctnnnnnnn nnnnncagtc tgyyctgayt    60
cagcct                                                              66
```

<210> SEQ ID NO 393
<211> LENGTH: 63
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(41)
<223> OTHER INFORMATION: a, c, t, g, unknown or other

<400> SEQUENCE: 393

```
acactctttc cctacacgac gctcttccga tctnnnnnnn naattttatg ctgactcagc    60
ccc                                                                 63
```

<210> SEQ ID NO 394
<211> LENGTH: 67
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(45)
<223> OTHER INFORMATION: a, c, t, g, unknown or other

<400> SEQUENCE: 394

```
acactctttc cctacacgac gctcttccga tctnnnnnnn nnnnnaattt tatgctgact    60
cagcccc                                                             67
```

<210> SEQ ID NO 395
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 395

```
aatgatacgg cgaccaccga gatctacacc ggttaaaaca ctctttccct acacgacgct    60
cttccgatct                                                          70
```

<210> SEQ ID NO 396
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 396

```
caagcagaag acggcatacg agataaattg gcgtgactgg agttcagacg tgtgctcttc    60
cgatct                                                              66
```

<210> SEQ ID NO 397
<211> LENGTH: 70
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 397
aatgatacgg cgaccaccga gatctacacg aacataaaca ctctttccct acacgacgct    60
cttccgatct                                                          70

<210> SEQ ID NO 398
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 398
caagcagaag acggcatacg agataataca aggtgactgg agttcagacg tgtgctcttc    60
cgatct                                                              66

<210> SEQ ID NO 399
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 399
aatgatacgg cgaccaccga gatctacaca ctggtaaaca ctctttccct acacgacgct    60
cttccgatct                                                          70

<210> SEQ ID NO 400
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 400
caagcagaag acggcatacg agataatggt cagtgactgg agttcagacg tgtgctcttc    60
cgatct                                                              66

<210> SEQ ID NO 401
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 401
gctgaggtga agaagcctgg gtcctcggtg aaggtctcct gcaaggcttc tggaggcacc    60
ttcagcagct atgctatcag ctgggtgcga caggcccctg gacaagggct tgagtggatg   120
ggagggatca tccctatctt tggtacagca aactacgcac agaagttcca gggcagagtc   180
acgattacca cggacgaatc cacgagcaca gcctacatgg agctgagcag cctgagatct   240
gaggacacgg ccgtgtatta ctgtgcgaga tattgtagta gtaccagctg ctatcacaac   300
tggttcgacc cctggggcca gggaaccctg gtcaccgtct cctca                   345

<210> SEQ ID NO 402

<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 402
gctgaggtga agaagcctgg gtcctcagtg aaggtctcct gcaaggcttc tggaggcacc      60
ttcagcagct atgctatcag ctgggtgcga caggcccctg gacaagggct tgagtggatg     120
ggagggatca tccctatctt tggtacagca aactacgcac agaagttcca gggcagagtc     180
acgattacca cggacgaatc cacgagcaca gcctacatgg agctgagcag cctgagatct     240
gaggacacgg ccgtgtatta ctgtgcgaga tactgttaca gtgccagttg ttatcacaac     300
tggttcgacc cctggggcca gggaacgctg gtcaccgtct cctca                     345

<210> SEQ ID NO 403
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 403
gctgaggtga agaagcctgg gtcctcggtg aaggtctcct gcaaggcttc tggaggcacc      60
ttcagcagct atgctatcag ctgggtgcga caggcccctg gacaagggct tgagtggatg     120
ggagggatca tccctatctt tggtacagca aactacgcac agaagttcca gggcagagtc     180
acgattaccg cggacaaatc cacgagcaca gcctacatgg agctgagcag cctgagatct     240
gaggacacgg ccgtgtatta ctgtgcgaga tactgttaca gtgccagttg ttatcacaac     300
tggttcgacc cctggggcca gggaacgctg gtcaccgtct cctca                     345

<210> SEQ ID NO 404
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 404
gctgaggtga agaagcctgg gtcctcagtg aaggtctcct gcaaggcttc tggaggcacc      60
ttcagcagct atgctatcag ctgggtgcga caggcccctg gacaagggct tgagtggatg     120
ggagggatca tccctttctt tggtacaaga gaccacgcac agaacttcca gggcagagtc     180
acgattacca cggacgaatc cacgagcaca gcctacatgg agctgagcag cctgagatct     240
gaggacacgg ccgtctatta ctgtgcgaga tattgtagta gtcccagttg ttatcacaac     300
tggttcgacc cctggggcca gggaaccctg gtcaccgtct cctca                     345

<210> SEQ ID NO 405
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 405
gctgaggtga agaagcctgg gtcctcagtg aaggtctcct gcaaggcttc tggaggcacc      60

```
ttcagcagct atgctatcag ctgggtgcga caggccsctg acaagggct tgagtggatg      120 ggagggatca tccctatctt tggtacagca aactacgcac agaagttcca gggcagagtc     180
acgattaccg cggacaaatc cacgagcaca gcctacatgg agctgagcag cctgagatct    240
gaggacacgg ccgtgtatta ctgtgcgaga tattgtagta gtgccagttg ctatcacaac    300
tggttcgacc cctggggcca gggaaccctg gtcaccgtct cctca                    345
```

```
<210> SEQ ID NO 406
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 406
gctgaggtga ggaagcctgg gtcctcagtg aaggtctcct gcaagatttc tggaggctcc     60
ctcaacagtt atggcatcag ctgggtgcga caggcccctg gtggacaagg gcttgagtgg    120 atggaggga tcatcccttt ctttggtaca gttatctatt cagacaatta ccaggacaga     180
gtctcgtttt cctcggacga atctacgacc acagcctaca tggagctgag aagcctaaga    240
tctgaggaca cggccgtgta ttactgtgcg agatattgtt atagtgccag ttgttatcac    300
aactggttcg acccctgggg ccagggaacc ctggtcaccg tctcctca                 348
```

```
<210> SEQ ID NO 407
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 407
gctgaggtga ggaagcctgg gtcctcagtg aaggtctcct gcaagatttc tggaggctcc     60
ctcaacagtt atggcatcag ctgggtgcga caggcccctg gtggacaagg gcttgagtgg    120
atgggaggga tcatcccttt ctttggtaca gttatctatt cagacaatta ccaggacaga    180
gtctcgtttt cctcggacga atctacgacc acagcctaca tggagctgag aagcctaaga    240
tctgaggaca cggccgtgta ttactgtgcg agatattgtt atagtgccag ttgttatcac    300
aactggttcg acccctgggg ccagggaacc ctggtcaccg tctccaca                 348
```

```
<210> SEQ ID NO 408
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 408
gctgaggtga ggaagcctgg gtcctcagtg aaggtctcct gcaagatttc tggaggctcc     60
ctcaacagtt atggcatcag ctgggtgcga caggcccctg gtggacaagg gcttgagtgg    120
atgggaggga tcatcccttt ctttggtaca gttatctatt cagacaatta ccaggacaga    180
gtctcgtttt cctcggacga atctacgacc acagcctaca tggagctgag aagcctaaga    240
tctgaggaca cggccgtgta ttactgtgcg aggtattgtt atagtgccag ttgttatcac    300
aactggttcg acccctgggg ccagggaacc ctggtcaccg tctccaca                 348
```

<210> SEQ ID NO 409
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 409
gctgaggtga agaagcctgg gtcctcagtt aaggtctcct gcaaggcttc tggaggcacc      60
ttcagcagca attctgtcac ctgggtgcgg caggcccctg gacacgggct tgagtggatg     120
ggaacaatcg tccctttctt tggtacaaga cactccgcag acaactttca gggcagagtc     180
acgatcacca cggacgaatc cacgaccaca gtgtacatgg agctgagcag cctgagatct     240
gacgacacgg ccgtgtatta ctgtgcgaga tcttgtgaga gtcccagttg ttaccacaac     300
tggttcgacc cctggggcca gggaaccctg gtcaccgtca cctca                     345

<210> SEQ ID NO 410
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 410
gctgaggtga agaagcctgg gtcctcagtg aaggtctcct gcaaggcttc tggaggcacc      60
ttcagcagca attctgtcac ctgggtgcgg caggcccctg gacacgggct tgagtggatg     120
ggaacaatca tccctttctt tggtacaaga cactacgcag acaactttca gggcagagtc     180
acgatcacca cggacgaatc cacgaccacg gtgtacatgg agctgagcag cctgagatct     240
gacgacacgg ccgtgtatta ctgtgcgcga tcttgtgaga gtcccagttg ttaccacaac     300
tggttcgacc cctggggcca gggaaccctg gtcaccgtca cctca                     345

<210> SEQ ID NO 411
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 411
gctgaggtga agaagcctgg gtcctcagtg aaggtctcct gcaaggcttc tggaggcacc      60
ttcagcagca attctgtcac ctgggtgcgg caggcccctg gacacgggct tgagtggatg     120
ggaacaatca tccctttctt tggtacaaga cactacgcag acaactttca ggacagagtc     180
acgatcacca cggacgaatc cacgaccaca gtgtatatgg aactgagcag cctgagatct     240
gacgacacgg ccctgtatta ctgtgcgaga tcttgtgaga gtcccagttg ttaccacaac     300
tggttcgacc cctggggcca gggaaccctg gtcaccgtca cctca                     345

<210> SEQ ID NO 412
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 412

```
gctgaggtga agaagcctgg gtcctcagtg aaggtctcct gcaaggcttc tggaggcacc      60
ttcagcaact atgctatcag ctgggtgcga caggcccctg gacaagggct tgagtggatg     120
ggaggggtca ccccttttctt tggtacgaga aactacgcag acatgttcca gggcagagtc    180
acgattacca cggacgaatc cacgagcaca gtctacatgg agctgagcag cctgagatct    240
gaggacacgg ccgtctatta ttgtgcgaga tattgtagta gtcccagctg ctatcacaag    300
tggttcgacc cctggggcca gggaaccctg gtcaccgtct cctca                     345
```

<210> SEQ ID NO 413
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 413

```
gctgaggtga agaagcctgg gtcctcagtg aaggtctcct gcaaggcttc tggaggcacc      60
ttcaacaact atgccatcag ctgggtgcga caggcccctg gacaagggct tgagtggatg     120
ggaggggtca ccccttttctt tggtacgaga aactacgccg acatgttcca ggacagaatc    180
acgattacca cggacgaatc cacgaccaca gtctacatgg aactgagcag cctgagatct    240
gaagacacgg ccgtctatta ttgtgcgaga tactgtagta atcccagctg ctatcacaag    300
tggttcgacc cctggggcca gggaaccctg gtcaccgtct cctca                     345
```

<210> SEQ ID NO 414
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 414

```
gctgaggtga agaagcctgg gtcctcagtg aaggtctcct gcaagccttc tggaggcacc      60
ttcagcggta gttatggtct cgcgtgggtg cggcaggccc ctggacaagg gcttgagtgg     120
atgggaggga tcatcccgtt ctttggtaca agaaactacg cagacgactt ccaggacaga    180
atcacgctta cgacggacga aaccacgacc acagcctaca tggagctgag cagcctgaga    240
tctgaggaca cggccgtgta ttactgtgcg agatattgta gtagtgccag ttgctatcac    300
aactggttcg acccctgggg ccagggaacc ctggtcaccg tctcctca                  348
```

<210> SEQ ID NO 415
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 415

```
gctgaggtga agaagcctgg gtcctcagtt aaggtctcct gcaagccttc tggaggcacc      60
ttcagcggta gttatggtct cgcgtgggtg cggcaggccc ctggacaagg gcttgagtgg     120
atgggaggga tcatcccttt ctttgggaca agaaactacg cagacgactt ccaggacaga    180
gtcacactaa ccacggacga aaccacgacc acagcctaca tggagctgag cagcctgaga    240
```

```
tctgaggaca cggccgtcta ttactgtgcg agatattgta gtagtgccag ttgctatcac    300
aactggttcg acccctgggg ccagggaacc ctggtcaccg tctcctca                 348
```

<210> SEQ ID NO 416
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 416

```
gctgaggtga agaagcctgg gtcctcagtg aaggtctcct gcagggcttc tggaggcccc    60
ttcaatagct atggtatcac ctgggtgcga caggcccctg acaagggct tgagtggatg    120 ggagggatca gcccttcctt tgggacacga aactacgcag agaggttcca agacagactc   180
acgattacca cggacgaatc cacgaccgca gcctacatgg agctgcgcag cctgacatct   240
gacgacacgg ccgtctatta ctgtgcgaga tattgttaca gtgccagttg ttatcacaac   300
tggttcgacc cctggggcca gggaaccctg gtcaccgtct cctca                   345
```

<210> SEQ ID NO 417
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 417

```
gctgaggtga agaagcctgg gtcctcagtg aaggtctcct gcagggcttc tggaggcccc    60
ttcaatagct atggtatcac ctgggtgcga caggcccctg acaagggct tgagtggatg    120 ggagggatca gcccttcctt tggtacacga aactacgcag agaggttcca agacagactc   180
acgattagca cggacgaatc cacgaccgca gcctacatgg agctgcgcag cctgacatct   240
gacgacacgg ccgtctatta ctgtgcgaga tattgttaca gtgccagttg ttatcacaac   300
tggttcgacc cctggggcca gggaaccctg gtcaccgtct cctca                   345
```

<210> SEQ ID NO 418
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 418

```
gctgaggtga agaagcctgg gtcctcagtg aaggtctcct gcagggcttc tggaggcccc    60
ttcaatagtt atggtatcac ctgggtgcga caggcccctg acaagggct tgagtggatg    120 ggagggatca gcccttcctt tgggacacga aactacgcag agaggttcca agacagactc   180
acgattacca cggacgagtc tacgaccgca gcctacatgg agctgcgcag cctgacatct   240
gacgacacgg ccgtctatta ctgtgcgaga tactgttaca gtgccagttg ttatcacaac   300
tggttcgacc cctggggcca gggaacgctg gtcaccgtct cctca                   345
```

<210> SEQ ID NO 419
<211> LENGTH: 345
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 419
gctgaggtga agaagcctgg gtcctcagtg aaggtctcct gcaaggcttc tggaggcacc      60
ttcagcagct atggtatcac ctgggtgcga caggcccctg gacaagggct tgagtggatg     120
ggagggatca tccctttctt tggtacaaga aactacgcag acaacttcca ggacagagtc     180
acgattacca cggacgaatc cacgaccaca gcctacatgg agctgagcag cctgagatct     240
gacgacacgg ccgtgtatta ctgtgcgaga tattgtagta gtgccagttg ttatcacaac     300
tggttcgacc cctggggcca gggaaccctg gtcaccgtct cctca                     345

<210> SEQ ID NO 420
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 420

Ala Glu Val Lys Lys Pro Gly Ser Ser Val Lys Val Ser Cys Lys Ala
1               5                   10                  15

Ser Gly Gly Thr Phe Ser Ser Tyr Ala Ile Ser Trp Val Arg Gln Ala
            20                  25                  30

Pro Gly Gln Gly Leu Glu Trp Met Gly Gly Ile Ile Pro Ile Phe Gly
        35                  40                  45

Thr Ala Asn Tyr Ala Gln Lys Phe Gln Gly Arg Val Thr Ile Thr Thr
    50                  55                  60

Asp Glu Ser Thr Ser Thr Ala Tyr Met Glu Leu Ser Ser Leu Arg Ser
65                  70                  75                  80

Glu Asp Thr Ala Val Tyr Tyr Cys Ala Arg Tyr Cys Ser Ser Thr Ser
                85                  90                  95

Cys Tyr Asp Asn Trp Phe Asp Pro Trp Gly Gln Gly Thr Leu Val Thr
            100                 105                 110

Val Ser Ser
        115

<210> SEQ ID NO 421
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 421

Ala Glu Val Lys Lys Pro Gly Ser Ser Val Lys Val Ser Cys Lys Ala
1               5                   10                  15

Ser Gly Gly Thr Phe Ser Ser Tyr Ala Ile Ser Trp Val Arg Gln Ala
            20                  25                  30

Pro Gly Gln Gly Leu Glu Trp Met Gly Gly Ile Ile Pro Ile Phe Gly
        35                  40                  45

Thr Ala Asn Tyr Ala Gln Lys Phe Gln Gly Arg Val Thr Ile Thr Thr
    50                  55                  60

Asp Glu Ser Thr Ser Thr Ala Tyr Met Glu Leu Ser Ser Leu Arg Ser
65                  70                  75                  80

Glu Asp Thr Ala Val Tyr Tyr Cys Ala Arg Tyr Cys Tyr Ser Ala Ser

```
                 85                  90                  95

Cys Tyr His Asn Trp Phe Asp Pro Trp Gly Gln Gly Thr Leu Val Thr
            100                 105                 110

Val Ser Ser
        115

<210> SEQ ID NO 422
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 422

Ala Glu Val Lys Lys Pro Gly Ser Ser Val Lys Val Ser Cys Lys Ala
1               5                   10                  15

Ser Gly Gly Thr Phe Ser Ser Tyr Ala Ile Ser Trp Val Arg Gln Ala
            20                  25                  30

Pro Gly Gln Gly Leu Glu Trp Met Gly Gly Ile Ile Pro Ile Phe Gly
        35                  40                  45

Thr Ala Asn Tyr Ala Gln Lys Phe Gln Gly Arg Val Thr Ile Thr Ala
    50                  55                  60

Asp Lys Ser Thr Ser Thr Ala Tyr Met Glu Leu Ser Ser Leu Arg Ser
65                  70                  75                  80

Glu Asp Thr Ala Val Tyr Tyr Cys Ala Arg Tyr Cys Tyr Ser Ala Ser
                85                  90                  95

Cys Tyr His Asn Trp Phe Asp Pro Trp Gly Gln Gly Thr Leu Val Thr
            100                 105                 110

Val Ser Ser
        115

<210> SEQ ID NO 423
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 423

Ala Glu Val Lys Lys Pro Gly Ser Ser Val Lys Val Ser Cys Lys Ala
1               5                   10                  15

Ser Gly Gly Thr Phe Ser Ser Tyr Ala Ile Ser Trp Val Arg Gln Ala
            20                  25                  30

Pro Gly Gln Gly Leu Glu Trp Met Gly Gly Ile Ile Pro Phe Phe Gly
        35                  40                  45

Thr Arg Asp His Ala Gln Asn Phe Gln Gly Arg Val Thr Ile Thr Thr
    50                  55                  60

Asp Glu Ser Thr Ser Thr Ala Tyr Met Glu Leu Ser Ser Leu Arg Ser
65                  70                  75                  80

Glu Asp Thr Ala Val Tyr Tyr Cys Ala Arg Tyr Cys Ser Ser Pro Ser
                85                  90                  95

Cys Tyr His Asn Trp Phe Asp Pro Trp Gly Gln Gly Thr Leu Val Thr
            100                 105                 110

Val Ser Ser
        115
```

```
<210> SEQ ID NO 424
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 424

Ala Glu Val Lys Lys Pro Gly Ser Ser Val Lys Val Ser Cys Lys Ala
1               5                   10                  15

Ser Gly Gly Thr Phe Ser Ser Tyr Ala Ile Ser Trp Val Arg Gln Ala
            20                  25                  30

Pro Gly Gln Gly Leu Glu Trp Met Gly Gly Ile Ile Pro Ile Phe Gly
        35                  40                  45

Thr Ala Asn Tyr Ala Gln Lys Phe Gln Gly Arg Val Thr Ile Thr Ala
    50                  55                  60

Asp Lys Ser Thr Ser Thr Ala Tyr Met Glu Leu Ser Ser Leu Arg Ser
65                  70                  75                  80

Glu Asp Thr Ala Val Tyr Tyr Cys Ala Arg Tyr Cys Ser Ser Ala Ser
                85                  90                  95

Cys Tyr His Asn Trp Phe Asp Pro Trp Gly Gln Gly Thr Leu Val Thr
            100                 105                 110

Val Ser Ser
        115

<210> SEQ ID NO 425
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 425

Ala Glu Val Arg Lys Pro Gly Ser Ser Val Lys Val Ser Cys Lys Ile
1               5                   10                  15

Ser Gly Gly Ser Leu Asn Ser Tyr Gly Ile Ser Trp Val Arg Gln Ala
            20                  25                  30

Pro Gly Gly Gln Gly Leu Glu Trp Met Gly Gly Ile Ile Pro Phe Phe
        35                  40                  45

Gly Thr Val Ile Tyr Ser Asp Asn Tyr Gln Asp Arg Val Ser Phe Ser
    50                  55                  60

Ser Asp Glu Ser Thr Thr Thr Ala Tyr Met Glu Leu Arg Ser Leu Arg
65                  70                  75                  80

Ser Glu Asp Thr Ala Val Tyr Tyr Cys Ala Arg Tyr Cys Tyr Ser Ala
                85                  90                  95

Ser Cys Tyr His Asn Trp Phe Asp Pro Trp Gly Gln Gly Thr Leu Val
            100                 105                 110

Thr Val Ser Ser
        115

<210> SEQ ID NO 426
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 426
```

```
Ala Glu Val Arg Lys Pro Gly Ser Ser Val Lys Val Ser Cys Lys Ile
1               5                   10                  15

Ser Gly Gly Ser Leu Asn Ser Tyr Gly Ile Ser Trp Val Arg Gln Ala
            20                  25                  30

Pro Gly Gly Gln Gly Leu Glu Trp Met Gly Gly Ile Ile Pro Phe Phe
            35                  40                  45

Gly Thr Val Ile Tyr Ser Asp Asn Tyr Gln Asp Arg Val Ser Phe Ser
        50                  55                  60

Ser Asp Glu Ser Thr Thr Thr Ala Tyr Met Glu Leu Arg Ser Leu Arg
65                  70                  75                  80

Ser Glu Asp Thr Ala Val Tyr Tyr Cys Ala Arg Tyr Cys Tyr Ser Ala
                85                  90                  95

Ser Cys Tyr His Asn Trp Phe Asp Pro Trp Gly Gln Gly Thr Leu Val
                100                 105                 110

Thr Val Ser Thr
            115
```

<210> SEQ ID NO 427
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 427

```
Ala Glu Val Arg Lys Pro Gly Ser Ser Val Lys Val Ser Cys Lys Ile
1               5                   10                  15

Ser Gly Gly Ser Leu Asn Ser Tyr Gly Ile Ser Trp Val Arg Gln Ala
            20                  25                  30

Pro Gly Gly Gln Gly Leu Glu Trp Met Gly Gly Ile Ile Pro Phe Phe
            35                  40                  45

Gly Thr Val Ile Tyr Ser Asp Asn Tyr Gln Asp Arg Val Ser Phe Ser
        50                  55                  60

Ser Asp Glu Ser Thr Thr Thr Ala Tyr Met Glu Leu Arg Ser Leu Arg
65                  70                  75                  80

Ser Glu Asp Thr Ala Val Tyr Tyr Cys Ala Arg Tyr Cys Tyr Ser Ala
                85                  90                  95

Ser Cys Tyr His Asn Trp Phe Asp Pro Trp Gly Gln Gly Thr Leu Val
                100                 105                 110

Thr Val Ser Thr
            115
```

<210> SEQ ID NO 428
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 428

```
Ala Glu Val Lys Lys Pro Gly Ser Ser Val Lys Val Ser Cys Lys Ala
1               5                   10                  15

Ser Gly Gly Thr Phe Ser Ser Asn Ser Val Thr Trp Val Arg Gln Ala
            20                  25                  30

Pro Gly His Gly Leu Glu Trp Met Gly Thr Ile Val Pro Phe Phe Gly
            35                  40                  45
```

```
Thr Arg His Ser Ala Asp Asn Phe Gln Gly Arg Val Thr Ile Thr Thr
            50                  55                  60

Asp Glu Ser Thr Thr Thr Val Tyr Met Glu Leu Ser Ser Leu Arg Ser
65                  70                  75                  80

Asp Asp Thr Ala Val Tyr Tyr Cys Ala Arg Ser Cys Glu Ser Pro Ser
                85                  90                  95

Cys Tyr His Asn Trp Phe Asp Pro Trp Gly Gln Gly Thr Leu Val Thr
                100                 105                 110

Val Thr Ser
        115

<210> SEQ ID NO 429
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 429

Ala Glu Val Lys Lys Pro Gly Ser Ser Val Lys Val Ser Cys Lys Ala
1               5                   10                  15

Ser Gly Gly Thr Phe Ser Ser Asn Ser Val Thr Trp Val Arg Gln Ala
                20                  25                  30

Pro Gly His Gly Leu Glu Trp Met Gly Thr Ile Ile Pro Phe Phe Gly
            35                  40                  45

Thr Arg His Tyr Ala Asp Asn Phe Gln Gly Arg Val Thr Ile Thr Thr
            50                  55                  60

Asp Glu Ser Thr Thr Thr Val Tyr Met Glu Leu Ser Ser Leu Arg Ser
65                  70                  75                  80

Asp Asp Thr Ala Val Tyr Tyr Cys Ala Arg Ser Cys Glu Ser Pro Ser
                85                  90                  95

Cys Tyr His Asn Trp Phe Asp Pro Trp Gly Gln Gly Thr Leu Val Thr
                100                 105                 110

Val Thr Ser
        115

<210> SEQ ID NO 430
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 430

Ala Glu Val Lys Lys Pro Gly Ser Ser Val Lys Val Ser Cys Lys Ala
1               5                   10                  15

Ser Gly Gly Thr Phe Ser Ser Asn Ser Val Thr Trp Val Arg Gln Ala
                20                  25                  30

Pro Gly His Gly Leu Glu Trp Met Gly Thr Ile Ile Pro Phe Phe Gly
            35                  40                  45

Thr Arg His Tyr Ala Asp Asn Phe Gln Asp Arg Val Thr Ile Thr Thr
            50                  55                  60

Asp Glu Ser Thr Thr Thr Val Tyr Met Glu Leu Ser Ser Leu Arg Ser
65                  70                  75                  80

Asp Asp Thr Ala Leu Tyr Tyr Cys Ala Arg Ser Cys Glu Ser Pro Ser
                85                  90                  95
```

Cys Tyr His Asn Trp Phe Asp Pro Trp Gly Gln Gly Thr Leu Val Thr
            100                 105                 110

Val Thr Ser
        115

<210> SEQ ID NO 431
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 431

Ala Glu Val Lys Lys Pro Gly Ser Ser Val Lys Val Ser Cys Lys Ala
1               5                   10                  15

Ser Gly Gly Thr Phe Ser Asn Tyr Ala Ile Ser Trp Val Arg Gln Ala
            20                  25                  30

Pro Gly Gln Gly Leu Glu Trp Met Gly Gly Val Thr Pro Phe Phe Gly
        35                  40                  45

Thr Arg Asn Tyr Ala Asp Met Phe Gln Gly Arg Val Thr Ile Thr Thr
    50                  55                  60

Asp Glu Ser Thr Ser Thr Val Tyr Met Glu Leu Ser Ser Leu Arg Ser
65                  70                  75                  80

Glu Asp Thr Ala Val Tyr Tyr Cys Ala Arg Tyr Cys Ser Ser Pro Ser
                85                  90                  95

Cys Tyr His Lys Trp Phe Asp Pro Trp Gly Gln Gly Thr Leu Val Thr
            100                 105                 110

Val Ser Ser
        115

<210> SEQ ID NO 432
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 432

Ala Glu Val Lys Lys Pro Gly Ser Ser Val Lys Val Ser Cys Lys Ala
1               5                   10                  15

Ser Gly Gly Thr Phe Asn Asn Tyr Ala Ile Ser Trp Val Arg Gln Ala
            20                  25                  30

Pro Gly Gln Gly Leu Glu Trp Met Gly Gly Val Thr Pro Phe Phe Gly
        35                  40                  45

Thr Arg Asn Tyr Ala Asp Met Phe Gln Asp Arg Ile Thr Ile Thr Thr
    50                  55                  60

Asp Glu Ser Thr Ser Thr Val Tyr Met Glu Leu Ser Ser Leu Arg Ser
65                  70                  75                  80

Glu Asp Thr Ala Val Tyr Tyr Cys Ala Arg Tyr Cys Ser Asn Pro Ser
                85                  90                  95

Cys Tyr His Lys Trp Phe Asp Pro Trp Gly Gln Gly Thr Leu Val Thr
            100                 105                 110

Val Ser Ser
        115

<210> SEQ ID NO 433

<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 433

Ala Glu Val Lys Lys Pro Gly Ser Ser Val Lys Val Ser Cys Lys Pro
1               5                   10                  15

Ser Gly Gly Thr Phe Ser Gly Ser Tyr Gly Leu Ala Trp Val Arg Gln
            20                  25                  30

Ala Pro Gly Gln Gly Leu Glu Trp Met Gly Gly Ile Ile Pro Phe Phe
        35                  40                  45

Gly Thr Arg Asn Tyr Ala Asp Asp Phe Gln Asp Arg Ile Thr Leu Thr
    50                  55                  60

Thr Asp Glu Thr Thr Thr Thr Ala Tyr Met Glu Leu Ser Ser Leu Arg
65                  70                  75                  80

Ser Glu Asp Thr Ala Val Tyr Tyr Cys Ala Arg Tyr Cys Ser Ser Ala
                85                  90                  95

Ser Cys Tyr His Asn Trp Phe Asp Pro Trp Gly Gln Gly Thr Leu Val
            100                 105                 110

Thr Val Ser Ser
        115

<210> SEQ ID NO 434
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 434

Ala Glu Val Lys Lys Pro Gly Ser Ser Val Lys Val Ser Cys Lys Pro
1               5                   10                  15

Ser Gly Gly Thr Phe Ser Gly Ser Tyr Gly Leu Ala Trp Val Arg Gln
            20                  25                  30

Ala Pro Gly Gln Gly Leu Glu Trp Met Gly Gly Ile Ile Pro Phe Phe
        35                  40                  45

Gly Thr Arg Asn Tyr Ala Asp Asp Phe Gln Asp Arg Val Thr Leu Thr
    50                  55                  60

Thr Asp Glu Thr Thr Thr Thr Ala Tyr Met Glu Leu Ser Ser Leu Arg
65                  70                  75                  80

Ser Glu Asp Thr Ala Val Tyr Tyr Cys Ala Arg Tyr Cys Ser Ser Ala
                85                  90                  95

Ser Cys Tyr His Asn Trp Phe Asp Pro Trp Gly Gln Gly Thr Leu Val
            100                 105                 110

Thr Val Ser Ser
        115

<210> SEQ ID NO 435
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 435

```
Ala Glu Val Lys Lys Pro Gly Ser Ser Val Lys Val Ser Cys Arg Ala
1               5                   10                  15

Ser Gly Gly Pro Phe Asn Ser Tyr Gly Ile Thr Trp Val Arg Gln Ala
            20                  25                  30

Pro Gly Gln Gly Leu Glu Trp Met Gly Gly Ile Ser Pro Phe Phe Gly
            35                  40                  45

Thr Arg Asn Tyr Ala Glu Arg Phe Gln Asp Arg Leu Thr Ile Thr Thr
            50                  55                  60

Asp Glu Ser Thr Thr Ala Ala Tyr Met Glu Leu Arg Ser Leu Thr Ser
65                  70                  75                  80

Asp Asp Thr Ala Val Tyr Tyr Cys Ala Arg Tyr Cys Tyr Ser Ala Ser
            85                  90                  95

Cys Tyr His Asn Trp Phe Asp Pro Trp Gly Gln Gly Thr Leu Val Thr
            100                 105                 110

Val Ser Ser
        115

<210> SEQ ID NO 436
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 436

Ala Glu Val Lys Lys Pro Gly Ser Ser Val Lys Val Ser Cys Arg Ala
1               5                   10                  15

Ser Gly Gly Pro Phe Asn Ser Tyr Gly Ile Thr Trp Val Arg Gln Ala
            20                  25                  30

Pro Gly Gln Gly Leu Glu Trp Met Gly Gly Ile Ser Pro Phe Phe Gly
            35                  40                  45

Thr Arg Asn Tyr Ala Glu Arg Phe Gln Asp Arg Leu Thr Ile Ser Thr
            50                  55                  60

Asp Glu Ser Thr Thr Ala Ala Tyr Met Glu Leu Arg Ser Leu Thr Ser
65                  70                  75                  80

Asp Asp Thr Ala Val Tyr Tyr Cys Ala Arg Tyr Cys Tyr Ser Ala Ser
            85                  90                  95

Cys Tyr His Asn Trp Phe Asp Pro Trp Gly Gln Gly Thr Leu Val Thr
            100                 105                 110

Val Ser Ser
        115

<210> SEQ ID NO 437
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 437

Ala Glu Val Lys Lys Pro Gly Ser Ser Val Lys Val Ser Cys Arg Ala
1               5                   10                  15

Ser Gly Gly Pro Phe Asn Ser Tyr Gly Ile Thr Trp Val Arg Gln Ala
            20                  25                  30

Pro Gly Gln Gly Leu Glu Trp Met Gly Gly Ile Ser Pro Ser Phe Gly
            35                  40                  45
```

Thr Arg Asn Tyr Ala Glu Arg Phe Gln Asp Arg Leu Thr Ile Thr Thr
            50                  55                  60

Asp Glu Ser Thr Thr Ala Ala Tyr Met Glu Leu Arg Ser Leu Thr Ser
65                  70                  75                  80

Asp Asp Thr Ala Val Tyr Tyr Cys Ala Arg Tyr Cys Tyr Ser Ala Ser
                85                  90                  95

Cys Tyr His Asn Trp Phe Asp Pro Trp Gly Gln Gly Thr Leu Val Thr
            100                 105                 110

Val Ser Ser
        115

<210> SEQ ID NO 438
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 438

Ala Glu Val Lys Lys Pro Gly Ser Ser Val Lys Val Ser Cys Lys Ala
1               5                   10                  15

Ser Gly Gly Thr Phe Ser Ser Tyr Gly Ile Thr Trp Val Arg Gln Ala
            20                  25                  30

Pro Gly Gln Gly Leu Glu Trp Met Gly Gly Ile Ile Pro Phe Phe Gly
        35                  40                  45

Thr Arg Asn Tyr Ala Asp Asn Phe Gln Asp Arg Val Thr Ile Thr Thr
            50                  55                  60

Asp Glu Ser Thr Thr Thr Ala Tyr Met Glu Leu Ser Ser Leu Arg Ser
65                  70                  75                  80

Asp Asp Thr Ala Val Tyr Tyr Cys Ala Arg Tyr Cys Ser Ser Ala Ser
                85                  90                  95

Cys Tyr His Asn Trp Phe Asp Pro Trp Gly Gln Gly Thr Leu Val Thr
            100                 105                 110

Val Ser Ser
        115

<210> SEQ ID NO 439
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 439

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Thr Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

```
Ala Arg Tyr Cys Ser Ser Thr Ser Cys Tyr Asp Asn Trp Phe Asp Pro
                100                 105                 110

Trp Gly Gln Gly Thr Leu Val Thr Val Ser Ser
        115                 120

<210> SEQ ID NO 440
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 440

Ala Glu Val Arg Lys Pro Gly Ser Ser Val Lys Val Ser Cys Lys Thr
1               5                   10                  15

Ser Gly Gly Ser Leu Asn Ser Tyr Gly Ile Ser Trp Val Arg Gln Ala
            20                  25                  30

Pro Gly Gly Gln Gly Leu Glu Trp Met Gly Gly Ile Ile Pro Phe Phe
        35                  40                  45

Gly Thr Val Ile Tyr Ser Asp Asn Tyr Gln Gly Arg Ala Ser Phe Ser
    50                  55                  60

Ser Asp Glu Ser Thr Thr Thr Ala Tyr Met Glu Leu Arg Ser Leu Arg
65                  70                  75                  80

Ser Glu Asp Thr Ala Val Tyr Tyr Cys Ala Arg Tyr Cys Tyr Ser Ala
                85                  90                  95

Ser Cys Tyr His Asn Trp Phe Asp Pro Trp Gly Gln Gly Thr Leu Val
                100                 105                 110

Thr Val Ser Thr
        115

<210> SEQ ID NO 441
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 441

Ala Glu Val Lys Lys Pro Gly Ser Ser Val Lys Val Ser Cys Lys Ala
1               5                   10                  15

Ser Gly Gly Thr Phe Ser Ser Asn Ser Val Thr Trp Val Arg Gln Ala
            20                  25                  30

Pro Gly His Gly Leu Glu Trp Met Gly Gly Ile Ile Pro Phe Phe Gly
        35                  40                  45

Thr Arg His Tyr Ala Asp Asn Phe Gln Gly Arg Val Thr Val Thr Thr
    50                  55                  60

Asp Glu Ser Thr Thr Thr Val Tyr Met Glu Leu Ser Ser Leu Arg Ser
65                  70                  75                  80

Asp Asp Thr Ala Val Tyr Tyr Cys Ala Arg Ser Cys Glu Ser Pro Ser
                85                  90                  95

Cys Tyr His Asn Trp Phe Asp Pro Trp Gly Gln Gly Thr Leu Val Thr
                100                 105                 110

Val Thr Ser
        115

<210> SEQ ID NO 442
<211> LENGTH: 115
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 442

Ala Glu Val Arg Lys Pro Gly Ser Ser Val Lys Val Ser Cys Lys Thr
1               5                   10                  15

Ser Gly Gly Ser Leu Asn Ser Tyr Gly Ile Ser Trp Val Arg Gln Ala
            20                  25                  30

Pro Gly Gln Gly Leu Glu Trp Met Gly Gly Ile Ile Pro Phe Phe Gly
        35                  40                  45

Thr Val Ile Tyr Ser Asp Asn Tyr Gln Gly Arg Ala Ser Phe Ser Ser
    50                  55                  60

Asp Glu Ser Thr Thr Ala Tyr Met Glu Leu Arg Ser Leu Arg Ser
65                  70                  75                  80

Glu Asp Thr Ala Val Tyr Tyr Cys Ala Arg Tyr Cys Tyr Ser Ala Ser
                85                  90                  95

Cys Tyr His Asn Trp Phe Asp Pro Trp Gly Gln Gly Thr Leu Val Thr
            100                 105                 110

Val Ser Thr
        115

<210> SEQ ID NO 443
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 443

Gly Gly Thr Phe Ser Ser Tyr Ala Ile Ser
1               5                   10

<210> SEQ ID NO 444
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 444

Trp Met Gly Gly Ile Ile Pro Ile Phe Gly Thr Ala Asn Tyr Ala Gln
1               5                   10                  15

Lys Phe Gln Gly
            20

<210> SEQ ID NO 445
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 445

Ala Arg Tyr Cys Ser Ser Thr Ser Cys Tyr Asp Asn Trp Phe Asp Pro
1               5                   10                  15

<210> SEQ ID NO 446
```

-continued

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 446

Gln Ser Ile Gly Ser Asn
1               5
```